US011319547B1

(12) United States Patent
Nuccio et al.

(10) Patent No.: US 11,319,547 B1
(45) Date of Patent: May 3, 2022

(54) PLANT TRANSFORMATION

(71) Applicant: Inari Agriculture, Inc., Cambridge, MA (US)

(72) Inventors: Michael Lee Nuccio, Salem, NH (US); Davide Sosso, Cambridge, MA (US); Tomáš Čermák, Brookline, MA (US); David J. Segal, Davis, CA (US)

(73) Assignee: Inari Agriculture Technology, Inc., Cambridge, MA (US)

( * ) Notice: Subject to any disclaimer, the term of this patent is extended or adjusted under 35 U.S.C. 154(b) by 0 days.

(21) Appl. No.: 16/844,438

(22) Filed: Apr. 9, 2020

Related U.S. Application Data

(60) Provisional application No. 62/833,150, filed on Apr. 12, 2019.

(51) Int. Cl.
*C12N 15/82* (2006.01)
(52) U.S. Cl.
CPC .................. *C12N 15/8223* (2013.01)
(58) Field of Classification Search
None
See application file for complete search history.

(56) References Cited

U.S. PATENT DOCUMENTS

| 7,256,322 | B2 | 8/2007 | Lowe et al. |
| 2017/0121722 | A1 | 5/2017 | Anand et al. |
| 2017/0342431 | A1 | 11/2017 | Gordon-Kamm et al. |
| 2019/0017061 | A1 | 1/2019 | Gordon-Kamm et al. |
| 2021/0010012 | A1* | 1/2021 | Gasior ............... C12N 15/8213 |
| 2021/0071189 | A1* | 3/2021 | Labs .................. C12N 15/8207 |

FOREIGN PATENT DOCUMENTS

WO 2018085693 A1 5/2018

OTHER PUBLICATIONS

Čermáak, et al. "A Multipurpose Toolkit to Enable Advanced Genome Engineering in Plants." 2017, The Plant Cell Online 29 (6): 1196-1217. doi: 10.1105/tpc.16.00922.
Gersbach, et al. "Synthetic Zinc Finger Proteins: The Advent of Targeted Gene Regulation and Genome Modification Technologies." 2014, Accounts of Chemical Research 47 (8): 2309-18. doi: 10.1021/ar500039w.
Gupta, et al. "Transcriptional Activation of *Brassica napus* β-Ketoacyl-ACP Synthase II with an Engineered Zinc Finger Protein Transcription Factor." 2012, Plant Biotechnology Journal 10 (7): 783-91. doi: 10.1111/i.1467-7652.2012.00695.x.
Heiderscheit, et al. "Reprogramming Cell Fate with Artificial Transcription Factors." 2018, FEBS Letters 592 (6): 888-900. doi: 10.1002/1873-3468.12993.
Holmes-Davis, et al. "Gene Regulation in Planta by Plant-Derived Engineered Zinc Finger Protein Transcription Factors." 2005, Plant Molecular Biology 57 (3): 411-23. doi: 10.1007/s11103-004-7820-x.
Jinek, et al. "A programmable dual-RNA-guided DNA endonuclease in adaptive bacterial immunity." Science, Aug. 17, 2012;337(6096):816-21. doi: 10.1126/science.1225829.
Lowe, et al. "Rapid Genotype 'Independent' *Zea mays* L. (Maize) Transformation via Direct Somatic Embryogenesis." 2018, In Vitro Cellular & Developmental Biology—Plant 54 (3): 240-52. doi: 10.1007/s11627-018-9905-2.
Lowe, et al. "Morphogenic Regulators Baby Boom and Wuschel Improve Monocot Transformation." 2016, The Plant Cell Online 28 (9): 1998-2015. doi: 10.1105/tpc.16.00124.
Mookkan, et al. "Selectable Marker Independent Transformation of Recalcitrant Maize Inbred B73 and Sorghum P898012 Mediated by Morphogenic Regulators Baby Boom and WUSCHEL2." 2017, Plant Cell Reports 36 (9) 1477-91. doi: 10.1007/s00299-017-2169-1.
Moore, et al. "Transcription Activator-like Effectors: A Toolkit for Synthetic Biology." 2014, ACS Synthetic Biology 3 (10): 708-16. doi: 10.1021/sb400137b.
Sanjana, et al. "A Transcription Activator-like Effector Toolbox for Genome Engineering." 2012, Nature Protocols 7 (1):171-92. doi: 10.1038/nprot.2011.431.
Schindele, et al. "Transforming plant biology and breeding with CRISPR/Cas9, Cas12 and Cas13." FEBS Lett. Jun. 2018; 592(12):1954-1967. doi:10.1002/1873-3468.13073.
Thakore, et al. "Design, Assembly, and Characterization of TALE-Based Transcriptional Activators and Repressors." 2016, Methods in Molecular Biology (Clifton, N.J.) 1338: 71-88. doi: 10.1007/978-1-4939-2932-0_7.
Zhang X, et al. "Multiplex gene regulation by CRISPR-ddCpf1" Cell Discov. Jun. 6, 2017;3:17018. doi: 10.1038/celldisc.2017.18.

* cited by examiner

*Primary Examiner* — Matthew R Keogh
*Assistant Examiner* — Brian James Sullivan
(74) *Attorney, Agent, or Firm* — McKee, Voorhees & Sease PLC

(57) ABSTRACT

Plant cells and related systems, methods, and compositions for improving the capacity of the plant cells to regenerate embryogenic plant tissues, plant organs, and whole plants are provided. Such plant cells and related systems, methods, and compositions provide for increased expression of the endogenous morphoregulators BABYBOOM (ODP2) and/or WUSCHEL2 (WUS2).

11 Claims, No Drawings
Specification includes a Sequence Listing.

PLANT TRANSFORMATION

REFERENCE TO RELATED APPLICATIONS

This application claims benefit of priority to U.S. Provisional Patent Application No. 62/833,150 filed Apr. 12, 2019, which is incorporated herein by reference in their entireties.

INCORPORATION OF SEQUENCE LISTING

The sequence listing contained in the file named "63200_195755_SEQLISTING_ST25.txt", which is 382,728 MB measured in Windows, which was created on Apr. 9, 2020 and electronically filed via EFS-Web on Apr. 9, 2020, is incorporated herein by reference in its entirety.

BACKGROUND

To overcome recalcitrance of corn to genetic transformation, transgenes encoding morphoregulators BABYBOOM (ODP2) and/or WUSCHEL2 (WUS2) have been transiently expressed in corn cells to stimulate somatic embryogenesis (Lowe et al. 2016, Lowe et al. 2018). Such somatic embryogenesis promotes formation of Type II embryogenic callus from which new shoots can be generated, allowing maize genotype independent genetic transformation and making previously recalcitrant tissues accessible to transformation. The expression of BABYBOOM (ODP2) and/or WUSCHEL2 (WUS2) has also been shown to promote embryogenesis in sorghum (Mookkan et al. 2017), wheat, and a variety of other plants including cotton (US Patent Appl. Pub. No. 20170342431; U.S. Pat. No. 7,256,322; also reviewed by Nagle et al., 2018).

It is not yet clear how BABYBOOM and WUSCHEL trigger this effect. BABYBOOM is known to induce somatic embryogenesis, the biology of which is beginning to be understood (Horstman et al. 2017; Jha and Kumar, 2019). WUSCHEL biology has been investigated primarily in *Arabidopsis* (Rodriguez et al. 2016; Schoof et al. 2000; Mayer et al. 1998; Laux et al. 1996). It has a major role in stem cell maintenance.

The genomic insertion of morphoregulator-encoding transgenes is not a universal agricultural biotechnology solution, and also stipulates market access consequences. Commercialization of transgenic plants, and their progeny, is restricted by country-specific regulations. Genomic insertion of transgenes can facilitate the introduction of gene editing reagents, for example when coupled with transgenes encoding CRISPR-Cas9 (Soda, Verma, and Giri 2017; W. Wang et al. 2018). Hence, transgenes often need to be segregated away from edited progeny which can require multiple crosses and lengthen development/production timelines and costs. Transgenes do enable the use of selectable markers which enrich for edited tissue, greatly improving editing efficiency. Due to this enrichment step transgenesis remains the primary method for producing edited plants, however several groups are experimenting with alternative selection tools (Zhang et al. 2016; Hamada et al. 2018).

SUMMARY

Disclosed herein are plant cells wherein expression of an endogenous ODP2 polypeptide and/or expression of an endogenous WUS2 polypeptide is transiently increased in comparison to the expression of the endogenous ODP2 and/or the endogenous WUS2 polypeptides in a control plant cell, and wherein the plant cell can form a regenerable plant structure. Also disclosed are tissue cultures of such plant cells and related methods wherein the cells are used to obtain genetically edited or genetically transformed regenerable plant structures (e.g., a somatic embryo, embryogenic callus, somatic meristem, organogenic callus, a shoot, or a shoot further comprising roots) or plants. In certain embodiments, the expression of the endogenous ODP2 polypeptide and/or the endogenous WUS2 polypeptide is transiently increased in the plant cell with at least one exogenous gene transcription agent that stimulates transcription of the endogenous ODP2 gene and/or with at least one exogenous gene transcription agent that stimulates transcription of the endogenous WUS2 gene. Such plant cells include both monocot (e.g., maize, wheat, sorghum, and rice) plant cells and dicot plant cells (e.g., *Brassica* sp., cotton, and soybean). Also provided are maize plant cells comprising at least one exogenous gene transcription agent that stimulates transcription of the endogenous WUS2 gene, wherein expression of the endogenous WUS2 polypeptide is increased in comparison to the expression of the endogenous WUS2 polypeptide in a control maize plant cell, wherein the endogenous WUS2 polypeptide is encoded by an endogenous polynucleotide that is operably linked to an endogenous maize WUS2 promoter of SEQ ID NO:4 or an allelic variant thereof, wherein the exogenous gene transcription agent(s) bind to DNA sequences in the endogenous maize WUS2 promoter corresponding to residues 100 to 225 of SEQ ID NO:4, and wherein the maize plant cells can form a regenerable maize plant structure.

Methods provided herein include methods of producing a regenerable plant structure, comprising introducing into the plant cell at least one exogenous gene transcription agent which transiently increases expression of an endogenous ODP2 polypeptide and/or at least one exogenous gene transcription agent which increases expression of an endogenous WUS2 polypeptide, wherein the expression is increased in comparison to the expression of the endogenous ODP2 and/or the endogenous WUS2 polypeptides in a control plant cell; and culturing the plant cell to produce the regenerable plant structure. In certain embodiments of the methods, the exogenous gene transcription agent comprises: (i) a domain or complex which binds to the promoter or 5' untranslated region (5' UTR) of the endogenous ODP2 gene or to the promoter or 5' UTR of the endogenous WUS2 gene; and (ii) a transcription activation domain, wherein the transcription activation domain is operably linked or operably associated with the domain or complex. Such methods can be applied to plant cells that include both monocot (e.g., maize, wheat, sorghum, and rice) plant cells and dicot plant cells (e.g., *Brassica* sp., cotton, and soybean). Also provided are methods of producing a regenerable maize plant structure, comprising: (i) introducing into a maize plant cell at least one exogenous gene transcription agent which transiently increases expression of an endogenous WUS2 polypeptide, wherein the expression is increased in comparison to the expression of the endogenous WUS2 polypeptide in a control maize plant cell, wherein the endogenous WUS2 polypeptide is encoded by an endogenous polynucleotide that is operably linked to an endogenous maize WUS2 promoter of SEQ ID NO:4 or an allelic variant thereof, and wherein the exogenous gene transcription agent(s) bind to DNA sequences in the endogenous maize WUS2 promoter corresponding to residues 100 to 225 of SEQ ID NO:4; and, (ii) culturing the maize plant cell to produce a regenerable maize plant structure.

DETAILED DESCRIPTION

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art. Where a term is provided in the singular, the inventors also contemplate embodiments described by the plural of that term.

The phrase "allelic variant" as used herein refers to a polynucleotide or polypeptide sequence variant that occurs in a different strain, variety, or isolate of a given organism.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the terms "correspond," "corresponding," and the like, when used in the context of an nucleotide position, mutation, and/or substitution in any given polynucleotide (e.g., an allelic variant of SEQ ID NO: 4) with respect to the reference polynucleotide sequence (e.g., SEQ ID NOs: 4, 101, 102, residues 130-210 of SEQ ID NO: 4) all refer to the position of the polynucleotide residue in the given sequence that has identity to the residue in the reference nucleotide sequence when the given polynucleotide is aligned to the reference polynucleotide sequence using a pairwise alignment algorithm (e.g., CLUSTAL O 1.2.4 with default parameters).

As used herein, the terms "Cpf1" and "Cas12a" are used interchangeably herein to refer to the same RNA directed nuclease.

The phrases "expression of an endogenous ODP2 polypeptide," "expression of an endogenous WUS2 polypeptide," "expression of the endogenous ODP2 polypeptide," and "expression of the endogenous WUS2 polypeptide" refer to the expression of an ODP2 polypeptide or WUS2 polypeptide respectively encoded by an endogenous ODP2 gene or endogenous WUS2 gene in a plant genome.

As used herein, the phrase "genome altering reagent" refers to any molecule or set of molecules that can result in either the site-specific or non-site specific insertion of an exogenous nucleic acid molecule into the genome or a site-specific or non-site specific insertion, deletion, and/or substitution of one or more nucleotide residues in the genome. A genome altering reagent can comprise a transgene, a vector comprising a transgene, a genome editing molecule(s), and/or polynucleotides encoding the genome editing molecule(s).

As used herein, the phrase "gene-editing" includes genome modification by homology directed repair (HDR), base editing, and non-homologous end-joining (NHEJ) mechanisms. Such gene-editing includes embodiments where a site specific nuclease and a donor template are provided.

As used herein, an "exogenous" agent or molecule refers to any agent or molecule from an external source that is provided to or introduced into a system, composition, plant cell culture, reaction system, or plant cell. In certain embodiments, the exogenous agent (e.g., polynucleotide, protein, or compound) from the external source can be an agent that is also found in a plant cell. In certain embodiments, the exogenous agent (e.g., polynucleotide, protein, or compound) from the external source can be an agent that is heterologous to the plant cell.

As used herein, a "heterologous" agent or molecule refers: (i) to any agent or molecule that is not found in a wild-type, untreated, or naturally occurring composition or plant cell; and/or (ii) to a polynucleotide or peptide sequence located in, e.g., a genome or a vector, in a context other than that in which the sequence occurs in nature. For example, a promoter that is operably linked to a gene other than the gene that the promoter is operably linked to in nature is a heterologous promoter.

The phrase "improved plant cell regenerative potential" as used herein refers to the ability of a given plant cell to form a somatic embryo, embryogenic callus, a somatic meristem, organogenic callus, a shoot, or a shoot further comprising roots in comparison to a control plant cell.

As used herein, the terms "include," "includes," and "including" are to be construed as at least having the features to which they refer while not excluding any additional unspecified features.

As used herein, the term "overproduced" where used herein with regards to various agents refers to providing the agent in an amount that is increased in comparison to the amount found in an untreated plant cell or plant.

As used herein, the phrase "plant cell" can refer either a plant cell having a plant cell wall or to a plant cell protoplast lacking a plant cell wall.

The term "polynucleotide" where used herein is a nucleic acid molecule containing two (2) or more nucleotide residues. Polynucleotides are generally described as single- or double-stranded. Where a polynucleotide contains double-stranded regions formed by intra- or intermolecular hybridization, the length of each double-stranded region is conveniently described in terms of the number of base pairs. Embodiments of the systems, methods, and compositions provided herein can employ or include: (i) one or more polynucleotides of 2 to 25 residues in length, one or more polynucleotides of more than 26 residues in length, or a mixture of both. Polynucleotides can comprise single- or double-stranded RNA, single- or double-stranded DNA, double-stranded DNA/RNA hybrids, chemically modified analogues thereof, or a mixture thereof. In certain embodiments, a polynucleotide can include a combination of ribonucleotides and deoxyribonucleotides (e.g., synthetic polynucleotides consisting mainly of ribonucleotides but with one or more terminal deoxyribonucleotides or synthetic polynucleotides consisting mainly of deoxyribonucleotides but with one or more terminal dideoxyribonucleotides), or can include non-canonical nucleotides such as inosine, thiouridine, or pseudouridine. In certain embodiments, the polynucleotide includes chemically modified nucleotides (see, e.g., Verma and Eckstein (1998) *Annu. Rev. Biochem.*, 67:99-134). Chemically modified nucleotides that can be used in the polynucleotides provided herein include: (i) phosphorothioate, phosphorodithioate, or methylphosphonate internucleotide linkage modifications of the phosphodiester backbone; (ii) nucleosides comprising modified bases and/or modified sugars; and/or (iii) detectable labels including a fluorescent moiety (e.g., fluorescein or rhodamine or a fluorescence resonance energy transfer or FRET pair of chromophore labels) or other label (e.g., biotin or an isotope). Polynucleotides provided or used herein also include modified nucleic acids, particularly modified RNAs, which are disclosed in U.S. Pat. No. 9,464,124, which is incorporated herein by reference in its entirety.

As used herein the term "synergistic" refers to an effect of combining at least two factors that exceeds the sum of the effects obtained when the factors are not combined.

As used herein, the phrase "target plant gene" can refer to either a gene located in the plant genome that is to be modified by gene editing molecules provided in a system, method, composition and/or plant cell provided herein or alternatively to a plant gene located in the plant genome that is targeted for increased expression (e.g., an ODP2 and/or an WUS2 gene). Embodiments of target plant genes include (protein-)coding sequence, non-coding sequence, and combinations of coding and non-coding sequences. Modifications of a target plant gene include nucleotide substitutions, insertions, and/or deletions in one or more elements of a plant gene that include a transcriptional enhancer or promoter, a 5' or 3' untranslated region, a mature or precursor RNA coding sequence, an intron, a splice donor and/or acceptor, a protein coding sequence, a polyadenylation site, and/or a transcriptional terminator. In certain embodiments, all copies or all alleles of a given target gene in a diploid or polyploid plant cell are modified to provide homozygosity of the modified target gene in the plant cell. In embodiments, where a desired trait is conferred by a loss-of-function mutation that is introduced into the target gene by gene editing, a plant cell, population of plant cells, plant, or seed is homozygous for a modified target gene with the loss-of-function mutation. In other embodiments, only a subset of the copies or alleles of a given target gene are modified to provide heterozygosity of the modified target gene in the plant cell. In certain embodiments where a desired trait is conferred by a dominant mutation that is introduced into the target gene by gene editing, a plant cell, population of plant cells, plant, or seed is heterozygous for a modified target gene with the dominant mutation. Traits imparted by such modifications to certain plant target genes include improved yield, resistance to insects, fungi, bacterial pathogens, and/or nematodes, herbicide tolerance, abiotic stress tolerance (e.g., drought, cold, salt, and/or heat tolerance), protein quantity and/or quality, starch quantity and/or quality, lipid quantity and/or quality, secondary metabolite quantity and/or quality, and the like, all in comparison to a control plant that lacks the modification. The plant having a genome modified by gene editing molecules provided in a system, method, composition and/or plant cell provided herein differs from a plant having a genome modified by traditional breeding (i.e., crossing of a male parent plant and a female parent plant), where unwanted and random exchange of genomic regions as well as random mitotically or meiotically generated genetic and epigenetic changes in the genome typically occurs during the cross and are then found in the progeny plants. Thus, in embodiments of the plant (or plant cell) with a modified genome, the modified genome is more than 99.9% identical to the original (unmodified) genome. In embodiments, the modified genome is devoid of random mitotically or meiotically generated genetic or epigenetic changes relative to the original (unmodified) genome. In embodiments, the modified genome includes a difference of epigenetic changes in less than 0.01% of the genome relative to the original (unmodified) genome. In embodiments, the modified genome includes: (a) a difference of DNA methylation in less than 0.01% of the genome, relative to the original (unmodified) genome; or (b) a difference of DNA methylation in less than 0.005% of the genome, relative to the original (unmodified) genome; or (c) a difference of DNA methylation in less than 0.001% of the genome, relative to the original (unmodified) genome. In embodiments, the gene of interest is located on a chromosome in the plant cell, and the modified genome includes: (a) a difference of DNA methylation in less than 0.01% of the portion of the genome that is contained within the chromosome containing the gene of interest, relative to the original (unmodified) genome; or (b) a difference of DNA methylation in less than 0.005% of the portion of the genome that is contained within the chromosome containing the gene of interest, relative to the original (unmodified) genome; or (c) a difference of DNA methylation in less than 0.001% of the portion of the genome that is contained within the chromosome containing the gene of interest, relative to the original (unmodified) genome. In embodiments, the modified genome has not more unintended changes in comparison to the original (unmodified) genome than $1 \times 10^{-8}$ mutations per base pair per replication. In certain embodiments, the modified genome has not more unintended changes than would occur at the natural mutation rate. Natural mutation rates can be determined empirically or are as described in the literature (Lynch, M., 2010; Clark et al., 2005).

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Plant cells and related systems, methods, and compositions that provide for improved plant cell regenerative potential in comparison to control plant cells are provided herein. In certain embodiments, improved plant cell regenerative potential is provided by transiently increasing the expression of an ODP2 polypeptide and/or WUS2 polypeptide respectively encoded by an endogenous ODP2 gene or endogenous WUS2 gene in a plant genome in the plant cells in comparison to a control plant cell. Such transient expression of the endogenous WUS2 and/or ODP2 genes can provide for desired improvements in the regenerative capacity of the plant cell while avoiding undesired effects of increasing expression of WUS2 and/or ODP2 in partially or fully regenerated plant structures, tissues, organs, and plants. Transient expression of the endogenous ODP2 and/or WUS2 genes can be for a period of time and/or in an amount sufficient to result in improved regenerative potential in comparison to a control plant cell. In certain embodiments, the transient increase in the expression of the endogenous ODP2 polypeptide and/or expression of the endogenous WUS2 polypeptide is for a period of about 1, 2, 4, 8, 12, 16, 20, 24, 30, or 36 hours to about 72, 96, 120, 144, 168, 192, 276, or 336 hours. In certain embodiments, the transient increase in the expression of the endogenous ODP2 polypeptide and/or expression of the endogenous WUS2 polypeptide is for a period of about 2, 4, 8, 12, or 16 hours to about 18, 20, 24, 30 or 36 hours. In certain embodiments, the transient increase in the expression of the endogenous ODP2 polypeptide and/or expression of the endogenous WUS2 polypeptide is for a period of about 18, 20, 24, 30 or 36 hours to about 60, 80, 100, 120, 168, or 192 hours. Such transient increases in expression of the endogenous ODP2 and/or WUS2 genes can be measured by methods whereby accumulated ODP2 and/or WUS2 gene products including mRNAs and/or proteins are measured. Useful methods of measuring ODP2 and/or WUS2 mRNAs include quantitative reverse transcriptase Polymerase Chain Reaction (qRT-PCR)-based and/or any hybridization-based assay. Useful methods for quantitating ODP2 and/or WUS2 include immunoassays (e.g., ELISAs, RIAs) and/or mass spectrometry-based methods. In certain embodiments, expression of endogenous ODP2 and/or WUS2 gene products including mRNAs and/or proteins are transiently increased by at least 1.5-, 2-, 3-, 5-, 10-fold, 20-fold, 50-fold, 100-fold, 500-fold, or 1000-fold in comparison to the corresponding endogenous ODP2 and/or WUS2 gene products in a control plant cell. In certain embodiments, expression of endogenous ODP2 and/or WUS2 gene products including mRNAs and/or proteins are transiently increased by at least 1.5-, 2-, or 3-fold to about 4-, 5-, 10-, 15-, 20-, 50-, 100-, 500-f, or 1000-fold in comparison to the corresponding endogenous ODP2 and/or WUS2 gene products in a control plant cell.

Endogenous ODP2 genes in plants that can be targeted for increased expression by methods provided herein include the endogenous ODP2 genes of both monocot and dicot plants. Such endogenous ODP2 genes include the ODP2 genes that encode ODP2 peptides disclosed in US Patent Application Publication Nos. 20190017061 and 20170121722, which are specifically incorporated herein by reference in their entireties with respect to such disclosure of such ODP2 genes and peptides. Endogenous ODP2 genes targeted for increased expression can encode ODP2 peptides that comprise APETALA2 (AP2) DNA binding motifs, and amino acid variants thereof. In certain embodiments, the plant cell is a maize plant cell and the endogenous ODP2 gene targeted for increased expression encodes a ODP2 polypeptide comprising an amino acid sequence having at least 95%, 96%, 97%, or 99% amino acid sequence identity across the entire length of SEQ ID NO:1. In certain embodiments, the plant cell is a maize plant cell and the endogenous ODP2 gene targeted for increased expression of the ODP2 polypeptide is the endogenous maize ODP2 gene located on maize chromosome 3. In certain embodiments, the plant cell is a maize plant cell and the endogenous ODP2 gene targeted for increased expression comprises an endogenous polynucleotide that is operably linked to an endogenous maize ODP2 promoter of SEQ ID NO:3, SEQ ID NO:71, or an allelic variant thereof.

Endogenous WUS2 genes in plants that can be targeted by methods provided herein include the endogenous WUS2 genes of both monocot and dicot plants. Such endogenous WUS2 genes include the WUS2 genes that encode WUS2 peptides disclosed in U.S. Pat. No. 7,256,322 and US Patent Application Publication No. 20170121722, which are specifically incorporated herein by reference in their entireties with respect to such disclosure of such WUS2 genes and peptides. Endogenous WUS2 genes targeted for increased expression can encode WUS2 peptides that comprise conserved homeodomain motifs such as the (E/R)TLPLFP motif (SEQ ID NO:109), the A(A/S)LEL(S/T)L motif (SEQ ID NO:110), a 25 amino acid motif located between the (E/R)TLPLFP (SEQ ID NO:109) and the A(A/S)LEL(S/T)L (SEQ ID NO:110) motifs, and amino acid variants thereof. In certain embodiments, the plant cell is a maize plant cell and the endogenous WUS2 gene targeted for increased expression encodes a WUS2 polypeptide comprising an amino acid sequence having at least 95%, 96%, 97%, or 99% amino acid sequence identity across the entire length of SEQ ID NO:2. In certain embodiments, the plant cell is a maize plant cell and the endogenous WUS2 gene targeted for increased expression of the endogenous WUS2 polypeptide the endogenous maize WUS2 gene located on maize chromosome 10. In certain embodiments, the plant cell is a maize plant cell and the endogenous WUS2 gene targeted for increased expression comprises an endogenous polynucleotide that is operably linked to an endogenous maize WUS2 promoter of SEQ ID NO:4 or an allelic variant thereof.

In certain embodiments, expression of the endogenous ODP2 and/or WUS2 gene is transiently increased by introducing at least one exogenous gene transcription agent that stimulates transcription of the endogenous ODP2 gene and/or with at least one exogenous gene transcription agent that stimulates transcription of the endogenous WUS2 gene. In certain embodiments, expression of the endogenous ODP2 and/or WUS2 gene is transiently increased by introducing an exogenous gene transcription agent that stimulates transcription of both the endogenous ODP2 gene and the endogenous WUS2 gene. In certain embodiments, additional exogenous polynucleotides encoding an ODP2 and/or WUS2 polypeptide are not provided to the cell since the exogenous transcription agents can increase the regenerative capacity of the plant cell by increasing expression of the endogenous ODP2 and/or WUS2 polypeptides encoded by the endogenous ODP2 and/or WUS2 genes. Features of the exogenous gene transcription agents that can increase expression of the endogenous ODP2 and WUS2 genes include: (a) a DNA binding domain that specifically binds a sequence within the promoter or 5' untranslated region (5' UTR) of the endogenous ODP2 and/or WUS2 gene; (b) a transcriptional activation domain (TAD) that is operably linked or operably associated with the DNA binding domain; and, where required, (c) a nuclear localization signal (NLS) that is operably linked to the DNA binding domain. In certain embodiments, the aforementioned exogenous transcription factors are artificial transcription factors (ATFs). In certain embodiments, an exogenous gene transcription agent that stimulates transcription of both the endogenous ODP2 gene and the endogenous WUS2 gene could comprise an artificial transcription factor comprising: (a) a first DNA binding domain that specifically binds the endogenous ODP2 gene promoter or 5' UTR, a second DNA binding domain that binds the endogenous WUS2 gene promoter or 5' UTR; (b) a TAD that is operably linked or operably associated with the DNA binding domains, and, where required (c) an NLS that is operably linked with the DNA binding domains. In certain embodiments, the ATFs comprise one or more of the features or elements within the features are wholly synthetic (e.g., non-naturally occurring) or wherein features from heterologous proteins are combined. Specific binding to the promoter or 5' untranslated region (5' UTR) of the endogenous ODP2 and/or WUS2 gene by the DNA binding domain can be shown by DNA binding assays. Protein-DNA binding assays that can be used include DNA electrophoretic mobility shift assays (EMSA); chromatin immunoprecipitation (ChIP)-based assays; enzyme-linked immunoassays, fluorescence-anisotropy-based assays, and surface plasmon resonance assays (Jantz and Berg, 2010). Specific DNA binding activity can also be demonstrated in competitive DNA binding assays wherein binding to the target DNA sequence is inhibited more efficiently (e.g., at lower concentrations) by the target DNA sequence located within the promoter or 5' untranslated region (5' UTR) of the endogenous ODP2 or WUS2 gene than by an unrelated, non-target DNA sequence. In certain embodiments, the DNA binding domains and/or artificial transcription factors used herein will bind the target DNA sequence with an affinity (KO of 10 nM or less, 5 nM or less, 2 nM or less, or 1 nM or less or will bind with an affinity of about 10 nM or 8 nM to about 1 nM or 0.5 nM. Other optional features of the artificial transcription factors include epitope tags that can facilitate detection and/or quantitation of expression as well as cell penetrating peptides that can facilitate entry into a target plant cell.

Transcriptional activation domains (TADs) used in the ATFs can be obtained from either naturally occurring transcription factors or can be wholly or partially synthetic. Any of an acidic, glutamine-rich, proline-rich, isoleucine-rich, and/or an alanine-rich TAD can be used (Ma, 2011). Examples of such TADs that can be used include the maize C1, the VP16, and the VP64 transcription activation domains. In certain embodiments, multiple VP64 TADs can be used (Li et al., 2018). Another example of a potent plant TAD that can be used in the ATFs provided herein is the EDLL motif that is found in AP2/ERF transcription factors (Tiwari et al., 2012). Yet another example of a potent plant TAD that can be used in the ATFs provided herein is a hybrid VP64-p65-Rta tripartite activator (VPR; SEQ ID NO: 91; Chavez et al., 2015).

Nuclear localization signals (NLS) that can be used in the ATF provided herein include monopartite and bipartite nuclear localization signals (Kosugi et al., 2009). Examples of monopartite NLS that can be used include NLS that comprise at least 4 consecutive basic amino acids such as the SV40 large T antigen NLS (PKKKRKV; SEQ ID NO:49) and another class having only three basic amino acids with a K(K/R)X(K/R) consensus sequence (SEQ ID NO:50). Examples of bipartite NLS that can be used in the ATFs provided herein include (K/R)(K/R)$X_{10-12}$(K/R)$_{3/5}$ (SEQ ID NO:51) where (K/R)$_{3/5}$ represents at least three of either lysine or arginine of five consecutive amino acids. An NLS can also comprise a plant-specific class 5 NLS having a consensus sequence of LGKR(K/R)(W/F/Y) (SEQ ID NO:52). Examples of specific NLS that can be used further include the maize opaque-2 nuclear localization signal and an extended SV40 large T antigen NLS (SEQ ID NO: 92).

In certain embodiments, the TAD and NLS elements can be operably linked to the DNA binding domain in an ATF via either a direct covalent linkage of the elements and domain or by a use of a linker peptide or flexible hinge polypeptide. Flexible hinge polypeptides include glycine-rich or glycine/serine containing peptide sequence. Such sequences can include, but are not limited to, a (Gly$_4$)n sequence, a (Gly$_4$Ser)n sequence of SEQ ID NO:53, a Ser(Gly$_4$Ser)n sequence of SEQ ID NO:54, combinations thereof, and variants thereof, wherein n is a positive integer equal to 1, 2, 3, 4, 5, 6, 7, 8, 9 or 10. In certain embodiments, such glycine-rich or glycine/serine containing hinge peptides can also contain threonyl and/or alanyl residues for flexibility as well as polar lysyl and/or glutamyl residues. Other examples of hinge peptides that can be used include immunoglobulin hinge peptides (Vidarsson et al., 2014).

A variety of cell-penetrating peptides (CPP) can also be used in the ATF provided herein. CPPs that can be used include a minimal undecapeptide protein transduction domain (corresponding to residues 47-57 of HIV-1 TAT comprising YGRKKRRQRRR; SEQ ID NO:55); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an *Drosophila* Antennapedia protein transduction domain (Noguchi et al. (2003) Diabetes 52(7): 1732-1737); a truncated human calcitonin peptide (Trehin et al. (2004) Pharm. Research 21: 1248-1256); polylysine (Wender et al. (2000) Proc. Natl. Acad. Sci. USA 97: 13003-13008); RRQRRTSKLMKR (SEQ ID NO:56); Transportan (e.g., GWTLNSAGYLLGKINLKALAALAKKIL (SEQ ID NO:57)); KALAWEAKLAKALAKALAKHLAKALAKALKCEA (SEQ ID NO:58); and RQIKIWFQNRRMKWKK (SEQ ID NO:59). Exemplary CPP amino acid sequences also include YGRKKRRQRRR (SEQ ID NO:60); RKKRRQRR (SEQ ID NO:61); YARAAARQARA (SEQ ID NO:62); THRLPRRRRRR (SEQ ID NO:63); and GGRRARRRRRR (SEQ ID NO:64).

In certain embodiments, a TAD can be operably associated with a DNA binding domain via a non-covalent interaction between a protein comprising the TAD and the DNA binding peptide. In certain embodiments, such operable associations can be provided by protein domains that bind to one another (e.g., dimerization or other multimerization domains). Examples of such dimerization domains include leucine zipper structures. Such operable associates are similar to those used in yeast two-hybrid systems where interacting proteins are identified via their ability to join a TAD to a DNA binding domain (Brückner et al., 2009). In certain embodiments, operable association can be achieved by using protein domains that interact through binding a common ligand (e.g., the iDimerize™ Regulated Transcription System that uses Dmr A, B, or C dimerization domains and ligands; Takara Bio, USA, Inc.). Such ligand-based systems have the advantage of allowing control of dimerization (and activation of the endogenous ODP2 and/or WUS2 gene expression) by ligand addition or removal.

In certain embodiments, the DNA binding domain can comprise an artificial zinc finger (AZF) DNA binding domain polypeptide which specifically binds a sequence within the promoter or 5' untranslated region (5' UTR) of the endogenous ODP2 and/or WUS2 gene. In certain embodiments, the AZF DNA binding domain specifically binds a target DNA sequence located within the promoter or 5' untranslated region (5' UTR) of the endogenous maize ODP2 and/or maize WUS2 gene. Such target sequences in the endogenous maize ODP2 promoter include SEQ ID NO:6, SEQ ID NO:9, and any allelic variants thereof having one or more nucleotide insertions, deletions, and/or substitutions found in other wild-type maize genomes. AZF DNA binding domains predicted to bind the maize ODP2 promoter target sequences of SEQ ID NO:6 or SEQ ID NO:9 include the polypeptides comprising SEQ ID NO:5 and SEQ ID NO:8, respectively, as well as variants thereof having at least 85%, 90%, 95%, 97%, 98%, or 99% sequence identity across the entire length of SEQ ID NO: 5 or 8; or one or more conservative and/or semi-conservative amino acid substitutions in SEQ ID NO: 5 or 8. Such target sequences in the endogenous maize WUS2 promoter include SEQ ID NO:12, SEQ ID NO:15, DNA sequences in the endogenous maize WUS2 promoter corresponding to residues 100 to 225 or 130 to 210 of SEQ ID NO:4 (or their complementary strand), SEQ ID NO:101, SEQ ID NO: 102 (in the minus or complementary strand of the dsDNA comprising SEQ ID NO: 4), and any allelic variants thereof having one or more nucleotide insertions, deletions, and/or substitutions found in other wild-type maize genomes. Such target sequences in the endogenous maize WUS2 promoter also include DNA sequences in the endogenous maize WUS2 promoter corresponding to residues 100 to 225 or 130 to 210 of SEQ ID NO:4 (or their complementary strand), and any allelic variants thereof having one or more nucleotide insertions, deletions, and/or substitutions found in other wild-type maize genomes. In certain embodiments, such allelic variants of the endogenous promoter WUS2 can have at least 80%, 85%, 90%, 95%, 97%, 98%, 98%, or 99% sequence identity to SEQ ID NO: 4, residues 100 to 225 or 130 to 210 of SEQ ID NO:4, SEQ ID NO:101, or SEQ ID NO: 102. In certain embodiments, the target sequences in the endogenous maize WUS2 promoter also include DNA sequences in the endogenous maize WUS2 promoter corresponding to: (i) residues 100, 105, 110, 115, 120, 125, 130, 132, 134, 135, 136, 137, or 138 to 155, 156, 157, 158, 160, 162, 165, or 170 of SEQ ID NO:4 (or their complementary strand); (ii) residues 171, 175, 180, 182, 183, 184, 185, 186, 187, or 188 to 202, 203, 204, 205, 206, 207, 208, 209, 210, 215, 220, or 225 of SEQ ID NO:4 (or their complementary strand); (iii) any combination of (i) and (ii); e.g., where two ATFs are used; or (iv) residues 100, 105, 110, 115, 120, 125, 130, 132, 134, 135, 136, 137, or 138 to 202, 203, 204, 205, 206, 207, 208, 209, 210, 215, 220, or 225 of SEQ ID NO:4 (or their complementary strand) of SEQ ID NO:4 (or their complementary strand). AZF-binding domains predicted to bind the maize WUS2 promoter target sequences of SEQ ID NO:12 or SEQ ID NO:15 include the polypeptides comprising SEQ ID NO:11 and SEQ ID NO:14, respectively, as well as variants thereof having at least 85%, 90%, 95%, 97%, 98%, or 99% sequence identity across the entire length of SEQ ID NO:11 or 14; or one or more conservative and/or semi-conservative amino acid substitutions in SEQ ID NO:11 or 14. AZF DNA binding domains predicted to bind the maize WUS2 promoter target sequences comprising SEQ ID NO:101 or 102 include the polypeptides comprising SEQ ID NO: 105 or 106, respectively, as well as variants thereof having at least 85%, 90%, 95%, 97%, 98%, or 99% sequence identity across the entire length of SEQ ID NO:105 or 106; or one or more conservative and/or semi-conservative amino acid substitutions in SEQ ID NO:105 or 106. AZF DNA binding domains predicted to bind the maize WUS2 promoter target sequences comprising SEQ ID NO:101, 102 and adjacent sequences or comprising subfragments (e.g., 9, 12, or 15 nucleotides) of SEQ ID NO:101 or 102 and adjacent sequences also include variants of SEQ ID NO:105 or 106 that further comprise additional zinc finger DNA binding motifs designed to bind the adjacent WUS2 promoter sequences. Artificial transcription factors (ATFs) comprising the aforementioned AZF DNA-binding polypeptides can further comprise operably linked nuclear localization peptides, cell-penetrating peptides, and transcription activation domains. Such ATFs predicted to bind and activate the endogenous ZmODP2 promoter include the ATFs set forth in SEQ ID NO:7 and 10, as well as variants thereof having at least 85%, 90%, 95%, 97%, 98%, or 99% sequence identity across the entire length of SEQ ID NO:7 or 10; or having at one or more conservative and/or semi-conservative amino acid substitutions in SEQ ID NO:7 or 10. Such ATFs predicted to bind and activate the endogenous maize WUS2 (ZmWUS2) promoter include the ATFs set forth in SEQ ID NO:13 and 16, as well as variants thereof having at least 85%, 90%, 95%, 97%, 98%, or 99% sequence identity across the entire length of SEQ ID NO:13 or 16; or having at one or more conservative and/or semi-conservative amino acid substitutions in SEQ ID NO:13 or 16. Such ATFs predicted to bind and activate the endogenous maize WUS2 (ZmWUS2) promoter include the ATFs set forth in SEQ ID NO:93 and 95, as well as variants thereof having at least 85%, 90%, 95%, 97%, 98%, or 99% sequence identity across the entire length of SEQ ID NO:93 and 95; or having at one or more conservative and/or semi-conservative amino acid substitutions in SEQ ID NO:93 and 95. In other embodiments, target AZF DNA binding sites in the promoter or 5'UTR sequences of other endogenous plant ODP2 or WUS2 genes can be selected and AZF DNA binding domains as well as AZF transcription factors which specifically bind the target binding sites can be designed to obtain AZF transcription factors that can increase expression of other endogenous plant ODP2 or WUS2 genes. In certain embodiments, target AZF DNA binding sites can be selected based on the presence of consecutive DNA triplets that can each be recognized by zinc finger domains comprising a $Cys_2$-$His_2$ zinc finger motif. Target AZF DNA binding sites can be selected for the absence of overlap with sequences in non-target genes (e.g., genes other than endogenous plant ODP2 or WUS2 genes). AZF DNA binding domains, including variants of the SEQ ID NO:11, 14, 105, and 106 AZF DNA binding domains, that target the selected AZF DNA binding sites can be constructed by joining zinc finger domains. In certain embodiments, the AZF will comprise about six (6) zinc finger domains joined by canonical TGEKP (SEQ ID NO: 48) linker peptides. In certain embodiments, rules governing the design of Zn-ATFs to bind specific DNA sequences that have been published (Sera and Uranga 2002; Gersbach, Gaj, and Barbas 2014) or provided online (on the world wide web at "zincfingers.org/default2.htm" and "scripps.edu/barbas/zfdesign/zfdesign-home.php" can be applied to the design of the AZF's which bind target AZF binding sites in the ODP2 or WUS2 promoters or 5'UTR or to the construction of variants of the SEQ ID NO:11, 14, 105, and 106 AZF DNA binding domains. Features of artificial transcription factors that comprise AZF-DNA binding domains for use in activating endogenous genes in plants and other organisms that have been described in various publications (van Tol and van der Zaal 2014; Heiderscheit et al. 2018; Van Eenennaam et al. 2004; Gupta et al. 2012; Stege et al. 2002; Sánchez et al. 2006; Holmes-Davis et al. 2005; Petolino and Davies 2013) can also be used in the design of artificial transcription factors comprising AZF-DNA binding domains that recognize plant ODP2 or WUS2 promoters or 5'UTR sequences or in the construction of variants of the SEQ ID NO:11, 14, 105, and 106 AZF DNA binding domains.

In certain embodiments, the DNA binding domain can comprise an artificial transcription activator-like effector (TALE) DNA binding polypeptide (aTALE) which comprises an 'repeat-variable di-residue' (RVD) containing domain that specifically binds a sequence within the promoter or 5' untranslated region (5' UTR) of the endogenous ODP2 or WUS2 gene. In certain embodiments, the TALE DNA binding polypeptide specifically binds a target DNA sequence located within the promoter or 5' untranslated region (5' UTR) of the endogenous maize ODP2 or maize WUS2 gene. Such target sequences in the endogenous maize ODP2 promoter include sequences within SEQ ID NO:3 or in SEQ ID NO:71, and any allelic variants thereof having one or more nucleotide insertions, deletions, and/or substitutions found in other wild-type maize genomes. TALE DNA-binding polypeptides predicted to bind the maize ODP2 (ZmODP2) promoter target sequences within SEQ ID NO:3 include the polypeptides comprising SEQ ID NO:23, SEQ ID NO:25, SEQ ID NO:27, SEQ ID NO:81, SEQ ID NO:84, and SEQ ID NO:87, as well as variants thereof having at least 85%, 90%, 95%, 97%, 98%, or 99% sequence identity across the entire length of SEQ ID NO:23, 25, 27, 81, 84, or 87; or one or more conservative and/or semi-conservative amino acid substitutions in SEQ ID NO: 23, 25, 27, 81, 84, or 87. Artificial transcription factors (ATFs) comprising the aforementioned TALE DNA binding polypeptides can further comprise operably linked nuclear localization peptides, cell-penetrating peptides, and operably linked or operably associated transcription activation domains. Such ATFs predicted to bind and activate the endogenous ZmODP2 promoter include the ATFs set forth in SEQ ID NO:24, 26, 28, 82, 85, or 88, as well as variants thereof having at least 85%, 90%, 95%, 97%, 98%, or 99% sequence identity across the entire length of SEQ ID NO:24, 26, 28, 82, 85, or 88; or having at one or more conservative and/or semi-conservative amino acid substitutions in SEQ ID NO:24, 26, 28, 82, 85, or 88. Any of the aforementioned ATFs predicted to bind the maize ODP2 promoter can be used either independently, in tandem pairs of ATFs predicted to bind at ~100 bp intervals in ZmODP2 promoter sequences located 5' to the ZmODP2 transcription start site, or as a set of three ATFs predicted to bind at ~100 bp intervals in ZmODP2 promoter sequences located 5' to the ZmODP2 transcription start site. In other embodiments, ATFs predicted to bind the maize ODP2 promoter can be used in tandem pairs of ATFs predicted to bind at ~50 bp intervals in ZmODP2 promoter sequences located 5' to the ZmODP2 transcription start site, or as a set of three ATFs predicted to bind at ~50 bp intervals in ZmODP2 promoter sequences located 5' to the ZmODP2 transcription start site. Such target sequences in the endogenous maize WUS2 promoter include sequences located within SEQ ID NO:4 and any allelic variants thereof having one or more nucleotide insertions, deletions, and/or substitutions found in other wild-type maize genomes. TALE DNA-binding polypeptides predicted to bind the maize WUS2 promoter target sequences within SEQ ID NO:4 include the polypeptides comprising SEQ ID NO:17, SEQ ID NO:19, SEQ ID NO:21, SEQ ID NO:72, SEQ ID NO:75, and SEQ ID NO:78, as well as variants thereof having at least 85%, 90%, 95%, 97%, 98%, or 99% sequence identity across the entire length of SEQ ID NO:17, 19, 21, 72, 75, or 78; or one or more conservative and/or semi-conservative amino acid substitutions in SEQ ID NO: 17, 19, 21, 72, 75, or 78. Artificial transcription factors (ATFs) comprising the aforementioned TALE DNA-binding polypeptides can further comprise operably linked nuclear localization peptides and transcription activation domains. Such ATFs predicted to bind and activate the endogenous ZmWUS2 promoter include the ATFs set forth in SEQ ID NO:18, 20, 22, 73, 76, or 79, as well as variants thereof having at least 85%, 90%, 95%, 97%, 98%, or 99% sequence identity across the entire length of SEQ ID NO:18, 20, 22, 73, 76, or 79; or having at one or more conservative and/or semi-conservative amino acid substitutions in SEQ ID NO:18, 20, 22, 73, 76, or 79. Any of the aforementioned ATFs comprising the aforementioned TALE DNA-binding polypeptides predicted to bind the maize WUS2 (ZmWUS2) promoter can be used either independently, in tandem pairs of ATFs predicted to bind at ~100 bp intervals in the maize WUS2 promoter sequences located 5' to the ZmWUS2 transcription start site, or as a set of three ATFs predicted to bind at ~100 bp intervals in ZmWUS2 promoter sequences located 5' to the ZmWUS2 transcription start site. In other embodiments, ATFs predicted to bind the maize WUS2 promoter can be used in tandem pairs of ATFs predicted to bind at ~50 bp intervals in ZmWUS2 promoter sequences located 5' to the ZmWUS2 transcription start site, or as a set of three ATFs predicted to bind at ~50 bp intervals in ZmWUS2 promoter sequences located 5' to the ZmWUS2 transcription start site. In other embodiments, target TALE DNA binding sites in the promoter or 5'UTR sequences of other endogenous plant ODP2 or WUS2 genes can be selected and TALE DNA binding domains as well as TALE transcription factors which specifically bind the target binding sites can be designed to obtain TALE transcription factors that can increase expression of other endogenous plant ODP2 or WUS2 genes. In certain embodiments, rules governing the design of TALEs to bind specific DNA sequences that have been published (Moore, Chandrahas, and Bleris 2014; Čermák et al. 2017; Sanjana et al. 2012; Thakore and Gersbach 2016) or provided online (on the https internet site "tale-nt.cac.cornell.edu/node/add/single-tale") can be applied to the design of the TALE's which bind target TALE binding sites in the ODP2 or WUS2 promoters or 5'UTR.

In certain embodiments, the DNA binding domain can comprise a complex of an RNA guided DNA binding polypeptide that is nuclease activity deficient and a guide RNA comprising a tracrRNA and crRNA polynucleotide sequence which corresponds to a sequence immediately adjacent to the 5' end of a protospacer adjacent motif (PAM) in the target ODP2 or WUS2 promoter or 5' UTR, where the complex specifically binds a sequence within the promoter or 5' untranslated region (5' UTR) of the endogenous ODP2 or WUS2 gene. RNA guided DNA binding polypeptides that are nuclease activity deficient are also referred to herein as nuclease activity deficient RNA-guided DNA binding polypeptides (ndRGDBP). In certain embodiments, the guide RNA is a single guide RNA (sgRNA) where the crRNA and the tracrRNA are covalently linked. In other embodiments, a dual guide RNA can be used where the crRNA and the tracrRNA are not covalently linked. In general, the crRNA typically comprises about an 18 or 19 to about a 21 or 22 nucleotide sequence which corresponds to the sequence immediately adjacent to the 5' end of a protospacer adjacent motif (PAM) (e.g., for Cas9 and similar RNA directed nucleases). In general, the crRNA typically comprises about a 20, 21, 22, 23, or 24 nucleotide sequence which corresponds to the sequence immediately adjacent to the 3' end of a PAM (e.g., for Cas12a (i.e., Cpf1) and similar RNA directed nucleases). Nuclease activity deficient RNA guided DNA binding polypeptides (ndRGDBP) used in such complexes can comprise RNA guided nucleases (Cas or Cas12a nucleases) having mutations that render the protein nuclease activity deficient (e.g., having a 99% or greater reduction in nuclease activity under physiological conditions in a plant cell nucleus). Such nuclease deficient variants of Cas like Cas9 or Cas12a proteins are referred to herein and elsewhere as "dCas" (e.g., dCas9, dCasJ, and the like) or "dCpf1" or "dCas12a" proteins (i.e., "dead Cas" or "dead Cpf1" or "dead Cas12a"). Domains in Cas or Cas12a proteins which can be disrupted to reduce or eliminate nuclease activity include HNH and RuvC-like nuclease domains. Mutations in the catalytic residues of the HNH and RuvC-like nuclease domains of Cas proteins can provide for nuclease-deficient RNA-guided DNA binding proteins (Jinek et al., 2012; Schindele et al., 2018). Examples of such mutations include the D10A and H840A mutations in the Cas9 protein and analogous mutations in the corresponding residues of other Cas9-like proteins identified by alignment with the Cas9 protein. Examples of a dCas9 protein include the polypeptide of SEQ ID NO:29. Other dCas proteins can be obtained by inactivation of nuclease domains include the dCasJ mutants obtained by mutating the CasJ protein of SEQ ID NO:47. Mutations in the nuclease domain of the CasJ include D901A and/or E1228A amino acid substitutions in the CasJ protein of SEQ ID NO:47 and analogous mutations in the corresponding residues of other CasJ proteins identified by alignment with the CasJ protein of SEQ ID NO:47. Mutations in the RuvC-like nuclease domains of Cas12a (i.e., Cpf1) proteins can provide for dCas12a nuclease-deficient RNA-guided DNA binding proteins. Examples of such mutations include the E993A mutation in the AsCpf1 protein (Zhang et al, 2017), the D917A, E1006A, E1028A, D1255A, and/or N1257A mutations in the AsCpf1 protein of SEQ ID NO:44, the D832A, E925A, and/or D1148A mutations in the LbCpf1 protein of SEQ ID NO:45, the D917A, E1006A, E1028A, D1255A, and/or N1257A mutations in the FnCpf1 protein of SEQ ID NO:46, and analogous mutations in the corresponding residues of other Cpf1 proteins identified by alignment with the Cpf1 proteins of SEQ ID NO:44, 45, or 46. Any of the aforementioned dCas9, dCas, dCasJ, or dCpf1 proteins can be used in artificial transcription factors (ATFs) provided herein that further comprise transcription activation domains, cell-penetrating peptides, and nuclear localization domains. Examples of such ATFs include the dCas9 ATF set forth in SEQ ID NO:30, SEQ ID NO:90, and variants thereof that retain RNA guided DNA binding activity and that are nuclease activity deficient. Such dCas9 ATF variants that retain RNA guided DNA binding activity and that are nuclease activity deficient include variants thereof having at least 85%, 90%, 95%, 97%, 98%, or 99% sequence identity across the entire length of SEQ ID NO:30 or 90; or having at one or more conservative and/or semi-conservative amino acid substitutions in SEQ ID NO:90. Such artificial transcription factors are used with guide RNAs (sgRNAs or crRNAs and a tracrRNA) to form an ATF/guide RNA complex which can specifically bind sequences in the plant ODP2 and/or WUS2 promoters or 5' UTR that is immediately adjacent to a protospacer adjacent motif (PAM) sequence. Guide RNAs that direct the dCas or dCpf1 ATF proteins to endogenous plant ODP2 or WUS2 genes can be obtained by identifying target sequences adjacent to PAM sequences in the plant ODP2 and/or WUS2 promoters or 5' UTR and synthesizing a crRNA or sgRNA that is complementary to that sequence. The type of RNA-guided DNA binding program typically informs the location of suitable PAM sites and design of crRNAs or sgRNAs. G-rich PAM sites, e.g., 5'-NGG are typically targeted for design of crRNAs or sgRNAs used with dCas9 proteins. T-rich PAM sites (e.g., 5'-TTTV [1], where "V" is A, C, or G) are typically targeted for design of crRNAs or sgRNAs used with dCpf1 proteins. PAM sites including TTN, CTN, TCN, CCN, TTTN, TCTN, TTCN, CTTN, ATTN, TCCN, TTGN, GTTN, CCCN, CCTN, TTAN, TCGN, CTCN, ACTN, GCTN, TCAN, GCCN, and CCGN targeted for design of crRNAs or sgRNAs used with dCasJ proteins (e.g., SEQ ID NO:47). Such crRNAs or sgRNAs can be complementary to sequences that are immediately adjacent to PAM sequences located on either strand of the OPD2 or WUS2 promoter. In certain embodiments the dCas or dCpf1 ATF proteins and guide RNAs are provided to the cell as a pre-assembled ribonucleoprotein (RNP) complex. For example, the ATF can be expressed in an expression host (e.g., *E. coli*), purified, and complexed with the guide RNA. In other embodiments, the dCas or dCpf1 ATF proteins and guide RNAs are provided separately to the plant cell. Guide RNAs that are synthesized and optionally including chemically modified ribonucleotides can also be used (O'Reilly et al., 2018; Yin et al., 2018). In other embodiments, the dCas or dCpf1 ATF proteins and guide RNAs are provided by introducing one or more polynucleotides encoding the dCas or dCpf1 ATF proteins and/or guide RNA(s) into the target plant cell. In certain embodiments, the guide RNAs are provided to the plant cell by introducing polynucleotides comprising a class III RNA polymerase III promoter that is operably linked to the DNA encoding the guide RNA (Long et al., 2018). Such RNA polymerase III promoters include U6 promoters from monocot plants (e.g., OsU6a, OsU6b, and OsU6c from rice) or dicot plants (e.g., GmU6 from soybean, GhU6 from cotton, and AtU6-1 or AtU6-29 from *Arabidopsis thaliana*). Useful U6 promoters from maize, tomato, or soybean are disclosed in WO 2015/131101, which is incorporated herein by reference in its entirety with respect to such promoters and their use. In certain embodiments, the plant cell is a maize plant and an ATF/guide RNA complex that specifically binds target DNA sequence located within the promoter or 5' untranslated region (5' UTR) of the endogenous maize ODP2 or maize WUS2 gene. Expression of the guide RNA can in certain embodiments be driven by a plant U6 spliceosomal RNA promoter, which can be native to the genome of the plant cell or from a different species, and claiming priority to U.S. Provisional Patent Application 61/945,700, incorporated herein by reference, or a homologue thereof; such a promoter is operably linked to DNA encoding the guide RNA for directing an endonuclease, followed by a suitable 3' element such as a U6 poly-T terminator. In another embodiment, an expression cassette for expressing guide RNAs in plants is used, wherein the promoter is a plant U3, 7SL (signal recognition particle RNA), U2, or U5 promoter, or chimerics thereof, e.g., as described in WO 2015/131101), incorporated herein by reference. Guide RNAs that can be used to target a dCas9 ATF to an endogenous maize ODP2 promoter can comprise crRNA molecules encoded by DNA molecules set forth as SEQ ID NO:31, 32, 33, 34, or 35. In certain embodiments, the dCas9 ATF and only one guide RNA comprising a crRNA encoded by SEQ ID NO:31, 32, 33, 34, or 35 are introduced into the maize plant cell to activate transcription of the endogenous maize ODP2 gene. In other embodiments, the dCas9 ATF and two, three, four, or five guide RNAs each comprising one crRNA molecules encoded by SEQ ID NO:31, 32, 33, 34, and/or 35 are introduced into the maize plant cell to activate transcription of the endogenous maize ODP2 gene. Guide RNAs that can be used to target a dCas9 ATF to an endogenous maize WUS2 promoter can comprise crRNA molecules encoded by DNA molecules set forth as SEQ ID NO:36, 37, 38, 39, or 40. In certain embodiments, the dCas9 ATF and only one guide RNA comprising a crRNA encoded by SEQ ID NO: 36, 37, 38, 39, or 40 are introduced into the maize plant cell to activate transcription of the endogenous maize WUS2 gene. In other embodiments, the dCas9 ATF and two, three, four, or five guide RNAs each comprising one crRNA molecule encoded by SEQ ID NO:31, 32, 33, 34, and/or 35 are introduced into the maize plant cell to activate transcription of the endogenous maize WUS2 gene. In certain embodiments, the crRNAs SEQ ID NO:31, 32, 33, 34, 35, 36, 37, 38, 39, or 40 further comprise a covalently linked tracrRNA and are thus provided as sgRNAs. In other embodiments, the crRNAs SEQ ID NO:31, 32, 33, 34, 35, 36, 37, 38, 39, or 40 are provided with a non-covalently linked tracrRNA to provide a dual guide RNA. In instances where an allelic variant of an endogenous maize ODP2 or WUS2 promoter that differs in sequence by one or more insertions, deletions, and/or substitutions from SEQ ID NO:3 or SEQ ID NO:4, respectively, a corresponding crRNA can be synthesized that is complementary to the allelic variant sequence and used in a single or dual guide RNA with a dCas ATF to activate transcription of the endogenous maize ODP2 gene or WUS2 gene that comprises the allelic variant promoter sequence.

In certain embodiments, the expression of the endogenous ODP2 and/or WUS2 genes are increased in isolated plant cells or plant protoplasts (i.e., are not located in undissociated or intact plant tissues, plant parts, or whole plants). In certain embodiments, the plant cells are obtained from any plant part or tissue or callus. In certain embodiments, the culture includes plant cells obtained from a plant tissue, a cultured plant tissue explant, whole plant, intact nodal bud, shoot apex or shoot apical meristem, root apex or root apical meristem, lateral meristem, intercalary meristem, seedling, whole seed, halved seed or other seed fragment, zygotic embryo, somatic embryo, immature embryo, ovule, pollen, microspore, anther, hypocotyl, cotyledon, leaf, petiole, stem, tuber, root, callus, or plant cell suspension. In certain embodiments, the plant cell is derived from the L1 or L2 layer of an immature or mature embryo of a monocot plant (e.g., maize, wheat, sorghum, or rice).

In certain embodiments, the expression of the endogenous ODP2 and/or WUS2 genes are increased in plant cells that are located in undissociated or intact plant tissues, plant parts, plant explants, or whole plants. In certain embodiments, the plant cell can be located in an intact nodal bud, a cultured plant tissue explant, shoot apex or shoot apical meristem, root apex or root apical meristem, lateral meristem, intercalary meristem, seedling, whole seed, halved seed or other seed fragment, zygotic embryo, somatic embryo, immature embryo, ovule, pollen, microspore, anther, hypocotyl, cotyledon, leaf, petiole, stem, tuber, root, or callus. In certain embodiments, the explants used include immature embryos. Immature embryos (e.g., immature maize embryos) include, 1.8-2.2 mm embryos, 1-7 mm embryos, and 3-7 mm embryos. In certain embodiments, the aforementioned embryos are obtained from mature ear-derived seed, leaf bases, leaves from mature plants, leaf tips, immature inflorescences, tassels, immature ears, and silks. In various aspects, the plant-derived explant used for transformation includes immature embryos, 1.8-2.2 mm embryos, 1-7 mm embryos, and 3.5-7 mm embryos. In an aspect, the embryos used in the disclosed methods can be derived from mature ear-derived seed, leaf bases, leaves from mature plants, leaf tips, immature inflorescences, tassel, immature ear, or silks. In certain embodiments, the plant cell is a pluripotent plant cell (e.g., a stem cell or meristem cell). In certain embodiments, the plant cell is located within the L1 or L2 layer of an immature or mature embryo of a monocot plant (e.g., maize, wheat, sorghum, or rice). In certain embodiments, methods of editing genomes of whole plants, seeds, embryos, explants, or meristematic tissue published in WO2018085693, which is incorporated herein by reference in its entirety, can be adapted for use in the plant cells and related systems, methods, compositions, or cultures provided herein.

In certain embodiments, the plant cells can comprise haploid, diploid, or polyploid plant cells or plant protoplasts, for example, those obtained from a haploid, diploid, or polyploid plant, plant part or tissue, or callus. In certain embodiments, plant cells in culture (or the regenerated plant, progeny seed, and progeny plant) are haploid or can be induced to become haploid; techniques for making and using haploid plants and plant cells are known in the art, see, e.g., methods for generating haploids in *Arabidopsis thaliana* by crossing of a wild-type strain to a haploid-inducing strain that expresses altered forms of the centromere-specific histone CENH3, as described by Maruthachalam and Chan in "How to make haploid *Arabidopsis thaliana*", protocol available at www[dot]openwetware[dot]org/images/d/d3/Haploid_Arabidopsis_protocol[dot]pdf; (Ravi et al. (2014) *Nature Communications,* 5:5334, doi: 10.1038/ncomms6334). Haploids can also be obtained in a wide variety of monocot plants (e.g., maize, wheat, rice, sorghum, barley) or dicot plants (e.g., soybean, *Brassica* sp. including canola, cotton, tomato) by crossing a plant comprising a mutated CENH3 gene with a wildtype diploid plant to generate haploid progeny as disclosed in U.S. Pat. No. 9,215,849, which is incorporated herein by reference in its entirety. Haploid-inducing maize lines that can be used to obtain haploid maize plants and/or cells include Stock 6, MHI (Moldovian Haploid Inducer), indeterminate gametophyte (ig) mutation, KEMS, RWK, ZEM, ZMS, KMS, and well as transgenic haploid inducer lines disclosed in U.S. Pat. No. 9,677,082, which is incorporated herein by reference in its entirety. Examples of haploid cells include but are not limited to plant cells obtained from haploid plants and plant cells obtained from reproductive tissues, e.g., from flowers, developing flowers or flower buds, ovaries, ovules, megaspores, anthers, pollen, megagametophyte, and microspores. In certain embodiments where the plant cell or plant protoplast is haploid, the genetic complement can be doubled by chromosome doubling (e.g., by spontaneous chromosomal doubling by meiotic non-reduction, or by using a chromosome doubling agent such as colchicine, oryzalin, trifluralin, pronamide, nitrous oxide gas, anti-microtubule herbicides, anti-microtubule agents, and mitotic inhibitors) in the plant cell or plant protoplast to produce a doubled haploid plant cell or plant protoplast wherein the complement of genes or alleles is homozygous; yet other embodiments include regeneration of a doubled haploid plant from the doubled haploid plant cell or plant protoplast. Another embodiment is related to a hybrid plant having at least one parent plant that is a doubled haploid plant provided by this approach. Production of doubled haploid plants provides homozygosity in one generation, instead of requiring several generations of self-crossing to obtain homozygous plants. The use of doubled haploids is advantageous in any situation where there is a desire to establish genetic purity (i.e. homozygosity) in the least possible time. Doubled haploid production can be particularly advantageous in slow-growing plants, such as fruit and other trees, or for producing hybrid plants that are offspring of at least one doubled-haploid plant.

In certain embodiments, the plant cells where expression of the endogenous ODP2 and/or WUS2 genes are increased, as well as the related methods, systems, compositions, or reaction mixtures provided herein can include plant cells obtained from or located in any monocot or dicot plant species of interest, for example, row crop plants, fruit-producing plants and trees, vegetables, trees, and ornamental plants including ornamental flowers, shrubs, trees, ground-covers, and turf grasses. In certain non-limiting embodiments, the plant cells are obtained from or located in alfalfa (*Medicago sativa*), almonds (*Prunus dulcis*), apples (*Malus x domestica*), apricots (*Prunus armeniaca, P. brigantine, P. mandshurica, P. mume, P. sibirica*), asparagus (*Asparagus officinalis*), bananas (*Musa* spp.), barley (*Hordeum vulgare*), beans (*Phaseolus* spp.), blueberries and cranberries (*Vaccinium* spp.), cacao (*Theobroma cacao*), canola and rapeseed or oilseed rape, (*Brassica napus*), carnation (*Dianthus caryophyllus*), carrots (*Daucus carota sativus*), cassava (*Manihot esculentum*), cherry (*Prunus avium*), chickpea (*Cider arietinum*), chicory (*Cichorium intybus*), chili peppers and other capsicum peppers (*Capsicum annuum, C. frutescens, C. chinense, C. pubescens, C. baccatum*), chrysanthemums (*Chrysanthemum* spp.), coconut (*Cocos nucifera*), coffee (*Coffea* spp. including *Coffea arabica* and *Coffea canephora*), cotton (*Gossypium hirsutum* L.), cowpea (*Vigna unguiculata*), cucumber (*Cucumis sativus*), currants and gooseberries (*Ribes* spp.), eggplant or aubergine (*Solanum melongena*), eucalyptus (*Eucalyptus* spp.), flax (*Linum usitatissumum* L.), geraniums (*Pelargonium* spp.), grapefruit (*Citrus x paradisi*), grapes (*Vitus* spp.) including wine grapes (*Vitus vinifera*), guava (*Psidium guajava*), hemp and cannabis (e.g., *Cannabis sativa* and *Cannabis* spp.), hops (*Humulus lupulus*), irises (*Iris* spp.), lemon (*Citrus limon*), lettuce (*Lactuca sativa*), limes (*Citrus* spp.), maize (*Zea mays* L.), mango (*Mangifera indica*), mangosteen (*Garcinia mangostana*), melon (*Cucumis melo*), millets (*Setaria* spp, *Echinochloa* spp, *Eleusine* spp, *Panicum* spp., *Pennisetum* spp.), oats (*Avena sativa*), oil palm (*Ellis quineensis*), olive (*Olea europaea*), onion (*Allium cepa*), orange (*Citrus sinensis*), papaya (*Carica papaya*), peaches and nectarines (*Prunus persica*), pear (*Pyrus* spp.), pea (*Pisa sativum*), peanut (*Arachis hypogaea*), peonies (*Paeonia* spp.), petunias (*Petunia* spp.), pineapple (*Ananas comosus*), plantains (*Musa* spp.), plum (*Prunus domestica*), poinsettia (*Euphorbia pulcherrima*), Polish canola (*Brassica rapa*), poplar (*Populus* spp.), potato (*Solanum tuberosum*), pumpkin (*Cucurbita pepo*), rice (*Oryza sativa* L.), roses (*Rosa* spp.), rubber (*Hevea brasiliensis*), rye (*Secale cereale*), safflower (*Carthamus tinctorius* L), sesame seed (*Sesame indium*), sorghum (*Sorghum bicolor*), soybean (*Glycine max* L.), squash (*Cucurbita pepo*), strawberries (*Fragaria* spp., *Fragaria* x *ananassa*), sugar beet (*Beta vulgaris*), sugarcanes (*Saccharum* spp.), sunflower (*Helianthus annus*), sweet potato (*Ipomoea batatas*), tangerine (*Citrus tangerina*), tea (*Camellia sinensis*), tobacco (*Nicotiana tabacum* L.), tomato (*Lycopersicon esculentum*), tulips (*Tulipa* spp.), turnip (*Brassica rapa rapa*), walnuts (*Juglans* spp. L.), watermelon (*Citrulus lanatus*), wheat (*Tritium aestivum*), or yams (*Discorea* spp.).

In certain embodiments, the plant cells where the expression of the endogenous ODP2 and/or WUS2 genes are increased can be plant cells that are (a) encapsulated or enclosed in or attached to a polymer (e.g., pectin, agarose, or other polysaccharide) or other support (solid or semi-solid surfaces or matrices, or particles or nanoparticles); (b) encapsulated or enclosed in or attached to a vesicle or liposome or other fluid compartment; or (c) not encapsulated or enclosed or attached. In certain embodiments, the plant cells can be in liquid or suspension culture, or cultured in or on semi-solid or solid media, or in a combination of liquid and solid or semi-solid media (e.g., plant cells or protoplasts cultured on solid medium with a liquid medium overlay, or plant cells or protoplasts attached to solid beads or a matrix and grown with a liquid medium). In certain embodiments, the plant cells encapsulated in a polymer (e.g., pectin, agarose, or other polysaccharide) or other encapsulating material, enclosed in a vesicle or liposome, suspended in a mixed-phase medium (such as an emulsion or reverse emulsion), or embedded in or attached to a matrix or other solid support (e.g., beads or microbeads, membranes, or solid surfaces).

In a related aspect, the disclosure provides arrangements of plant cells having improved plant cell regenerative potential in the systems, methods, and compositions described herein, such as arrangements of plant cells convenient for screening purposes or for high-throughput and/or multiplex transformation or gene editing experiments. In an embodiment, the disclosure provides an arrangement of multiple plant cells comprising: (a) an exogenous gene transcription agent which transiently increases expression of an endogenous ODP2 polypeptide and/or an exogenous gene transcription agent which increases expression of an endogenous WUS2 polypeptide; and optionally (b) genome altering reagent(s). In certain embodiments, the arrangements of plant cells can further comprise at least one chemical, enzymatic, or physical delivery agent. In another embodiment, the disclosure provides an array including a plurality of containers, each including at least one plant cell or plant protoplast having improved plant cell regenerative potential.

In an embodiment, the disclosure provides arrangements of plant cells having the exogenous gene transcription agent(s) and optionally the genome altering reagents, wherein the plant cells are in an arrayed format, for example, in multi-well plates, encapsulated or enclosed in vesicles, liposomes, or droplets (useful, (e.g., in a microfluidics device), or attached discretely to a matrix or to discrete particles or beads; a specific embodiment is such an arrangement of multiple plant cells having improved plant cell regenerative potential provided in an arrayed format, further including at least one genome altering reagent(s) (e.g., an RNA-guided DNA nuclease, at least one guide RNA, or a ribonucleoprotein including both an RNA-guided DNA nuclease and at least one guide RNA), which may be different for at least some locations on the array or even for each location on the array, and optionally at least one chemical, enzymatic, or physical delivery agent.

In the systems and methods provided herein, plant cells can be exposed to one exogenous gene transcription agent which transiently increases expression of an endogenous ODP2 polypeptide and/or at least one exogenous gene transcription agent which increases expression of an endogenous WUS2 polypeptide and/or genome altering reagents in any temporal order. In certain embodiments, the genome altering reagents and aforementioned exogenous gene transcription agent(s) are provided simultaneously. In other embodiments, the genome altering reagents are provided after the exogenous gene transcription agent(s) are provided. In other embodiments, the genome altering reagents are provided before the exogenous gene transcription agent(s) are provided. In summary, the genome altering reagents can be provided to a plant cell either previous to, concurrently with, or subsequent to exposing the plant cell to the exogenous gene transcription agent(s).

Plant cells having improved plant cell regenerative potential conferred by an increase in the transient expression of the endogenous ODP2 and/or WUS2 genes are provided herein. Also provided by the disclosure are compositions derived from or grown from the plant cell or plant protoplast having improved plant cell regenerative potential, provided by the systems and methods disclosed herein; such compositions include multiple protoplasts or cells, callus, a somatic embryo, a somatic meristem, embryogenic callus, or a regenerated plant grown from the plant cell or plant protoplast having improved plant cell regenerative potential. Improved plant cell regenerative potential in plant cells that have been subjected to a transient increase in ODP2 and/or WUS2 gene expression can be assessed by a variety of techniques. In certain embodiments, such techniques can compare the numbers and/or amount of regenerable plant structures (e.g., immature embryos, somatic embryos, embryogenic calli, somatic meristems, organogenic calli, shoots, or shoots further comprising roots) formed and/or recovered from a given number of plant cells subjected to the transient increase in endogenous ODP2 and/or WUS2 gene expression versus control plant cells that were not subjected to the transient increase in ODP2 and/or WUS2 gene expression. In certain embodiments, it is understood that the plant cells can be directly subjected to the transient increase in endogenous ODP2 and/or WUS2 gene expression (e.g., by or indirectly (e.g., by exposure, contact, or other signaling of neighboring cells The principle attributes of tissues targeted for transient expression of the ATFs provided would be the presence of dividing cells and the ability to grow in tissue culture media. These tissues include, but are not limited to dividing cells from young maize leaf, meristems and scutellar tissue from about 8 or 10 to about 12 or 14 days after pollination (DAP) embryos. The isolation of maize embryos has been described in several publications (Brettschneider, Becker, and Lörz 1997; Leduc et al. 1996; Frame et al. 2011; K. Wang and Frame 2009). In certain embodiments, basal leaf tissues (e.g., leaf tissues located about 0 to 3 cm from the ligule of a maize plant; Kirienko, Luo, and Sylvester 2012) are targeted for transient expression of the ATFs. In certain embodiments, such increases in numbers and/or amounts of regenerable plant structures can be observed in about 1, 2, or 3 to about 7, 10, 14, 30, or 60 days following the transient increase in endogenous ODP2 and/or WUS2 gene expression. Methods for obtaining regenerable plant structures and regenerating plants from the plant cells provided herein can be adapted from methods disclosed in US Patent Application Publication No. 20170121722, which is incorporated herein by reference in its entirety and specifically with respect to such disclosure. In certain embodiments, single plant cells subjected to the transient increase in endogenous ODP2 and/or WUS2 gene expression will give rise to single regenerable plant structures. In certain embodiments, the single regenerable plant cell structure can form from a single cell on, or within, an explant that has been subjected to the transient increase in endogenous ODP2 and/or WUS2 gene expression and optionally subjected to treatment with a genome altering reagent. In certain embodiments, initiation or formation of the single plant cell regenerable structure can occur where single-cell-derived cell or tissue proliferation (e.g., growth of callus, non-differentiated callus, embryogenic callus and organogenic callus) occurring before initiation of the regenerable plant structure is reduced or absent. In certain embodiments, regenerable plant structures from plant cells subjected to the transient increase in endogenous ODP2 and/or WUS2 gene expression and optionally a genome altering reagent can be form the regenerable plant structure in the absence of exogenous cytokinin or with levels of cytokinin that are lower than those required to initiate formation of the regenerable structure from a control cell. In certain embodiments, regenerable plant structures from plant cells subjected to the transient increase in endogenous ODP2 and/or WUS2 gene expression and optionally a genome altering reagent can be identified and/or selected via a positive growth selection based on the ability of those plant cells to initiate and/or form the regenerable plant structures more rapidly than adjacent plant cells that have not been subjected to the transient increase in endogenous ODP2 and/or WUS2 gene expression. In certain embodiments, such positive growth selection can obviate or reduce the need to use a traditional negative selection system where an antibiotic or herbicide is used to inhibit growth of adjacent, non-transformed cells that do not contain a gene that confers resistance to the antibiotic or herbicide. Nonetheless, embodiments where a selectable marker gene conferring resistance to an antibiotic, herbicide, or other agent can be introduced into the plant cell at least temporarily during initiation and/or formation of the regenerable plant cell structures to facilitate identification and recovery.

In some embodiments, methods provided herein can include the additional step of growing or regenerating a plant from a plant cell that had been subjected to an increase in the transient expression of the endogenous ODP2 and/or WUS2 genes or from a regenerable plant structure obtained from that plant cell. In certain embodiments, the plant can further comprise an inserted transgene, a target gene edit, or genome edit as provided by the methods and compositions disclosed herein. In certain embodiments, callus is produced from the plant cell, and plantlets and plants produced from such callus. In other embodiments, whole seedlings or plants are grown directly from the plant cell without a callus stage. Thus, additional related aspects are directed to whole seedlings and plants grown or regenerated from the plant cell or plant protoplast having a target gene edit or genome edit, as well as the seeds of such plants. In certain embodiments wherein the plant cell or plant protoplast is subjected to genetic or epigenetic modification (for example, stable or transient expression of a transgene, gene silencing, epigenetic silencing, or genome editing by means of, e.g., an RNA-guided DNA nuclease), the grown or regenerated plant exhibits a phenotype associated with the genetic or epigenetic modification. In certain embodiments, the grown or regenerated plant includes in its genome two or more genetic or epigenetic modifications that in combination provide at least one phenotype of interest. In certain embodiments, a heterogeneous population of plant cells having a target gene edit or genome edit, at least some of which include at least one genetic or epigenetic modification, is provided by the method; related aspects include a plant having a phenotype of interest associated with the genetic or epigenetic modification, provided by either regeneration of a plant having the phenotype of interest from a plant cell or plant protoplast selected from the heterogeneous population of plant cells having a target gene or genome edit, or by selection of a plant having the phenotype of interest from a heterogeneous population of plants grown or regenerated from the population of plant cells having a target gene edit or genome edit. Examples of phenotypes of interest include herbicide resistance, improved tolerance of abiotic stress (e.g., tolerance of temperature extremes, drought, or salt) or biotic stress (e.g., resistance to nematode, bacterial, or fungal pathogens), improved utilization of nutrients or water, modified lipid, carbohydrate, or protein composition, improved flavor or appearance, improved storage characteristics (e.g., resistance to bruising, browning, or softening), increased yield, altered morphology (e.g., floral architecture or color, plant height, branching, root structure). In an embodiment, a heterogeneous population of plant cells having a target gene edit or genome edit (or seedlings or plants grown or regenerated therefrom) is exposed to conditions permitting expression of the phenotype of interest; e.g., selection for herbicide resistance can include exposing the population of plant cells having a target gene edit or genome edit (or seedlings or plants grown or regenerated therefrom) to an amount of herbicide or other substance that inhibits growth or is toxic, allowing identification and selection of those resistant plant cells (or seedlings or plants) that survive treatment. Methods for obtaining regenerable plant structures and regenerating plants from plant cells or regenerable plant structures can be adapted from published procedures (Roest and Gilissen, Acta Bot. Neerl., 1989, 38(1), 1-23; Bhaskaran and Smith, Crop Sci. 30(6):1328-1337; Ikeuchi et al., Development, 2016, 143: 1442-1451). Methods for obtaining regenerable plant structures and regenerating plants from plant cells or regenerable plant structures can also be adapted from US Patent Application Publication No. 20170121722, which is incorporated herein by reference in its entirety and specifically with respect to such disclosure. Also provided are heterogeneous populations, arrays, or libraries of such plants, succeeding generations or seeds of such plants grown or regenerated from the plant cells or plant protoplasts, having a target gene edit or genome edit, parts of the plants (including plant parts used in grafting as scions or rootstocks), or products (e.g., fruits or other edible plant parts, cleaned grains or seeds, edible oils, flours or starches, proteins, and other processed products) made from the plants or their seeds. Embodiments include plants grown or regenerated from the plant cells having a target gene edit or genome edit, wherein the plants contain cells or tissues that do not have a genetic or epigenetic modification, e.g., grafted plants in which the scion or rootstock contains a genetic or epigenetic modification, or chimeric plants in which some but not all cells or tissues contain a genetic or epigenetic modification. Plants in which grafting is commonly useful include many fruit trees and plants such as many citrus trees, apples, stone fruit (e.g., peaches, apricots, cherries, and plums), avocados, tomatoes, eggplant, cucumber, melons, watermelons, and grapes as well as various ornamental plants such as roses. Grafted plants can be grafts between the same or different (generally related) species. Additional related aspects include a hybrid plant provided by crossing a first plant grown or regenerated from a plant cell or plant protoplast having a target gene edit or genome edit and having at least one genetic or epigenetic modification, with a second plant, wherein the hybrid plant contains the genetic or epigenetic modification; also contemplated is seed produced by the hybrid plant. Also envisioned as related aspects are progeny seed and progeny plants, including hybrid seed and hybrid plants, having the regenerated plant as a parent or ancestor. The plant cells and derivative plants and seeds disclosed herein can be used for various purposes useful to the consumer or grower. The intact plant itself may be desirable, e.g., plants grown as cover crops or as ornamentals. In other embodiments, processed products are made from the plant or its seeds, such as extracted proteins, oils, sugars, and starches, fermentation products, animal feed or human food, wood and wood products, pharmaceuticals, and various industrial products.

An exogenous gene transcription agent that stimulates transcription of the endogenous ODP2 gene and/or the endogenous WUS2 gene can be provided to a cell (e.g., a plant cell or plant protoplast) by any suitable technique. In certain embodiments, the exogenous gene transcription agent is provided by directly contacting a plant cell with the exogenous gene transcription agent or the polynucleotide that encodes the exogenous gene transcription agent. In certain embodiments, the exogenous gene transcription agent is provided by transporting the exogenous gene transcription agent or a polynucleotide that encodes exogenous gene transcription agent into a plant cell or plant protoplast using a chemical, enzymatic, or physical agent. In certain embodiments, the exogenous gene transcription agent is provided by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of a plant cell or plant protoplast with a polynucleotide encoding the exogenous gene transcription agent; see, e.g., Broothaerts et al. (2005) *Nature*, 433:629-633. In an embodiment, the exogenous gene transcription agent is provided by transcription in a plant cell or plant protoplast of a DNA that encodes the exogenous gene transcription agent and is stably integrated in the genome of the plant cell or is provided to the plant cell or plant protoplast in the form of a plasmid or expression vector (e.g., a viral vector) that encodes the exogenous gene transcription agent. In certain embodiments, the exogenous gene transcription agent is provided to the plant cell or plant protoplast as a polynucleotide that encodes exogenous gene transcription agent, e.g., in the form of an RNA (e.g., mRNA or RNA containing an internal ribosome entry site (IRES)) encoding the exogenous gene transcription agent. Genome altering reagents can also be introduced into the plant cells by similar techniques.

Transient expression of an exogenous gene transcription agent that stimulates transcription of the endogenous ODP2 gene and/or the endogenous WUS2 gene (e.g., expression of an guide RNA from a DNA, or expression and translation of an ATF or RNA-guided DNA binding polypeptide from a DNA encoding the ATF or polypeptide), can be achieved by a variety of techniques. Certain embodiments are useful in effectuating transient expression of the endogenous ODP2 and/or WUS2 gene without remnants of the exogenous gene transcription agents that provide for the transient expression or selective genetic markers occurring in progeny. In certain embodiments, the exogenous gene transcription agents are provided directly to the plant cells, systems, methods, and compositions as isolated molecules, as isolated or semi-purified products of a cell free synthetic process (e.g., in vitro translation), or as isolated or semi-purified products of in a cell-based synthetic process (e.g., such as in a bacterial or other cell lysate). In certain embodiments, artificial transcription factors (ATFs) are targeted to the plant cell or cell nucleus in a manner that insures transient expression (e.g., by methods adapted from Gao et al. 2016; or Li et al. 2009). In certain embodiments, the exogenous gene transcription agent is delivered into the plant cell by delivery of the agent itself in the absence of any polynucleotide that encodes the agent. Examples of exogenous gene transcription agents that can be delivered in the absence of any encoding polynucleotides include polypeptide ATFs (e.g., aZFPs or aTALEs), RNA-guided DNA binding polypeptide, and RNA guides. RNA-guided DNA binding polypeptide/RNA guides can be delivered separately and/or as RNP complexes. In certain embodiments, ATF proteins can be produced in a heterologous system, purified and delivered to plant cells by particle bombardment (e.g., by methods adapted from Martin-Ortigosa and Wang 2014). In embodiments where the exogenous gene transcription agents are delivered in the absence of any encoding polynucleotides, the delivered agent is expected to degrade over time in the absence of ongoing expression from any introduced encoding polynucleotides to result in transient endogenous ODP2 gene and/or the endogenous WUS2 gene expression. In certain embodiments, the exogenous gene transcription agent is delivered into the plant cell by delivery of a polynucleotide that encodes the agent. In certain embodiments, ATFs can be encoded on a bacterial plasmid and delivered to plant tissue by particle bombardment (e.g., by methods adapted from Hamada et al. 2018; or Kirienko, Luo, and Sylvester 2012). In certain embodiments, ATFs can be encoded on a T-DNA and transiently transferred to plant cells using *agrobacterium* (e.g., by methods adapted from Leonelli et al. 2016; or Wu et al. 2014). In certain embodiments, ATFs can be encoded in a viral genome and delivered to plants (e.g., by methods adapted from Honig et al. 2015). In certain embodiments, ATFs can be encoded in mRNA or an RNA comprising an IRES and delivered to target plant cells. In certain embodiments where the exogenous gene transcription agent comprises an RNA-guided DNA binding polypeptide and an RNA guide, the polypeptide or guide can be delivered by a combination of: (i) an encoding polynucleotide for either polypeptide or the guide; and (ii) either polypeptide or the guide itself in the absence of an encoding polynucleotide. In certain embodiments, the exogenous gene transcription agent is delivered into the plant cell by delivery of a polynucleotide that encodes the agent. In certain embodiments, the polynucleotide that encodes the exogenous gene transcription agent is not integrated into a plant cell genome (e.g., as a polynucleotide lacking sequences that provide for integration, by agroinfiltration on an integration deficient T-DNA vector or system, or in a viral vector), is not operably linked to polynucleotides which provide for autonomous replication, and/or only provided with factors (e.g., viral replication proteins) that provide for autonomous replication. Suitable techniques for transient expression including biolistic and other delivery of polynucleotides, agroinfiltration, and use of viral vectors disclosed by Canto, 2016 and others can be adapted for transient expression of the agents provided herein. Transient expression of the agent encoded by a non-integrated polynucleotide effectuated by excision of the polynucleotide and/or regulated expression of the agent. In certain embodiments, the polynucleotide that encodes the exogenous gene transcription agent is integrated into a plant cell genome (e.g., a nuclear or plastid genome) and transient expression of the agent is effectuated by excision of the polynucleotide and/or regulated expression of the agent. Excision of a polynucleotide encoding the agent can be provided by use of site-specific recombination systems (e.g., Cre-Lox, FLP-FRT). Regulated expression of the agent can be effectuated by methods including: (i) operable linkage of the polynucleotide encoding the agent to a developmentally-regulated, de-repressable, and/or inducible promoter; and/or (ii) introduction of a polynucleotide (e.g., dsRNA or amiRNA) that can induce siRNA-mediated inhibition of the agent. Suitable site-specific recombination systems as well as developmentally-regulated, de-repressable, and/or inducible promoters include those disclosed in US Patent Application Publication No. 20170121722, which is incorporated herein by reference in its entirety and specifically with respect to such disclosure. In any of the aforementioned embodiments, transient expression of the endogenous ODP2 and/or WUS2 genes can also be achieved by using an exogenous gene transcription agent comprising a DNA binding domain or complex and a transcription activation domain (TAD) that can be operably associated through binding a common ligand (e.g., the iDimerize™ Regulated Transcription System that uses Dmr A, B, or C dimerization domains and ligands; Takara Bio, USA, Inc.). In such embodiments, transient expression of the endogenous ODP2 and/or WUS2 genes can occur upon addition of the common ligand.

Polynucleotides that can be used to effectuate transient expression of an exogenous gene transcription agent (e.g., a polynucleotide encoding an ATF, RNA-guided DNA binding polypeptide, and/or a guide RNA) include: (a) double-stranded RNA; (b) single-stranded RNA; (c) chemically modified RNA; (d) double-stranded DNA; (e) single-stranded DNA; (f) chemically modified DNA; or (g) a combination of (a)-(f). Certain embodiments of the polynucleotide further include additional nucleotide sequences that provide useful functionality; non-limiting examples of such additional nucleotide sequences include an aptamer or riboswitch sequence, nucleotide sequence that provides secondary structure such as stem-loops or that provides a sequence-specific site for an enzyme (e.g., a sequence-specific recombinase or endonuclease site), T-DNA (e.g., DNA sequence encoding an exogenous gene transcription agent is enclosed between left and right T-DNA borders from *Agrobacterium* spp. or from other bacteria that infect or induce tumors in plants), a DNA nuclear-targeting sequence, a regulatory sequence such as a promoter sequence, and a transcript-stabilizing or -destabilizing sequence. Certain embodiments of the polynucleotide include those wherein the polynucleotide is complexed with, or covalently or non-covalently bound to, a non-nucleic acid element, e.g., a carrier molecule, an antibody, an antigen, a viral movement protein, a cell-penetrating or pore-forming peptide, a polymer, a detectable label, a quantum dot, or a particulate or nanoparticulate.

Various treatments are useful in delivery of an exogenous gene transcription agent that stimulates transcription of the endogenous ODP2 gene and/or the endogenous WUS2 gene to a plant cell. In certain embodiments, one or more treatments is employed to deliver the agent (e.g., comprising a polynucleotide, polypeptide or combination thereof) into a plant cell or plant protoplast, e.g., through barriers such as a cell wall, a plasma membrane, a nuclear envelope, and/or other lipid bilayer. In certain embodiments, a polynucleotide-, polypeptide-, or RNP-containing composition comprising the agent(s) are delivered directly, for example by direct contact of the composition with a plant cell. Aforementioned compositions can be provided in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a plant, plant part, plant cell, or plant explant (e.g., through abrasion or puncture or otherwise disruption of the cell wall or cell membrane, by spraying or dipping or soaking or otherwise directly contacting, by microinjection). For example, a plant cell or plant protoplast is soaked in a liquid exogenous gene transcription agent-containing composition, whereby the agent is delivered to the plant cell. In certain embodiments, the agent-containing composition is delivered using negative or positive pressure, for example, using vacuum infiltration or application of hydrodynamic or fluid pressure. In certain embodiments, the agent-containing composition is introduced into a plant cell or plant protoplast, e.g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e.g., delivery of materials to cells employing microfluidic flow through a cell-deforming constriction as described in US Published Patent Application 2014/0287509, incorporated by reference in its entirety herein. Other techniques useful for delivering the agent-containing composition to a plant cell or plant protoplast include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e.g., abrasion with carborundum or other particulate abrasive or scarification with a file or sandpaper) or chemical scarification (e.g., treatment with an acid or caustic agent); and electroporation. In certain embodiments, the agent-containing composition is provided by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of the plant cell or plant protoplast with a polynucleotide encoding the agent (e.g., ATF, RNA guided ATF, and/or guide RNA); see, e.g., Broothaerts et al. (2005) Nature, 433:629-633. Any of these techniques or a combination thereof are alternatively employed on the plant explant, plant part or tissue or intact plant (or seed) from which a plant cell is optionally subsequently obtained or isolated; in certain embodiments, the agent-containing composition is delivered in a separate step after the plant cell has been isolated. In certain embodiments, the aforementioned methods can also be used to introduce a genome altering reagent into the plant cell.

In embodiments, a treatment employed in delivery of a exogenous gene transcription agent that stimulates transcription of the endogenous ODP2 gene and/or the endogenous WUS2 gene to a plant cell is carried out under a specific thermal regime, which can involve one or more appropriate temperatures, e.g., chilling or cold stress (exposure to temperatures below that at which normal plant growth occurs), or heating or heat stress (exposure to temperatures above that at which normal plant growth occurs), or treating at a combination of different temperatures. In certain embodiments, a specific thermal regime is carried out on the plant cell, or on a plant, plant explant, or plant part from which a plant cell or plant protoplast is subsequently obtained or isolated, in one or more steps separate from the agent delivery. In certain embodiments, the aforementioned methods can also be used to introduce a genome altering reagent into the plant cell.

In certain embodiments of the plant parts, systems, methods, and compositions provided herein, a whole plant or plant part or seed, or an isolated plant cell, a plant explant, or the plant or plant part from which a plant cell or plant protoplast is obtained or isolated, is treated with one or more delivery agents which can include at least one chemical, enzymatic, or physical agent, or a combination thereof. In certain embodiments, an exogenous gene transcription agent that stimulates transcription of the endogenous ODP2 gene and/or the endogenous WUS2 gene further includes one or more than one chemical, enzymatic, or physical agents for delivery. Treatment with the chemical, enzymatic or physical agent can be carried out simultaneously with the agent delivery or in one or more separate steps that precede or follow the agent delivery. In certain embodiments, a chemical, enzymatic, or physical agent, or a combination of these, is associated or complexed with the polynucleotide composition, with the donor template polynucleotide, with the exogenous gene transcription agent; examples of such associations or complexes include those involving non-covalent interactions (e.g., ionic or electrostatic interactions, hydrophobic or hydrophilic interactions, formation of liposomes, micelles, or other heterogeneous composition) and covalent interactions (e.g., peptide bonds, bonds formed using cross-linking agents). In non-limiting examples, the exogenous gene transcription agent is provided as a liposomal complex with a cationic lipid; the exogenous gene transcription agent is provided as a complex with a carbon nanotube; and/or exogenous gene transcription agent is provided as a fusion protein between the agent and a cell-penetrating peptide. Examples of agents useful for delivering the exogenous gene transcription agent(s) include the various cationic liposomes and polymer nanoparticles reviewed by Zhang et al. (2007) *J. Controlled Release,* 123:1-10, and the cross-linked multilamellar liposomes described in US Patent Application Publication 2014/0356414 A1, incorporated by reference in its entirety herein. In any of the aforementioned embodiments, it is further contemplated that the aforementioned methods can also be used to introduce a genome altering reagent into the plant cell.

In certain embodiments, the chemical agent used to deliver an exogenous gene transcription agent that stimulates transcription of the endogenous ODP2 gene and/or the endogenous WUS2 gene can comprise:

(a) solvents (e.g., water, dimethylsulfoxide, dimethylformamide, acetonitrile, N-pyrrolidine, pyridine, hexamethylphosphoramide, alcohols, alkanes, alkenes, dioxanes, polyethylene glycol, and other solvents miscible or emulsifiable with water or that will dissolve phosphonucleotides in non-aqueous systems);

(b) fluorocarbons (e.g., perfluorodecalin, perfluoromethyldecalin);

(c) glycols or polyols (e.g., propylene glycol, polyethylene glycol);

(d) surfactants, including cationic surfactants, anionic surfactants, non-ionic surfactants, and amphiphilic surfactants, e.g., alkyl or aryl sulfates, phosphates, sulfonates, or carboxylates; primary, secondary, or tertiary amines; quaternary ammonium salts; sultaines, betaines; cationic lipids; phospholipids; tallowamine; bile acids such as cholic acid; long chain alcohols; organosilicone surfactants including non-ionic organosilicone surfactants such as trisiloxane ethoxylate surfactants or a silicone polyether copolymer such as a copolymer of polyalkylene oxide modified heptamethyl trisiloxane and allyloxypolypropylene glycol methylether (commercially available as SILWET L-77™ brand surfactant having CAS Number 27306-78-1 and EPA Number CAL. REG. NO. 5905-50073-AA, Momentive Performance Materials, Inc., Albany, N.Y.); specific examples of useful surfactants include sodium lauryl sulfate, the Tween series of surfactants, Triton-X100, Triton-X114, CHAPS and CHAPSO, Tergitol-type NP-40, Nonidet P-40;

(e) lipids, lipoproteins, lipopolysaccharides;

(f) acids, bases, caustic agents;

(g) peptides, proteins, or enzymes (e.g., cellulase, pectolyase, maceroenzyme, pectinase), including cell-penetrating or pore-forming peptides (e.g., (BO100)2K8, Genscript; poly-lysine, poly-arginine, or poly-homoarginine peptides; gamma zein, see US Patent Application publication 2011/0247100, incorporated herein by reference in its entirety; transcription activator of human immunodeficiency virus type 1 ("HIV-1 Tat") and other Tat proteins, see, e.g., www[dot]lifetein[dot]com/Cell_Penetrating_Peptides[dot] html and Järver (2012) *Mol. Therapy-Nucleic Acids,* 1:e27, 1-17); octa-arginine or nona-arginine; poly-homoarginine (see Unnamalai et al. (2004) *FEBS Letters,* 566:307-310); see also the database of cell-penetrating peptides CPPsite 2.0 publicly available at crdd[dot]osdd[dot]net/raghava/cpp-site/

(h) RNase inhibitors;

(i) cationic branched or linear polymers such as chitosan, poly-lysine, DEAE-dextran, polyvinylpyrrolidone ("PVP"), or polyethylenimine ("PEI", e.g., PEI, branched, MW 25,000, CAS #9002-98-6; PEI, linear, MW 5000, CAS #9002-98-6; PEI linear, MW 2500, CAS #9002-98-6);

(j) dendrimers (see, e.g., US Patent Application Publication 2011/0093982, incorporated herein by reference in its entirety);

(k) counter-ions, amines or polyamines (e.g., spermine, spermidine, putrescine), osmolytes, buffers, and salts (e.g., calcium phosphate, ammonium phosphate);

(l) polynucleotides (e.g., non-specific double-stranded DNA, salmon sperm DNA);

(m) transfection agents (e.g., Lipofectin®, Lipofectamine®, and Oligofectamine®, and Invivofectamine® (all from Thermo Fisher Scientific, Waltham, Mass.), PepFect (see Ezzat et al. (2011) *Nucleic Acids Res.,* 39:5284-5298), Transit® transfection reagents (Minis Bio, LLC, Madison, Wis.), and poly-lysine, poly-homoarginine, and poly-arginine molecules including octo-arginine and nono-arginine as described in Lu et al. (2010) *J. Agric. Food Chem.,* 58:2288-2294);

(n) antibiotics, including non-specific DNA double-strand-break-inducing agents (e.g., phleomycin, bleomycin, talisomycin); and/or (o) antioxidants (e.g., glutathione, dithiothreitol, ascorbate).

In any of the aforementioned embodiments, it is further contemplated that the aforementioned chemical agents can also be used to introduce a genome altering reagent into the plant cell.

In certain embodiments, the chemical agent is provided simultaneously with the exogenous gene transcription agent that stimulates transcription of the endogenous ODP2 gene and/or the endogenous WUS2 gene. In certain embodiments, exogenous gene transcription agent is covalently or non-covalently linked or complexed with one or more chemical agents; for example, an ATF or RNA guided DNA binding protein can be covalently linked to a peptide or protein (e.g., a cell-penetrating peptide or a pore-forming peptide) or non-covalently complexed with cationic lipids, polycations (e.g., polyamines), or cationic polymers (e.g., PEI). In certain embodiments, the exogenous gene transcription agent is complexed with one or more chemical agents to form, e.g., a solution, liposome, micelle, emulsion, reverse emulsion, suspension, colloid, or gel. In any of the aforementioned embodiments, it is further contemplated that genome altering reagents comprising polynucleotides and/or polypeptides can be also be delivered as described above.

In certain embodiments, the physical agent for delivery of an exogenous gene transcription agent that stimulates transcription of the endogenous ODP2 gene and/or the endogenous WUS2 gene is at least one selected from the group consisting of particles or nanoparticles (e.g., particles or nanoparticles made of materials such as carbon, silicon, silicon carbide, gold, tungsten, polymers, or ceramics) in various size ranges and shapes, magnetic particles or nanoparticles (e.g., silenceMag Magnetotransfection™ agent, OZ Biosciences, San Diego, Calif.), abrasive or scarifying agents, needles or microneedles, matrices, and grids. In certain embodiments, particulates and nanoparticulates are useful in delivery of the exogenous gene transcription agent. Useful particulates and nanoparticles include those made of metals (e.g., gold, silver, tungsten, iron, cerium), ceramics (e.g., aluminum oxide, silicon carbide, silicon nitride, tungsten carbide), polymers (e.g., polystyrene, polydiacetylene, and poly(3,4-ethylenedioxythiophene) hydrate), semiconductors (e.g., quantum dots), silicon (e.g., silicon carbide), carbon (e.g., graphite, graphene, graphene oxide, or carbon nanosheets, nanocomplexes, or nanotubes), and composites (e.g., polyvinylcarbazole/graphene, polystyrene/graphene, platinum/graphene, palladium/graphene nanocomposites). In certain embodiments, such particulates and nanoparticulates are further covalently or non-covalently functionalized, or further include modifiers or cross-linked materials such as polymers (e.g., linear or branched polyethylenimine, polylysine), polynucleotides (e.g., DNA or RNA), polysaccharides, lipids, polyglycols (e.g., polyethylene glycol, thiolated polyethylene glycol), polypeptides or proteins, and detectable labels (e.g., a fluorophore, an antigen, an antibody, or a quantum dot). In various embodiments, such particulates and nanoparticles are neutral, or carry a positive charge, or carry a negative charge. Embodiments of compositions including particulates include those formulated, e.g., as liquids, colloids, dispersions, suspensions, aerosols, gels, and solids. Embodiments include nanoparticles affixed to a surface or support, e.g., an array of carbon nanotubes vertically aligned on a silicon or copper wafer substrate. Embodiments include polynucleotide compositions including particulates (e.g., gold or tungsten or magnetic particles) delivered by a Biolistic-type technique or with magnetic force. The size of the particles used in Biolistics is generally in the "microparticle" range, for example, gold microcarriers in the 0.6, 1.0, and 1.6 micrometer size ranges (see, e.g., instruction manual for the Helios® Gene Gun System, Bio-Rad, Hercules, Calif.; Randolph-Anderson et al. (2015) "Sub-micron gold particles are superior to larger particles for efficient Biolistic® transformation of organelles and some cell types", Bio-Rad US/EG Bulletin 2015), but successful Biolistics delivery using larger (40 nanometer) nanoparticles has been reported in cultured animal cells; see O'Brian and Lummis (2011) *BMC Biotechnol.*, 11:66-71. Other embodiments of useful particulates are nanoparticles, which are generally in the nanometer (nm) size range or less than 1 micrometer, e.g., with a diameter of less than about 1 nm, less than about 3 nm, less than about 5 nm, less than about 10 nm, less than about 20 nm, less than about 40 nm, less than about 60 nm, less than about 80 nm, and less than about 100 nm. Specific, non-limiting embodiments of nanoparticles commercially available (all from Sigma-Aldrich Corp., St. Louis, Mo.) include gold nanoparticles with diameters of 5, 10, or 15 nm; silver nanoparticles with particle sizes of 10, 20, 40, 60, or 100 nm; palladium "nanopowder" of less than 25 nm particle size; single-, double-, and multi-walled carbon nanotubes, e.g., with diameters of 0.7-1.1, 1.3-2.3, 0.7-0.9, or 0.7-1.3 nm, or with nanotube bundle dimensions of 2-10 nm by 1-5 micrometers, 6-9 nm by 5 micrometers, 7-15 nm by 0.5-10 micrometers, 7-12 nm by 0.5-10 micrometers, 110-170 nm by 5-9 micrometers, 6-13 nm by 2.5-20 micrometers. In certain embodiments, physical agents for delivery of an exogenous gene transcription agents can include materials such as gold, silicon, cerium, or carbon, e.g., gold or gold-coated nanoparticles, silicon carbide whiskers, carborundum, porous silica nanoparticles, gelatin/silica nanoparticles, nanoceria or cerium oxide nanoparticles (CNPs), carbon nanotubes (CNTs) such as single-, double-, or multi-walled carbon nanotubes and their chemically functionalized versions (e.g., carbon nanotubes functionalized with amide, amino, carboxylic acid, sulfonic acid, or polyethylene glycol moeities), and graphene or graphene oxide or graphene complexes. Such physical agents that can be adapted for delivery of exogenous gene transcription agents include those disclosed in Wong et al. (2016) *Nano Lett.*, 16:1161-1172; Giraldo et al. (2014) *Nature Materials*, 13:400-409; Shen et al. (2012) *Theranostics*, 2:283-294; Kim et al. (2011) *Bioconjugate Chem.*, 22:2558-2567; Wang et al. (2010) *J. Am. Chem. Soc. Comm.*, 132:9274-9276; Zhao et al. (2016) *Nanoscale Res. Lett.*, 11:195-203; and Choi et al. (2016) *J. Controlled Release*, 235:222-235. See also, for example, the various types of particles and nanoparticles, their preparation, and methods for their use, e.g., in delivering polynucleotides and polypeptides to cells, disclosed in US Patent Application Publications 2010/0311168, 2012/0023619, 2012/0244569, 2013/0145488, 2013/0185823, 2014/0096284, 2015/0040268, 2015/0047074, and 2015/0208663, all of which are incorporated herein by reference in their entirety. In any of the aforementioned embodiments, it is further contemplated that genome altering reagents comprising polynucleotides and/or polypeptides can be also be delivered as described above.

In certain embodiments wherein the exogenous gene transcription agents comprise a gRNA (or polynucleotide encoding the gRNA) is provided in a composition that further includes an RNA guided DNA binding polypeptide that is nuclease activity deficient (or a polynucleotide that encodes the same), one or more one chemical, enzymatic, or physical agent can similarly be employed. In certain embodiments, the RNA guide and the nuclease activity deficient RNA-guided DNA binding polypeptide (ndRGDBP) or polynucleotide encoding the same) are provided separately, e.g., in a separate composition. Such compositions can include other chemical or physical agents (e.g., solvents, surfactants, proteins or enzymes, transfection agents, particulates or nanoparticulates), such as those described above as useful in the polynucleotide compositions. For example, porous silica nanoparticles are useful for delivering a DNA recombinase into maize cells; see, e.g., Martin-Ortigosa et al. (2015) *Plant Physiol.*, 164:537-547, and can be adapted to providing a ndRGDBP or polynucleotide encoding the same into a maize or other plant cell. In one embodiment, the polynucleotide composition includes a gRNA and the ndRGDBP, and further includes a surfactant and a cell-penetrating peptide (CPP) which can be operably linked to the ndRGDBP. In an embodiment, the polynucleotide composition includes a plasmid or viral vector that encodes both the gRNA and the ndRGDBP, and further includes a surfactant and carbon nanotubes. In an embodiment, the polynucleotide composition includes multiple gRNAs and an mRNA encoding the ndRGDBP, and further includes particles (e.g., gold or tungsten particles), and the polynucleotide composition is delivered to a plant cell or plant protoplast by Biolistics. In any of the aforementioned embodiments, it is further contemplated that other polynucleotides of interest including genome altering reagents can also be delivered before, during, or after delivery of the gRNA and the ndRGDBP.

In certain embodiments, the plant, plant explant, or plant part from which a plant cell is obtained or isolated is treated with one or more chemical, enzymatic, or physical agent(s) in the process of obtaining, isolating, or treating the plant cell. In certain embodiments, the plant cell, plant, plant explant, or plant part is treated with an abrasive, a caustic agent, a surfactant such as Silwet L-77 or a cationic lipid, or an enzyme such as cellulase. In any of the aforementioned embodiments, it is further contemplated that other polynucleotides of interest including genome altering reagents can also be delivered before, during, or after delivery of the endogenous gene transcription agents.

In certain embodiments, one or more than one chemical, enzymatic, or physical agent, separately or in combination with the polynucleotide composition encoding the exogenous gene transcription agent that stimulates transcription of the endogenous ODP2 gene and/or the endogenous WUS2 gene, is provided/applied at a location in the plant or plant part other than the plant location, part, or tissue from which the plant cell is treated, obtained, or isolated. In certain embodiments, the polynucleotide composition is applied to adjacent or distal cells or tissues and is transported (e.g., through the vascular system or by cell-to-cell movement) to the meristem from which plant cells are subsequently isolated. In certain embodiments, the polynucleotide-containing composition is applied by soaking a seed or seed fragment or zygotic or somatic embryo in the polynucleotide-containing composition, whereby the polynucleotide is delivered to the plant cell. In certain embodiments, a flower bud or shoot tip is contacted with a polynucleotide-containing composition, whereby the polynucleotide is delivered to cells in the flower bud or shoot tip from which desired plant cells (e.g., plant cells subjected to a transient increase in expression of the endogenous ODP2 gene and/or the endogenous WUS2 gene) are obtained. In certain embodiments, a polynucleotide-containing composition is applied to the surface of a plant or of a part of a plant (e.g., a leaf surface), whereby the polynucleotide(s) are delivered to tissues of the plant from which desired plant cells are obtained. In certain embodiments a whole plant or plant tissue is subjected to particle- or nanoparticle-mediated delivery (e.g., Biolistics or carbon nanotube or nanoparticle delivery) of a polynucleotide-containing composition, whereby the polynucleotide(s) are delivered to cells or tissues from which plant cells are subsequently obtained. In any of the aforementioned embodiments, it is further contemplated that other polynucleotides of interest including genome altering reagents can also be delivered before, during, or after delivery of the endogenous gene transcription agents.

Genome altering reagents include gene editing molecules for inducing a genetic modification in the plant cells having improved plant cell regenerative potential provided herein. In certain embodiments, such genome altering reagents can include: (i) a polynucleotide selected from the group consisting of an RNA guide for an RNA-guided nuclease, a DNA encoding an RNA guide for an RNA-guided nuclease; (ii) a nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), Argonaute, a meganuclease or engineered meganuclease; (iii) a polynucleotide encoding one or more nucleases capable of effectuating site-specific modification of a target nucleotide sequence; and/or (iv) a donor template polynucleotide. In certain embodiments, at least one delivery agent is selected from the group consisting of solvents, fluorocarbons, glycols or polyols, surfactants; primary, secondary, or tertiary amines and quaternary ammonium salts; organosilicone surfactants; lipids, lipoproteins, lipopolysaccharides; acids, bases, caustic agents; peptides, proteins, or enzymes; cell-penetrating peptides; RNase inhibitors; cationic branched or linear polymers; dendrimers; counter-ions, amines or polyamines, osmolytes, buffers, and salts; polynucleotides; transfection agents; antibiotics; chelating agents such as ammonium oxalate, EDTA, EGTA, or cyclohexane diamine tetraacetate, non-specific DNA double-strand-break-inducing agents; and antioxidants; particles or nanoparticles, magnetic particles or nanoparticles, abrasive or scarifying agents, needles or microneedles, matrices, and grids. In certain embodiments, the plant cell, system, method, or composition comprising the plant cells provided herein further includes (a) at least one plant cell having a Cas9, a Cpf1, a CasY, a CasX, a C2c1, or a C2c3 nuclease; (b) at least one guide RNA; and (c) optionally, at least one chemical, enzymatic, or physical delivery agent.

Gene editing molecules of use in the systems, methods, compositions, and reaction mixtures provided herein include molecules capable of introducing a double-strand break ("DSB") in double-stranded DNA, such as in genomic DNA or in a target gene located within the genomic DNA as well as accompanying guide RNA or donor template polynucleotides. Examples of such gene editing molecules include: (a) a nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), an Argonaute, and a meganuclease or engineered meganuclease; (b) a polynucleotide encoding one or more nucleases capable of effectuating site-specific alteration (such as introduction of a DSB) of a target nucleotide sequence; (c) a guide RNA (gRNA) for an RNA-guided nuclease, or a DNA encoding a gRNA for an RNA-guided nuclease; and (d) donor template polynucleotides.

CRISPR-type genome editing can be adapted for use in the plant cells, systems, methods, and compositions provided herein in several ways. CRISPR elements, i.e., gene editing molecules comprising CRISPR endonucleases and CRISPR single-guide RNAs or polynucleotides encoding the same, are useful in effectuating genome editing without remnants of the CRISPR elements or selective genetic markers occurring in progeny. In certain embodiments, the CRISPR elements are provided directly to the plant cells, systems, methods, and compositions as isolated molecules, as isolated or semi-purified products of a cell free synthetic process (e.g., in vitro translation), or as isolated or semi-purified products of in a cell-based synthetic process (e.g., such as in a bacterial or other cell lysate). In certain embodiments, genome-inserted CRISPR elements are useful in plant lines adapted for use in the systems, methods, and compositions provide herein. In certain embodiments, plants or plant cells used in the systems, methods, and compositions provided herein can comprise a transgene that expresses a CRISPR endonuclease (e.g., a Cas9, a Cpf1-type or other CRISPR endonuclease). In certain embodiments, one or more CRISPR endonucleases with unique PAM recognition sites can be used. Cpf1 endonuclease and corresponding guide RNAs and PAM sites are disclosed in US Patent Application Publication 2016/0208243 A1, which is incorporated herein by reference for its disclosure of DNA encoding Cpf1 endonucleases and guide RNAs and PAM sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for gene editing mediated trait introgression (e.g., for introducing a trait into a new genotype without backcrossing to a recurrent parent or with limited backcrossing to a recurrent parent). Multiple endonucleases can be provided in expression cassettes with the appropriate promoters to allow multiple genome editing in a spatially or temporally separated fashion in either in chromosome DNA or episome DNA.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1. Other CRISPR nucleases useful for editing genomes include C2c1 and C2c3 (see Shmakov et al. (2015) *Mol. Cell*, 60:385-397) and CasX and CasY (see Burstein et al. (2016) *Nature*, doi:10.1038/nature21059). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in US Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety.

For the purposes of gene editing, CRISPR arrays can be designed to contain one or multiple guide RNA sequences corresponding to a desired target DNA sequence; see, for example, Cong et al. (2013) *Science*, 339:819-823; Ran et al. (2013) *Nature Protocols*, 8:2281-2308. At least 16 or 17 nucleotides of gRNA sequence are required by Cas9 for DNA cleavage to occur; for Cpf1 at least 16 nucleotides of gRNA sequence are needed to achieve detectable DNA cleavage and at least 18 nucleotides of gRNA sequence were reported necessary for efficient DNA cleavage in vitro; see Zetsche et al. (2015) *Cell*, 163:759-771. In practice, guide RNA sequences are generally designed to have a length of 17-24 nucleotides (frequently 19, 20, or 21 nucleotides) and exact complementarity (i.e., perfect base-pairing) to the targeted gene or nucleic acid sequence; guide RNAs having less than 100% complementarity to the target sequence can be used (e.g., a gRNA with a length of 20 nucleotides and 1-4 mismatches to the target sequence) but can increase the potential for off-target effects. The design of effective guide RNAs for use in plant genome editing is disclosed in US Patent Application Publication 2015/0082478 A1, the entire specification of which is incorporated herein by reference. More recently, efficient gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing); see, for example, Cong et al. (2013) *Science*, 339:819-823; Xing et al. (2014) *BMC Plant Biol.*, 14:327-340. Chemically modified sgRNAs have been demonstrated to be effective in genome editing; see, for example, Hendel et al. (2015) *Nature Biotechnol.*, 985-991. The design of effective gRNAs for use in plant genome editing is disclosed in US Patent Application Publication 2015/0082478 A1, the entire specification of which is incorporated herein by reference.

Other nucleases capable of effecting site-specific modification of a target nucleotide sequence in the systems, methods, and compositions provided herein include zinc-finger nucleases (ZFNs), transcription activator-like effector nucleases (TAL-effector nucleases or TALENs), Argonaute proteins, and a meganuclease or engineered meganuclease. Zinc finger nucleases (ZFNs) are engineered proteins comprising a zinc finger DNA-binding domain fused to a nucleic acid cleavage domain, e.g., a nuclease. The zinc finger binding domains provide specificity and can be engineered to specifically recognize any desired target DNA sequence. For a review of the construction and use of ZFNs in plants and other organisms, see, e.g., Urnov et al. (2010) *Nature Rev. Genet.*, 11:636-646. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotide bases outside their target triplet. Typically, the engineered zinc finger DNA binding domain has a novel binding specificity, compared to a naturally-occurring zinc finger protein. Engineering methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e.g., U.S. Pat. Nos. 6,453,242 and 6,534,261, both incorporated herein by reference in their entirety. Exemplary selection methods (e.g., phage display and yeast two-hybrid systems) are well known and described in the literature. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e.g., see U.S. Pat. Nos. 6,479,626; 6,903,185; and 7,153,949, incorporated herein by reference in their entirety. The nucleic acid cleavage domain is non-specific and is typically a restriction endonuclease, such as FokI. This endonuclease must dimerize to cleave DNA. Thus, cleavage by FokI as part of a ZFN requires two adjacent and independent binding events, which must occur in both the correct orientation and with appropriate spacing to permit dimer formation. The requirement for two DNA binding events enables more specific targeting of long and potentially unique recognition sites. FokI variants with enhanced activities have been described; see, e.g., Guo et al. (2010) *J. Mol. Biol.*, 400:96-107.

Transcription activator like effectors (TALEs) are proteins secreted by certain *Xanthomonas* species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare genome editing proteins, referred to as TAL-effector nucleases or TALENs. As in the case of ZFNs, a restriction endonuclease, such as FokI, can be conveniently used. For a description of the use of TALENs in plants, see Mahfouz et al. (2011) *Proc. Natl. Acad. Sci. USA*, 108:2623-2628 and Mahfouz (2011) *GM Crops*, 2:99-103.

Argonautes are proteins that can function as sequence-specific endonucleases by binding a polynucleotide (e.g., a single-stranded DNA or single-stranded RNA) that includes sequence complementary to a target nucleotide sequence) that guides the Argonaut to the target nucleotide sequence and effects site-specific alteration of the target nucleotide sequence; see, e.g., US Patent Application Publication 2015/0089681, incorporated herein by reference in its entirety.

In related embodiments, zinc finger nucleases, TALENs, and Argonautes are used in conjunction with other functional domains. For example, the nuclease activity of these nucleic acid targeting systems can be altered so that the enzyme binds to but does not cleave the DNA. Examples of functional domains include transposase domains, integrase domains, recombinase domains, resolvase domains, invertase domains, protease domains, DNA methyltransferase domains, DNA hydroxylmethylase domains, DNA demethylase domains, histone acetylase domains, histone deacetylase domains, nuclease domains, repressor domains, activator domains, nuclear-localization signal domains, transcription-regulatory protein (or transcription complex recruiting) domains, cellular uptake activity associated domains, nucleic acid binding domains, antibody presentation domains, histone modifying enzymes, recruiter of histone modifying enzymes; inhibitor of histone modifying enzymes, histone methyltransferases, histone demethylases, histone kinases, histone phosphatases, histone ribosylases, histone deribosylases, histone ubiquitinases, histone deubiquitinases, histone biotinases and histone tail proteases. Non-limiting examples of functional domains include a transcriptional activation domain, a transcription repression domain, and an SHH1, SUVH2, or SUVH9 polypeptide capable of reducing expression of a target nucleotide sequence via epigenetic modification; see, e.g., US Patent Application Publication 2016/0017348, incorporated herein by reference in its entirety. Genomic DNA may also be modified via base editing using a fusion between a catalytically inactive Cas9 (dCas9) fused to a cytidine deaminase which converts cytosine (C) to uridine (U), thereby effecting a C to T substitution; see Komor et al. (2016) *Nature*, 533:420-424. In other embodiments, adenine base editors (ABEs) can be used to convert A/T base pairs to G/C base pairs in genomic DNA (Gaudelli et al., 2017).

Other genome altering reagents used in plant cells and methods provided herein include transgenes or vectors comprising the same. Such transgenes can confer useful traits that include herbicide tolerance, pest tolerance (e.g., tolerance to insects, nematodes, or plant pathogenic fungi and bacteria), improved yield, increased and/or qualitatively improved oil, starch, and protein content, improved abiotic stress tolerance (e.g., improved or enhanced water use efficiency or drought tolerance, osmotic stress tolerance, high salinity stress tolerance, heat stress tolerance, enhanced cold tolerance, including cold germination tolerance), and the like. Such transgenes include both transgenes that confer the trait by expression of an exogenous protein as well as transgenes that confer the trait by inhibiting expression of endogenous plant genes (e.g., by inducing an siRNA response which inhibits expression of the endogenous plant genes). Transgenes that can provide such traits are disclosed in US Patent Application Publication Nos. 20170121722 and 20170275636, which are each incorporated herein by reference in their entireties and specifically with respect to such disclosures.

In some embodiments, one or more polynucleotides or vectors driving expression of one or more polynucleotides encoding any of the aforementioned exogenous gene transcription agents and/or genome altering reagents are introduced into a plant cell. In certain embodiments, a polynucleotide vector comprises a regulatory element such as a promoter operably linked to one or more polynucleotides encoding exogenous gene transcription agents or genome altering reagents. In such embodiments, expression of these polynucleotides can be controlled by selection of the appropriate promoter, particularly promoters functional in a plant cell; useful promoters include constitutive, conditional, inducible, and temporally or spatially specific promoters (e.g., a tissue specific promoter, a developmentally regulated promoter, or a cell cycle regulated promoter). Developmentally regulated promoters that can be used include Phospholipid Transfer Protein (PLTP), fructose-1,6-bisphosphatase protein, NAD(P)-binding Rossmann-Fold protein, adipocyte plasma membrane-associated protein-like protein, Rieske [2Fe-2S] iron-sulfur domain protein, chlororespiratory reduction 6 protein, D-glycerate 3-kinase, chloroplastic-like protein, chlorophyll a-b binding protein 7, chloroplastic-like protein, ultraviolet-B-repressible protein, Soul heme-binding family protein, Photosystem I reaction center subunit psi-N protein, and short-chain dehydrogenase/reductase protein that are disclosed in US Patent Application Publication No. 20170121722, which is incorporated herein by reference in its entirety and specifically with respect to such disclosure. In certain embodiments, the promoter is operably linked to nucleotide sequences encoding multiple guide RNAs, wherein the sequences encoding guide RNAs are separated by a cleavage site such as a nucleotide sequence encoding a microRNA recognition/cleavage site or a self-cleaving ribozyme (see, e.g., Ferré-D'Amaré and Scott (2014) Cold Spring Harbor Perspectives Biol., 2:a003574). In certain embodiments, the promoter is an RNA polymerase III promoter operably linked to a nucleotide sequence encoding one or more guide RNAs. In certain embodiments, the promoter operably linked to one or more polynucleotides is a constitutive promoter that drives gene expression in plant cells. In certain embodiments, the promoter drives gene expression in the nucleus or in an organelle such as a chloroplast or mitochondrion. Examples of constitutive promoters include a CaMV 35S promoter as disclosed in U.S. Pat. Nos. 5,858,742 and 5,322,938, a rice actin promoter as disclosed in U.S. Pat. No. 5,641,876, a maize chloroplast aldolase promoter as disclosed in U.S. Pat. No. 7,151,204, and the nopaline synthase (NOS) and octopine synthase (OCS) promoters from *Agrobacterium tumefaciens*. In certain embodiments, the promoter operably linked to one or more polynucleotides encoding elements of a genome-editing system is a promoter from figwort mosaic virus (FMV), a RUBISCO promoter, or a pyruvate phosphate dikinase (PPDK) promoter, which is active in photosynthetic tissues. Other contemplated promoters include cell-specific or tissue-specific or developmentally regulated promoters, for example, a promoter that limits the expression of the nucleic acid targeting system to germline or reproductive cells (e.g., promoters of genes encoding DNA ligases, recombinases, replicases, or other genes specifically expressed in germline or reproductive cells). In certain embodiments, the genome alteration is limited only to those cells from which DNA is inherited in subsequent generations, which is advantageous where it is desirable that expression of the genome-editing system be limited in order to avoid genotoxicity or other unwanted effects. All of the patent publications referenced in this paragraph are incorporated herein by reference in their entirety.

Expression vectors or polynucleotides provided herein may contain a DNA segment near the 3' end of an expression cassette that acts as a signal to terminate transcription and directs polyadenylation of the resultant mRNA, and may also support promoter activity. Such a 3' element is commonly referred to as a "3'-untranslated region" or "3'-UTR" or a "polyadenylation signal." In some cases, plant gene-based 3' elements (or terminators) consist of both the 3'-UTR and downstream non-transcribed sequence (Nuccio et al., 2015). Useful 3' elements include: *Agrobacterium tumefaciens* nos 3', tml 3', tmr 3', tms 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in US Patent Application Publication 2002/0192813 A1, incorporated herein by reference.

In certain embodiments, a vector or polynucleotide comprising an expression cassette includes additional components, e.g., a polynucleotide encoding a drug resistance or herbicide gene or a polynucleotide encoding a detectable marker such as green fluorescent protein (GFP) or beta-glucuronidase (gus) to allow convenient screening or selection of cells expressing the vector or polynucleotide. Selectable markers include genes that confer resistance to herbicidal compounds, such as glyphosate, sulfonylureas, glufosinate ammonium, bromoxynil, imidazolinones, and 2,4-dichlorophenoxyacetate (2,4-D). Since the transient expression of endogenous ODP2 and/or WUS2 genes can accelerate somatic embryogenesis and embryo maturation, selectable marker genes, selective agents, and conditions can be adjusted to minimize formation of un-edited or untransformed regenerable plant structures (e.g., "escapes"). Such selectable marker genes and selective agents include the maize HRA gene (Lee et al., 1988, EMBO J 7:1241-1248) which confers resistance to sulfonylureas and imidazolinones, the CP4 gene that confers resistance to glyphosate (U.S. Reissue Pat. RE039247, specifically incorporated herein by reference in its entirety and with respect to such genes and related selection methods), the GAT gene which confers resistance to glyphosate (Castle et al., 2004, Science 304: 1151-1154), genes that confer resistance to spectinomycin such as the aadA gene (Svab et al., 1990, Plant Mol Biol. 14:197-205) and the bar gene that confers resistance to glufosinate ammonium (White et al., 1990, Nucl. Acids Res. 25:1062), and PAT (or moPAT for corn, see Rasco-Gaunt et al., 2003, Plant Cell Rep. 21:569-76; also see Sivamani et al., 2019) and the PMI gene that permits growth on mannose-containing medium (Negrotto et al., 2000, Plant Cell Rep. 22:684-690).

Embodiments

Various embodiments of the plant cells and methods provided herein are included in the following non-limiting list of embodiments.

1. A plant cell wherein expression of an endogenous ODP2 polypeptide and/or expression of an endogenous WUS2 polypeptide is increased in comparison to the expression of the endogenous ODP2 and/or the endogenous WUS2 polypeptides in a control plant cell, wherein the plant cell can form a regenerable plant structure, and optionally wherein the plant cell is a monocot plant cell or optionally wherein the plant cell is a maize, wheat, sorghum, or rice plant cell.

2. The plant cell of embodiment 1, wherein an exogenous polynucleotide encoding an ODP2 and/or WUS2 polypeptide is absent before and/or during the increase in expression of the endogenous ODP2 polypeptide and/or the endogenous WUS2 polypeptide.

3. The plant cell of embodiment 1 or 2, wherein the increase in expression of the endogenous ODP2 polypeptide and/or expression of the endogenous WUS2 polypeptide is sufficient to increase in proliferation, somatic embryogenesis, and/or regeneration capacity of the plant cell in comparison to the control plant cell.

4. The plant cell of any one of embodiments 1, 2, or 3, wherein the increase in expression of the endogenous ODP2 polypeptide and/or expression of the endogenous WUS2 polypeptide is sufficient to increase in transformation efficiency and/or endogenous gene editing efficiency of the plant cell in comparison to the control plant cell.

5. The plant cell of any one of embodiments 1-3, or 4, wherein the increase in the expression of the endogenous ODP2 polypeptide and/or expression of the endogenous WUS2 polypeptide is for a period of about 12, 24, 30, or 36 hours to about 168 or 192 hours.

6. The plant cell of any one of embodiments 1-4, or 5, wherein said cell is located within or obtained from a cultured plant tissue explant, an immature embryo, a mature embryo, a leaf, and/or callus.

7. The plant cell of embodiment 6, wherein the plant tissue explant, embryo, or callus exhibits an increase in proliferation, somatic embryogenesis, and/or regeneration capacity in comparison to the control plant tissue explant, embryo, or callus which was not subjected to an increase in expression of the endogenous ODP2 polypeptide and/or the endogenous WUS2 polypeptide.

8. The plant cell of embodiment 6, wherein the plant tissue explant, embryo, or callus exhibits an increase in transformation efficiency and/or endogenous gene editing efficiency in comparison to the control plant tissue explant, embryo, or callus which was not subjected to an increase in expression of the endogenous ODP2 polypeptide and/or the endogenous WUS2 polypeptide.

9. The plant cell of any one of embodiments 1 to 8 wherein the plant cell, plant tissue explant, embryo, or callus comprises inbred germplasm, haploid germplasm, and/or a regeneration-recalcitrant germplasm.

10. The plant cell of any one of embodiments 1 to 8, wherein the plant cell is derived from the L1 or L2 layer of an immature or mature embryo.

11. The plant cell of any one of embodiments 1 to 8, wherein the plant cell is a maize plant cell and the ODP2 polypeptide comprises an amino acid sequence having at least 95%, 96%, 97%, or 99% amino acid sequence identity across the entire length of SEQ ID NO:1.

12. The plant cell of embodiment 11, wherein the endogenous ODP2 polypeptide is encoded by the endogenous maize ODP2 gene located on maize chromosome 3 and/or that is encoded by an endogenous polynucleotide that is operably linked to an endogenous maize ODP2 promoter of SEQ ID NO:3, SEQ ID NO:71, or an allelic variant thereof.

13. The plant cell of any one of embodiments 1 to 12, wherein the plant cell is a maize plant cell and the endogenous WUS2 polypeptide comprises an amino acid sequence having at least 95%, 96%, 97%, or 99% amino acid sequence identity across the entire length of SEQ ID NO:2.

14. The plant cell of embodiment 13, wherein the endogenous WUS2 polypeptide is encoded by the endogenous maize WUS2 gene located on maize chromosome 10 and/or that is encoded by an endogenous polynucleotide that is operably linked to an endogenous maize WUS2 promoter of SEQ ID NO:4 or an allelic variant thereof.

15. The plant cell of any one of embodiments 1 to 14, wherein the expression of the endogenous ODP2 polypeptide and/or the endogenous WUS2 polypeptide is transiently increased with at least one exogenous gene transcription agent that stimulates transcription of the endogenous ODP2 gene and/or with at least one exogenous gene transcription agent that stimulates transcription of the endogenous WUS2 gene.

16. The plant cell of embodiment 15, wherein the exogenous gene transcription agent is provided as: (i) an exogenous protein; or (ii) as an exogenous protein and an exogenous guide RNA.

17. The plant cell of embodiment 16, wherein the exogenous protein of either (i) or (ii) is provided in the cell in the absence of an exogenous polynucleotide that encodes the protein.

18. The plant cell of embodiment 16, wherein the exogenous protein of either (i) or (ii) is provided in the cell by an exogenous polynucleotide comprising a promoter that is operably linked to a polynucleotide that encodes the protein or by an exogenous RNA molecule that encodes the protein.

19. The plant cell of embodiment 18, wherein the exogenous RNA molecule that encodes the protein comprises an mRNA or an RNA with an internal ribosome entry site (IRES).

20. The plant cell of embodiment 19, wherein the exogenous polynucleotide or exogenous RNA are operably linked to a polynucleotide comprising a viral vector or T-DNA in the cell.

21. The plant cell of embodiment 20, wherein the exogenous protein, exogenous polynucleotide, and/or exogenous guide RNA are in part associated with an exogenous particle within the cell.

22. The plant cell of embodiment 15, wherein the exogenous gene transcription agent comprises: (i) a domain or complex which binds to the promoter or 5' untranslated region (5' UTR) of the endogenous ODP2 gene or to the promoter or 5' UTR of the endogenous WUS2 gene; and (ii) a transcription activation domain, wherein the transcription activation domain is operably linked or operably associated with the domain or complex.

23. The plant cell of embodiment 22, wherein the exogenous gene transcription agent further comprises an operably linked nuclear localization signal (NLS).

24. The plant cell of embodiment 22, wherein the domain that binds the promoter or 5' UTR comprises an artificial zinc finger (AZF) DNA binding domain polypeptide or an artificial transcription activator-like effector (TALE) DNA binding polypeptide.

25. The plant cell of embodiment 24, wherein the plant cell is a maize plant cell and the artificial zinc finger DNA binding domain that binds the ODP2 promoter comprises: (i) a polypeptide having at least 85%, 90%, 95%, 97%, 98%, or 99% sequence identity across the entire length of SEQ ID NO: 5 or 8; or (ii) a polypeptide having at one or more conservative and/or semi-conservative amino acid substitutions in SEQ ID NO: 5 or 8.

26. The plant cell of embodiment 24, wherein the plant cell is a maize plant cell and the artificial zinc finger DNA binding domain that binds the WUS2 promoter comprises: (i) a polypeptide having at least 85%, 90%, 95%, 97%, 98%, or 99% sequence identity across the entire length of SEQ ID NO: 11 or 14; or comprises a polypeptide having at one or more conservative and/or semi-conservative amino acid substitutions in SEQ ID NO: 11 or 14.

27. The plant cell of embodiment 24, wherein the plant cell is a maize plant cell and the artificial TALE DNA binding polypeptide that binds the ODP2 promoter comprises: (i) a polypeptide having at least 85%, 90%, 95%, 97%, 98%, or 99% sequence identity across the entire length of SEQ ID NO: 27, 81, 84, or 87; or (ii) a polypeptide having at one or more conservative and/or semi-conservative amino acid substitutions in SEQ ID NO: 23, 25, 27, 81, 84, or 87.

28. The plant cell of embodiment 24, wherein the plant cell is a maize plant cell and the artificial TALE DNA binding domain that binds the WUS2 promoter comprises: (i) a polypeptide having at least 85%, 90%, 95%, 97%, 98%, or 99% sequence identity across the entire length of SEQ ID NO: 17, 19, 21, 72, 75, or 78; or (ii) a polypeptide having at one or more conservative and/or semi-conservative amino acid substitutions in SEQ ID NO: 17, 19, 21, 72, 75, or 78.

29. The plant cell of embodiment 22, wherein the complex that binds the promoter or 5' UTR comprises: (i) an RNA guided DNA binding polypeptide that is nuclease activity deficient and a guide RNA comprising about an 18 or 19 to about a 21 or 22 nucleotide polynucleotide sequence which is complementary to a sequence immediately adjacent to a protospacer adjacent motif (PAM) in the promoter or 5' UTR; or (ii) a 20, 21, 22, 23, or 24 nucleotide polynucleotide sequence which is complementary to a sequence immediately adjacent to a protospacer adjacent motif (PAM) in the promoter or 5' UTR.

30. The plant cell of embodiment 29, wherein the RNA guided DNA binding polypeptide comprises a dCAS9 polypeptide, comprises a polypeptide having at least 85%, 90%, 95%, 97%, 98%, or 99% sequence identity across the entire length of SEQ ID NO: 29, or comprises a polypeptide having at one or more conservative and/or semi-conservative amino acid substitutions in SEQ ID NO: 29.

31. The plant cell of embodiment 29, wherein the RNA guided DNA binding polypeptide comprises; (i) a dCpf1 polypeptide;
(ii) a polypeptide having one or more conservative and/or semi-conservative amino acid substitutions in SEQ ID NO: 44 or at least 85%, 90%, 95%, 97%, 98%, or 99% sequence identity across the entire length of SEQ ID NO: 44 and a D917A, E1006A, E1028A, D1255A, and/or N1257A amino acid substitution;
(iii) a polypeptide having one or more conservative and/or semi-conservative amino acid substitutions in SEQ ID NO: 45 or at least 85%, 90%, 95%, 97%, 98%, or 99% sequence identity across the entire length of SEQ ID NO: 45 and a D832A, E925A, and/or D1148A amino acid substitution;
(iv) a polypeptide having one or more conservative and/or semi-conservative amino acid substitutions in SEQ ID NO: 46 or at least 85%, 90%, 95%, 97%, 98%, or 99% sequence identity across the entire length of SEQ ID NO: 46 and a D917A, E1006A, E1028A, D1255A, and/or N1257A amino acid substitution; or
(v) a polypeptide having one or more conservative and/or semi-conservative amino acid substitutions in SEQ ID NO: 47 or at least 85%, 90%, 95%, 97%, 98%, or 99% sequence identity across the entire length of SEQ ID NO: 47 and a D901A and/or E1228A amino acid substitution.

32. The plant cell of embodiment 29, wherein the plant cell is a maize plant cell and the guide RNA comprises a sequence that is complementary to either strand of an ODP2 promoter comprising SEQ ID NO: 3 or SEQ ID NO: 71 or to either strand of an WUS2 promoter comprising SEQ ID NO: 4, wherein the complementary sequence is immediately adjacent to a protospacer adjacent motif (PAM) in SEQ ID NO: 3, 71, or 4.

33. The plant cell of embodiment 32, wherein the guide RNA comprises an RNA encoded by SEQ ID NO: 31, 32, 33, 34, or 35 that is complementary to a sequence in the endogenous maize ODP2 promoter.

34. The plant cell of embodiment 32, wherein the guide RNA comprises an RNA encoded by SEQ ID NO: 36, 37, 38, 39, or 40 that is complementary to a sequence in the endogenous maize WUS2 promoter.

35. The plant cell of any one of embodiments 1 to 34, wherein the cell comprises at least two exogenous gene transcription agents that stimulate transcription of the endogenous ODP2 gene and/or at least two exogenous gene transcription agents that stimulate transcription of the endogenous WUS2 gene.

36. The plant cell of embodiment 35, wherein the exogenous gene transcription agents comprise a transcriptional activation domain that is operably linked to or operably associated with: (i) an artificial zinc finger (AZF) DNA binding domain polypeptide; (ii) an artificial TALE DNA binding polypeptide; (iii) an RNA guided DNA binding polypeptide that is nuclease activity deficient and a guide RNA, or any combination thereof.

37. The plant cell of embodiment 35, wherein the plant cell is a maize plant cell and the exogenous gene transcription agents that stimulate transcription of the endogenous WUS2 gene comprise a combination of at least two artificial TALE transcription factors comprising a transcriptional activation domain and an artificial TALE DNA binding polypeptide of SEQ ID NO:17, SEQ ID NO:19, SEQ ID NO:21, SEQ ID NO:72, SEQ ID NO:75, and SEQ ID NO:78.

38. The plant cell of embodiment 35, wherein the plant cell is a maize plant cell and the exogenous gene transcription agents that stimulate transcription of the endogenous ODP2 gene comprise a combination of at least two distinct artificial TALE transcription factors that each comprise a transcriptional activation domain that is operably linked to or operably associated with an artificial TALE DNA sequence recognition domain polypeptide of SEQ ID NO:23, SEQ ID NO:25, SEQ ID NO:27, SEQ ID NO:81, SEQ ID NO:84, or SEQ ID NO:87.

39. The plant cell of any one of embodiments 1 to 38, wherein the cell further comprises a genome altering reagent.

40. The plant cell of any one of embodiments 1 to 39, wherein the regenerable plant structure comprises a somatic embryo, embryogenic callus, somatic meristem, organogenic callus, a shoot, or a shoot further comprising roots.

41. A method of producing a regenerable plant structure, comprising:
(i) introducing into a plant cell at least one exogenous gene transcription agent which transiently increases expression of an endogenous ODP2 polypeptide and/or at least one exogenous gene transcription agent which transiently increases expression of an endogenous WUS2 polypeptide, wherein the expression is increased in comparison to the expression of the endogenous ODP2 and/or the endogenous WUS2 polypeptides in a control plant cell; and,
(ii) culturing the plant cell to produce a regenerable plant structure;
optionally wherein the plant cell is a monocot plant cell or optionally wherein the monocot plant cell is a maize, wheat, sorghum, or rice plant cell.

42. The method of embodiment 41, wherein an exogenous polynucleotide encoding an ODP2 and/or WUS2 polypeptide is absent before and/or during the transient increase in expression of the endogenous ODP2 polypeptide and/or the endogenous WUS2 polypeptide.

43. The method of embodiment 41 or 42, wherein the transient increase in expression of the endogenous ODP2 polypeptide and/or expression of the endogenous WUS2 polypeptide is sufficient to increase proliferation, somatic embryogenesis, and/or regeneration capacity of the plant cell in comparison to the control plant cell.

44. The method of any one of embodiments 41 to 43, wherein the transient increase in expression of the endogenous ODP2 polypeptide and/or expression of the endogenous WUS2 polypeptide is sufficient to increase transformation efficiency and/or endogenous gene editing efficiency in comparison to the control plant cell.

45. The method of any one of embodiments 41 to 44, wherein the transient increase in the expression of the endogenous ODP2 polypeptide and/or expression of the endogenous WUS2 polypeptide is for a period of about 24, 30, or 36 hours to about 168 or 192 hours.

46. The method of any one of embodiments 41 to 45, wherein the exogenous gene transcription agent is introduced by electroporation, particle bombardment, transfection, *Agrobacterium*-mediated transformation or viral vector-mediated transfer.

47. The method of embodiment 41, wherein the exogenous gene transcription agent is introduced as: (i) an exogenous protein; or (ii) as an exogenous protein and an exogenous guide RNA, wherein said protein and said guide RNA are optionally complexed as a RNP.

48. The method of embodiment 47, wherein the exogenous protein of either (i) or (ii) is introduced in the cell in the absence of an exogenous polynucleotide that encodes the protein.

49. The method of embodiment 47, wherein the exogenous protein of either (i) or (ii) is introduced in the cell by an exogenous polynucleotide comprising a promoter that is operably linked to a polynucleotide that encodes the protein or an exogenous RNA molecule that encodes the protein.

50. The method of embodiment 49, wherein the exogenous polynucleotide or exogenous RNA are operably linked to a polynucleotide comprising a viral vector or T-DNA in the cell.

51. The method of embodiment 49, wherein the exogenous polynucleotide is not integrated into the nuclear or plastid genome of the plant cell.

52. The method of any one of embodiments 41 to 51, wherein said plant cell is located within or obtained from a cultured plant tissue explant, an immature embryo, a mature embryo, a leaf, and/or callus.

53. The method of embodiment 52, wherein the plant cell is derived from the L1 or L2 layer of an immature or mature embryo.

54. The method of any one of embodiments 41 to 53, wherein the plant cell, plant tissue explant, embryo, or callus comprises inbred germplasm, haploid germplasm, and/or a regeneration-recalcitrant germplasm.

55. The method of any one of embodiments 41 to 54, wherein the regenerable plant structure comprises a somatic embryo, embryogenic callus, somatic meristem, organogenic callus, a shoot, or a shoot further comprising roots.

56. The method of any one of embodiments 41 to 55, wherein the culturing comprises growing of the plant cell in plant cell growth media comprising an auxin concentration sufficient to induce formation of a somatic embryo, embryogenic callus, somatic meristem, and/or organogenic callus.

57. The method of embodiment 56, wherein the culturing further comprises growing the somatic embryo, embryogenic callus, somatic meristem, and/or organogenic callus in plant cell growth media comprising concentrations of auxin and cytokinin sufficient to induce formation of a shoot.

58. The method of embodiment 57, wherein the culturing further comprises growing the shoot in a plant cell growth media until the shoot forms roots.

59. The method of any one of embodiments 41 to 58, further comprising the step of introducing a genome altering reagent into the cell at step (i), (ii), or (i) and (ii).

60. The method of embodiment 59, wherein the genome altering reagent comprises a transgene, a vector comprising a transgene, or genome editing molecules.

61. The method of embodiment 60, wherein the vector comprises a T-DNA or viral vector.

62. The method of embodiment 59, wherein the genome editing molecules comprise an RNA-guided nuclease or a polynucleotide encoding an RNA-guided nuclease, a guide RNA or a polynucleotide encoding a guide RNA, and optionally a donor template polynucleotide or a polynucleotide encoding a donor template polynucleotide.

63. The method of embodiment 62, wherein the RNA-guided nuclease and guide RNA are introduced as a ribonucleoprotein (RNP) complex.

64. The method of embodiment 59, wherein the genome editing molecules comprise a transcription activator-like nuclease (TALEN) protein or a polynucleotide encoding a TALEN protein and optionally a donor template polynucleotide or a polynucleotide encoding a donor template polynucleotide.

65. The method of embodiment 59, wherein the genome editing molecules comprise a zinc finger nuclease (ZnfN) protein or a polynucleotide encoding a ZnfN protein and optionally a donor template polynucleotide or a polynucleotide encoding a donor template polynucleotide.

66. The method of any one of embodiments 41 to 65, wherein the plant cell is a maize plant cell and the ODP2 polypeptide comprises an amino acid sequence having at least 95%, 96%, 97%, or 99% amino acid sequence identity across the entire length of SEQ ID NO:1.

67. The method of embodiment 66, wherein the endogenous ODP2 polypeptide is encoded by the endogenous maize ODP2 gene located on maize chromosome 3 and/or that is encoded by an endogenous polynucleotide that is operably linked to an endogenous maize ODP2 promoter of SEQ ID NO:3, SEQ ID NO:71, or an allelic variant thereof.

68. The method of any one of embodiments 41 to 67, wherein the plant cell is a maize plant cell and the endogenous WUS2 polypeptide comprises an amino acid sequence having at least 95%, 96%, 97%, or 99% amino acid sequence identity across the entire length of SEQ ID NO:2.

69. The method of embodiment 68, wherein the endogenous WUS2 polypeptide is encoded by the endogenous maize WUS2 gene located on maize chromosome 10 and/or that is encoded by an endogenous polynucleotide that is operably linked to an endogenous maize WUS2 promoter of SEQ ID NO:4 or an allelic variant thereof.

70. The method of any one of embodiments 41 to 69, wherein the exogenous gene transcription agent is introduced as: (i) an exogenous protein or exogenous polynucleotide encoding the protein; or (ii) as an exogenous protein or exogenous polynucleotide encoding the protein and an exogenous guide RNA.

71. The method of embodiment 70, wherein the exogenous protein of either (i) or (ii) is introduced into the cell in the absence of an exogenous polynucleotide that encodes the protein.

72. The method of embodiment 71, wherein the exogenous protein of either (i) or (ii) is introduced into the cell by an exogenous polynucleotide comprising a promoter that is operably linked to a polynucleotide that encodes the protein or by an exogenous RNA molecule that encodes the protein.

73. The method of embodiment 72, wherein the exogenous RNA molecule that encodes the protein comprises an mRNA or an RNA with an internal ribosome entry site (IRES).

74. The method of embodiment 72, wherein the exogenous polynucleotide or exogenous RNA are operably linked to a polynucleotide comprising a viral vector or T-DNA and wherein the polynucleotide comprising a viral vector or T-DNA is introduced into the cell.

75. The method of embodiment 70, wherein the exogenous protein, exogenous polynucleotide, and/or exogenous guide RNA are introduced into the cell by particle bombardment of the cell.

76. The method of any one of embodiments 41 to 75, wherein the exogenous gene transcription agent comprises: (i) a domain or complex which binds to the promoter or 5' untranslated region (5' UTR) of the endogenous ODP2 gene or to the promoter or 5' UTR of the endogenous WUS2 gene; and (ii) a transcription activation domain, wherein the transcription activation domain is operably linked or operably associated with the domain or complex.

77. The method of embodiment 76, wherein the exogenous gene transcription agent further comprises an operably linked nuclear localization signal (NLS).

78. The method of embodiment 76, wherein the domain that binds the promoter or 5' UTR comprises an artificial zinc finger (AZF) DNA binding domain polypeptide or an artificial transcription activator-like effector (TALE) DNA binding polypeptide.

79. The method of embodiment 78, wherein the artificial zinc finger DNA binding domain that binds the ODP2 promoter comprises: (i) a polypeptide having at least 85%, 90%, 95%, 97%, 98%, or 99% sequence identity across the entire length of SEQ ID NO: 5 or 8; or (ii) a polypeptide having at one or more conservative and/or semi-conservative amino acid substitutions in SEQ ID NO: 5 or 8.

80. The method of embodiment 78, wherein the artificial zinc finger DNA binding domain that binds the WUS2 promoter comprises: (i) a polypeptide having at least 85%, 90%, 95%, 97%, 98%, or 99% sequence identity across the entire length of SEQ ID NO: 11 or 14; or comprises a polypeptide having at one or more conservative and/or semi-conservative amino acid substitutions in SEQ ID NO: 11 or 14.

81. The method of embodiment 78, wherein the artificial TALE DNA binding polypeptide that binds the ODP2 promoter comprises: (i) a polypeptide having at least 85%, 90%, 95%, 97%, 98%, or 99% sequence identity across the entire length of SEQ ID NO: 23, 25, 27, 81, 84, or 87; or (ii) a polypeptide having at one or more conservative and/or semi-conservative amino acid substitutions in SEQ ID NO: 23, 25, 27, 81, 84, or 87.

82. The method of embodiment 78, wherein the artificial TALE DNA binding domain that binds the WUS2 promoter comprises: (i) a polypeptide having at least 85%, 90%, 95%, 97%, 98%, or 99% sequence identity across the entire length of SEQ ID NO: 17, 19, 21, 72, 75, or 78; or (ii) a polypeptide having at one or more conservative and/or semi-conservative amino acid substitutions in SEQ ID NO: 17, 19, 21, 72, 75, or 78.

83. The method of embodiment 76, wherein the complex that binds the promoter or 5' UTR comprises: (i) an RNA guided DNA binding polypeptide that is nuclease activity deficient and a guide RNA comprising about an 18 or 19 to about a 21 or 22 nucleotide polynucleotide sequence with is complementary to a sequence immediately adjacent to a protospacer adjacent motif (PAM) in the promoter or 5' UTR; or (ii) a 20, 21, 22, 23, or 24 nucleotide polynucleotide sequence which is complementary to a sequence immediately adjacent to a protospacer adjacent motif (PAM) in the promoter or 5' UTR. 84. The method of embodiment 83, wherein the RNA guided DNA binding polypeptide comprises a dCAS9 polypeptide, comprises a polypeptide having at least 85%, 90%, 95%, 97%, 98%, or 99% sequence identity across the entire length of SEQ ID NO: 29, or comprises a polypeptide having at one or more conservative and/or semi-conservative amino acid substitutions in SEQ ID NO: 29.

85. The method of embodiment 83, wherein the RNA guided DNA binding polypeptide comprises:
(i) a dCpf1 polypeptide;
(ii) a polypeptide having one or more conservative and/or semi-conservative amino acid substitutions in SEQ ID NO: 44 or at least 85%, 90%, 95%, 97%, 98%, or 99% sequence identity across the entire length of SEQ ID NO: 44 and a D917A, E1006A, E1028A, D1255A, and/or N1257A amino acid substitution;
(iii) a polypeptide having one or more conservative and/or semi-conservative amino acid substitutions in SEQ ID NO: 45 or at least 85%, 90%, 95%, 97%, 98%, or 99% sequence identity across the entire length of SEQ ID NO: 45 and a D832A, E925A, and/or D1148A amino acid substitution;
(iv) a polypeptide having one or more conservative and/or semi-conservative amino acid substitutions in SEQ ID NO: 46 or at least 85%, 90%, 95%, 97%, 98%, or 99% sequence identity across the entire length of SEQ ID NO: 46 and a D917A, E1006A, E1028A, D1255A, and/or N1257A amino acid substitution; or
(v) a polypeptide having one or more conservative and/or semi-conservative amino acid substitutions in SEQ ID NO: 47 or at least 85%, 90%, 95%, 97%, 98%, or 99% sequence identity across the entire length of SEQ ID NO: 47 and a D901A and/or E1228A amino acid substitution.

86. The method of embodiment 83, wherein the guide RNA comprises a sequence that is complementary to either strand of an ODP2 promoter comprising SEQ ID NO: 3 or SEQ ID NO: 71 or to either strand of an WUS2 promoter comprising SEQ ID NO: 4, wherein the complementary sequence is immediately adjacent to a protospacer adjacent motif (PAM) in SEQ ID NO: 3, 71, or 4.

87. The method of embodiment 86, wherein the guide RNA comprises an RNA encoded by SEQ ID NO: 31, 32, 33, 34, or 35 that is complementary to a sequence in the endogenous maize ODP2 promoter.

88. The method of embodiment 86, wherein the plant cell is a maize plant cell and the guide RNA comprises an RNA encoded by SEQ ID NO: 36, 37, 38, 39, or 40 that is complementary to a sequence in the endogenous maize WUS2 promoter.

89. The method of any one of embodiments 41 to 88, wherein at least two exogenous gene transcription agents that stimulate transcription of the endogenous ODP2 gene and/or at least two exogenous gene transcription agents that stimulate transcription of the endogenous WUS2 gene are introduced into a plant cell at step (i).

90. The method of embodiment 89, wherein the exogenous gene transcription agents comprise a transcriptional activation domain that is operably linked to or operably associated with: (i) an artificial zinc finger (AZF) DNA binding domain polypeptide; (ii) an artificial TALE DNA binding polypeptide; (iii) an RNA guided DNA binding polypeptide that is nuclease activity deficient and a guide RNA, or any combination thereof.

91. The method of embodiment 89, wherein the plant cell is a maize plant cell and the exogenous gene transcription agents that stimulate transcription of the endogenous WUS2 gene comprise a combination of at least two artificial TALE transcription factors comprising a transcriptional activation domain and an artificial TALE DNA binding polypeptide of SEQ ID NO:17, SEQ ID NO:19, SEQ ID NO:21, SEQ ID NO:72, SEQ ID NO:75, or SEQ ID NO:78.

92. The method of embodiment 89, wherein the plant cell is a maize plant cell and the exogenous gene transcription agents that stimulate transcription of the endogenous ODP2 gene comprise a combination of at least two distinct artificial TALE transcription factors that each comprise a transcriptional activation domain that is operably linked to or operably associated with an artificial TALE DNA sequence recognition domain polypeptide of SEQ ID NO:23, SEQ ID NO:25, SEQ ID NO:27, SEQ ID NO:81, SEQ ID NO:84, or SEQ ID NO:87.

93. The plant cell of any one of embodiments 1, 5, 7, 8, 9, 15-20, or 21, wherein the plant cell is a maize plant cell comprising at least one exogenous gene transcription agent that stimulates transcription of the endogenous WUS2 gene, wherein expression of the endogenous WUS2 polypeptide is increased in comparison to the expression of the endogenous WUS2 polypeptide in a control maize plant cell, wherein the endogenous WUS2 polypeptide is encoded by an endogenous polynucleotide that is operably linked to an endogenous maize WUS2 promoter of SEQ ID NO:4 or an allelic variant thereof, wherein the exogenous gene transcription agent(s) bind to DNA sequences in the endogenous maize WUS2 promoter corresponding to residues 100 to 225 of SEQ ID NO:4, and wherein the maize plant cell can form a regenerable maize plant structure.

94. The maize plant cell of embodiment 93, wherein the exogenous gene transcription agent(s) bind to DNA sequences in the endogenous maize WUS2 promoter corresponding to residues 130 to 210 of SEQ ID NO:4

95. The maize plant cell of embodiment 93, wherein an exogenous polynucleotide encoding a WUS2 polypeptide is absent before and/or during the increase in expression of the endogenous WUS2 polypeptide.

96. The maize plant cell of embodiment 93, wherein the increase in expression of the endogenous WUS2 polypeptide is sufficient to increase proliferation, somatic embryogenesis, and/or regeneration capacity of the maize plant cell in comparison to the control plant cell.

97. The maize plant cell of embodiment 93, wherein the increase in expression of the endogenous WUS2 polypeptide is sufficient to increase transformation efficiency and/or endogenous gene editing efficiency of the plant cell in comparison to the control plant cell.

98. The maize plant cell of embodiment 93, wherein said cell is located within or obtained from a cultured plant tissue explant, an immature embryo, a mature embryo, a leaf, and/or callus or optionally wherein the plant cell is located with or derived from the L1 or L2 layer of the immature or mature embryo.

99. The maize plant cell of embodiment 93, wherein the endogenous WUS2 polypeptide comprises an amino acid sequence having at least 95%, 96%, 97%, or 99% amino acid sequence identity across the entire length of SEQ ID NO:2.

100. The maize plant cell of embodiment 93, wherein the exogenous gene transcription agent comprises: (i) a DNA binding domain which binds to the endogenous WUS2 gene; (ii) a transcription activation domain, wherein the transcription activation domain is operably linked or operably associated with the DNA binding domain; and optionally (iii) an operably linked nuclear localization signal (NLS).

101. The maize plant cell of embodiment 100, wherein the DNA binding domain that binds the WUS2 promoter comprises an artificial zinc finger (AZF) DNA binding domain polypeptide.

102. The maize plant cell of embodiment 101, at least one AZF DNA binding domain polypeptide binds to any one of SEQ ID NO:101 or 102.

103. The maize plant cell of embodiment 101, wherein at least two exogenous gene transcription agents comprising an AZF DNA binding domain polypeptide are provided and wherein one of the AZF DNA binding domain polypeptides binds to a DNA sequence comprising SEQ ID NO:101 and one of the AZF DNA binding domain polypeptides binds to a DNA sequence comprising SEQ ID NO:102.

104. The maize plant cell of embodiment 102, wherein the AZF DNA binding domain polypeptide comprises a polypeptide having at least 95%, 98%, 99%, or 100% sequence identity to SEQ ID NO:105 or SEQ ID NO:106.

105. The maize plant cell of embodiment 101, wherein at least two exogenous gene transcription agents comprising an AZF DNA binding domain polypeptide are provided and wherein one of the AZF DNA binding domain polypeptides comprises a polypeptide having at least 95%, 98%, 99%, or 100% sequence identity to SEQ ID NO:105 and one of the AZF DNA binding domain polypeptides comprises a polypeptide having at least 95%, 98%, 99%, or 100% sequence identity to SEQ ID NO:106.

106. The maize plant cell of embodiment 101, wherein the exogenous gene transcription agent comprises a polypeptide having at least 90%, 95%, 98%, 99%, or 100% sequence identity to SEQ ID NO: 93 or 95.

107. The maize plant cell of embodiment 101, wherein at least two exogenous gene transcription agents are provided and wherein one of the exogenous gene transcription agents comprises a polypeptide having at least 95%, 98%, 99%, or 100% sequence identity to SEQ ID NO:93 and one of the exogenous gene transcription agents comprises a polypeptide having at least 95%, 98%, 99%, or 100% sequence identity to SEQ ID NO:95.

108. The method of any one of embodiments 41, 43-60, or 61 for producing a regenerable plant structure, wherein the regenerable plant structure is a regenerable maize plant structure, comprising:
(i) introducing into a maize plant cell at least one exogenous gene transcription agent which transiently increases expression of an endogenous WUS2 polypeptide, wherein the expression is increased in comparison to the expression of the endogenous WUS2 polypeptide in a control maize plant cell, wherein the endogenous WUS2 polypeptide is encoded by an endogenous polynucleotide that is operably linked to an endogenous maize WUS2 promoter of SEQ ID NO:4 or an allelic variant thereof, and wherein the exogenous gene transcription agent(s) bind to DNA sequences in the endogenous maize WUS2 promoter corresponding to residues 100 to 225 of SEQ ID NO:4; and,
(ii) culturing the maize plant cell to produce a regenerable maize plant structure.

109. The method of embodiment 108, wherein the exogenous gene transcription agent comprises: (i) an artificial zinc finger (AZF) DNA binding domain which binds to of the endogenous WUS2 gene; (ii) a transcription activation domain, wherein the transcription activation domain is operably linked or operably associated with the domain or complex; and optionally (iii) an operably linked nuclear localization signal (NLS).

110. The method of embodiment 109, wherein at least one AZF DNA binding domain polypeptide binds to any one of SEQ ID NO:101 or 102 or wherein one AZF DNA binding domain polypeptides binds to a DNA molecule comprising SEQ ID NO:101 and one of the AZF DNA binding domain polypeptides binds to a DNA molecule comprising SEQ ID NO:102.

111. The method of embodiment 109, wherein the AZF DNA binding domain polypeptide comprises a polypeptide having at least 95%, 98%, 99%, or 100% sequence identity to SEQ ID NO:105 or SEQ ID NO:106.

112. The method of embodiment 109, at least two exogenous gene transcription agents comprising an AZF DNA binding domain polypeptide are provided and wherein one of the AZF DNA binding domain polypeptides comprises a polypeptide having at least 95%, 98%, 99%, or 100% sequence identity to SEQ ID NO:105 and one of the AZF DNA binding domain polypeptides comprises a polypeptide having at least 95%, 98%, 99%, or 100% sequence identity to SEQ ID NO:106.

113. The method of embodiment 109, wherein the exogenous gene transcription agent comprises a polypeptide having at least 90%, 95%, 98%, 99%, or 100% sequence identity to SEQ ID NO: 93 or 95.

114. The method of embodiment 109, wherein at least two exogenous gene transcription agents are provided and wherein one of the exogenous gene transcription agents comprises a polypeptide having at least 95%, 98%, 99%, or 100% sequence identity to SEQ ID NO:93 and one of the exogenous gene transcription agents comprises a polypeptide having at least 95%, 98%, 99%, or 100% sequence identity to SEQ ID NO:95.

115. The method of embodiment 108, wherein the exogenous gene transcription agent(s) bind to DNA sequences in the endogenous maize WUS2 promoter corresponding to residues 130 to 210 of SEQ ID NO:4.

EXAMPLES

Example 1. Artificial Zinc Finger Transcription Factors (ATF) for Increasing Expression of the Endogenous Maize ODP2 and WUS2 Genes This example provides artificial Zinc Finger Transcription Factors (ATF) for increasing expression of the endogenous maize ODP2 and WUS2 genes.

Two high quality target binding sites for an ATF (SEQ ID NO: 6 and 9) were identified in the maize ODP2 promoter region of approximately 500 bp (SEQ ID NO:3) which is proximal to the ODP2 gene transcription initiation site (e.g., mRNA cap site). A ZNF DNA binding domain (SEQ ID NO:5) and an ATF comprising that DNA binding domain (SEQ ID NO:7) were designed to bind the ZmODP2 promoter at SEQ ID NO:6. A ZNF DNA binding domain (SEQ ID NO:8) and an ATF comprising that DNA binding domain (SEQ ID NO:10) was designed to bind the ZmODP2 promoter at SEQ ID NO:9. Each of the ATFs comprise the maize opaque-2 nuclear localization signal, the artificial zinc finger DNA binding domain, and 60 amino acids from the maize C1 transcriptional activation domain.

Two high quality target binding sites for an ATF (SEQ ID NO:12 and 15) were identified in the maize WUS2 promoter region of approximately 500 bp (SEQ ID NO:4) which is proximal to the WUS2 gene transcription initiation site (e.g., mRNA cap site). A ZNF DNA binding domain (SEQ ID NO:11) and an ATF comprising that DNA binding domain (SEQ ID NO:13) was designed to bind the ZmWUS2 promoter at SEQ ID NO:12. A ZNF DNA binding domain (SEQ ID NO:14) and an ATF comprising that DNA binding domain (SEQ ID NO:16) was designed to bind the ZmWUS2 promoter at SEQ ID NO:15. Each of the ATFs comprise the maize opaque-2 nuclear localization signal, the artificial zinc finger DNA binding domain, and 60 amino acids from the maize C1 transcriptional activation domain.

Example 2. Artificial Transcription Activator-Like Effectors (aTALEs) for Increasing Expression of the Endogenous Maize ODP2 and WUS2 Genes This example provides artificial Transcription activator-like effectors (aTALEs) for increasing expression of the endogenous maize ODP2 and WUS2 genes.

Three high quality target binding sites (SEQ ID NO: 65, 66, and 67) for three aTALEs that are spaced at intervals of about 100 nucleotides were identified in the maize WUS2 promoter region of approximately 500 bp (SEQ ID NO:4) which is proximal to the WUS2 gene transcription initiation site. A TALE DNA binding protein (SEQ ID NO:17) and an ATF comprising that DNA binding protein (SEQ ID NO:18) was designed to bind the ZmWUS2 promoter at SEQ ID NO:65. A TALE DNA binding protein (SEQ ID NO:19) and an ATF comprising that DNA binding protein (SEQ ID NO:20) was designed to bind the ZmWUS2 promoter at SEQ ID NO:66. A TALE DNA binding protein (SEQ ID NO:21) and an ATF comprising that DNA binding protein (SEQ ID NO:22) was designed to bind the ZmWUS2 promoter at SEQ ID NO:67. Each of the ATFs comprise the DNA binding protein, SV40 NLS, a 3×FLAG sequence, a VP64 transcription activation domain, and a 6×His (Histidine) domain. The aTALE ATFs targeting the WUS2 promoter can function independently or in tandem.

Three high quality target binding sites (SEQ ID NO: 74, 77, and 80) for three aTALEs were identified in the maize WUS2 promoter region of approximately 500 bp (SEQ ID NO:4) which is proximal to the WUS2 gene transcription initiation site. A TALE DNA binding protein (SEQ ID NO: 72) and an ATF comprising that DNA binding protein (SEQ ID NO: 73) was designed to bind the ZmWUS2 promoter at SEQ ID NO: 74. A TALE DNA binding protein (SEQ ID NO: 75) and an ATF comprising that DNA binding protein (SEQ ID NO: 76) was designed to bind the ZmWUS2 promoter at SEQ ID NO: 77. A TALE DNA binding protein (SEQ ID NO:78) and an ATF comprising that DNA binding protein (SEQ ID NO:79) was designed to bind the ZmWUS2 promoter at SEQ ID NO: 80. Each of the ATFs comprise a 6×His (Histidine) domain, the DNA binding protein, SV40 NLS, and a VP64 transcription activation domain. The aTALE ATFs targeting the WUS2 promoter can function independently or in tandem.

Three high quality target binding sites (SEQ ID NO: 68, 69, and 70) for three aTALEs that are spaced at intervals of about 100 nucleotides were identified in the maize ODP2 promoter region of approximately 500 bp (SEQ ID NO: 3) which is proximal to the ODP2 gene transcription initiation codon. A TALE DNA binding protein (SEQ ID NO:23) and an ATF comprising that DNA binding protein (SEQ ID NO:24) was designed to bind the ZmODP2 promoter at SEQ ID NO:68. A TALE DNA binding protein (SEQ ID NO:25) and an ATF comprising that DNA binding protein (SEQ ID NO:26) was designed to bind the ZmODP2 promoter at SEQ ID NO:69. A TALE DNA binding protein (SEQ ID NO:27) and an ATF comprising that DNA binding protein (SEQ ID NO:28) was designed to bind the ZmODP2 promoter at SEQ ID NO:70. Each of the ATFs comprise the DNA binding domain, SV40 NLS, a 3×FLAG sequence, a VP64 transcription activation domain, and a 6×His (Histidine) domain. The three aTALE ATFs targeting the ODP2 promoter can function independently or in tandem.

Three high quality target binding sites (SEQ ID NO: 83, 86, and 89) for three aTALEs were identified in the maize ODP2 promoter region of approximately 500 bp (SEQ ID NO: 3) which is proximal to the ODP2 gene transcription initiation codon. A TALE DNA binding protein (SEQ ID NO: 81) and an ATF comprising that DNA binding protein (SEQ ID NO:82) was designed to bind the ZmODP2 promoter at SEQ ID NO: 83. A TALE DNA binding protein (SEQ ID NO: 84) and an ATF comprising that DNA binding protein (SEQ ID NO: 85) was designed to bind the ZmODP2 promoter at SEQ ID NO: 86. A TALE DNA binding protein (SEQ ID NO: 87) and an ATF comprising that DNA binding protein (SEQ ID NO: 88) was designed to bind the ZmODP2 promoter at SEQ ID NO: 89. Each of the ATFs comprise a 6×His (Histidine) domain, the DNA binding domain, SV40 NLS, and a VP64 transcription activation domain. The three aTALE ATFs targeting the ODP2 promoter can function independently or in tandem.

Example 3. Construction of dCas9 Transcription Activators and Guide RNAs Targeting ZmWUS2 and ZmODP2

This example describes an ATF comprising a nuclease deficient Cas9 DNA binding domain, guide RNAs, and vectors useful for the expression of the guide RNAs. Such ATFs and guide RNAs are designed to increase expression of the endogenous maize ODP2 and WUS2 genes.

Five crRNA (SEQ ID NO:31, 32, 33, 34, and 35) were constructed which are complementary to sequences immediately adjacent to PAM sequences in the −250 to −100 region of the maize ODP2 promoter (SEQ ID NO:3) relative to the transcription start site. Five single guide RNAs (sgRNA) incorporating the crRNA can be obtained with the sgRNA expression cassette of SEQ ID NO:41. The aforementioned sgRNAs can be expressed by substituting the aforementioned crRNA sequences for the 20 "N" (i.e., a,c,g, or t) residues in the vector of SEQ ID NO: 41 which provides for operable linkage of the crRNA sequences to a U6 promoter and sgRNA encoding sequences and introducing the vector with the substitution into a suitable host cell (e.g., a meristematic cell, a somatic cell or a reproductive cell). A dCas9 nuclease deficient RNA guided DNA binding domain (SEQ ID NO:29) is obtained and a polypeptide comprising that DNA binding domain, an SV40 NLS, a 3×FLAG sequence, a VP64 transcription activation domain, and a 6×His (Histidine) domain (SEQ ID NO:30) is designed to bind the ZmODP2 promoter when complexed with the aforementioned sgRNAs.

Five crRNA (SEQ ID NO: 36, 37, 38, 39 and 40) are constructed which are complementary to sequences immediately adjacent to PAM sequences in the −250 to −100 region of the maize WUS2 promoter (SEQ ID NO:4) relative to the transcription start site. Five single guide RNAs (sgRNA) incorporating the crRNA can be obtained with the sgRNA expression cassette of SEQ ID NO:41. The aforementioned sgRNAs can be expressed by substituting the aforementioned crRNA sequences for the 20 "N" (i.e., a,c,g, or t) residues in the vector of SEQ ID NO: 41 which provides for operable linkage of the crRNA sequences to a U6 promoter and sgRNA encoding sequences and introducing the vector with the substitution into a suitable host cell (e.g., a meristematic cell, a somatic cell or a reproductive cell). A dCas9 nuclease deficient RNA guided DNA binding domain (SEQ ID NO:29) is obtained and a polypeptide comprising that DNA binding domain, an SV40 NLS, a 3×FLAG sequence, a VP64 transcription activation domain, and a 6×His (Histidine) domain (SEQ ID NO:30) was designed to bind the ZmWUS2 promoter when complexed with the aforementioned sgRNAs.

In certain cases, the dCas9 polypeptide is expressed in *E. coli*, purified, and complexed in vitro with the corresponding sgRNA for delivery to a plant cell. Alternatively, the Cas9 protein and sgRNAs can be expressed from a plasmid that is delivered to the target plant cells or plant tissues.

Example 4. Use of ATFs to Obtain Regenerable Plant Structures

Developing maize embryos 8-14 days after pollination (DAP) from a variety or of a genotype that typically does not respond to biolistic or *agrobacterium*-mediated transformation are excised and placed on sterile plant growth media, scutellar side up. A plasmid encoding transcription activation ATFs that target the maize ODP2 and WUS2 promoter proximal regions is delivered using biolistics. The plasmid may also encode a marker gene such as GFP (or variants thereof) or mCherry fluorescent proteins to identify cells containing the plasmid.

The expected positive result is formation of regenerable plant structures comprising callus or pro-embryogenic masses from tissue that received the plasmid containing the transcription activation ATF genes after one week and no such formations on control tissue that received plasmid lacking the transcription activation ATF genes.

Example 5. Isolation of Corn Transformation Target Tissue and Biolistic Delivery of Transcription Activators in Target Tissue Ears representing the target plant genotype are harvested approximately 8-14 DAP. The tips of developing kernels are removed with a scalpel. A fine spatula is used to gently remove the embryo from the kernel, which is then placed on callus induction media (e.g. 4 g $L^{-1}$ N6 salts plus N6 vitamins, 2 mg $L^{-1}$ 2,4-D, 2.8 g $L^{-1}$ L-proline, 30 g $L^{-1}$ sucrose, 100 mg $L^{-1}$ casein hydrolysate, 100 mg $L^{-1}$ myo-inositol, 25 µM silver nitrate, 2.5 g $L^{-1}$ gelrite, pH 5.8). Embryo size is about 1.5-2.5 mm. After approximately 200 embryos are harvested, they are arranged onto four plates containing about 50 embryos each. Ideally, the scutellar surface is facing up.

The ATFs targeting ZmODP2 and ZmWUS2 (e.g., ZfATF including SEQ ID NO:7, 10, 13, and/or 16; aTALE including SEQ ID NO:18, 20, 22, 24, 26, and/or 28; a dCas-NLS-TAD and guide RNAs including dCas9-NLS-TAD (SEQ ID NO: 30) and sgRNAs comprising crRNAs of SEQ ID NO:31, 32, 33, 34, 35, 36, 37, 38, 39, and/or 40 are encoded on plasmid DNA using suitable gene cassettes to drive their expression. The plasmid DNA is a standard high-copy *E. coli* vector that may or may not contain a selectable marker gene. The plasmid DNA is prepared using standard molecular biology procedures, examined for integrity and quantified. The plasmid DNA is complexed with 0.6 µm gold particles as described, for example in (Hamada et al. 2018; K. Wang and Frame 2009). The embryos are transferred to osmotic media (4 g $L^{-1}$N6 salts plus N6 vitamins, 2 mg $L^{-1}$ 2,4-D, 0.7 g L-proline, 30 g $L^{-1}$ sucrose, 100 mg $L^{-1}$ casein hydrolysate, 100 mg $L^{-1}$ myo-inositol, 36.4 g $L^{-1}$ sorbitol, 36.4 g mannitol, 25 µM silver nitrate, 2.5 g gelrite, pH 5.8) four hours prior to bombardment. The gold particles are loaded into a BioRad PDS-1000 helium gene gun and delivered to target plant tissue following manufacturer's instructions or variations developed by other researchers. Bombarded embryos are incubated overnight in the dark at 28° C.

The following morning embryos are moved onto callus induction media as above, but with 0.8 mg L$^{-1}$ 2,4-D and cultured in dark at 28° C. for about 5-7 days. The tissue is examined for the formation of regenerable plant structures comprising pro-embryogenic masses starting at 5 days after bombardment. ATF efficacy is scored on the basis of pro-embryogenic mass formation compared to control tissue which received plasmid DNA lacking the ATF genes.

Example 6. Regeneration of Plants from Transformed Target Tissue

After 6-7 days on callus induction medium, the embryos are moved onto shoot formation medium (e.g. MS, 60 g L$^{-1}$ sucrose, 0.5 mg L$^{-1}$ zeatin, 0.1 mg L$^{-1}$ thidiazuron, 1 mg/L BAP, 0.1 mg L$^{-1}$ imazapyr, pH 5.8). After 2 weeks on shoot formation medium, embryos are moved to rooting medium (e.g. MS, 40 g L$^{-1}$ sucrose, 0.1 mg L$^{-1}$ imazapyr, pH 5.8) and placed under GE Ecolux® (General Electric; Boston, Mass.) fluorescent lights G (60 μmol m$^{-2}$ s$^{-1}$) with a 16-h photoperiod at 26° C. Once adequate shoots with roots form, plantlets are transferred to soil and grown to maturity in an appropriate growth environment like a greenhouse or growth chamber.

Example 7. Selection of Promoter Sequences Common Across Corn Lines for Targeting by ATFs The promoter regions of ODP2 and WUS are sequenced and analyzed for the presence of conserved regions. These consistent sequences are desirable because the same ATF reagents can be used in diverse corn germplasm to obtain regenerable plant structures. ATF reagents can be designed to bind and activate a conserved ODP2 promoter sequence of 312 bp (SEQ ID NO:71), that is 99% identical among B73, B104, PH207, Mo17, 2FACC, LH214, LH123HT and ICI441.

Example 8. Expression of Endogenous WUS2 in Corn Protoplasts Transfected with ATFs Corn protoplasts were transfected with vectors expressing the ATFs ZnFng-WUS1, 2, 3, and/or −4 (SEQ ID NOs: 93, 95, 97, and/or 99, respectively) or expressing GFP as a control. Endogenous RNA was extracted, and the level of WUS2 mRNA expression is quantified by RT-PCR relative to expression of the Act1 gene.

GFP, ZnFng-WUS3, or ZnFng-WUS4 expression did not significantly affect endogenous WUS2 transcription over background levels in mock transfected protoplasts. In contrast, ZnFng-WUS1 and ZnFng-WUS2 increased WUS2 transcription over the background levels in mock transfected protoplasts. ZnFng-WUS1 promotes WUS2 expression increase to about 10% relative to actin and normalized by transfection efficiency (in the 8-12% range in different experiments). ZnFng-WUS2 promoted a WUS2 expression increase of about 50% relative to actin and normalized by transfection efficiency (in the 15 to 60% range in different experiments). Mock transfected protoplasts had a nearly zero WUS2 expression level relative to actin.

Example 9. Biological Sequences

This example provides non-limiting embodiments of proteins, promoters, and coding sequences referred to herein. Biological sequences and their SEQ ID NOs are set forth in Table 1.

TABLE 1

Biological Sequences

| SEQ ID NO: | DESCRIPTION | SEQUENCE | COMMENTS |
|---|---|---|---|
| 1 | Endogenous Maize ODP2 polypeptide | MATVNNWLAFSLSPQELPPSQTTDSTLI SAATADHVSGDVCFNIPQDWSMRGSEL SALVAEPKLEDFLGGISFSEQHHKSNCN LIPSTSSTVCYASSAASTGYHHQLYQPT SSALHFADSVMVASSAGVHDGGSMLS AAAANGVAGAASANGGGIGLSMIKNW LRSQPAPMQPRAAAAEGAQGLSLSMN MAGTTQGAAGMPLLAGERARAPESVS TSAQGGAVVVTAPKEDSGGSGVAGAL VAVSTDTGGSGGASADNTARKTVDTFG QRTSIYRGVTRHRWTGRYEAHLWDNS CRREGQTRKGRQVYLGGYDKEEKAAR AYDLAALKYWGATTTTNFPVSNYEKEL EDMKHMTRQEFVASLRRKSSGFSRGAS IYRGVTRHHQHGRWQARIGRVAGNKD LYLGTFSTQEEAAEAYDIAAIKFRGLNA VTNFDMSRYDVKSILDSSALPIGSAAKR LKEAEAAASAQHHHAGVVSYDVGRIAS QLGDGGALAAAYGAHYHGAAWPTIAF QPGAATTGLYHPYAQQPMRGGGWCKQ EQDHAVIAAAHSLQDLHHLNLGAAGA HDFFSAGQQAAAAAMHGLASIDSASL EHSTGSNSVVYNGGVGDSNGASAVGS GGGYMMPMSAAGATTTSAMVSHEQM HARAYDEAKQAAQMGYESYLVNAEN NGGGRMSAWGTVVSAAAAAAASSND NIAADVGHGGAQLFSVWNDT | |
| 2 | Endogenous Maize WUS2 polypeptide | MAANAGGGGAGGGSGSGSVAAPAVCR PSGSRWTPTPEQIRMLKELYYGCGIRSP SSEQIQRITAMLRQHGKIEGKNVFYWFQ NHKARERQKRRLTSLDVNVPAAGAAD | |

TABLE 1-continued

Biological Sequences

| SEQ ID NO: | DESCRIPTION | SEQUENCE | COMMENTS |
|---|---|---|---|
| | | ATTSQLGVLSLSSPPSGAAPPSPTLGFYA AGNGGGSAGLLDTSSDWGSSGAAMAT ETCFLQDYMGVTDTGSSSQWPCFSSSD TIMAAAAAAARVATTRAPETLPLFPTC GDDDDDDSQPPPRPRHAVPVPAGETIR GGGGSSSSYLPFWGAGAASTTAGATSS VAIQQQHQLQEQYSFYSNSTQLAGTGS QDVSASAAALELSLSSWCSPYPAAGSM | |
| 3 | Endogenous Maize ODP2 promoter and 5'-UTR | AAATGGCCGTGACAACGTATACTATT ATCGAGTAAAAGGTCGCCACTTTAGT AGTACATGTACATGCATGCGCAGATA CATCATCAGGTACTCATATATGGGCA CACATATAGACATGTTTTGAGGAAAA TGAGACAAAGTATAGTGGAGACTTCC CTAGAAAGCAGAAGAAAAAGAAGTG GTTTATGTTCCGTTAAATCATACTACA ACTTTTTTTATTATACTCTCCATTTTG TCATCATTAGGTACTCATATATGGGCA CACATATAGTACTGCCAATTTTTCTTG CTAAAAAAAGTTCCACTATATATATG TATGTATGCACAAATAAACTAATTTTC TTAGAAAAGAAAACCGGTGTAATACA TACTAAGGGCTAGTTTGGGAACCCTG GTTTTCTAAGGAATTTTATTTTTCCAA AAAAAATAGTTTATTTTTCCTTCGGAA ATTAGGAATCTCT<u>TATA</u>AAATTCGAGT TCCCAAACTATTC*TAATATATATatcat actctccatcagtctatatatagattacatatagtaagtatag agtatctcgctatcacatagtgccactaatcttctggagtgta ccagttgtataaatatctatcagtatcagcactactgtttgctg aatacccaaaatctctgcttgacttctcttccctaaccttttgc actgtccaaaatggcttcctgatccctcacttcctcgaatcat tctaagaagaaactcaagccgctaccattaggggcagatta attgctgcactttcagataatctacc* | 500 bp promoter sequence; TATA box underlined; 5'-UTR in lower case italics |
| 4 | Endogenous Maize WUS2 promoter and 5'-UTR | CATTGAACAATGGAGCTGCAAGAGCAATGATG CACTAGCTAGTGTAATGCAGTGCATGCATGGT AGATTGGTAGCTAGCCTTTGCAGTTTGCACCA GGCACCAGCAGCAGCTAGAAGACGACAGACG ACAGGGGCTT<u>GACTAGGTTGCGGAAGGG</u>CAG TTGCCAGTTGCCACAAGGGGAGCCTG<u>GACCTC TGCATCCTCCTC</u>ATGATAGCTCTGTCTCTCTCA CACACACACACAGTCACACAGAGACACGCAAA TGACTTCTGTCTCTAACTCTTCCAAATTTCGAA GCGGCCAATGCAAGAGCCAGCCCCCGGCCGT ATGTCAACTTCACTTGTCTCTCTCCAAAAGATA TCGTATCACCCATGGGCAATGGCCATGACCCC CCTCCCAGCCCCAACC<u>TATAT</u>CACCTAGCGCAG CTACGCTCTCTTCTCCCGCTCTCGCTCTCTGCTG GCTGCATGCTAGCTACCTTCTAGCTATCTAGCC TCTAGCTCCAATGCACTCCCTCCTTATAAACAA GGAACCCTCCTTCGGCTCTCTTGCCATAGACCG GACACCGGAGAGCTAGGTCACAGAAGCGCTC AGGAAGGCCGCTGCGCTGAGATAGAGGC | 609 bp WUS2 promoter and 5'UTR sequence: TATA box underlined; binding sites for ZnFng-WUS1 AZF DNA BINDING SITE (SEQ ID NO: 101) at nucleotides 138-155 and ZnFng-WUS2 AZF DNA BINDING SITE (Reverse complement of SEQ ID NO: 102) at nucleotides 185-202 to double underlined and in bold |
| 5 | Zinc Finger DNA binding domain targeting ZmODP2 gene sequence at position 73 | LEPGEKPYKCPECGKSFSQSSSLVRHQR TH<u>TGEKP</u>YKCPECGKSFSRADNLTEHQ RTH<u>TGEKP</u>YKCPECGKSFSTSGNLTEHQ RTH<u>TGEKP</u>YKCPECGKSFSTSGNLTEHQ RTH<u>TGEKP</u>YKCPECGKSFSQKSSLIAHQ RTH<u>TGEKP</u>YKCPECGKSFSRADNLTEH QRTHTGKKTS | TGEKP linkers separating zinc fingers are underlined |
| 6 | ZmODP2 gene sequence at position 73 | 5'-cagatacatcatcaggta-3' | |
| 7 | Complete Zf ATF targeting ZmODP2 at position 73 | <u>Mrkrkesnresarrsrrsryrkkv</u>LEPGEKPYKCPE CGKSFSQSSSLVRHQRTHTGEKPYKCPE CGKSFSRADNLTEHQRTHTGEKPYKCP | maize opaque-2 nuclear localization signal |

TABLE 1-continued

Biological Sequences

| SEQ ID NO: | DESCRIPTION | SEQUENCE | COMMENTS |
|---|---|---|---|
| | | ECGKSFSTSGNLTEHQRTHTGEKPYKCP ECGKSFSTSGNLTEHQRTHTGEKPYKCP ECGKSFSQKSSLIAHQRTHTGEKPYKCP ECGKSFSRADNLTEHQRTHTGKKTS<u>AG SSDDCSSAASVSLRVGSHDEPCFSGDGD GDWMDDVRALASFLESDEDWLRCQTA GQLA</u> | is lower case and underlined; maize C1 transcription activation domain double underlined |
| 8 | Zinc Finger DNA binding domain targeting ZmODP2 gene sequence at position 51 | LEPGEKPYKCPECGKSFSQSGDLRRHQ RTHTGEKPYKCPECGKSFSTSGNLTEHQ RTHTGEKPYKCPECGKSFSQSSSLVRHQ RTHTGEKPYKCPECGKSFSTSGNLTEHQ RTHTGEKPYKCPECGKSFSQSSSLVRHQ RTHTGEKPYKCPECGKSFSQSSSLVRHQ RTHTGKKTS | |
| 9 | ZmODP2 gene sequence at position 51 | 5'-gtagtacatgtacatgca-3' | |
| 10 | Complete Zf ATF targeting ZmODP2 at position 51 | <u>Mrkrkesnresarrsrrsryrkkv</u>LEPGEKPYKCPE CGKSFSQSGDLRRHQRTHTGEKPYKCP ECGKSFSTSGNLTEHQRTHTGEKPYKCP ECGKSFSQSSSLVRHQRTHTGEKPYKCP ECGKSFSTSGNLTEHQRTHTGEKPYKCP ECGKSFSQSSSLVRHQRTHTGEKPYKCP ECGKSFSQSSSLVRHQRTHTGKKTS<u>AGS SDDCSSAASVSLRVGSHDEPCFSGDGD GDWMDDVRALASFLESDEDWLRCQTA GQLA</u> | maize opaque-2 nuclear localization signal is lower case and underlined; maize C1 transcription activation domain double underlined |
| 11 | Zinc Finger DNA binding domain targeting ZmWUS2 gene sequence at position 83 | LEPGEKPYKCPECGKSFSQAGHLASHQ RTHTGEKPYKCPECGKSFSTSGNLTEHQ RTHTGEKPYKCPECGKSFSRSDKLTEHQ RTHTGEKPYKCPECGKSFSRNDALTEH QRTHTGEKPYKCPECGKSFSQSSNLVR HQRTHTGEKPYKCPECGKSFSTTGNLT VHQRTHTGKKTS | |
| 12 | ZmWUS2 gene sequence at position 83 | 5'-AATGAACTGCGGCATTGA-3' | |
| 13 | Complete Zf ATF targeting ZmWUS2 at position 83 | <u>Mrkrkesnresarrsrrsryrkkv</u>LEPGEKPYKCPE CGKSFSQAGHLASHQRTHTGEKPYKCP ECGKSFSTSGNLTEHQRTHTGEKPYKCP ECGKSFSRSDKLTEHQRTHTGEKPYKCP ECGKSFSRNDALTEHQRTHTGEKPYKC PECGKSFSQSSNLVRHQRTHTGEKPYK CPECGKSFSTTGNLTVHQRTHTGKKTS <u>AGSSDDCSSAASVSLRVGSHDEPCFSGD GDGDWMDDVRALASFLESDEDWLRCQ TAGQLA</u> | maize opaque-2 nuclear localization signal is lower case and underlined; maize C1 transcription activation domain double underlined |
| 14 | Zinc Finger DNA binding domain targeting ZmWUS2 gene sequence at position 92 | LEPGEKPYKCPECGKSFSRSDNLVRHQ RTHTGEKPYKCPECGKSFSRRDELNVH QRTHTGEKPYKCPECGKSFSSPADLTRH QRTHTGEKPYKCPECGKSFSQAGHLAS HQRTHTGEKPYKCPECGKSFSTSGNLTE HQRTHTGEKPYKCPECGKSFSRSDKLTE HQRTHTGKKTS | |
| 15 | ZmWUS2 gene sequence at position 92 | 5'-CGGCATTGAACAATGGAG-3' | |
| 16 | Complete Zf ATF targeting ZmWUS2 at position 92 | <u>Mrkrkesnresarrsrrsryrkkv</u>LEPGEKPYKCPE CGKSFSRSDNLVRHQRTHTGEKPYKCP ECGKSFSRRDELNVHQRTHTGEKPYKC PECGKSFSSPADLTRHQRTHTGEKPYKC PECGKSFSQAGHLASHQRTHTGEKPYK CPECGKSFSTSGNLTEHQRTHTGEKPYK CPECGKSFSRSDKLTEHQRTHTGKKTS<u>A GSSDDCSSAASVSLRVGSHDEPCFSGDG</u> | maize opaque-2 nuclear localization signal is lower case and underlined; maize C1 transcription activation domain double underlined |

TABLE 1-continued

Biological Sequences

| SEQ ID NO: | DESCRIPTION | SEQUENCE | COMMENTS |
|---|---|---|---|
| | | DGDWMDDVRALASFLESDEDWLRCQT AGQLA | |
| 17 | ZmWUS2-TALE-1 N-terminus, RVD, and C-terminal domain | mapkkkrkvdykdhdgdykdhdidykddddkgtvdlrt lgysqqqqekikpkyrstvaqhhealvghgfthahivalsq hpaalgtvavkyqdmiaalpeatheaivgvgkqwsgaral ealltvagelrgpplqldtgqllkiakrggvtaveavhawrna ltgaplnltpeqvvaiLTPEQVVAIAS<u>NH</u>GGKQ ALETVQRLLPVLCQAHGLTPEQVVAIAS <u>NH</u>GGKQALETVQRLLPVLCQAHGLTPE QVVAIAS<u>HD</u>GGKQALETVQRLLPVLCQ AHGLTPEQVVAIAS<u>HD</u>GGKQALETVQR LLPVLCQAHGLTPEQVVAIAS<u>HD</u>GGKQ ALETVQRLLPVLCQAHGLTPEQVVAIAS <u>NG</u>GGKQALETVQRLLPVLCQAHLTPEQ VVAIAS<u>HD</u>GGKQALETVQRLLPVLCQA HGLTPEQVVAIAS<u>NG</u>GGKQALETVQRL LPVLCQAHGLTPEQVVAIAS<u>NH</u>GGKQA LETVQRLLPVLCQAHGLTPEQVVAIAS<u>H</u> <u>D</u>GGKQALETVQRLLPVLCQAHGLTPEQ VVAIAS<u>NI</u>GGKQALETVQRLLPVLCQA HGLTPEQVVAIAS<u>NG</u>GGKQALETVQRL LPVLCQAHGLTPEQVVAIAS<u>HD</u>GGKQA LETVQRLLPVLCQAHGLTPEQVVAIAS<u>H</u> <u>D</u>GGKQALETVQRLLPVLCQAHGLTPEQ VVAIAS<u>NG</u>GGKQALETVQRLLPVLCQA HGLTPEQVVAIAS<u>HD</u>GGKQALETVQRL LPVLCQAHGLTPEQVVAIAS<u>HD</u>GGKQA LETVQRLLPVLCQAHGLTPEQVVAIAS<u>N</u> <u>G</u>GGKQALETVQRLLPVLCQAHGLTPEQ VVAIAS<u>HD</u>GGKQALETVQRLLPVLCQA HGLTPEQVVAIAS<u>NI</u>GGKQALETVQRLL PVLCQAHGLTPEQVVAIAS<u>NG</u>GGKQAL ETVQRLLPVLCQAHGLTPEQVVAIAS<u>N</u> <u>H</u>GGKQALETVQRLLPVLCQAHGLTPEQ VVAIAS<u>NI</u>GGKQALETVQRLLPVLCQA HGLTPEQVVAIAS<u>NG</u>GGKQALETVQRL LPVLCQAHGLTPEQVVAIAS<u>NI</u>GGKQAL ETVQRLLPVLCQAHGLTPEQVVAIAS<u>N</u> <u>H</u>GGKQALETVQRLLPVLCQAHGLTPEQ VVAIAS<u>HD</u>GGKQALETVQRLLPVLCQA HGLTPEQVVAIAS<u>NG</u>GG*sivaqlsrpdpalaalt ndhlvalaclggrpaldavkkglphapalikrtnrripertsh rva* | N-terminus in lower case; RVD domain in in uppercase with hypervariable diresidues double underlined; C-terminus in lowercase italics; Binds upstream of the ZmWUS2 transcription start site |
| 18 | ZmWUS2-TALE-1 Artificial Transcription Factor | mapkkkrkvdykdhdgdykdhdidykddddkgtvdlrt lgysqqqqekikpkvrstvaqhhealvghgfthahivalsq hpaalgtvavkyqdmiaalpeatheaivgvgkqwsgaral ealltvagelrgpplqldtgqllkiakrggvtaveavhawrna ltgaplnltpeqvvailtpeqvvaiasnhggkqaletvqrllp vlcqahgltpeqvvaiasnhggkqaletvqrllpvlcqahgl tpeqvvaiashdggkqaletvqrllpvlcqahgltpeqvvai ashdggkqaletvqrllpvlcqahgltpeqvvaiashdggk qaletvqrllpvlcqahgltpeqvvaiasngggkqaletvqrl lpvlcqahltpeqvvaiashdggkqaletvqrllpvlcqahg ltpeqvvaiasngggkqaletvqrllpvlcqahgltpeqvva iasnhggkqaletvqrllpvlcqahgltpeqvvaiashdggk qaletvqrllpvlcqahgltpeqvvaiasniggkqaletvqrll pvlcqahgltpeqvvaiasngggkqaletvqrllpvlcqahg ltpeqvvaiashdggkqaletvqrllpvlcqahgltpeqvva iashdggkqaletvqrllpvlcqahgltpeqvvaiasngggk qaletvqrllpvlcqahgltpeqvvaiashdggkqaletvqrl lpvlcqahgltpeqvvaiashdggkqaletvqrllpvlcqah gltpeqvvaiasngggkqaletvqrllpvlcqahgltpeqvv aiashdggkqaletvqrllpvlcqahgltpeqvvaiasnigg kqaletvqrllpvlcqahgltpeqvvaiasngggkqaletvq rllpvlcqahgltpeqvvaiasnhggkqaletvqrllpvlcqa hgltpeqvvaiasniggkqaletvqrllpvlcqahgltpeqv vaiasngggkqaletvqrllpvlcqahgltpeqvvaiasnig gkqaletvqrllpvlcqahgltpeqvvaiasnhggkqaletv qrllpvlcqahgltpeqvvaiashdggkqaletvqrllpvlcq ahgltpeqvvaiasngggsivaqlsrpdpalaaltndhlvala clggrpaldavkkglphapalikrtnrripertshrva<u>PKK</u> | ZmWUS2-TALE-1 N terminus, RVD domain, C-terminus in lower case; SV40 Nuclear Localization Sequence in uppercase, underlined; 3 x FLAG sequence lowercase, underlined; VP64 transcriptional activation domain is lowercase, double underlined, italics; 6 x His tag at C-terminus |

TABLE 1-continued

Biological Sequences

| SEQ ID NO: | DESCRIPTION | SEQUENCE | COMMENTS |
|---|---|---|---|
| | | KRKVSSdykdhdqdykdhdidykddddkAAGG<br>GGSGRAdalddfdldmlgsdalddfdldmlgsdalddf<br>dldmlgsdalddfdldmlHHHHHH | |
| 19 | ZmWUS2-TALE-2 N-terminus, RVD, and C-terminal domain | mapkkkrkvdykdhdgdykdhdidykddddkgtvdlrt<br>lgysqqqekikpkvrstvaqhhealvghgfthahivalsq<br>hpaalgtvavkyqdmiaalpeatheaivgvgkqwsgaral<br>ealltvagelrgpplqldtgqllkiakrggvtaveavhawrna<br>ltgaplnltpeqvvaiLTPEQVVAIASHDGGKQ<br>ALETVQRLLPVLCQAHGLTPEQVVAIAS<br>NGGGKQALETVQRLLPVLCQAHGLTPE<br>QVVAIASNGGGKQALETVQRLLPVLCQ<br>AHGLTPEQVVAIASHDGGKQALETVQR<br>LLPVLCQAHGLTPEQVVAIASHDGGKQ<br>ALETVQRLLPVLCQAHGLTPEQVVAIAS<br>NIGGKQALETVQRLLPVLCQAHGLTPE<br>QVVAIASNIGGKQALETVQRLLPVLCQ<br>AHGLTPEQVVAIASNIGGKQALETVQR<br>LLPVLCQAHGLTPEQVVAIASNGGGKQ<br>ALETVQRLLPVLCQAHGLTPEQVVAIAS<br>NGGGKQALETVQRLLPVLCQAHGLTPE<br>QVVAIASHDGGKQALETVQRLLPVLCQ<br>AHGLTPEQVVAIASHDGGKQALETVQR<br>LLPVLCQAHGLTPEQVVAIASNHGGKQ<br>ALETVQRLLPVLCQAHGLTPEQVVAIAS<br>NIGGKQALETVQRLLPVLCQAHGLTPE<br>QVVAIASNIGGKQALETVQRLLPVLCQ<br>AHGLTPEQVVAIASNHGGKQALETVQR<br>LLPVLCQAHGLTPEQVVAIASHDGGKQ<br>ALETVQRLLPVLCQAHGLTPEQVVAIAS<br>NHGGKQALETVQRLLPVLCQAHGLTPE<br>QVVAIASNHGGKQALETVQRLLPVLCQ<br>AHGLTPEQVVAIASHDGGKQALETVQR<br>LLPVLCQAHGLTPEQVVAIASHDGGKQ<br>ALETVQRLLPVLCQAHGLTPEQVVAIAS<br>NIGGKQALETVQRLLPVLCQAHGLTPE<br>QVVAIASNIGGKQALETVQRLLPVLCQ<br>AHGLTPEQVVAIASNGGGKQALETVQR<br>LLPVLCQAHGLTPEQVVAIASNHGGKQ<br>ALETVQRLLPVLCQAHGLTPEQVVAIAS<br>HDGGKQALETVQRLLPVLCQAHGLTPE<br>QVVAIASNIGGKQALETVQRLLPVLCQ<br>AHGLTPEQVVAIASNIGGKQALETVQR<br>LLPVLCQAHGLTPEQVVAIASNGGGsiva<br>qlsrpdpalaaltndhlvalaclggrpaldavkkglphapal<br>ikrtnrripertshrva | N-terminus in lower case; RVD domain in in uppercase with hypervariable diresidues underlined; C-terminus in lowercase italics; Binds upstream of the ZmWUS2 transcription start site |
| 20 | ZmWUS2-TALE-2 Artificial Transcription Factor | mapkkkrkvdykdhdgdykdhdidykddddkgtvdlrt<br>lgysqqqekikpkvrstvaqhhealvghgfthahivalsq<br>hpaalgtvavkyqdmiaalpeatheaivgvgkqwsgaral<br>ealltvagelrgpplqldtgqllkiakrggvtaveavhawrna<br>ltgaplnltpeqvvailtpeqvvaiashdggkqaletvqrllp<br>vlcqahgltpeqvvaiasngggkqaletvqrllpylcqahgl<br>tpeqvvaiasngggkqaletvqrllpylcqahgltpeqvvai<br>ashdggkqaletvqrllpylcqahgltpeqvvaiashdggk<br>qaletvqrllpvlcqahgltpeqvvaiasniggkqaletvqrll<br>pvlcqahgltpeqvvaiasniggkqaletvqrllpvlcqahg<br>ltpeqvvaiasniggkqaletvqrllpvlcqahgltpeqvvai<br>asngggkqaletvqrllpvlcqahgltpeqvvaiasngggk<br>qaletvqrllpvlcqahgltpeqvvaiashdggkqaletvqrl<br>lpvlcqahgltpeqvvaiashdggkqaletvqrllpvlcqah<br>gltpeqvvaiasnhggkqaletvqrllpvlcqahgltpeqvv<br>aiasniggkqaletvqrllpvlcqahgltpeqvvaiasniggk<br>qaletvqrllpvlcqahgltpeqvvaiasnhggkqaletvqrl<br>lpvlcqahgltpeqvvaiashdggkqaletvqrllpvlcqah<br>gltpeqvvaiasnhggkqaletvqrllpvlcqahgltpeqvv<br>aiasnhggkqaletvqrllpvlcqahgltpeqvvaiashdgg<br>kqaletvqrllpvlcqahgltpeqvvaiashdggkqaletvq<br>rllpvlcqahgltpeqvvaiasniggkqaletvqrllpvlcqa<br>hgltpeqvvaiasniggkqaletvqrllpvlcqahgltpeqv<br>vaiasngggkqaletvqrllpvlcqahgltpeqvvaiasnhg<br>gkqaletvqrllpvlcqahgltpeqvvaiashdggkqaletv<br>qrllpvlcqahgltpeqvvaiasniggkqaletvqrllpvlcq<br>ahgltpeqvvaiasniggkqaletvqrllpvlcqahgltpeq | ZmWUS2-TALE-2 N terminus, RVD domain, C-terminus in lower case; SV40 Nuclear Localization Sequence in uppercase, double underlined; 3 x FLAG sequence lowercase, underlined; VP64 transcriptional activation domain is lowercase, double underlined, italics; 6 x His tag at C-terminus |

TABLE 1-continued

Biological Sequences

| SEQ ID NO: | DESCRIPTION | SEQUENCE | COMMENTS |
|---|---|---|---|
| | | vvaiasngggsivaqlsrpdpalaaltndhlvalaclggrpal davkkglphapalikrtnrripertshrvaPKKKRKVS SdykdhdqdykdhdidykddddkAAGGGGSGR A*dalddfdldmlgsdalddfdldmlgsdalddfdldmlgs dalddfdldml*HHHHHH | |
| 21 | ZmWUS2-TALE-3 N-terminus, RVD, and C-terminal domain | mapkkkrkvdykdhdgdykdhdidykddddkgtvdlrt lgysqqqqekikpkvrstvaqhhealvghgfthahivalsq hpaalgtvavkyqdmiaaalpeatheaivgvgkqwsgaral ealltvagelrgpplqldtgqllkiakrggvtaveavhawrna ltgaplnltpeqvvaiLTPEQVVAIAS<u>NI</u>GGKQA LETVQRLLPVLCQAHGLTPEQVVAIAS<u>N</u> GGGKQALETVQRLLPVLCQAHGLTPEQ VVAIAS<u>HD</u>GGKQALETVQRLLPVLCQA HGLTPEQVVAIAS<u>NH</u>GGKQALETVQRL LPVLCQAHGLTPEQVVAIAS<u>N</u>GGGKQA LETVQRLLPVLCQAHGLTPEQVVAIAS<u>N</u> IGGKQALETVQRLLPVLCQAHGLTPEQ VVAIAS<u>N</u>GGGKQALETVQRLLPVLCQA HGLTPEQVVAIAS<u>HD</u>GGKQALETVQRL LPVLCQAHGLTPEQVVAIAS<u>NI</u>GGKQAL ETVQRLLPVLCQAHGLTPEQVVAIAS<u>H</u> <u>D</u>GGKQALETVQRLLPVLCQAHGLTPEQ VVAIAS<u>HD</u>GGKQALETVQRLLPVLCQA HGLTPEQVVAIAS<u>HD</u>GGKQALETVQRL LPVLCQAHGLTPEQVVAIAS<u>NI</u>GGKQAL ETVQRLLPVLCQAHGLTPEQVVAIAS<u>N</u> GGGKQALETVQRLLPVLCQAHGLTPEQ VVAIAS<u>NH</u>GGKQALETVQRLLPVLCQA HGLTPEQVVAIAS<u>NH</u>GGKQALETVQRL LPVLCQAHGLTPEQVVAIAS<u>HD</u>GGKQA LETVQRLLPVLCQAHGLTPEQVVAIAS<u>N</u> IGGKQALETVQRLLPVLCQAHGLTPEQ VVAIAS<u>N</u>GGGKQALETVQRLLPVLCQA HGLTPEQVVAIAS<u>NH</u>GGKQALETVQRL LPVLCQAHGLTPEQVVAIAS<u>NI</u>GGKQAL ETVQRLLPVLCQAHGLTPEQVVAIAS<u>H</u> <u>D</u>GGKQALETVQRLLPVLCQAHGLTPEQ VVAIAS<u>HD</u>GGKQALETVQRLLPVLCQA HGLTPEQVVAIAS<u>HD</u>GGKQALETVQRL LPVLCQAHGLTPEQVVAIASHDGGKQA LETVQRLLPVLCQAHGLTPEQVVAIAS<u>H</u> <u>D</u>GGKQALETVQRLLPVLCQAHGLTPEQ VVAIAS<u>HD</u>GGKQALETVQRLLPVLCQA HGLTPEQVVAIAS<u>N</u>GGG*sivaqlsrpdpalaalt ndhlvalaclggrpaldavkkglphapalikrtnrripertsh rva* | N-terminus in lower case; RVD domain in uppercase with hypervariable diresidues underlined; C-terminus in lowercase italics; Binds upstream of the ZmWUS2 transcription start site |
| 22 | ZmWUS2-TALE-3 Artificial Transcription Factor | mapkkkrkvdykdhdgdykdhdidykddddkgtvdlrt lgysqqqqekikpkvrstvaqhhealvghgfthahivalsq hpaalgtvavkyqdmiaaalpeatheaivgvgkqwsgaral ealltvagelrgpplqldtgqllkiakrggvtaveavhawrna ltgaplnltpeqvvailtpeqvvaiasniggkqaletvqrllpv lcqahgltpeqvvaiasngggkqaletvqrllpvlcqahglt peqvvaiashdggkqaletvqrllpvlcqahgltpeqvvaia snhggkqaletvqrllpvlcqahgltpeqvvaiasngggkq aletvqrllpvlcqahgltpeqvvaiasniggkqaletvqrllp vlcqahgltpeqvvaiasngggkqaletvqrllpvlcqahgl tpeqvvaiashdggkqaletvqrllpvlcqahgltpeqvvai asniggkqaletvqrllpvlcqahgltpeqvvaiashdggkq aletvqrllpvlcqahgltpeqvvaiashdggkqaletvqrll pvlcqahgltpeqvvaiashdggkqaletvqrllpvlcqahg ltpeqvvaiasniggkqaletvqrllpvlcqahgltpeqvvai asngggkqaletvqrllpvlcqahgltpeqvvaiasnhggk qaletvqrllpvlcqahgltpeqvvaiasnhggkqaletvqrl lpvlcqahgltpeqvvaiashdggkqaletvqrllpvlcqah gltpeqvvaiasniggkqaletvqrllpvlcqahgltpeqvv aiasngggkqaletvqrllpvlcqahgltpeqvvaiasnhgg kqaletvqrllpvlcqahgltpeqvvaiasniggkqaletvqr llpvlcqahgltpeqvvaiashdggkqaletvqrllpvlcqa hgltpeqvvaiashdggkqaletvqrllpvlcqahgltpeqv vaiashdggkqaletvqrllpvlcqahgltpeqvvaiashdg gkqaletvqrllpvlcqahgltpeqvvaiashdggkqaletv qrllpvlcqahgltpeqvvaiashdggkqaletvqrllpvlcq | ZmWUS2-TALE-3 N terminus, RVD domain, C-terminus in lower case; SV40 Nuclear Localization Sequence in uppercase, underlined; 3 x FLAG sequence lowercase, underlined; VP64 transcriptional activation domain is lowercase, double underlined, italics; 6 x His tag at C-terminus |

TABLE 1-continued

Biological Sequences

| SEQ ID NO: | DESCRIPTION | SEQUENCE | COMMENTS |
|---|---|---|---|
| | | ahgltpeqvvaiasngggsivaqlsrpdpalaaltndhlvala clggrpaldavkkglphapalikrtnrripertshrva<u>PKK KRKVS</u>dykdhdqdykdhdidykddddkAAGG GGSGRA*dalddfdldmlgsdalddfdldmlgsdalddf dldmlgsdalddfdldml*HHHHHH | |
| 23 | Zm ODP2-TALE-1 N-terminus, RVD, and C-terminal domain | mapkkkrkvdykdhdgdykdhdidykddddkgtvdlrt lgysqqqqekikpkvrstvaqhhealvghgfthahivalsq hpaalgtvavkyqdmiaalpeatheaivgvgkqwsgaral ealltvagelrgpplqldtgqllkiakrggvtaveavhawrna ltgaplnltpeqvvaiLTPEQVVAIAS<u>NI</u>GGKQA LETVQRLLPVLCQAHGLTPEQVVAIAS<u>N</u> GGGKQALETVQRLLPVLCQAHGLTPEQ VVAIAS<u>NG</u>GGKQALETVQRLLPVLCQA HGLTPEQVVAIAS<u>HD</u>GGKQALETVQRL LPVLCQAHGLTPEQVVAIAS<u>HD</u>GGKQA LETVQRLLPVLCQAHGLTPEQVVAIAS<u>N</u> GGGKQALETVQRLLPVLCQAHGLTPEQ VVAIAS<u>NI</u>GGKQALETVQRLLPVLCQA HGLTPEQVVAIAS<u>NI</u>GGKQALETVQRLL PVLCQAHGLTPEQVVAIAS<u>NG</u>GGKQAL ETVQRLLPVLCQAHGLTPEQVVAIAS<u>NI</u> GGKQALETVQRLLPVLCQAHGLTPEQV VAIAS<u>NG</u>GGKQALETVQRLLPVLCQAH GLTPEQVVAIAS<u>NI</u>GGKQALETVQRLLP VLCQAHGLTPEQVVAIAS<u>NG</u>GGKQALE TVQRLLPVLCQAHGLTPEQVVAIAS<u>NI</u>G GKQALETVQRLLPVLCQAHGLTPEQVV AIAS<u>NG</u>GGKQALETVQRLLPVLCQAHG LTPEQVVAIAS<u>NI</u>GGKQALETVQRLLPV LCQAHGLTPEQVVAIAS<u>NG</u>GGKQALET VQRLLPVLCQAHGLTPEQVVAIAS<u>HD</u> GKQALETVQRLLPVLCQAHGLTPEQVV AIAS<u>NI</u>GGKQALETVQRLLPVLCQAHGL TPEQVVAIAS<u>NG</u>GGKQALETVQRLLPV LCQAHGLTPEQVVAIAS<u>NI</u>GGKQALET VQRLLPVLCQAHGLTPEQVVAIAS<u>HD</u> GKQALETVQRLLPVLCQAHGLTPEQVV AIAS<u>NG</u>GGKQALETVQRLLPVLCQAHG LTPEQVVAIAS<u>HD</u>GGKQALETVQRLLP VLCQAHGLTPEQVVAIAS<u>NG</u>GGKQALE TVQRLLPVLCQAHGLTPEQVVAIAS<u>HD</u> GGKQALETVQRLLPVLCQAHGLTPEQV VAIAS<u>HD</u>GGKQALETVQRLLPVLCQAH GLTPEQVVAIAS<u>NI</u>GGKQALETVQRLLP VLCQAHGLTPEQVVAIAS<u>NGG</u>*sivaqlsr pdpalaaltndhlvalaclggrpaldavkkglphapalikrt nrripertshrva* | N-terminus in lower case; RVD domain in uppercase with hypervariable diresidues underlined; C-terminus in lowercase italics; Binds upstream of the ZmODP2 transcription start site |
| 24 | Zm ODP2-TALE-1 Artificial Transcription Factor | mapkkkrkvdykdhdgdykdhdidykddddkgtvdlrt lgysqqqqekikpkvrstvaqhhealvghgfthahivalsq hpaalgtvavkyqdmiaalpeatheaivgvgkqwsgaral ealltvagelrgpplqldtgqllkiakrggvtaveavhawrna ltgaplnltpeqvvailtpeqvvaiasniggkqaletvqrllpv lcqahgltpeqvvaiasngggkqaletvqrllpvlcqahglt peqvvaiasngggkqaletvqrllpvlcqahgltpeqvvaia shdggkqaletvqrllpvlcqahgltpeqvvaiashdggkq aletvqrllpvlcqahgltpeqvvaiasngggkqaletvqrll pvlcqahgltpeqvvaiasniggkqaletvqrllpvlcqahg ltpeqvvaiasniggkqaletvqrllpvlcqahgltpeqvvai asngggkqaletvqrllpvlcqahgltpeqvvaiasniggkq aletvqrllpvlcqahgltpeqvvaiasngggkqaletvqrll pvlcqahgltpeqvvaiasniggkqaletvqrllpvlcqahg ltpeqvvaiasngggkqaletvqrllpvlcqahgltpeqvva iasniggkqaletvqrllpvlcqahgltpeqvvaiasngggk qaletvqrllpvlcqahgltpeqvvaiasniggkqaletvqrll pvlcqahgltpeqvvaiasngggkqaletvqrllpvlcqahg ltpeqvvaiashdggkqaletvqrllpvlcqahgltpeqvva iasniggkqaletvqrllpvlcqahgltpeqvvaiasngggk qaletvqrllpvlcqahgltpeqvvaiasniggkqaletvqrll pvlcqahgltpeqvvaiashdggkqaletvqrllpvlcqahg ltpeqvvaiasngggkqaletvqrllpvlcqahgltpeqvva iashdggkqaletvqrllpvlcqahgltpeqvvaiasngggk qaletvqrllpvlcqahgltpeqvvaiashdggkqaletvqrl | Zm ODP2-TALE-1 N terminus, RVD domain, C-terminus in lower case; SV40 Nuclear Localization Sequence in uppercase, underlined; 3 x FLAG sequence lowercase, underlined; VP64 transcriptional activation domain is lowercase, double underlined, italics; 6 x His tag at C-terminus |

TABLE 1-continued

Biological Sequences

| SEQ ID NO: | DESCRIPTION | SEQUENCE | COMMENTS |
|---|---|---|---|
| | | lpylcqahgltpeqvvaiashdggkqaletvqrllpvlcqah gltpeqvvaiasnggkqaletvqrllpvlcqahgltpeqvv aiasngggsivaqlsrpdpalaaltndhlvalaclggrpalda vkkglphapalikrtnrripertshrva<u>PKKKRKV</u>ss<i>dy kdhdqdykdhdidykddddk</i>AAGGGGSGRA<i><u>dal ddfdldmlqsdalddfdldmlqsdalddfdldmlqsdaldd fdldml</u></i>hhhhhh | |
| 25 | Zm ODP2-TALE-2 N-terminus, RVD, and C-terminal domain | mapkkkrkvdykdhdgdykdhdidykddddkgtvdlrt lgysqqqekikpkvrstvaqhhealvghgfthahivalsq hpaalgtvavkyqdmiaalpeatheaivgvgkqwsgaral ealltvagelrgpplqldtgqllkiakrggvtaveavhawrna ltgaplnltpeqvvaiLTPEQVVAIAS<u>HD</u>GGKQ ALETVQRLLPVLCQAHGLTPEQVVAIAS <u>NG</u>GGKQALETVQRLLPVLCQAHGLTPE QVVAIAS<u>NG</u>GGKQALETVQRLLPVLCQ AHGLTPEQVVAIAS<u>HD</u>GGKQALETVQR LLPVLCQAHGLTPEQVVAIAS<u>NG</u>GGKQ ALETVQRLLPVLCQAHGLTPEQVVAIAS <u>NH</u>GGKQALETVQRLLPVLCQAHGLTPE QVVAIAS<u>NH</u>GGKQALETVQRLLPVLCQ AHGLTPEQVVAIAS<u>NI</u>GGKQALETVQR LLPVLCQAHGLTPEQVVAIAS<u>NH</u>GGKQ ALETVQRLLPVLCQAHGLTPEQVVAIAS <u>NG</u>GGKQALETVQRLLPVLCQAHGLTPE QVVAIAS<u>NH</u>GGKQALETVQRLLPVLCQ AHGLTPEQVVAIAS<u>NG</u>GGKQALETVQR LLPVLCQAHGLTPEQVVAIAS<u>NI</u>GGKQA LETVQRLLPVLCQAHGLTPEQVVAIAS<u>H</u> <u>D</u>GGKQALETVQRLLPVLCQAHGLTPEQ VVAIAS<u>HD</u>GGKQALETVQRLLPVLCQA HGLTPEQVVAIAS<u>NI</u>GGKQALETVQRLL PVLCQAHGLTPEQVVAIAS<u>NH</u>GGKQAL ETVQRLLPVLCQAHGLTPEQVVAIAS<u>N</u> <u>G</u>GGKQALETVQRLLPVLCQAHGLTPEQ VVAIAS<u>NG</u>GGKQALETVQRLLPVLCQA HGLTPEQVVAIAS<u>NH</u>GGKQALETVQRL LPVLCQAHGLTPEQVVAIAS<u>NG</u>GGKQA LETVQRLLPVLCQAHGLTPEQVVAIAS<u>N</u> <u>I</u>GGKQALETVQRLLPVLCQAHGLTPEQ VVAIAS<u>NG</u>GGKQALETVQRLLPVLCQA HGLTPEQVVAIAS<u>NI</u>GGKQALETVQRLL PVLCQAHGLTPEQVVAIAS<u>NI</u>GGKQALE TVQRLLPVLCQAHGLTPEQVVAIAS<u>NI</u>G GKQALETVQRLLPVLCQAHGLTPEQVV AIAS<u>NG</u>GGKQALETVQRLLPVLCQAHG LTPEQVVAIAS<u>NI</u>GGKQALETVQRLLPV LCQAHGLTPEQVVAIAS<u>NG</u>GG<i>sivaqlsrpd palaaltndhlvalaclggrpaldavkkglphapalikrtnr ripertshrva</i> | N-terminus in lower case; RVD domain in uppercase with hypervariable diresidues underlined; C-terminus in lowercase italics; Binds upstream of the ZmODP2 transcription start site |
| 26 | Zm ODP2-TALE-2 Artificial Transcription Factor | mapkkkrkvdykdhdgdykdhdidykddddkgtvdlrt lgysqqqekikpkvrstvaqhhealvghgfthahivalsq hpaalgtvavkyqdmiaalpeatheaivgvgkqwsgaral ealltvagelrgpplqldtgqllkiakrggvtaveavhawrna ltgaplnltpeqvvailtpeqvvaiashdggkqaletvqrllp vlcqahgltpeqvvaiasngggkqaletvqrllpvlcqahgl tpeqvvaiasngggkqaletvqrllpvlcqahgltpeqvvai ashdggkqaletvqrllpvlcqahgltpeqvvaiasngggk qaletvqrllpvlcqahgltpeqvvaiasnhggkqaletvqrl lpvlcqahgltpeqvvaiasnhggkqaletvqrllpvlcqah gltpeqvvaiasniggkqaletvqrllpvlcqahgltpeqvv aiasnhggkqaletvqrllpvlcqahgltpeqvvaiasnggg kqaletvqrllpvlcqahgltpeqvvaiasnhggkqaletvq rllpvlcqahgltpeqvvaiasngggkqaletvqrllpvlcqa hgltpeqvvaiasniggkqaletvqrllpvlcqahgltpeqv vaiashdggkqaletvqrllpvlcqahgltpeqvvaiashdg gkqaletvqrllpvlcqahgltpeqvvaiasniggkqaletv qrllpvlcqahgltpeqvvaiasnhggkqaletvqrllpvlcq ahgltpeqvvaiasngggkqaletvqrllpvlcqahgltpeq vvaiasngggkqaletvqrllpvlcqahgltpeqvvaiasnh ggkqaletvqrllpvlcqahgltpeqvvaiasngggkqalet vqrllpvlcqahgltpeqvvaiasniggkqaletvqrllpvlc qahgltpeqvvaiasngggkqaletvqrllpvlcqahgltpe | N terminus, RVD domain, C-terminus in lower case; SV40 Nuclear Localization Sequence in uppercase, underlined; 3 x FLAG sequence lowercase, underlined; VP64 transcriptional activation domain is lowercase, double underlined, italics; 6 x His tag at C-terminus |

TABLE 1-continued

Biological Sequences

| SEQ ID NO: | DESCRIPTION | SEQUENCE | COMMENTS |
|---|---|---|---|
| | | qvvaiasniggkqaletvqrllpvlcqahgltpeqvvaiasni ggkqaletvqrllpvlcqahgltpeqvvaiasngggkqalet vqrllpvlcqahgltpeqvvaiasnggkqaletvqrllpvlc qahgltpeqvvaiasniggkqaletvqrllpvlcqahgltpe qvvaiasngggsivaqlsrpdpalaaltndhlvalaclggrp aldavkkglphapalikrtnrripertshrva<u>PKKKRKV</u> <u>SS</u><u>dykdhdgdykdhdidykddddk</u>AAGGGGSGR A<i><u>dalddfdldmlgsdalddfdldmlgsdalddfdldmlgs</u></i> <i><u>dalddfdldml</u></i>HHHHHH | |
| 27 | Zm ODP2-TALE-3 N-terminus, RVD, and C-terminal domain | mapkkkrkvdykdhdgdykdhdidykddddkgtvdlrt lgysqqqekikpkvrstvaqhhealvghgfthahivalsq hpaalgtvavkyqdmiaalpeatheaivgvgkqwsgaral ealltvagelrgpplqldtgqllkiakrggvtaveavhawrna ltgaplnltpeqvvaiLTPEQVVAIAS<u>NH</u>GGKQ ALETVQRLLPVLCQAHGLTPEQVVAIAS <u>HD</u>GGKQALETVQRLLPVLCQAHGLTPE QVVAIAS<u>NI</u>GGKQALETVQRLLPVLCQ AHGLTPEQVVAIAS<u>HD</u>GGKQALETVQR LLPVLCQAHGLTPEQVVAIAS<u>NG</u>GGKQ ALETVQRLLPVLCQAHGLTPEQVVAIAS <u>NH</u>GGKQALETVQRLLPVLCQAHGLTPE QVVAIAS<u>NG</u>GGKQALETVQRLLPVLCQ AHGLTPEQVVAIAS<u>HD</u>GGKQALETVQR LLPVLCQAHGLTPEQVVAIAS<u>HD</u>GGKQ ALETVQRLLPVLCQAHGLTPEQVVAIAS <u>NI</u>GGKQALETVQRLLPVLCQAHGLTPE QVVAIAS<u>NI</u>GGKQALETVQRLLPVLCQ AHGLTPEQVVAIAS<u>NI</u>GGKQALETVQR LLPVLCQAHGLTPEQVVAIAS<u>NI</u>GGKQA LETVQRLLPVLCQAHGLTPEQVVAIAS<u>N</u> GGGKQALETVQRLLPVLCQAHGLTPEQ VVAIAS<u>NH</u>GGKQALETVQRLLPVLCQA HGLTPEQVVAIAS<u>NH</u>GGKQALETVQRL LPVLCQAHGLTPEQVVAIAS<u>HD</u>GGKQA LETVQRLLPVLCQAHGLTPEQVVAIAS<u>N</u> GGGKQALETVQRLLPVLCQAHGLTPEQ VVAIAS<u>NG</u>GGKQALETVQRLLPVLCQA HGLTPEQVVAIAS<u>HD</u>GGKQALETVQRL LPVLCQAHGLTPEQVVAIAS<u>HD</u>GGKQA LETVQRLLPVLCQAHGLTPEQVVAIAS<u>N</u> GGGKQALETVQRLLPVLCQAHGLTPEQ VVAIAS<u>NH</u>GGKQALETVQRLLPVLCQA HGLTPEQVVAIAS<u>NI</u>GGKQALETVQRLL PVLCQAHGLTPEQVVAIAS<u>NG</u>GGKQAL ETVQRLLPVLCQAHGLTPEQVVAIAS<u>H</u> <u>D</u>GGKQALETVQRLLPVLCQAHGLTPEQ VVAIAS<u>HD</u>GGKQALETVQRLLPVLCQA HGLTPEQVVAIAS<u>HD</u>GGKQALETVQRL LPVLCQAHGLTPEQVVAIAS<u>HD</u>GGKQA LETVQRLLPVLCQAHGLTPEQVVAIAS<u>N</u> GGG<i>sivaqlsrpdpalaaltndhlvalaclggrpaldavk kglphapalikrtnrripertshrva</i> | N-terminus in lower case; RVD domain in uppercase with hypervariable diresidues underlined; C-terminus in lowercase italics; Binds upstream of the ZmODP2 transcription start site |
| 28 | Zm ODP2-TALE-3 Artificial Transcription Factor | mapkkkrkvdykdhdgdykdhdidykddddkgtvdlrt lgysqqqekikpkvrstvaqhhealvghgfthahivalsq hpaalgtvavkyqdmiaalpeatheaivgvgkqwsgaral ealltvagelrgpplqldtgqllkiakrggvtaveavhawrna ltgaplnltpeqvvailtpeqvvaiasnhggkqaletvqrllp vlcqahgltpeqvvaiashdggkqaletvqrllpvlcqahgl tpeqvvaiasniggkqaletvqrllpvlcqahgltpeqvvaia shdggkqaletvqrllpvlcqahgltpeqvvaiasngggkq aletvqrllpvlcqahgltpeqvvaiasnhggkqaletvqrll pvlcqahgltpeqvvaiasngggkqaletvqrllpvlcqahg ltpeqvvaiashdggkqaletvqrllpvlcqahgltpeqvva iashdggkqaletvqrllpvlcqahgltpeqvvaiasniggk qaletvqrllpvlcqahgltpeqvvaiasniggkqaletvqrll pvlcqahgltpeqvvaiasniggkqaletvqrllpvlcqahg ltpeqvvaiasniggkqaletvqrllpvlcqahgltpeqvvai asngggkqaletvqrllpvlcqahgltpeqvvaiasnhggk qaletvqrllpvlcqahgltpeqvvaiasnhggkqaletvqrl lpvlcqahgltpeqvvaiashdggkqaletvqrllpvlcqah gltpeqvvaiasngggkqaletvqrllpvlcqahgltpeqvv aiasngggkqaletvqrllpvlcqahgltpeqvvaiashdgg | N terminus, RVD domain, C-terminus in lower case; SV40 Nuclear Localization Sequence in uppercase, underlined; 3 x FLAG sequence lowercase, underlined; VP64 transcriptional activation domain is lowercase, double underlined, italics; 6 x His tag at C-terminus |

TABLE 1-continued

Biological Sequences

| SEQ ID NO: | DESCRIPTION | SEQUENCE | COMMENTS |
|---|---|---|---|
| | | kqaletvqrllpvlcqahgltpeqvvaiashdggkqaletvq<br>rllpvlcqahgltpeqvvaiasngggkqaletvqrllpvlcqa<br>hgltpeqvvaiasnhggkqaletvqrllpvlcqahgltpeqv<br>vaiasniggkqaletvqrllpvlcqahgltpeqvvaiasngg<br>gkqaletvqrllpvlcqahgltpeqvvaiashdggkqaletv<br>qrllpvlcqahgltpeqvvaiashdggkqaletvqrllpvlcq<br>ahgltpeqvvaiashdggkqaletvqrllpvlcqahgltpeq<br>vvaiashdggkqaletvqrllpvlcqahgltpeqvvaiasng<br>ggsivaqlsrpdpalaaltndhlvalaclggrpaldavkkglp<br>hapalikrtnrripertshrva<u>PKKKRKVS</u><u>dykdhdg</u><br><u>dykdhdidykddddk</u>AAGGGGSGRA<u>*dalddfdld*</u><br><u>*mlgsdalddfdldmlgsdalddfdldmlgsdalddfdldml*</u><br>HHHHHH | |
| 29 | dCAS9 RNA guided DNA binding polypeptide | mdkkysiglaigtnsvgwavitdeykvpskkfkvlgntdr<br>hsikknligallfdsgetaeatrlkrtarrrytrrknricylqeifs<br>nemakvddsffhrleesflveedkkherhpifgnivdevay<br>hekyptiyhlrkklvdstdkadlrliylalahmikfrghflieg<br>dlnpdnsdvdklfiqlvqtynqlfeenpinasgvdakailsa<br>rlsksrrlenliaqlpgekknglfgnlialslgltpnfksnfdla<br>edaklqlskdtydddldnllaqigdqyadlflaaknlsdaills<br>dilrvnteitkaplsasmikrydehhqdltllkalvrqqlpek<br>ykeiffdqskngyagyidggasqeefykfikpilekmdgte<br>ellvklnredllrkqrtfdngsiphqihlgelhailrrqedfypf<br>lkdnrekiekiltfripyyvgplargnsrfawmtrkseetitp<br>wnfeevvdkgasaqsfiermtnfdknlpnekvlpkhslly<br>eyftvyneltkvkyvtegmrkpaflsgeqkkaivdllfktnr<br>kvtvkqlkedyfkkiecfdsveisgvedrfnaslgtyhdllki<br>ikdkdfldneenedilediviltltlfedremieerlktyahlfd<br>dkvmkqlkrrrytgwgrlsrklingirdkqsgktildflksd<br>gfanrnfmqlihddsltfkediqkaqvsgqgdslhehianla<br>gspaikkgilqtvkvvdelvkvmgrhkpeniviemarenq<br>ttqkgqknsrermkrieegikelgsqilkehpventqlqnek<br>lylyylqngrdmyvdqeldinrlsdydvdaivpqsflkdds<br>idnkvltrsdknrgksdnvpseevvkkmknywrqllnakl<br>itqrkfdnltkaergglseldkagfikrqlvetrqitkhvaqild<br>srmntkydendklirevkvitlksklvsdfrkdfqfykvrei<br>nnyhhahdaylnavvgtalikkypklesefvygdykvyd<br>vrkmiakseqeigkatakyffysnimnffkteitlangeirkr<br>plietngetgeivwdkgrdfatvrkvlsmpqvnivkktevq<br>tggfskesilpkrnsdkliarkkdwdpkkyggfdsptvays<br>vlvvakvekgkskklksvkellgitimerssfeknpidflea<br>kgykevkkdliiklpkyslfelengrkrmlasagelqkgnel<br>alpskyvnflylashyeklkgspedneqkqlfveqhkhyld<br>eiieqisefskrviladanldkvlsaynkhrdkpireqaenii<br>hlftltnlgapaafkyfdttidrkrytstkevldatlihqsitgly<br>etridlsqlggd | dCas9 domain |
| 30 | dCAS9 RNA guided DNA binding polypeptide with Nuclear Localization and Transcription Activator sequences with C-terminal 6 x His domain | mdkkysiglaigtnsvgwavitdeykvpskkfkvlgntdr<br>hsikknligallfdsgetaeatrlkrtarrrytrrknricylqeifs<br>nemakvddsffhrleesflveedkkherhpifgnivdevay<br>hekyptiyhlrkklvdstdkadlrliylalahmikfrghflieg<br>dlnpdnsdvdklfiqlvqtynqlfeenpinasgvdakailsa<br>rlsksrrlenliaqlpgekknglfgnlialslgltpnfksnfdla<br>edaklqlskdtydddldnllaqigdqyadlflaaknlsdaills<br>dilrvnteitkaplsasmikrydehhqdltllkalvrqqlpek<br>ykeiffdqskngyagyidggasqeefykfikpilekmdgte<br>ellvklnredllrkqrtfdngsiphqihlgelhailrrqedfypf<br>lkdnrekiekiltfripyyvgplargnsrfawmtrkseetitp<br>wnfeevvdkgasaqsfiermtnfdknlpnekvlpkhslly<br>eyftvyneltkvkyvtegmrkpaflsgeqkkaivdllfktnr<br>kvtvkqlkedyfkkiecfdsveisgvedrfnaslgtyhdllki<br>ikdkdfldneenedilediviltltlfedremieerlktyahlfd<br>dkvmkqlkrrrytgwgrlsrklingirdkqsgktildflksd<br>gfanrnfmqlihddsltfkediqkaqvsgqgdslhehianla<br>gspaikgilqtvkvvdelvkvmgrhkpeniviemarenq<br>ttqkgqknsrermkrieegikelgsqilkehpventqlqnek<br>lylyylqngrdmyvdqeldinrlsdydvdaivpqsflkdds<br>idnkvltrsdknrgksdnvpseevvkkmknywrqllnakl<br>itqrkfdnltkaergglseldkagfikrqlvetrqitkhvaqild<br>srmntkydendklirevkvitlksklvsdfrkdfqfykvrei<br>nnyhhahdaylnavvgtalikkypklesefvygdykvyd<br>vrkmiakseqeigkatakyffysnimnffkteitlangeirkr<br>plietngetgeivwdkgrdfatvrkvlsmpqvnivkktevq | dCas9 domain is in lower case, SV40 NLS is uppercase and underlined, 3 x FLAG sequence is lower case and underlined, the VP64 domain is lower case, underlined, and italicized; 6 x His domain at C-terminus |

TABLE 1-continued

Biological Sequences

| SEQ ID NO: | DESCRIPTION | SEQUENCE | COMMENTS |
|---|---|---|---|
| | | tggfskesilpkrnsdkliarkkdwdpkkyggfdsptvays vlvvakvekgkskklksvkellgitimerssfeknpidflea kgykevkkdliiklpkyslfelengrkrmlasagelqkgnel alpskyvnflylashyeklkgspedneqkqlfveqhkhyld eiieqisefskrviladanldkvlsaynkhrdkpireqaenii hlftltnlgapaafkyfdttidrkrytstkevldatlihqsitgly etridlsqlggdGS<u>PKKKRKVS</u>S<u>dykdhdqdykdh didykddddk</u>AAGGGGSGRA<u>*dalddfdldmlgsd alddfdldmlgsdalddfdldmlgsdalddfdldml*</u>HHH HHH | |
| 31 | ODP2_promoter_crRNA-1 encoding sequence | TTATTTTTCCTTCGGAAATT | T (Thymine) residues are U (uracil) residues in encoded RNA |
| 32 | ODP2_promoter_crRNA-2 encoding sequence | AAAATAGTTTATTTTTCCTT | T (Thymine) residues are U (uracil) residues in encoded RNA |
| 33 | ODP2_promoter_crRNA-3 encoding sequence | TTGGGAACCCTGGTTTTCTA | T (Thymine) residues are U (uracil) residues in encoded RNA |
| 34 | ODP2_promoter_crRNA-4 encoding sequence | AAGGGCTAGTTTGGGAACCC | T (Thymine) residues are U (uracil) residues in encoded RNA |
| 35 | ODP2_promoter_crRNA-5 encoding sequence encoding sequence | TACATACTAAGGGCTAGTTT | T (Thymine) residues are U (uracil) residues in encoded RNA |
| 36 | WUS2_promoter_crRNA-1 encoding sequence | AAAAGATATCGTATCACCCA | T (Thymine) residues are U (uracil) residues in encoded RNA |
| 37 | WUS2_promoter_crRNA-2 encoding sequence | GCAATGCAAGAGCCAGCCCC | T (Thymine) residues are U (uracil) residues in encoded RNA |
| 38 | WUS2_promoter_crRNA-3 encoding sequence | GACTCTTCCAAATTCCGAAG | T (Thymine) residues are U (uracil) residues in encoded RNA |
| 39 | WUS2_promoter_crRNA-4 encoding sequence | CAGTTGCCACAAGGGGAGCC | T (Thymine) residues are U (uracil) residues in encoded RNA |
| 40 | WUS2_promoter_crRNA-5 encoding sequence | GGCAGTTACCAGTTGCCACA | T (Thymine) residues are U (uracil) residues in encoded RNA |
| 41 | sgRNA expression cassette for the tethering approach | aaaataaatggtaaaatgtcaaatcaaaactaggctgcagtat gcagagcagagtcatgatgatactacttactacaccgattcttg tgtgcagaaaaatatgttaaaataattgaatctttctctagccaa atttgacaacaatgtacaccgttcatattgagagacgatgcttct tgtttgctttcggtggaagctgcatatactcaacattactccttca gcgagttttccaactgagtcccacattgcccagacctaacacg gtattcttgtttataatgaaatgtgccaccacatggattgNNN NNNNNNNNNNNNNNNNN<u>gttttagagctaga aatagcaagttaaaataaggctagtccgttatcaacttgaaaaa gtggcaccgagtcggtgctttttt</u> | GmU6 promoter in lower case; encoded sgRNA target sequence is in upper case, wherein the N x 20 sequence can be SEQ ID NO: 31, 32, 33, 34, 35, 36, 37, 38, 39, or 40; or any other crRNA; |

TABLE 1-continued

Biological Sequences

| SEQ ID NO: | DESCRIPTION | SEQUENCE | COMMENTS |
|---|---|---|---|
| | | | remainder of the encoded sgRNA is in lower case and underlined |
| 42 | maize opaque-2 nuclear localization signal | RKRKESNRESARRSRRSRYRKKV | |
| 43 | 60 amino acids from the maize C1 transcriptional activation domain | AGSSDDCSSAASVSLRVGSHDEPCFSGD GDGDWMDDVRALASFLESDEDWLRCQ TAGQLA | |
| 44 | As Cpf1 (wild type) | MTQFEGFTNLYQVSKTLRFELIPQGKTL KHIQEQGFIEEDKARNDHYKELKPIIDRI YKTYADQCLQLVQLDWENLSAAIDSYR KEKTEETRNALIEEQATYRNAIHDYFIG RTDNLTDAINKRHAEIYKGLFKAELFNG KVLKQLGTVTTTEHENALLRSFDKFTT YFSGFYENRKNVFSAEDISTAIPHRIVQD NFPKFKENCHIFTRLITAVPSLREHFENV KKAIGIFVSTSIEEVFSFPFYNQLLTQTQI DLYNQLLGGISREAGTEKIKGLNEVLNL AIQKNDETAHIIASLPHRFIPLFKQILSDR NTLSFILEEFKSDEEVIQSFCKYKTLLRN ENVLETAEALFNELNSIDLTHIFISHKKL ETISSALCDHWDTLRNALYERRISELTG KITKSAKEKVQRSLKHEDINLQEIISAAG KELSEAFKQKTSEILSHAHAALDQPLPT TLKKQEEKEILKSQLDSLLGLYHLLDWF AVDESNEVDPEFSARLTGIKLEMEPSLS FYNKARNYATKKPYSVEKFKLNFQMPT LASGWDVNKEKNNGAILFVKNGLYYL GIMPKQKGRYKALSFEPTEKTSEGFDK MYYDYFPDAAKMIPKCSTQLKAVTAHF QTHTTPILLSNNFIEPLEITKEIYDLNNPE KEPKKFQTAYAKKTGDQKGYREALCK WIDFTRDFLSKYTKTTSIDLSSLRPSSQY KDLGEYYAELNPLLYHISFQRIAEKEIM DAVETGKLYLFQIYNKDFAKGHHGKPN LHTLYWTGLFSPENLAKTSIKLNGQAEL FYRPKSRMKRMAHRLGEKMLNKKLKD QKTPIPDTLYQELYDYVNHRLSHDLSDE ARALLPNVITKEVSHEIIKDRRFTSDKFF FHVPITLNYQAANSPSKFNQRVNAYLK EHPETPIIGIDRGERNLIYITVIDSTGKILE QRSLNTIQQFDYQKKLDNREKERVAAR QAWSVVGTIKDLKQGYLSQVIHEIVDL MIHYQAVVVLENLNFGFKSKRTGIAEK AVYQQFEKMLIDKLNCLVLKDYPAEKV GGVLNPYQLTDQFTSFAKMGTQSGFLF YVPAPYTSKIDPLTGFVDPFVWKTIKNH ESRKHFLEGFDFLHYDVKTGDFILHFK MNRNLSFQRGLPGFMPAWDIVFEKNET QFDAKGTPFIAGKRIVPVIENHRFTGRY RDLYPANELIALLEEKGIVFRDGSNILPK LLENDDSHAIDTMVALIRSVLQMRNSN AATGEDYINSPVRDLNGVCFDSRFQNPE WPMDADANGAYHIALKGQLLLNHLKE SKDLKLQNGISNQDWLAYIQELRN | *Acidaminococcus sp.* (As) dCpf1 variants include D917A, E1006A, E1028A, D1255A, and/or N1257A amino acid substitutions in the wild type sequence; wild-type residues that can be substituted to obtain dCpf1 variants shown in bold and underlined |
| 45 | LbCpf1 (wild type) | MSKLEKFTNCYSLSKTLRFKAIPVGKTQ ENIDNKRLLVEDEKRAEDYKGVKKLLD RYYLSFINDVLHSIKLKNLNNYISLFRK KTRTEKENKELENLEINLRKEIAKAFKG NEGYKSLFKKDIIETILPEFLDDKDEIAL VNSFNGFTTAFTGFFDNRENMFSEEAKS TSIAFRCINENLTRYISNMDIFEKVDAIF DKHEVQEIKEKILNSDYDVEDFFEGEFF NFVLTQEGIDVYNAIIGGFVTESGEKIKG LNEYINLYNQKTKQKLPKFKPLYKQVL SDRESLSFYGEGYTSDEEVLEVFRNTLN KNSEIFSSIKKLEKLFKNFDEYSSAGIFV | *Lachnospiraceae bacterium* (Lb) dCpf1 variants include D832A, E925A, and/or D1148A amino acid substitutions in the wild type sequence; wild-type residues that can be substituted to obtain dCpf1 |

TABLE 1-continued

Biological Sequences

| SEQ ID NO: | DESCRIPTION | SEQUENCE | COMMENTS |
|---|---|---|---|
| | | KNGPAISTISKDIFGEWNVIRDKWNAEY DDIHLKKKAVVTEKYEDDRRKSFKKIG SFSLEQLQEYADADLSVVEKLKEIIIQKV DEIYKVYGSSEKLFDADFVLEKSLKKN DAVVAIMKDLLDSVKSFENYIKAFFGE GKETNRDESFYGDFVLAYDILLKVDHIY DAIRNYVTQKPYSKDKFKLYFQNPQFM GGWDKDKETDYRATILRYGSKYYLAI MDKKYAKCLQKIDKDDVNGNYEKINY KLLPGPNKMLPKVFFSKKWMAYYNPS EDIQKIYKNGTFKKGDMFNLNDCHKLI DFFKDSISRYPKWSNAYDFNFSETEKYK DIAGFYREVEEQGYKVSFESASKKEVD KLVEEGKLYMFQIYNKDFSDKSHGTPN LHTMYFKLLFDENNHGQIRLSGGAELF MRRASLKKEELVVHPANSPIANKNPDN PKKTTTLSYDVYKDKRFSEDQYELHIPI AINKCPKNIFKINTEVRVLLKHDDNPYV IGIDRGERNLLYIVVVDGKGNIVEQYSL NEIINNFNGIRIKTDYHSLLDKKEKERFE ARQNWTSIENIKELKAGYISQVVHKICE LVEKYDAVIALEDLNSGFKNSRVKVEK QVYQKFEKMLIDKLNYMVDKKSNPCA TGGALKGYQITNKFESFKSMSTQNGFIF YIPAWLTSKIDPSTGFVNLLKTKYTSIAD SKKFISSFDRIMYVPEEDLFEFALDYKN FSRTDADYIKKWKLYSYGNRIRIFRNPK KNNVFDWEEVCLTSAYKELFNKYGINY QQGDIRALLCEQSDKAFYSSFMALMSL MLQMRNSITGRTDVDFLISPVKNSDGIF YDSRNYEAQENAILPKNADANGAYNIA RKVLWAIGQFKKAEDEKLDKVKIAISN KEWLEYAQTSVKH | variants shown in bold and underlined |
| 46 | Fn Cpf1 (wild type) | MSIYQEFVNKYSLSKTLRFELIPQGKTL ENIKARGLILDDEKRAKDYKKAKQIID YHQFFIEEILSSVCISEDLLQNYSDVYFK LKKSDDDNLQKDFKSAKDTIKKQISEYI KDSEKFKNLFNQNLIDAKKGQESDLIL WLKQSKDNGIELFKANSDITDIDEALEII KSFKGWTTYFKGFHENRKNVYSSNDIP TSIIYRIVDDNLPKFLENKAKYESLKDK APEAINYEQIKKDLAEELTFDIDYKTSE VNQRVFSLDEVFEIANFNNYLNQSGITK FNTIIGGKFVNGENTKRKGINEYINLYS QQINDKTLKKYKMSVLFKQILSDTESKS FVIDKLEDDSDVVTTMQSFYEQIAAFKT VEEKSIKETLSLLFDDLKAQKLDLSKIYF KNDKSLTDLSQQVFDDYSVIGTAVLEYI TQQIAPKNLDNPSKKEQELIAKKTEKAK YLSLETIKLALEEFNKHRDIDKQCRFEEI LANFAAIPMIFDEIAQNKDNLAQISIKYQ NQGKKDLLQASAEDDVKAIKDLLDQT NNLLHKLKIFHISQSEDKANILDKDEHF YLVFEECYFELANIVPLYNKIRNYITQKP YSDEKFKLNFENSTLANGWDKNKEPDN TAILFIKDDKYYLGVMNKKNNKIFDDK AIKENKGEGYKKIVYKLLPGANKMLPK VFFSAKSIKFYNPSEDILRIRNHSTHTKN GSPQKGYEKFEFNIEDCRKFIDFYKQSIS KHPEWKDFGFRFSDTQRYNSIDEFYRE VENQGYKLTFENISESYIDSVVNQGKLY LFQIYNKDFSAYSKGRPNLHTLYWKAL FDERNLQDVVYKLNGEAELFYRKQSIP KKITHPAKEAIANKNKDNPKKESVFEY DLIKDKRFTEDKFFHCPITINFKSSGAN KFNDEINLLLKEKANDVHILSIDRGERH LAYYTLVDGKGNIIKQDTFNIIGNDRMK TNYHDKLAAIEKDRDSARKDWKKINNI KEMKEGYLSQVVHEIAKLVIEYNAIVVF EDLNFGFKRGRFKVEKQVYQKLEKMLI EKLNYLVFKDNEFDKTGGVLRAYQLTA PFETFKKMGKQTGIIYYVPAGFTSKICP VTGFVNQLYPKYESVSKSQEFFSKFDKI | *Francisella novicida* (Fn) dCpf1 variants include FnCpf1 amino acid substitutions in the wild type sequence; wild-type residues that can be substituted to obtain dCpf1 variants shown in bold and underlined |

TABLE 1-continued

Biological Sequences

| SEQ ID NO: | DESCRIPTION | SEQUENCE | COMMENTS |
|---|---|---|---|
| | | CYNLDKGYFEFSFDYKNFGDKAAKGK WTIASFGSRLINFRNSDKNHNWDTREV YPTKELEKLLKDYSIEYGHGECIKAAIC GESDKKFFAKLTSVLNTILQMRNSKTGT ELDYLISPVADVNGNFFDSRQAPKNMP QDADANGAYHIGLKGLMLLGRIKNNQ EGKKLNLVIKNEEYFEFVQNRNN | |
| 47 | CasJ (wild type) | MQQYQVSKTVRFGLTLKNSEKKHATH LLLKDLVNVSEERIKNEITKDDKNQSEL SFFNEVIETLDLMDKYIKDWENCFYRT DQIQLTKEYYKVIAKKACFDWFWTND RGMKFPTSSIISFNSLKSSDKSKTSDNLD RKKKILDYWKGNIFKTQKAIKDVLDITE DIQKAIEEKKSHREINRVNHRKMGIHLI HLINDTLVPLCNGSIFFGNISKLDFCESE NEKLIDFASTEKQDERKFLLSKINEIKQY FEDNGGNVPFARATLNRHTANQKPDRY NEEIKKLVNELGVNSLVRSLKSKTIEEIK THFEFENKNKINELKNSFVLSIVEKIQLF KYKTIPASVRFLLADYFEEQKLSTKEEA LTIFEEIGKPQNIGFDYIQLKEKDNFTLK KYPLKQAFDYAWENLARLDQNPKANQ FSVDECKRFFKEVFSMEMDNINFKTYA LLLALKEKTTAFDKKGEGAAKNKSEIIE QIKGVFEELDQPFKIIANTLREEVIKKED ELNVLKRQYRETDRKIKTLQNEIKKIKN QIKNLENSKKYSFPEIIKWIDLTEQEQLL DKNKQAKSNYQKAKGDLGLIRGSQKTS INDYFYLTDKVYRKLAQDFGKKMADL REKLLDKNDVNKIKYLSYIVKDNQGYQ YTLLKPLEDKNAEIIELKSEPNGDLKLFE IKSLTSKTLNKFIKNKGAYKEFHSAEFE HKKIKEDWKNYKYNSDFIVKLKKCLSH SDMANTQNWKAFGWDLDKCKSYETIE KEIDQKSYQLVEIKLSKTTIEKWVKENN YLLLPIVNQDITAEKLKVNTNQFTKDW QHIFEKNPNHRLHPEFNIAYRQPTKDYA KEGEKRYSRFQLTGQFMYEYIPQDANY ISRKEQITLFNDKEEQKIQVETFNNQIAK ILNAEDFYVIGIDRGITQLATLCVLNKN GVIQGGFEIFTREFDYTNKQWKHTKLK ENRNILDISNLKVETTVNGEKVLVDLSE VKTYLRDENGEPMKNEKGVILTKDNLQ KIKLKQLAYDRKLQYKMQHEPELVLSF LDRLENKEQIPNLLASTKLISAYKEGTA YADIDIEQFWNILQTFQTIVDKFGGIENA KKTMEFRQYTELDASFDLKNGVVANM VGVVKFIMEKYNYKTFIALEDLTFAFG QSIDGINGERLRSTKEDKEVDFKEQENS TLAGLGTYHFFEMQLLKKLSKTQIGNEI KHFVPAFRSTENYEKIVRKDKNVKAKI VSYPFGIVSFVNPRNTSISCPNCKNANK SNRIKKENDRILCKHNIEKTKGNCGFDT ANFDENKLRAENKGKNFKYISSGDANA AYNIAVKLLEDKIFEINKK | dCasJ variants include D901A and/or E1228A amino acid substitutions in the wild type sequence; wild-type residues that can be substituted to obtain dCasJ variants shown in bold and underlined |
| 48 | Zinc finger linker peptide | TGEKP | |
| 49 | SV40 large T antigen NLS | PKKKRKV | |
| 50 | Class II monopartite NLS consensus | K(K/R)X(K/R) | |
| 51 | Bipartite NLS consensus | $(K/R)(K/R)X_{10-12}(K/R)_{3/5}$ | where $K/R_{3/5}$ represents at least three of either lysine or arginine of five consecutive amino acids |

TABLE 1-continued

Biological Sequences

| SEQ ID NO: | DESCRIPTION | SEQUENCE | COMMENTS |
|---|---|---|---|
| 52 | Class 5 Plant NLS | LGKR(K/R)(W/F/Y) | |
| 53 | (Gly4Ser)n | GGGGS | n is equal to 1, 2, 3, 4, 5, 6, 7, 8, 9 or 10 |
| 54 | Ser(Gly$_4$Ser)n | SGGGGS | n is equal to 1, 2, 3, 4, 5, 6, 7, 8, 9 or 10 |
| 55 | cell-penetrating peptide (CPP) | YGRKKRRQRRR | |
| 56 | cell-penetrating peptide (CPP) | RRQRRTSKLMKR | |
| 57 | cell-penetrating peptide (CPP) | GWTLNSAGYLLGKINLKALAALAKKIL | |
| 58 | cell-penetrating peptide (CPP) | KALAWEAKLAKALAKALAKHLAKALAKALKCEA | |
| 59 | cell-penetrating peptide (CPP) | RQIKIWFQNRRMKWKK | |
| 60 | cell-penetrating peptide (CPP) | YGRKKRRQRRR | |
| 61 | cell-penetrating peptide (CPP) | RKKRRQRR | |
| 62 | cell-penetrating peptide (CPP) | YARAAARQARA | |
| 63 | cell-penetrating peptide (CPP) | THRLPRRRRRR | |
| 64 | cell-penetrating peptide (CPP) | GGRRARRRRRR | |
| 65 | ZmWUS2-TALE-1 binding site | TGGCCCTCTGCATCCTCCTCATGATAGCT | |
| 66 | ZmWUS2-TALE-2 binding site | TCTTCCAAATTCCGAAGCGGCCAATGCAAT | |
| 67 | ZmWUS2-TALE-3 binding site | TATCGTATCACCCATGGCCATGACCCCCCT | |
| 68 | ZmODP2-TALE-1 binding site | TATTCCTAATATATATATCATACTCTCCAT | |
| 69 | ZmODP2-TALE-2 binding site | TCTTCTGGAGTGTACCAGTTGTATAAATAT | |
| 70 | ZmODP2-TALE-3 binding site | TGCACTGTCCAAAATGGCTTCCTGATCCCCT | |
| 71 | Conserved Maize ODP2 promoter | GTACTCATATATGGGCACACATATAGACATGTTTTGAGGAAAATGAGACAAAGTATAGTGGAGACTTCCCTAGAAAGCAGAAGAAAAGAAGTGGTTTATGTTCCGTTAAATCATACTACAACTTTTTTTTATTATACTCTCCATTTTGTCATCATTAGGTACTCATATATGGGCACACATATAGTACTGCCAATTTTCTTGCTAAAAAAGTTCCACTATATATGTATGTATGCACAAATAAACTAATTTTCTTAGAAAAGAAAACCGGTGTAATACATACTAAGGGCTAGTTTGGGAACCCTGGTT | |
| 72 | ZmWUS2-TALE-1b N-terminus, | msrtrlpsppapspafsadsfsdllrqfdpslfntslfdslppfgahhteaatgewdevqsglraadappptmrvavtaarppr | N terminus of TALE and RVD |

TABLE 1-continued

Biological Sequences

| SEQ ID NO: | DESCRIPTION | SEQUENCE | COMMENTS |
|---|---|---|---|
| | RVD, and C-terminal domain | akpaprrraaqpsdaspaaqvdlrtlgysqqqekikpkvr stvaqhhealvghgfthahivalsqhpaalgtvavkyqdmi aalpeatheaivgvgkqwsgaralealltvagelrgpplqldt gqllkiakrggvtaveavhawrnaltgaplnltetltpeqvva iasnhggkqaletvqrllpylcqahgltpeqvvaiasnhggk qaletvqrllpylcqahgltpeqvvaiashdggkqaletvqrl lpvlcqahgltpeqvvaiashdggkqaletvqrllpvlcqah gltpeqvvaiashdggkqaletvqrllpvlcqahgltpeqvv aiasngggkqaletvqrllpvlcqahgltpeqvvaiashdgg kqaletvqrllpvlcqahgltpeqvvaiasngggkqaletvq rllpvlcqahgltpeqvvaiasnhggkqaletvqrllpvlcqa hgltpeqvvaiashdggkqaletvqrllpvlcqahgltpeqv vaiasniggkqaletvqrllpvlcqahgltpeqvvaiasngg gkqaletvqrllpvlcqahgltpeqvvaiashdggkqaletv qrllpvlcqahgltpeqvvaiashdggkqaletvqrllpvlcq ahgltpeqvvaiasngggkqaletvqrllpvlcqahgltpeq vvaiashdggkqaletvqrllpvlcqahgltpeqvvaiashd ggkqaletvqrllpvlcqahgasqltpeqvvaiasngggRP ALESIVAQLSRPDPALAALTNDHLVALA CLGGRPALDAVKKGLPHAPALIKRTNR RIPERTSHRVADHAQVVRVLGFFQCHS HPAQAFDDAMTQFGMSRHGLLQLFRR VGVTELEARSGTLPPASQRWDRILQAS GMKRAKPSPTSTQTPDQASLHAFADSL ERDLDAPSPMHEGDQTRAS | domain in lower case; truncated TAL terminal domain in upper case and underlined |
| 73 | ZmWUS2-TALE-1b ATF | MHHHHHHmsrtrlpsppapspafsadsfsdllrqfdps lfntslfdslppfgahhteaatgewdevqsglraadappptm rvavtaarppprakpaprrraaqpsdaspaaqvdlrtlgysqq qqekikpkvrstvaqhhealvghgfthahivalsqhpaalgt vavkyqdmiaalpeatheaivgvgkqwsgaralealltva gelrgpplqldtgqllkiakrggvtaveavhawrnaltgapl nltetltpeqvvaiasnhggkqaletvqrllpvlcqahgltpe qvvaiasnhggkqaletvqrllpvlcqahgltpeqvvaiash dggkqaletvqrllpvlcqahgltpeqvvaiashdggkqale tvqrllpvlcqahgltpeqvvaiashdggkqaletvqrllpvl cqahgltpeqvvaiasngggkqaletvqrllpvlcqahgltp eqvvaiashdggkqaletvqrllpvlcqahgltpeqvvaias ngggkqaletvqrllpvlcqahgltpeqvvaiasnhggkqa letvqrllpvlcqahgltpeqvvaiashdggkqaletvqrllp vlcqahgltpeqvvaiasniggkqaletvqrllpvlcqahglt peqvvaiasngggkqaletvqrllpvlcqahgltpeqvvaia shdggkqaletvqrllpvlcqahgltpeqvvaiashdggkq aletvqrllpvlcqahgltpeqvvaiasngggkqaletvqrll pvlcqahgltpeqvvaiashdggkqaletvqrllpvlcqahg ltpeqvvaiashdggkqaletvqrllpvlcqahgasqltpeq vvaiasngggRPALESIVAQLSRPDPALAAL TNDHLVALACLGGRPALDAVKKGLPH APALIKRTNRRIPERTSHRVADHAQVVR VLGFFQCHSHPAQAFDDAMTQFGMSR HGLLQLFRRVGVTELEARSGTLPPASQR WDRILQASGMKRAKPSPTSTQTPDQAS LHAFADSLERDLDAPSPMHEGDQTRAS *aspkkkrkveasgs*GRAdalddfdldmlgsdalddfdld mlgsdalddfdldmlgsdalddfdldml | 6 x His tag at N-terminus residues 2-7 in upper case; N terminus of TALE, RVD domain, C-terminus in lower case; truncated TAL terminal domain in upper case and underlined, extended SV40 Nuclear Localization Sequence in lowercase, double underlined, italics; VP64 transcriptional activation domain is lowercase, underlined |
| 74 | ZmWUS2-TALE-1b binding site | TGGCCCTCTGCATCCTCCT | |
| 75 | ZmWUS2-TALE-2b N-terminus, RVD, and C-terminal domain | msrtrlpsppapspafsadsfsdllrqfdpslfntslfdslppf gahhteaatgewdevqsglraadappptmrvavtaarppr akpaprrraaqpsdaspaaqvdlrtlgysqqqekikpkvr stvaqhhealvghgfthahivalsqhpaalgtvavkyqdmi aalpeatheaivgvgkqwsgaralealltvagelrgpplqldt gqllkiakrggvtaveavhawrnaltgaplnltetltpeqvva iasnhggkqaletvqrllpvlcqahgltpeqvvaiasngggk qaletvqrllpvlcqahgltpeqvvaiasnhggkqaletvqrl lpvlcqahgltpeqvvaiasngggkqaletvqrllpvlcqah gltpeqvvaiashdggkqaletvqrllpvlcqahgltpeqvv aiasniggkqaletvqrllpvlcqahltpeqvvaiasniggkq aletvqrllpvlcqahgltpeqvvaiashdggkqaletvqrll pvlcqahgltpeqvvaiasngggkqaletvqrllpvlcqahg ltpeqvvaiasngggkqaletvqrllpvlcqahgltpeqvva iashdggkqaletvqrllpvlcqahgltpeqvvaiasniggk | N terminus of TALE and RVD domain in lower case; truncated TAL terminal domain in upper case and underlined |

TABLE 1-continued

Biological Sequences

| SEQ ID NO: | DESCRIPTION | SEQUENCE | COMMENTS |
|---|---|---|---|
| | | qaletvqrllpvlcqahgltpeqvvaiashdggkqaletvqrl lpvlcqahgltpeqvvaiasngggkqaletvqrllpvlcqah gltpeqvvaiasngggkqaletvqrllpvlcqahgltpeqvv aiasnhggkqaletvqrllpvlcqahgasqltpeqvvaiasn ggg<u>RPALESIVAQLSRPDPALAALTNDHL VALACLGGRPALDAVKKGLPHAPALIK RTNRRIPERTSHRVADHAQVVRVLGFF QCHSHPAQAFDDAMTQFGMSRHGLLQ LFRRVGVTELEARSGTLPPASQRWDRIL QASGMKRAKPSPTSTQTPDQASLHAFA DSLERDLDAPSPMHEGDQTRAS</u> | |
| 76 | ZmWUS2-TALE-2b ATF | MHHHHHHmsrtrlpsppapspafsadsfsdllrqfdps lfntslfdslppfgahhteaatgewdevqsglraadappptm rvavtaarpprakpaprrraaqpsdaspaaqvdlrtlgysqq qqekikpkvrstvaqhhealvghgfthahivalsqhpaalgt vavkyqdmiaalpeatheaivgvgkqwsgaralealltva gelrgpplqldtgqllkiakrggvtaveavhawrnaltgapl nltetltpeqvvaiasnhggkqaletvqrllpvlcqahgltpe qvvaiasngggkqaletvqrllpvlcqahgltpeqvvaiasn hggkqaletvqrllpvlcqahgltpeqvvaiasngggkqale tvqrllpvlcqahgltpeqvvaiashdggkqaletvqrllpvl cqahgltpeqvvaiasniggkqaletvqrllpvlcqahltpeq vvaiasniggkqaletvqrllpvlcqahgltpeqvvaiashd ggkqaletvqrllpvlcqahgltpeqvvaiasngggkqalet vqrllpvlcqahgltpeqvvaiasngggkqaletvqrllpvlc qahgltpeqvvaiashdggkqaletvqrllpvlcqahgltpe qvvaiasniggkqaletvqrllpvlcqahgltpeqvvaiash dggkqaletvqrllpvlcqahgltpeqvvaiasngggkqale tvqrllpvlcqahgltpeqvvaiasngggkqaletvqrllpvl cqahgltpeqvvaiasnhggkqaletvqrllpvlcqahgas qltpeqvvaiasnggg<u>RPALESIVAQLSRPDPA LAALTNDHLVALACLGGRPALDAVKK GLPHAPALIKRTNRRIPERTSHRVADHA QVVRVLGFFQCHSHPAQAFDDAMTQF GMSRHGLLQLFRRVGVTELEARSGTLP PASQRWDRILQASGMKRAKPSPTSTQT PDQASLHAFADSLERDLDAPSPMHEGD QTRAS</u>*aspkkkrkveasgs*GRAdalddfdldmlqsd alddfdldmlqsdalddfdldmlqsdalddfdldml | 6 x His tag at N-terminus residues 2-7 in upper case; N terminus of TALE, RVD domain, C-terminus in lower case; truncated TAL terminal domain in upper case and underlined, extended SV40 Nuclear Localization Sequence in lowercase, double underlined, italics; VP64 transcriptional activation domain is lowercase, underlined |
| 77 | ZmWUS2-TALE-2b binding site | TGTGTCAACTTCACTTGT | |
| 78 | ZmWUS2-TALE-3b N-terminus, RVD, and C-terminal domain | msrtrlpsppapspafsadsfsdllrqfdpslfntslfdslppf gahhteaatgewdevqsglraadappptmrvavtaarppr akpaprrraaqpsdaspaaqvdlrtlgysqqqqekikpkvr stvaqhhealvghgfthahivalsqhpaalgtvavkyqdmi aalpeatheaivgvgkqwsgaralealltvagelrgpplqldt gqllkiakrggvtaveavhawrnaltgaplnltetltpeqvva iashdggkqaletvqrllpvlcqahgltpeqvvaiasnhggk qaletvqrllpvlcqahgltpeqvvaiasngggkqaletvqrl lpvlcqahgltpeqvvaiasniggkqaletvqrllpvlcqah gltpeqvvaiasngggkqaletvqrllpvlcqahgltpeqvv aiashdggkqaletvqrllpvlcqahgltpeqvvaiasnigg kqaletvqrllpvlcqahgltpeqvvaiashdggkqaletvq rllpvlcqahgltpeqvvaiashdggkqaletvqrllpvlcqa hgltpeqvvaiashdggkqaletvqrllpvlcqahgltpeqv vaiasniggkqaletvqrllpvlcqahgltpeqvvaiasngg gkqaletvqrllpvlcqahgltpeqvvaiasnhggkqaletv qrllpvlcqahgltpeqvvaiasnhggkqaletvqrllpvlcq ahgltpeqvvaiashdggkqaletvqrllpvlcqahgltpeq vvaiashdggkqaletvqrllpvlcqahgltpeqvvaiasni ggkqaletvqrllpvlcqahgasqltpeqvvaiasnggg<u>RP ALESIVAQLSRPDPALAALTNDHLVALA CLGGRPALDAVKKGLPHAPALIKRTNR RIPERTSHRVADHAQVVRVLGFFQCHS HPAQAFDDAMTQFGMSRHGLLQLFRR VGVTELEARSGTLPPASQRWDRILQAS GMKRAKPSPTSTQTPDQASLHAFADSL ERDLDAPSPMHEGDQTRAS</u> | N terminus of TALE and RVD domain in lower case; truncated TAL terminal domain in upper case and underlined |
| 79 | ZmWUS2-TALE-3b ATF | MHHHHHHmsrtrlpsppapspafsadsfsdllrqfdps lfntslfdslppfgahhteaatgewdevqsglraadappptm | 6 x His tag at N-terminus residues |

TABLE 1-continued

Biological Sequences

| SEQ ID NO: | DESCRIPTION | SEQUENCE | COMMENTS |
|---|---|---|---|
| | | rvavtaarpprakpaprrraaqpsdaspaaqvdlrtlgysqq qqekikpkvrstvaqhhealvghgfthahivalsqhpaalgt vavkyqdmiaalpeatheaivgvgkqwsgaraleallltva gelrgpplqldtgqllkiakrggvtaveavhawrnaltgapl nltetltpeqvvaiashdggkqaletvqrllpvlcqahgltpe qvvaiasnhggkqaletvqrllpvlcqahgltpeqvvaiasn gggkqaletvqrllpvlcqahgltpeqvvaiasniggkqale tvqrllpvlcqahgltpeqvvaiasngggkqaletvqrllpvl cqahgltpeqvvaiashdggkqaletvqrllpvlcqahgltp eqvvaiasniggkqaletvqrllpvlcqahgltpeqvvaias hdggkqaletvqrllpvlcqahgltpeqvvaiashdggkqa letvqrllpvlcqahgltpeqvvaiashdggkqaletvqrllp vlcqahgltpeqvvaiasniggkqaletvqrllpvlcqahglt peqvvaiasngggkqaletvqrllpvlcqahgltpeqvvaia snhggkqaletvqrllpvlcqahgltpeqvvaiasnhggkq aletvqrllpvlcqahgltpeqvvaiashdggkqaletvqrll pylcqahgltpeqvvaiashdggkqaletvqrllpvlcqahg ltpeqvvaiasniggkqaletvqrllpvlcqahgasqltpeqv vaiasngggRPALESIVAQLSRPDPALAALT NDHLVALACLGGRPALDAVKKGLPHA PALIKRTNRRIPERTSHRVADHAQVVRV LGFFQCHSHPAQAFDDAMTQFGMSRH GLLQLFRRVGVTELEARSGTLPPASQR WDRILQASGMKRAKPSPTSTQTPDQAS LHAFADSLERDLDAPSPMHEGDQTRAS aspkkkrkveasgsGRAdalddfdldmlgsdalddfdld mlgsdalddfdldmlgsdalddfdldml | 2-7 in upper case; N terminus of TALE, RVD domain, C-terminus in lower case; truncated TAL terminal domain in upper case and underlined, extended SV40 Nuclear Localization Sequence in lowercase, double underlined, italics; VP64 transcriptional activation domain is lowercase, underlined |
| 80 | ZmWUS2-TALE-3b binding site | TCGTATCACCCATGGCCAT | |
| 81 | ZmODP2-TALE-1b N-terminus, RVD, and C-terminal domain | msrtrlpsppapspafsadsfsdllrqfdpslfntslfdslppf gahhteaatgewdevqsglraadapppmrvavtaarppr akpaprrraaqpsdaspaaqvdlrtlgysqqqqekikpkvr stvaqhhealvghgfthahivalsqhpaalgtvavkyqdmi aalpeatheaivgvgkqwsgaraleallltvagelrgpplqldt gqllkiakrggvtaveavhawrnaltgaplnltetltpeqvva iashdggkqaletvqrllpvlcqahgltpeqvvaiashdggk qaletvqrllpvlcqahgltpeqvvaiasngggkqaletvqrl lpvlcqahgltpeqvvaiasniggkqaletvqrllpvlcqah gltpeqvvaiasniggkqaletvqrllpvlcqahgltpeqvv aiasngggkqaletvqrllpvlcqahgltpeqvvaiasnigg kqaletvqrllpvlcqahgltpeqvvaiasngggkqaletvq rllpvlcqahgltpeqvvaiasniggkqaletvqrllvlcqa hgltpeqvvaiasngggkqaletvqrllpvlcqahgltpeqv vaiasniggkqaletvqrllpvlcqahgltpeqvvaiasngg gkqaletvqrllpvlcqahgltpeqvvaiasniggkqaletv qrllpvlcqahgltpeqvvaiasngggkqaletvqrllpvlcq ahgltpeqvvaiashdggkqaletvqrllpvlcqahgltpeq vvaiasniggkqaletvqrllpvlcqahgasqltpeqvvaias ngggRPALESIVAQLSRPDPALAALTNDH LVALACLGGRPALDAVKKGLPHAPALI KRTNRRIPERTSHRVADHAQVVRVLGF FQCHSHPAQAFDDAMTQFGMSRHGLL QLFRRVGVTELEARSGTLPPASQRWDRI LQASGMKRAKPSPTSTQTPDQASLHAF ADSLERDLDAPSPMHEGDQTRAS | N terminus of TALE and RVD domain in lower case; truncated TAL terminal domain in upper case and underlined |
| 82 | ZmODP2-TALE-1b ATF | MHHHHHHmsrtrlpsppapspafsadsfsdllrqfdps lfntslfdslppfgahhteaatgewdevqsglraadappptm rvavtaarpprakpaprrraaqpsdaspaaqvdlrtlgysqq qqekikpkyrstvaqhhealvghgfthahivalsqhpaalgt vavkyqdmiaalpeatheaivgvgkqwsgaraleallltva gelrgpplqldtgqllkiakrggvtaveavhawrnaltgapl nltetltpeqvvaiashdggkqaletvqrllpvlcqahgltpe qvvaiashdggkqaletvqrllpvlcqahgltpeqvvaiasn gggkqaletvqrllpvlcqahgltpeqvvaiasniggkqale tvqrllpvlcqahgltpeqvvaiasniggkqaletvqrllpvlc qahgltpeqvvaiasngggkqaletvqrllpvlcqahgltpe qvvaiasniggkqaletvqrllpvlcqahgltpeqvvaiasn gggkqaletvqrllpvlcqahgltpeqvvaiasniggkqale tvqrllpvlcqahgltpeqvvaiasngggkqaletvqrllpvl cqahgltpeqvvaiasniggkqaletvqrllpvlcqahgltpe qvvaiasngggkqaletvqrllpvlcqahgltpeqvvaiasn | 6 x His tag at N-terminus residues 2-7 in upper case; N terminus of TALE, RVD domain, C-terminus in lower case; truncated TAL terminal domain in upper case and underlined, extended SV40 Nuclear Localization Sequence in |

TABLE 1-continued

Biological Sequences

| SEQ ID NO: | DESCRIPTION | SEQUENCE | COMMENTS |
|---|---|---|---|
| | | iggkqaletvqrllpvlcqahgltpeqvvaiasngggkqale tvqrllpvlcqahgltpeqvvaiashdggkqaletvqrllpvl cqahgltpeqvvaiasniggkqaletvqrllpvlcqahgasq ltpeqvvaiasnggg<u>RPALESIVAQLSRPDPAL AALTNDHLVALACLGGRPALDAVKKG LPHAPALIKRTNRRIPERTSHRVADHAQ VVRVLGFFQCHSHPAQAFDDAMTQFG MSRHGLLQLFRRVGVTELEARSGTLPP ASQRWDRILQASGMKRAKPSPTSTQTP DQASLHAFADSLERDLDAPSMHEGDQ TRAS</u>*aspkkkrkveasgs*GRA<u>dalddfdldmlqsdal ddfdldmlqsdalddfdldmlqsdalddfdldml</u> | lowercase, double underlined, italics; VP64 transcriptional activation domain is lowercase, underlined |
| 83 | ZmODP2-TALE-1b binding site | TCCTAATATATATATCAT | |
| 84 | ZmODP2-TALE-2b N-terminus, RVD, and C-terminal domain | msrtrlpsppapspafsadsfsdllrqfdpslfntslfdslppf gahhteaatgewdevqsglraadappptmrvavtaarppr akpaprrraaqpsdaspaaqvdlrtlgysqqqqekikpkvr stvaqhhealvghgfthahivalsqhpaalgtvavkyqdmi aalpeatheaivgvgkqwsgaraleailtvagelrgpplqldt gqllkiakrggvtaveavhawrnaltgaplnltetltpeqvva iasnhggkqaletvqrllpvlcqahgltpeqvvaiasngggk qaletvqrllpvlcqahgltpeqvvaiasniggkqaletvqrll pvlcqahgltpeqvvaiashdggkqaletvqrllpvlcqahg ltpeqvvaiashdggkqaletvqrllpvlcqahgltpeqvva iasniggkqaletvqrllpvlcqahgltpeqvvaiasnhggk qaletvqrllpvlcqahgltpeqvvaiasngggkqaletvqrl lpvlcqahgltpeqvvaiasngggkqaletvqrllpvlcqah gltpeqvvaiasnhggkqaletvqrllpvlcqahgltpeqvv aiasngggkqaletvqrllpvlcqahgltpeqvvaiasnigg kqaletvqrllpvlcqahgltpeqvvaiasngggkqaletvq rllpvlcqahgltpeqvvaiasniggkqaletvqrllpvlcqa hgltpeqvvaiasniggkqaletvqrllpvlcqahgltpeqv vaiasniggkqaletvqrllpvlcqahgasqltpeqvvaiasn ggg<u>RPALESIVAQLSRPDPALAALTNDHL VALACLGGRPALDAVKKGLPHAPALIK RTNRRIPERTSHRVADHAQVVRVLGFF QCHSHPAQAFDDAMTQFGMSRHGLLQ LFRRVGVTELEARSGTLPPASQRWDRIL QASGMKRAKPSPTSTQTPDQASLHAFA DSLERDLDAPSMHEGDQTRAS</u> | N terminus of TALE and RVD domain in lower case; truncated TAL terminal domain in upper case and underlined |
| 85 | ZmODP2-TALE-2b ATF | M<u>HHHHHH</u>msrtrlpsppapspafsadsfsdllrqfdps lfntslfdslppfgahhteaatgewdevqsglraadappptm rvavtaarpprakpaprrraaqpsdaspaaqvdlrtlgysqq qqekikpkvrstvaqhhealvghgfthahivalsqhpaalgt vavkyqdmiaalpeatheaivgvgkqwsgaralealltva gelrgpplqldtgqllkiakrggvtaveavhawrnaltgapl nltetltpeqvvaiasnhggkqaletvqrllpvlcqahgltpe qvvaiasngggkqaletvqrllpvlcqahgltpeqvvaiasn iggkqaletvqrllpvlcqahgltpeqvvaiashdggkqale tvqrllpvlcqahgltpeqvvaiashdggkqaletvqrllpvl cqahgltpeqvvaiasniggkqaletvqrllpvlcqahgltpe qvvaiasnhggkqaletvqrllpvlcqahgltpeqvvaiasn gggkqaletvqrllpvlcqahgltpeqvvaiasngggkqale tvqrllpvlcqahgltpeqvvaiasnhggkqaletvqrllpvl cqahgltpeqvvaiasngggkqaletvqrllpvlcqahgltp eqvvaiasniggkqaletvqrllpvlcqahgltpeqvvaias ngggkqaletvqrllpvlcqahgltpeqvvaiasniggkqal etvqrllpvlcqahgltpeqvvaiasniggkqaletvqrllpvl cqahgltpeqvvaiasngggkqaletvqrllpvlcqahgasq ltpeqvvaiasnggg<u>RPALESIVAQLSRPDPAL AALTNDHLVALACLGGRPALDAVKKG LPHAPALIKRTNRRIPERTSHRVADHAQ VVRVLGFFQCHSHPAQAFDDAMTQFG MSRHGLLQLFRRVGVTELEARSGTLPP ASQRWDRILQASGMKRAKPSPTSTQTP DQASLHAFADSLERDLDAPSMHEGDQ TRAS</u>*aspkkkrkveasgs*GRA<u>dalddfdldmlqsdal ddfdldmlqsdalddfdldmlqsdalddfdldml</u> | 6 x His tag at N-terminus residues 2-7 in upper case; N terminus of TALE, RVD domain, C-terminus in lower case; truncated TAL terminal domain in upper case and underlined, extended SV40 Nuclear Localization Sequence in lowercase, double underlined, italics; VP64 transcriptional activation domain is lowercase, underlined |
| 86 | ZmODP2-TALE-2b binding site | TGTACCAGTTGTATAAAT | |

TABLE 1-continued

Biological Sequences

| SEQ ID NO: | DESCRIPTION | SEQUENCE | COMMENTS |
|---|---|---|---|
| 87 | ZmODP2-TALE-3b N-terminus, RVD, and C-terminal domain | msrtrlpsppapspafsadsfsdllrqfdpslfntslfdslppf gahhteaatgewdevqsglraadappptmrvavtaarppr akpaprrraaqpsdaspaaqvdlrtlgysqqqqekikpkvr stvaqhhealvghgfthahivalsqhpaalgtvavkyqdmi aalpeatheaivgvgkqwsgaralealltvagelrgpplqldt gqllkiakrggvtaveavhawrnaltgaplnltetltpeqvva iasnhggkqaletvqrllpvlcqahgltpeqvvaiasngggk qaletvqrllpvlcqahgltpeqvvaiashdggkqaletvqrl lpvlcqahgltpeqvvaiashdggkqaletvqrllpvlcqah gltpeqvvaiasnggkqaletvqrllpvlcqahgltpeqvv aiasnggkqaletvqrllpvlcqahgltpeqvvaiasniggk qaletvqrllpvlcqahgltpeqvvaiasniggkqaletvqrll pvlcqahgltpeqvvaiasngggkqaletvqrllpvlcqahg ltpeqvvaiasnhggkqaletvqrllpvlcqahgltpeqvva iasnhggkqaletvqrllpvlcqahgltpeqvvaiashdggk qaletvqrllpvlcqahgltpeqvvaiasngggkqaletvqrl lpvlcqahgltpeqvvaiasngggkqaletvqrllpvlcqah gltpeqvvaiashdggkqaletvqrllpvlcqahgltpeqvv aiashdggkqaletvqrllpvlcqahgasqltpeqvvaiasn gggRPALESIVAQLSRPDPALAALTNDHL VALACLGGRPALDAVKKGLPHAPALIK RTNRRIPERTSHRVADHAQVVRVLGFF QCHSHPAQAFDDAMTQFGMSRHGLLQ LFRRVGVTELEARSGTLPPASQRWDRIL QASGMKRAKPSPTSTQTPDQASLHAFA DSLERDLDAPSPMHEGDQTRAS | N terminus of TALE and RVD domain in lower case; truncated TAL terminal domain in upper case and underlined |
| 88 | ZmODP2-TALE-3b ATF | MHHHHHHmsrtrlpsppapspafsadsfsdllrqfdps lfntslfdslppfgahhteaatgewdevqsglraadappptm rvavtaarpprakpaprrraaqpsdaspaaqvdlrtlgysqq qqekikpkvrstvaqhhealvghgfthahivalsqhpaalgt vavkyqdmiaalpeatheaivgvgkqwsgaralealltva gelrgpplqldtgqllkiakrggvtaveavhawrnaltgapl nitetltpeqvvaiasnhggkqaletvqrllpvlcqahgltpe qvvaiasngggkqaletvqrllpvlcqahgltpeqvvaiash dggkqaletvqrllpvlcqahgltpeqvvaiashdggkqale tvqrllpvlcqahgltpeqvvaiasniggkqaletvqrllpvlc qahgltpeqvvaiasniggkqaletvqrllpvlcqahgltpe qvvaiasniggkqaletvqrllpvlcqahgltpeqvvaiasni ggkqaletvqrllpvlcqahgltpeqvvaiasngggkqalet vqrllpvlcqahgltpeqvvaiasnhggkqaletvqrllpvlc qahgltpeqvvaiasnhggkqaletvqrllpvlcqahgltpe qvvaiashdggkqaletvqrllpvlcqahgltpeqvvaiasn gggkqaletvqrllpvlcqahgltpeqvvaiasngggkqale tvqrllpvlcqahgltpeqvvaiashdggkqaletvqrllpvl cqahgltpeqvvaiashdggkqaletvqrllpvlcqahgas qltpeqvvaiasnggg*RPALESIVAQLSRPDPA LAALTNDHLVALACLGGRPALDAVKK GLPHAPALIKRTNRRIPERTSHRVADHA QVVRVLGFFQCHSHPAQAFDDAMTQF GMSRHGLLQLFRRVGVTELEARSGTLP PASQRWDRILQASGMKRAKPSPTSTQT PDQASLHAFADSLERDLDAPSPMHEGD QTRAS*aspkkkrkveasqsGRAdalddfdldmlqsd alddfdldmlgsdalddfdldmlgsdalddfdldml | 6 x His tag at N-terminus residues 2-7 in upper case; N terminus of TALE, RVD domain, C-terminus in lower case; truncated TAL terminal domain in upper case and underlined, SV40 Nuclear Localization Sequence in lowercase, double underlined, italics; VP64 transcriptional activation domain is lowercase, underlined |
| 89 | ZmODP2-TALE-3b binding site | TGTCCAAAATGGCTTCCT | |
| 90 | dCAS9 RNA guided DNA binding polypeptide with Nuclear Localization and Transcription Activator sequences with N-terminal 6 x His domain | MHHHHHHmdkkysiglaigtnsvgwavitdeykvp skkfkvlgntdrhsikknligallfdsgetaeatrlkrtarrrytr rknricylqeifsnemakvddsffhrleesflveedkkherh pifgnivdevayhekyptiyhlrkklvdstdkadlrliylala hmikfrghfliegdlnpdnsdvdklfiqlvqtynqlfeenpi nasgvdakailsarlsksrrlenliaqlpgekknglfgnlialsl gltpnfksnfdlaedaklqlskdtydddldnllaqigdqyadl flaaknlsdaillsdilrynteitkaplsasmikrydehhqdltl lkalvrqqlpekykeiffdqskngyagyidggasqeefykfi kpilekmdgteellvklnredllrkqrtfdngsiphqihlgel hailrrqedfypflkdnrekiekiltfripyyvgplargnsrfa wmtrkseetitpwnfeevvdkgasaqsfiermtnfdknlp nekvlpkhsllyeyftvyneltkvkyvtegmrkpaflsgeq kkaivdllfktnrkvtvkqlkedyfkkiecfdsveisgvedrf | 6 x His tag at N-terminus residues 2-7 in upper case; dCas9 domain in lowercase; extended SV40 Nuclear Localization Signal in lowercase, underlined; VP64 transcriptional activation domain in lowercase, |

TABLE 1-continued

Biological Sequences

| SEQ ID NO: | DESCRIPTION | SEQUENCE | COMMENTS |
|---|---|---|---|
| | | naslgtyhdllkiikdkdfldneenedilediv1t1t1fedremi eerlktyahlfddkvmkqlkrrrytgwgrlsrklingirdkq sgktildflksdgfanrnfmqlihddsltfkediqkaqvsgq gdslhehianlagspaikkgilqtvkvvdelvkvmgrhkp eniviemarenqttqkgqknsrermkrieegikelgsqilke hpventqlqneklylyylqngrdmyvdqeldinrlsdydv daivpqsflkddsidnkvltrsdknrgksdnvpseevvkk mknywrqllnaklitqrkfdnitkaergglseldkagfikrql vetrqitkhvaqildsrmntkydendklirevkvitlksklvs dfrkdfqfykvreinnyhhandaylnavvgtalikkypkle sefvygdykvydvrkmiakseqeigkatakyffysnimnf fkteitlangeirkrplietngetgeivwdkgrdfatvrkvls mpqvnivkktevqtggfskesilpkrnsdkliarkkdwdp kkyggfdsptvaysvlvvakvekgkskklksvkellgitim erssfeknpidfleakgykevkkdliiklpkyslfelengrkr mlasagelqkgnelalpskyvnflylashyeklkgspedne qkqlfveqhkhyldeiieqisefskrviladanldkvlsayn khrdkpireqaeniihlftltnlgapaafkyfdttidrkrytstk evldatlihqsitglyetridlsqlggdGS*pkkkrkv*SSAA GGGGSGRA*dalddfdldmlgsdalddfdldmlgsda lddfdldmlgsdalddfdldml* | italics, and double underlined |
| 91 | VPR (VP64-p65-Rta) tripartite transcriptional activator | EASGSGRADALDDFDLDMLGSDALDDF DLDMLGSDALDDFDLDMLGSDALDDF DLDMLINSRSSGSPKKKRKVGSQYLPD TDDRHRIEEKRKRTYETFKSIMKKSPFS GPTDPRPPPRRIAVPSRSSASVPKPAPQP YPFTSSLSTINYDEFPTMVFPSGQISQAS ALAPAPPQVLPQAPAPAPAPAMVSALA QAPAPVPVLAPGPPQAVAPPAPKPTQA GEGTLSEALLQLQFDDEDLGALLGNST DPAVFTDLASVDNSEFQQLLNQGIPVAP HTTEPMLMEYPEAITRLVTGAQRPPDPA PAPLGAPGLPNGLLSGDEDFSSIADMDF SALLGSGSGSRDSREGMFLPKPEAGSAI SDVFEGREVCQPKRIRPFHPPGSPWANR PLPASLAPTPTGP VHEPVGSLTPAPVPQPLDPAPAVTPEAS HLLEDPDEETSQAVKALREMADTVIPQ KEEAAICGQMDLSHPPPRGHLDELTTTL ESMTEDLNLDSPLTPELNEILDTFLNDE CLLHAMHISTGLSIFDTSLF | |
| 92 | Extended SV40 Nuclear Localization Domain | ASPKKKRKVEASGS | |
| 93 | ZnFng-WUS1 ATF | mgPKKKRKVgrlepgekpykcpecgksfsrsdklvr hqrthtgekpykcpecgksfsqssnlvrhqrthtgekpykc pecgksfsrsddlvrhqrthtgekpykcpecgksfstsgslv rhqrthtgekpykcpecgksfsrednlhthqrthtgekpykc pecgksfsdpgnlvrhqrthtgaaa*dalddfdldmldalddf dldmldalddfdldmldalddfdldml* | SV40 Nuclear Localization Sequence in uppercase, underlined; VP64 transcriptional activation domain is lowercase, double underlined, italics |
| 94 | ZnFng-WUS1 ATF Coding | ATGGGCCCTAAGAAGAAGCGCAAGGT CGGACGCCTTGAGCCCGGCGAAAAGC CATATAAATGCCCAGAGTGTGGCAAG AGCTTCAGCCGCAGCGACAAGCTTGT TCGCCATCAACGCACTCACACCGGCG AGAAGCCTTACAAGTGTCCAGAGTGC GGCAAGAGCTTCAGCCAGAGCAGCAA CCTCGTTCGCCATCAAAGGACCCACA CTGGAGAGAAACCATATAAGTGCCCA GAATGCGGAAAAAGCTTCTCCCGCAG CGATGATCTCGTCCGCCACCAGAGGA CTCACACCGGAGAGAAGCCTTATAAG TGCCCAGAGTGTGGCAAGTCCTTCTCC ACCAGCGGAAGCCTCGTTCGCCATCA GCGCACCCATACTGGAGAAAAACCTT | |

TABLE 1-continued

Biological Sequences

| SEQ ID NO: | DESCRIPTION | SEQUENCE | COMMENTS |
|---|---|---|---|
| | | ACAAGTGCCCAGAGTGTGGAAAAAGC<br>TTTAGCCGCGAGGACAATCTCCATAC<br>CCATCAACGCACCCACACTGGCGAAA<br>AGCCTTACAAATGTCCAGAGTGCGGC<br>AAGTCCTTTTCCGACCCCGGCAACCTT<br>GTTAGGCATCAAAGGACTCATACCGG<br>AGCTGCCGCTGACGCTCTTGACGATTT<br>TGATCTCGACATGCTCGACGCTCTCGA<br>TGATTTCGACCTTGACATGCTTGATGC<br>CCTCGACGATTTCGATCTCGATATGCT<br>TGATGCTCTTGACGACTTCGACCTTGA<br>TATGCTCTGA | |
| 95 | ZnFng-WUS2 ATF | mg<u>PKKKRKV</u>grlepgekpykcpecgksfsdpgalvr<br>hqrthtgekpykcpecgksfsrsdnlvrhqrthtgekpykc<br>pecgksfsqsgdlrrhqrthtgekpykcpecgksfstsgnlv<br>rhqrthtgekpykcpecgksfsrsdnlvrhqrthtgekpykc<br>pecgksfsrsdnlvrhqrthtgaaa*<u>dalddfdldmldalddf<br>dldmldalddfdldmldalddfdldml</u>* | SV40 Nuclear Localization Sequence in uppercase, underlined; VP64 transcriptional activation domain is lowercase, double underlined, italics |
| 96 | ZnFng-WUS2 ATF coding | ATGGGACCAAAAAAGAAGCGCAAGG<br>TCGGACGCCTTGAGCCCGGCGAAAAG<br>CCATATAAGTGCCCAGAGTGCGGCAA<br>GTCCTTCTCCGATCCCGGCGCCCTCGT<br>TAGGCATCAGAGGACCCACACTGGAG<br>AGAAGCCATACAAGTGTCCAGAGTGC<br>GGAAAAAGCTTCAGCCGCTCCGACAA<br>CCTCGTCCGCCATCAGCGCACCCACA<br>CCGGAGAGAAACCATACAAGTGCCCA<br>GAGTGCGGAAAGTCCTTCAGCCAGTC<br>CGGAGATCTTCGCCGCCATCAAAGGA<br>CTCATACCGGCGAGAAGCCTTATAAA<br>TGCCCAGAGTGTGGAAAATCCTTCAG<br>CACCAGCGGCAATCTCGTTCGCCACC<br>AGAGGACTCACACTGGCGAGAAGCCA<br>TATAAATGTCCAGAATGTGGCAAAAG<br>CTTTTCTCGCTCCGATAACCTCGTTCG<br>CCACCAACGCACCCATACTGGAGAAA<br>AACCTTACAAATGCCCAGAGTGTGGA<br>AAGAGCTTCTCTCGCAGCGACAACCT<br>TGTCCGCCACCAGCGCACTCATACTG<br>GAGCTGCCGCCGACGCCCTCGACGAT<br>TTCGACCTCGATATGCTTGACGCCCTC<br>GATGATTTCGACCTTGATATGCTTGAT<br>GCCCTCGATGACTTCGATCTCGACATG<br>CTCGACGCCCTTGACGACTTTGATCTC<br>GATATGCTCTGA | |
| 97 | ZnFng-WUS3 ATF | mg<u>PKKKRKV</u>grlepgekpykcpecgksfsqlahlra<br>hqrthtgekpykcpecgksfsqsgdlrrhqrthtgekpykc<br>pecgksfsttgnltvhqrthtgekpykcpecgksfsdcrdlar<br>hqrthtgekpykcpecgksfsrsddlvrhqrthtgekpykc<br>pecgksfsqssnlvrhqrthtgaaa*<u>dalddfdldmldalddf<br>dldmldalddfdldmldalddfdldml</u>* | SV40 Nuclear Localization Sequence in uppercase, underlined; VP64 transcriptional activation domain is lowercase, double underlined, italics |
| 98 | ZnFng-WUS3 ATF coding | ATGGGCCCTAAAAAGAAGCGCAAGGT<br>CGGACGCCTTGAGCCCGGCGAAAAAC<br>CTTACAAGTGCCCAGAATGCGGAAAA<br>TCCTTTAGCCAGCTCGCCCACCTTCGC<br>GCCCATCAGCGCACTCATACCGGAGA<br>GAAGCCATATAAATGCCCAGAGTGTG<br>GAAAGTCCTTCTCCCAGAGCGGCGAT<br>CTTCGCCGCCACCAGCGCACCCACAC<br>TGGAGAAAAACCTTATAAGTGTCCAG<br>AATGCGGCAAGAGCTTCAGCACCACC<br>GGCAACCTCACCGTTCACCAGAGGAC | |

TABLE 1-continued

Biological Sequences

| SEQ ID NO: | DESCRIPTION | SEQUENCE | COMMENTS |
|---|---|---|---|
| | | CCATACCGGCGAGAAGCCATACAAGT GTCCAGAGTGTGGCAAAAGCTTCAGC GACTGCCGCGATCTTGCTCGCCATCA AAGGACTCATACTGGAGAGAAGCCTT ACAAGTGTCCAGAGTGCGGCAAGTCC TTCAGCCGCTCCGATGACCTCGTTCGC CATCAGCGCACCCACACCGGCGAAAA GCCATATAAGTGTCCAGAGTGCGGAA AGAGCTTTTCCCAGAGCAGCAACCTT GTTAGGCACCAACGCACCCATACTGG AGCTGCCGCTGATGCTCTCGACGACTT CGACCTCGACATGCTTGACGCTCTCG ACGATTTCGATCTTGATATGCTTGATG CCCTCGATGATTTCGATCTCGACATGC TCGATGCTCTCGATGATTTTGACCTTG ACATGCTTTGA | |
| 99 | ZnFng-WUS4 ATF | mg<u>PKKKRKV</u>grlepgekpykcpecgksfsrsdklyr hqrthtgekpykcpecgksfstsgslvrhqrthtgekpykcp ecgksfsrednlhthqrthtgekpykcpecgksfsqksslia hqrthtgekpykcpecgksfsrsdelvrhqrthtgekpykc pecgksfsrednlhthqrthtgaaa<u>*dalddfdldmldalddf dldmldalddfdldmldalddfdldml*</u> | SV40 Nuclear Localization Sequence in uppercase, underlined; VP64 transcriptional activation domain is lowercase, double underlined, italics |
| 100 | ZnFng-WUS4 ATF coding | ATGGGACCAAAGAAGAAAAGGAAGG TCGGCCGCCTTGAGCCCGGCGAAAAG CCTTATAAGTGTCCAGAGTGTGGAAA ATCCTTCTCTCGCAGCGATAAGCTCGT TAGGCACCAACGCACCCATACTGGCG AAAAACCATATAAGTGCCCAGAGTGT GGAAAGTCCTTTAGCACTAGCGGCAG CCTTGTTAGGCACCAGCGCACCCACA CCGGCGAAAAGCCTTACAAGTGTCCA GAATGTGGCAAGAGCTTCTCCCGCGA GGATAATCTCCACACTCATCAGCGCA CCCATACCGGCGAGAAACCTTACAAG TGTCCAGAATGCGGAAAAAGCTTCAG CCAAAAAAGCAGCCTCATCGCTCATC AGAGGACTCATACCGGAGAGAAGCCT TATAAATGCCCAGAGTGCGGAAAATC CTTCAGCCGCAGCGACGAACTCGTCC GCCATCAACGCACTCACACCGGAGAA AAACCATACAAATGTCCAGAGTGCGG CAAGTCCTTTAGCCGCGAGGACAACC TCCACACCCATCAAAGGACCCACACT GGGAGCCGCTGCTGATGCCCTCGACGA CTTCGATCTTGACATGCTTGATGCTCT CGATGATTTCGATCTCGACATGCTTGA CGCCCTCGACGATTTCGACCTCGATAT GCTCGACGCCCTTGACGACTTTGACCT TGATATGCTCTGA | |
| 101 | ZnFng-WUS1- binding site in maize WUS2 promoter | GACTAGGTTGCGGAAGGG | |
| 102 | ZnFng-WUS2- binding site (minus strand) in maize WUS2 promoter | GAGGAGGATGCAGAGGTC | |
| 103 | ZnFng-WUS3- binding site in maize WUS2 promoter | GAAGCGGCCAATGCAAGA | |

TABLE 1-continued

Biological Sequences

| SEQ ID NO: | DESCRIPTION | SEQUENCE | COMMENTS |
|---|---|---|---|
| 104 | ZnFng-WUS4-binding site (minus strand) in maize WUS2 promoter | TAGGTGATATAGGTTGGG | |
| 105 | ZnFng-WUS1 AZF DNA BINDING DOMAIN | mggrlepgekpykcpecgksfsrsdklvrhqrthtgekpy kcpecgksfsqssnlvrhqrthtgekpykcpecgksfsrsd dlvrhqrthtgekpykcpecgksfstsgslvrhqrthtgekp ykcpecgksfsrednlhthqrthtgekpykcpecgksfsdp gnlvrhqrthtgaaa | Binds SEQ ID NO: 101 |
| 106 | ZnFng-WUS2 AZF DNA BINDING DOMAIN | mggrlepgekpykcpecgksfsdpgalvrhqrthtgekpy kcpecgksfsrsdnlvrhqrthtgekpykcpecgksfsqsg dlrrhqrthtgekpykcpecgksfstsgnlvrhqrthtgekp ykcpecgksfsrsdnlvrhqrthtgekpykcpecgksfsrs dnlvrhqrthtgaaa | Binds SEQ ID NO: 102 |
| 107 | ZnFng-WUS3 AZN DNA BINDING DOMAIN | mggrlepgekpykcpecgksfsqlahlrahqrthtgekpy kcpecgksfsqsgdlrrhqrthtgekpykcpecgksfsttgn ltvhqrthtgekpykcpecgksfsdcrdlarhqrthtgekpy kcpecgksfsrsddlvrhqrthtgekpykcpecgksfsqss nlvrhqrthtgaaa | Binds SEQ ID NO: 103 |
| 108 | ZnFng-WUS4 AZF DNA BINDING DOMAIN | mggrlepgekpykcpecgksfsrsdklvrhqrthtgekpy kcpecgksfstsgslvrhqrthtgekpykcpecgksfsredn lhthqrthtgekpykcpecgksfsqkssliahqrthtgekpy kcpecgksfsrsdelvrhqrthtgekpykcpecgksfsred nlhthqrthtgaaa | Binds SEQ ID NO: 104 |

The breadth and scope of the present disclosure should not be limited by any of the above-described Examples, but should be defined only in accordance with the preceding embodiments, the following claims, and their equivalents.

REFERENCES

Booher, Nicholas J., and Adam J. Bogdanove. 2014. "Tools for TAL Effector Design and Target Prediction." *Methods (San Diego, Calif)* 69 (2): 121-27. doi: 10.1016/j.ymeth.2014.06.006.

Brettschneider, R., D. Becker, and H. Lörz. 1997. "Efficient Transformation of Scutellar Tissue of Immature Maize Embryos." *Theoretical and Applied Genetics* 94 (6-7): 737-48. doi: 10.1007/s001220050473.

Brückner A, Polge C, Lentze N, Auerbach D, Schlattner U. Yeast two-hybrid, a powerful tool for systems biology. Int J Mol Sci. 2009 Jun. 18; 10(6):2763-88. doi:10.3390/ijms10062763.

Canto T. Transient Expression Systems in Plants: Potentialities and Constraints. Adv Exp Med Biol. 2016; 896: 287-301. doi:10.1007/978-3-319-27216-0_18.

Čermák, Tomáš, Shaun J. Curtin, Javier Gil-Humanes, Radim Čegan, Thomas J. Y. Kono, Eva Konečná, Joseph J. Belanto, et al. 2017. "A Multipurpose Toolkit to Enable Advanced Genome Engineering in Plants." *The Plant Cell Online* 29 (6): 1196-1217. doi: 10.1105/tpc.16.00922.

Chavez A, Scheiman J, Vora S, Pruitt B W, Tuttle M, P R Iyer E, Lin S, Kiani S, Guzman CD, Wiegand D J, Ter-Ovanesyan D, Braff J L, Davidsohn N, Housden B E, Perrimon N, Weiss R, Aach J, Collins I J, Church G M. Highly efficient Cas9-mediated transcriptional programming. Nat Methods. 2015 April; 12(4):326-8. doi: 10.1038/nmeth.3312.

Richard M. Clark, Simon Tavaré, John Doebley, Estimating a Nucleotide Substitution Rate for Maize from Polymorphism at a Major Domestication Locus, *Molecular Biology and Evolution*, Volume 22, Issue 11, November 2005, Pages 2304-2312, doi: 10.1093/molbev/msi228.

Frame, Bronwyn, Marcy Main, Rosemarie Schick, and Kan Wang. 2011. "Genetic Transformation Using Maize Immature Zygotic Embryos." *Methods in Molecular Biology (Clifton, N.J.)* 710: 327-41. https://doi.org/10.1007/978-1-61737-988-8_22.

Gao, Caixia, Jin-Long Qiu, Jinxing Liu, Kunling Chen, Yanpeng Wang, Yi Zhang, Yuan Zong, and Zhen Liang. 2016. "Efficient and Transgene-Free Genome Editing in Wheat through Transient Expression of CRISPR/Cas9 DNA or RNA." *Nature Communications* 7 (August): 12617. doi: 10.1038/ncomms12617.

Gaudelli N M, Komor A C, Rees H A, Packer M S, Badran A H, Bryson D I, Liu D R. Programmable base editing of A•T to G•C in genomic DNA without DNA cleavage. Nature. 2017 Nov. 23; 551(7681):464-471. doi: 10.1038/nature24644.

Gersbach, Charles A., Thomas Gaj, and Carlos F. Barbas. 2014. "Synthetic Zinc Finger Proteins: The Advent of Targeted Gene Regulation and Genome Modification Technologies." *Accounts of Chemical Research* 47 (8): 2309-18. doi: 10.1021/ar500039w.

Gupta, Manju, Russell C. DeKelver, Asha Palta, Carla Clifford, Sunita Gopalan, Jeffrey C. Miller, Stephen Novak, et al. 2012. "Transcriptional Activation of *Brassica Napus* β-Ketoacyl-ACP Synthase II with an Engineered Zinc Finger Protein Transcription Factor." *Plant Biotechnology Journal* 10 (7): 783-91. doi: 10.1111/j.1467-7652.2012.00695.x.

Hamada, Haruyasu, Yuelin Liu, Yozo Nagira, Ryuji Miki, Naoaki Taoka, and Ryozo Imai. 2018. "Biolistic-Delivery-Based Transient CRISPR/Cas9 Expression Enables in *Planta* Genome Editing in Wheat." *Scientific Reports* 8 (1): 14422. \ doi: 10.1038/s41598-018-32714-6.

Heiderscheit, Evan A., Asuka Eguchi, Mackenzie C. Spurgat, and Aseem Z. Ansari. 2018. "Reprogramming Cell Fate with Artificial Transcription Factors." *FEBS Letters* 592 (6): 888-900. doi: 10.1002/1873-3468.12993.

Holmes-Davis, Rachel, Guofu Li, Andrew C. Jamieson, Edward J. Rebar, Qiang Liu, Yanhong Kong, Casey C. Case, and Philip D. Gregory. 2005. "Gene Regulation in *Planta* by Plant-Derived Engineered Zinc Finger Protein Transcription Factors." *Plant Molecular Biology* 57 (3): 411-23. doi: 10.1007/s11103-004-7820-x.

Honig, Arik, Ira Marton, Michal Rosenthal, J. Jeff Smith, Michael G. Nicholson, Derek Jantz, Amir Zuker, and Alexander Vainstein. 2015. "Transient Expression of Virally Delivered Meganuclease In *Planta* Generates Inherited Genomic Deletions." *Molecular Plant* 8 (8): 1292-94. doi: 10.1016/j.molp.2015.04.001.

Horstman, Anneke, Mengfan Li, Iris Heidmann, Mieke Weemen, Baojian Chen, Jose M. Muino, Gerco C. Angenent, and Kim Boutilier. 2017. "The BABY BOOM Transcription Factor Activates the LEC1-ABI3-FUS3-LEC2 Network to Induce Somatic Embryogenesis." *Plant Physiology* 175 (2): 848-57. doi: 10.1104/pp. 17.00232.

Jantz D, Berg J M. Probing the DNA-binding affinity and specificity of designed zinc finger proteins. Biophys J. 2010 Mar. 3; 98(5):852-60. doi:10.1016/j.bpj 0.2009.11.021.

Jha P, and Kumar V. BABY BOOM (BBM): a candidate transcription factor gene in plant biotechnology. *Biotechnol Lett.* 2018 December; 40(11-12):1467-1475. doi: 10.1007/s10529-018-2613-5.

Jinek M, Chylinski K, Fonfara I, Hauer M, Doudna J A, Charpentier E. Aprogrammable dual-RNA-guided DNA endonuclease in adaptive bacterial immunity. Science. 2012 Aug. 17; 337(6096):816-21. doi: 10.1126/science.1225829.

Kirienko D R, Luo A, Sylvester A W. Reliable transient transformation of intact maize leaf cells for functional genomics and experimental study. Plant Physiol. 2012 August; 159(4):1309-18. doi: 10.1104/pp. 112.199737.

Kosugi S, Hasebe M, Matsumura N, Takashima H, Miyamoto-Sato E, Tomita M, Yanagawa H. Six classes of nuclear localization signals specific to different binding grooves of importin alpha. J Biol Chem. 2009 Jan. 2; 284(1):478-85. doi: 10.1074/jbc.M807017200.

Laux, T., K. F. Mayer, J. Berger, and G. Jurgens. 1996. "The WUSCHEL Gene Is Required for Shoot and Floral Meristem Integrity in *Arabidopsis.*" *Development* 122 (1): 87-96.

Leduc, Nathalie, Elisabeth Matthys-Rochon, Mireille Rougier, Lloyd Mogensen, Preben Holm, Jean-Louis Magnard, and Christian Dumas. 1996. "Isolated Maize Zygotes Mimicin VivoEmbryonic Development and Express Microinjected Genes When Culturedin Vitro." *Developmental Biology* 177 (1): 190-203. doi: 10.1006/dbio.1996.0155.

Leonelli, Lauriebeth, Erika Erickson, Dagmar Lyska, and Krishna K. Niyogi. 2016. "Transient Expression in *Nicotiana Benthamiana* for Rapid Functional Analysis of Genes Involved in Non-Photochemical Quenching and Carotenoid Biosynthesis." *The Plant Journal: For Cell and Molecular Biology* 88 (3): 375-86. doi: 10.1111/tpj.13268.

Li, Jian-Feng, Eunsook Park, Albrecht G. von Arnim, and Andreas Nebenführ. 2009. "The FAST Technique: A Simplified *Agrobacterium*-Based Transformation Method for Transient Gene Expression Analysis in Seedlings of *Arabidopsis* and Other Plant Species." *Plant Methods* 5 (1): 6. doi: 10.1186/1746-4811-5-6.

Li Z, Zhang D, Xiong X, Yan B, Xie W, Sheen J, Li J F. A potent Cas9-derived gene activator for plant and mammalian cells. Nat Plants. 2017 December; 3(12):930-936. doi: 10.1038/s41477-017-0046-0.

Liu, Wusheng, Joshua S. Yuan, and C. Neal Stewart. 2013. "Advanced Genetic Tools for Plant Biotechnology." *Nature Reviews. Genetics* 14 (11): 781-93. doi: 10.1038/nrg3583.

Liu, Yuchen, Jinghong Han, Zhicong Chen, Hanwei Wu, Hongsong Dong, and Guohui Nie. 2017. "Engineering Cell Signaling Using Tunable CRISPR-Cpf1-Based Transcription Factors." *Nature Communications* 8 (1): 2095. doi: 10.1038/s41467-017-02265-x.

Long L, Guo D D, Gao W, Yang W W, Hou L P, Ma X N, Miao Y C, Botella J R, Song C P. Optimization of CRISPR/Cas9 genome editing in cotton by improved sgRNA expression. Plant Methods. 2018 Oct. 3; 14:85. doi: 10.1186/s13007-018-0353-0.

Lowe, Keith, Mauricio La Rota, George Hoerster, Craig Hastings, Ning Wang, Mark Chamberlin, Emily Wu, Todd Jones, and William Gordon-Kamm. 2018. "Rapid Genotype 'Independent' *Zea Mays* L. (Maize) Transformation via Direct Somatic Embryogenesis." *In Vitro Cellular & Developmental Biology—Plant* 54 (3): 240-52. doi: 10.1007/s11627-018-9905-2.

Lowe, Keith, Emily Wu, Ning Wang, George Hoerster, Craig Hastings, Myeong-Je Cho, Chris Scelonge, et al. 2016. "Morphogenic Regulators Baby Boom and Wuschel Improve Monocot Transformation." *The Plant Cell Online* 28 (9): 1998-2015. doi: 10.1105/tpc.16.00124.

Lynch M. Evolution of the mutation rate. Trends Genet. 2010 August; 26(8):345-52. doi: 10.1016/j.tig.2010.05.003

Ma J. Transcriptional activators and activation mechanisms. Protein Cell. 2011 November; 2(11):879-88. doi: 10.1007/s13238-011-1101-7.

Mahfouz, Magdy M., Lixin Li, Md Shamimuzzaman, Anjar Wibowo, Xiaoyun Fang, and Jian-Kang Zhu. 2011. "De Novo-Engineered Transcription Activator-like Effector (TALE) Hybrid Nuclease with Novel DNA Binding Specificity Creates Double-Strand Breaks." *Proceedings of the National Academy of Sciences* 108 (6): 2623-28 doi: 10.1073/pnas.1019533108.

Martin-Ortigosa, Susana, and Kan Wang. 2014. "Proteolistics: A Biolistic Method for Intracellular Delivery of Proteins." *Transgenic Research* 23 (5): 743-56. doi: 10.1007/s11248-014-9807-y.

Mayer, Klaus F. X, Heiko Schoof, Achim Haecker, Michael Lenhard, Gerd Jürgens, and Thomas Laux. 1998. "Role of WUSCHEL in Regulating Stem Cell Fate in the *Arabidopsis* Shoot Meristem." *Cell* 95 (6): 805-15. doi: 10.1016/S0092-8674(00)81703-1.

Mookkan, Muruganantham, Kimberly Nelson-Vasilchik, Joel Hague, Zhanyuan J. Zhang, and Albert P. Kausch. 2017. "Selectable Marker Independent Transformation of Recalcitrant Maize Inbred B73 and Sorghum P898012 Mediated by Morphogenic Regulators BABY BOOM and WUSCHEL2" *Plant Cell Reports* 36 (9): 1477-91. doi: 10.1007/s00299-017-2169-1.

Moore, Richard, Anita Chandrahas, and Leonidas Bleris. 2014. "Transcription Activator-like Effectors: A Toolkit for Synthetic Biology." *ACS Synthetic Biology* 3 (10): 708-16. doi: 10.1021/sb400137b.

Nagle M, Déjardin A, Pilate G, Strauss S H. Opportunities for Innovation in Genetic Transformation of Forest Trees. Front Plant Sci. 2018 Oct. 2; 9:1443. doi: 10.3389/fpls.2018.01443

Nuccio M., Chen X., Conville J., Zhou A., Liu X. (2015) Plant Trait Gene Expression Cassette Design. In: Azhakanandam K., Silverstone A., Daniell H., Davey M. (eds) Recent Advancements in Gene Expression and Enabling Technologies in Crop Plants. Springer, New York, N.Y.

O'Reilly D, Kartje Z J, Ageely E A, Malek-Adamian E, Habibian M, Schofield A, Barkau C L, Rohilla K J, DeRossett L B, Weigle A T, Damha M J, Gagnon K T. Extensive CRISPR RNA modification reveals chemical compatibility and structure-activity relationships for Cas9 biochemical activity. Nucleic Acids Res. 2019 Jan. 25; 47(2):546-558. doi: 10.1093/nar/gky1214.

Petolino, Joseph F., and John P. Davies. 2013. "Designed Transcriptional Regulators for Trait Development." *Plant Science* 201-202 (March): 128-36. doi: 10.1016/j.plantsci.2012.12.006.

Rodriguez, Kevin, Mariano Perales, Stephen Snipes, Ram Kishor Yadav, Mercedes Diaz-Mendoza, and G. Venugopala Reddy. 2016. "DNA-Dependent Homodimerization, Sub-Cellular Partitioning, and Protein Destabilization Control WUSCHEL Levels and Spatial Patterning." *Proceedings of the National Academy of Sciences of the United States of America* 113 (41): E6307-15. doi: 10.1073/pnas.1607673113.

Sánchez, Juan Pablo, Christopher Ullman, Michael Moore, Yen Choo, and Nam-Hai Chua. 2006. "Regulation of *Arabidopsis Thaliana* 4-Coumarate: Coenzyme-A Ligase-1 Expression by Artificial Zinc Finger Chimeras." *Plant Biotechnology Journal* 4 (1): 103-14. doi: 10.1111/j.1467-7652.2005.00161.x.

Sanjana, Neville E., Le Cong, Yang Zhou, Margaret M. Cunniff, Guoping Feng, and Feng Zhang. 2012. "A Transcription Activator-like Effector Toolbox for Genome Engineering." *Nature Protocols* 7 (1): 171-92. doi: 10.1038/nprot.2011.431.

Sivamani, E., Nalapalli, S., Prairie, A. et al. *Mol Biol Rep* (2019). https://doi.org/10.1007/s11033-019-04737-3.

Schindele P, Wolter F, Puchta H. Transforming plant biology and breeding with CRISPR/Cas9, Cas12 and Cas13. *FEBS Lett.* 2018 June; 592(12):1954-1967. doi:10.1002/1873-3468.13073.

Schoof, Heiko, Michael Lenhard, Achim Haecker, Klaus F. X Mayer, Gerd Jürgens, and Thomas Laux. 2000. "The Stem Cell Population of *Arabidopsis* Shoot Meristems Is Maintained by a Regulatory Loop between the CLAVATA and WUSCHEL Genes." *Cell* 100 (6): 635-44. doi: 10.1016/50092-8674(00)80700-X.

Sera, Takashi, and Carla Uranga. 2002. "Rational Design of Artificial Zinc-Finger Proteins Using a Nondegenerate Recognition Code Table." *Biochemistry* 41 (22): 7074-81.

Soda, Neelam, Lokesh Verma, and Mender Giri. 2017. "CRISPR-Cas9 Based Plant Genome Editing: Significance, Opportunities and Recent Advances." *Plant Physiology and Biochemistry*, October. doi: 10.1016/j.plaphy.2017.10.024.

Stege, Justin T., Xuen Guan, Thao Ho, Roger N. Beachy, and Carlos F. Barbas. 2002. "Controlling Gene Expression in Plants Using Synthetic Zinc Finger Transcription Factors." *The Plant Journal: For Cell and Molecular Biology* 32 (6): 1077-86.

Thakore, Pratiksha I., and Charles A. Gersbach. 2016. "Design, Assembly, and Characterization of TALE-Based Transcriptional Activators and Repressors." *Methods in Molecular Biology (Clifton, N.J.)* 1338: 71-88. doi: 10.1007/978-1-4939-2932-0_7.

Tiwari S B, Belachew A, Ma S F, Young M, Ade J, Shen Y, Marion C M, Holtan H E, Bailey A, Stone J K, Edwards L, Wallace A D, Canales R D, Adam L, Ratcliffe O J, Repetti P P. The EDLL motif: a potent plant transcriptional activation domain from AP2/ERF transcription factors. Plant J. 2012 June; 70(5):855-65. doi: 10.1111/j.1365-313X.2012.04935.x.

Tol, Niels van, and Bert J. van der Zaal. 2014. "Artificial Transcription Factor-Mediated Regulation of Gene Expression." *Plant Science: An International Journal of Experimental Plant Biology* 225 (August): 58-67. doi: 10.1016/j.plantsci.2014.05.015.

Urnov, Fyodor D., Edward J. Rebar, Michael C. Holmes, H. Steve Zhang, and Philip D. Gregory. 2010. "Genome Editing with Engineered Zinc Finger Nucleases." *Nature Reviews. Genetics* 11 (9): 636-46. doi: 10.1038/nrg2842.

Van Eenennaam, Alison L., Guofu Li, Mylavarapu Venkatramesh, Charlene Levering, Xiaosong Gong, Andrew C. Jamieson, Edward J. Rebar, Christine K. Shewmaker, and Casey C. Case. 2004. "Elevation of Seed Alpha-Tocopherol Levels Using Plant-Based Transcription Factors Targeted to an Endogenous Locus." *Metabolic Engineering* 6 (2): 101-8. doi: 10.1016/j.ymben.2003.11.001.

Vidarsson G, Dekkers G, Rispens T. IgG subclasses and allotypes: from structure to effector functions. Front Immunol. 2014 Oct. 20; 5:520. doi: 10.3389/fimmu.2014.00520.

Wang, Kan, and Bronwyn Frame. 2009. "Biolistic Gun-Mediated Maize Genetic Transformation." *Methods in Molecular Biology (Clifton, N.J.)* 526: 29-45. doi: 10.1007/978-1-59745-494-0_3.

Wang, Wei, Qianli Pan, Fei He, Alina Akhunova, Shiaoman Chao, Harold Trick, and Eduard Akhunov. 2018. "Transgenerational CRISPR-Cas9 Activity Facilitates Multiplex Gene Editing in Allopolyploid Wheat." *The CRISPR Journal* 1 (1): 65-74. doi: 10.1089/crispr.2017.0010.

Wu, Hung-Yi, Kun-Hsiang Liu, Yi-Chieh Wang, Jing-Fen Wu, Wan-Ling Chiu, Chao-Ying Chen, Shu-Hsing Wu, Jen Sheen, and Erh-Min Lai. 2014. "AGROBEST: An Efficient *Agrobacterium*-Mediated Transient Expression Method for Versatile Gene Function Analyses in *Arabidopsis* Seedlings." *Plant Methods* 10 (1): 19. doi: 10.1186/1746-4811-10-19.

Yin H, Song C Q, Suresh S, Wu Q, Walsh S, Rhym L H, Mintzer E, Bolukbasi M F, Zhu L J, Kauffman K, Mou H, Oberholzer A, Ding J, Kwan S Y, Bogorad R L, Zatsepin T, Koteliansky V, Wolfe S A, Xue W, Langer R, Anderson D G. Structure-guided chemical modification of guide RNA enables potent non-viral in vivo genome editing. Nat. Biotechnol. 2017 December; 35(12):1179-1187. doi: 10.1038/nbt.4005.

Zhang X, Wang J, Cheng Q, Zheng X, Zhao G, Wang J. Multiplex gene regulation by CRISPR-ddCpf1. Cell Discov. 2017 Jun. 6; 3:17018. doi: 10.1038/celldisc.2017.18.

Zhang, Yi, Zhen Liang, Yuan Zong, Yanpeng Wang, Jinxing Liu, Kunling Chen, Jin-Long Qiu, and Caixia Gao. 2016. "Efficient and Transgene-Free Genome Editing in Wheat through Transient Expression of CRISPR/Cas9 DNA or RNA." *Nature Communications* 7 (August): 12617. doi: 10.1038/ncomms12617.

What is claimed is:

1. A maize plant cell comprising at least one exogenous gene transcription agent that comprises the polypeptide of SEQ ID NO:95 and stimulates transcription of the endogenous WUS2 gene, wherein expression of the endogenous WUS2 polypeptide is increased in comparison to the expression of the endogenous WUS2 polypeptide in a control maize plant cell, wherein the endogenous WUS2 polypeptide is encoded by an endogenous polynucleotide that is operably linked to an endogenous maize WUS2 promoter of SEQ ID NO:4 or an allelic variant thereof, wherein the at least one exogenous gene transcription agent comprises an artificial zinc finger (AZF) DNA binding domain polypeptide that binds to the DNA sequence of SEQ ID NO:102 in the endogenous maize WUS2 promoter of SEQ ID NO:4, and wherein the maize plant cell can form a regenerable maize plant structure.

2. The maize plant cell of claim 1, wherein an exogenous polynucleotide encoding a WUS2 polypeptide is absent before and/or during the increase in expression of the endogenous WUS2 polypeptide.

3. The maize plant cell of claim 1, wherein the increase in expression of the endogenous WUS2 polypeptide is sufficient to increase proliferation, somatic embryogenesis, and/or regeneration capacity of the maize plant cell in comparison to the control plant cell.

4. The maize plant cell of claim 1, wherein the increase in expression of the endogenous WUS2 polypeptide is sufficient to increase transformation efficiency and/or endogenous gene editing efficiency of the plant cell in comparison to the control plant cell.

5. The maize plant cell of claim 1, wherein said cell is located within or obtained from a cultured plant tissue explant, an immature embryo, a mature embryo, a leaf, and/or callus or optionally wherein the plant cell is located with or derived from the L1 or L2 layer of the immature or mature embryo.

6. The maize plant cell of claim 1, wherein the endogenous WUS2 polypeptide comprises an amino acid sequence having at least 95%, 96%, 97%, or 99% amino acid sequence identity across the entire length of SEQ ID NO:2.

7. The maize plant cell of claim 1, wherein at least two exogenous gene transcription agents comprising an AZF DNA binding domain polypeptide are provided and wherein one of the AZF DNA binding domain polypeptides binds to a DNA sequence comprising SEQ ID NO:101 and one of the AZF DNA binding domain polypeptides binds to a DNA sequence comprising SEQ ID NO:102.

8. The maize plant cell of claim 1, wherein at least two exogenous gene transcription agents are provided and wherein one of the exogenous gene transcription agents comprises the polypeptide of SEQ ID NO:93 and one of the exogenous gene transcription agents comprises the polypeptide of SEQ ID NO:95.

9. A method of producing a regenerable maize plant structure, comprising:
(i) introducing into a maize plant cell at least one exogenous gene transcription agent which comprises the polypeptide of SEQ ID NO:95 and transiently increases expression of an endogenous WUS2 polypeptide, wherein the expression is increased in comparison to the expression of the endogenous WUS2 polypeptide in a control maize plant cell, wherein the endogenous WUS2 polypeptide is encoded by an endogenous polynucleotide that is operably linked to an endogenous maize WUS2 promoter of SEQ ID NO:4 or an allelic variant thereof, and wherein the at least one exogenous gene transcription agent comprises an AZF DNA binding domain polypeptide that binds to the DNA sequence of SEQ ID NO:102 in the endogenous maize WUS2 promoter of SEQ ID NO:4; and,
(ii) culturing the maize plant cell to produce a regenerable maize plant structure.

10. The method of claim 9, wherein at least two exogenous gene transcription agents comprising an AZF DNA binding domain polypeptide are provided and wherein one of the AZF DNA binding domain polypeptides binds to a DNA molecule comprising SEQ ID NO:101 and one of the AZF DNA binding domain polypeptides binds to a DNA molecule comprising SEQ ID NO:102.

11. The method of claim 9, wherein at least two exogenous gene transcription agents are provided and wherein one of the exogenous gene transcription agents comprises the polypeptide of SEQ ID NO:93 and one of the exogenous gene transcription agents comprises the polypeptide of SEQ ID NO:95.

* * * * *

SEQUENCE LISTING

<160> NUMBER OF SEQ ID NOS: 110

<210> SEQ ID NO 1
<211> LENGTH: 709
<212> TYPE: PRT
<213> ORGANISM: Zea mays

<400> SEQUENCE: 1

```
Met Ala Thr Val Asn Asn Trp Leu Ala Phe Ser Leu Ser Pro Gln Glu
1               5                   10                  15

Leu Pro Pro Ser Gln Thr Thr Asp Ser Thr Leu Ile Ser Ala Ala Thr
            20                  25                  30

Ala Asp His Val Ser Gly Asp Val Cys Phe Asn Ile Pro Gln Asp Trp
        35                  40                  45

Ser Met Arg Gly Ser Glu Leu Ser Ala Leu Val Ala Glu Pro Lys Leu
    50                  55                  60

Glu Asp Phe Leu Gly Gly Ile Ser Phe Ser Gln His His Lys Ser
65                  70                  75                  80

Asn Cys Asn Leu Ile Pro Ser Thr Ser Ser Thr Val Cys Tyr Ala Ser
                85                  90                  95

Ser Ala Ala Ser Thr Gly Tyr His His Gln Leu Tyr Gln Pro Thr Ser
            100                 105                 110

Ser Ala Leu His Phe Ala Asp Ser Val Met Val Ala Ser Ser Ala Gly
        115                 120                 125

Val His Asp Gly Gly Ser Met Leu Ser Ala Ala Ala Asn Gly Val
    130                 135                 140

Ala Gly Ala Ala Ser Ala Asn Gly Gly Gly Ile Gly Leu Ser Met Ile
145                 150                 155                 160

Lys Asn Trp Leu Arg Ser Gln Pro Ala Pro Met Gln Pro Arg Ala Ala
                165                 170                 175

Ala Ala Glu Gly Ala Gln Gly Leu Ser Leu Ser Met Asn Met Ala Gly
            180                 185                 190

Thr Thr Gln Gly Ala Ala Gly Met Pro Leu Leu Ala Gly Glu Arg Ala
        195                 200                 205

Arg Ala Pro Glu Ser Val Ser Thr Ser Ala Gln Gly Gly Ala Val Val
    210                 215                 220

Val Thr Ala Pro Lys Glu Asp Ser Gly Gly Ser Gly Val Ala Gly Ala
225                 230                 235                 240

Leu Val Ala Val Ser Thr Asp Thr Gly Gly Ser Gly Gly Ala Ser Ala
                245                 250                 255

Asp Asn Thr Ala Arg Lys Thr Val Asp Thr Phe Gly Gln Arg Thr Ser
            260                 265                 270

Ile Tyr Arg Gly Val Thr Arg His Arg Trp Thr Gly Arg Tyr Glu Ala
        275                 280                 285

His Leu Trp Asp Asn Ser Cys Arg Arg Glu Gly Gln Thr Arg Lys Gly
    290                 295                 300

Arg Gln Val Tyr Leu Gly Gly Tyr Asp Lys Glu Glu Lys Ala Ala Arg
305                 310                 315                 320

Ala Tyr Asp Leu Ala Ala Leu Lys Tyr Trp Gly Ala Thr Thr Thr Thr
                325                 330                 335

Asn Phe Pro Val Ser Asn Tyr Glu Lys Glu Leu Glu Asp Met Lys His
            340                 345                 350

Met Thr Arg Gln Glu Phe Val Ala Ser Leu Arg Arg Lys Ser Ser Gly
        355                 360                 365
```

Phe Ser Arg Gly Ala Ser Ile Tyr Arg Gly Val Thr Arg His His Gln
    370                 375                 380

His Gly Arg Trp Gln Ala Arg Ile Gly Arg Val Ala Gly Asn Lys Asp
385                 390                 395                 400

Leu Tyr Leu Gly Thr Phe Ser Thr Gln Glu Glu Ala Ala Glu Ala Tyr
                405                 410                 415

Asp Ile Ala Ala Ile Lys Phe Arg Gly Leu Asn Ala Val Thr Asn Phe
            420                 425                 430

Asp Met Ser Arg Tyr Asp Val Lys Ser Ile Leu Asp Ser Ser Ala Leu
        435                 440                 445

Pro Ile Gly Ser Ala Ala Lys Arg Leu Lys Glu Ala Glu Ala Ala Ala
    450                 455                 460

Ser Ala Gln His His His Ala Gly Val Val Ser Tyr Asp Val Gly Arg
465                 470                 475                 480

Ile Ala Ser Gln Leu Gly Asp Gly Gly Ala Leu Ala Ala Ala Tyr Gly
                485                 490                 495

Ala His Tyr His Gly Ala Ala Trp Pro Thr Ile Ala Phe Gln Pro Gly
            500                 505                 510

Ala Ala Thr Thr Gly Leu Tyr His Pro Tyr Ala Gln Gln Pro Met Arg
        515                 520                 525

Gly Gly Gly Trp Cys Lys Gln Glu Gln Asp His Ala Val Ile Ala Ala
    530                 535                 540

Ala His Ser Leu Gln Asp Leu His His Leu Asn Leu Gly Ala Ala Gly
545                 550                 555                 560

Ala His Asp Phe Phe Ser Ala Gly Gln Gln Ala Ala Ala Ala Ala Ala
                565                 570                 575

Met His Gly Leu Ala Ser Ile Asp Ser Ala Ser Leu Glu His Ser Thr
            580                 585                 590

Gly Ser Asn Ser Val Val Tyr Asn Gly Gly Val Gly Asp Ser Asn Gly
        595                 600                 605

Ala Ser Ala Val Gly Ser Gly Gly Tyr Met Met Pro Met Ser Ala
    610                 615                 620

Ala Gly Ala Thr Thr Thr Ser Ala Met Val Ser His Glu Gln Met His
625                 630                 635                 640

Ala Arg Ala Tyr Asp Glu Ala Lys Gln Ala Ala Gln Met Gly Tyr Glu
                645                 650                 655

Ser Tyr Leu Val Asn Ala Glu Asn Gly Gly Arg Met Ser Ala
            660                 665                 670

Trp Gly Thr Val Val Ser Ala Ala Ala Ala Ala Ala Ser Ser Asn
        675                 680                 685

Asp Asn Ile Ala Ala Asp Val Gly His Gly Gly Ala Gln Leu Phe Ser
    690                 695                 700

Val Trp Asn Asp Thr
705

<210> SEQ ID NO 2
<211> LENGTH: 325
<212> TYPE: PRT
<213> ORGANISM: Zea mays

<400> SEQUENCE: 2

Met Ala Ala Asn Ala Gly Gly Gly Ala Gly Gly Gly Ser Gly Ser
1               5                   10                  15

Gly Ser Val Ala Ala Pro Ala Val Cys Arg Pro Ser Gly Ser Arg Trp
            20                  25                  30

Thr Pro Thr Pro Glu Gln Ile Arg Met Leu Lys Glu Leu Tyr Tyr Gly
            35                  40                  45

Cys Gly Ile Arg Ser Pro Ser Ser Glu Gln Ile Gln Arg Ile Thr Ala
     50                  55                  60

Met Leu Arg Gln His Gly Lys Ile Glu Gly Lys Asn Val Phe Tyr Trp
 65                  70                  75                  80

Phe Gln Asn His Lys Ala Arg Glu Arg Gln Lys Arg Arg Leu Thr Ser
                 85                  90                  95

Leu Asp Val Asn Val Pro Ala Ala Gly Ala Ala Asp Ala Thr Thr Ser
            100                 105                 110

Gln Leu Gly Val Leu Ser Leu Ser Ser Pro Ser Gly Ala Ala Pro
        115                 120                 125

Pro Ser Pro Thr Leu Gly Phe Tyr Ala Ala Gly Asn Gly Gly Ser
    130                 135                 140

Ala Gly Leu Leu Asp Thr Ser Ser Asp Trp Gly Ser Ser Gly Ala Ala
145                 150                 155                 160

Met Ala Thr Glu Thr Cys Phe Leu Gln Asp Tyr Met Gly Val Thr Asp
                165                 170                 175

Thr Gly Ser Ser Ser Gln Trp Pro Cys Phe Ser Ser Asp Thr Ile
            180                 185                 190

Met Ala Ala Ala Ala Ala Ala Arg Val Ala Thr Thr Arg Ala Pro
        195                 200                 205

Glu Thr Leu Pro Leu Phe Pro Thr Cys Gly Asp Asp Asp Asp Asp
    210                 215                 220

Ser Gln Pro Pro Pro Arg Pro Arg His Ala Val Pro Val Pro Ala Gly
225                 230                 235                 240

Glu Thr Ile Arg Gly Gly Gly Ser Ser Ser Tyr Leu Pro Phe
                245                 250                 255

Trp Gly Ala Gly Ala Ala Ser Thr Thr Ala Gly Ala Thr Ser Ser Val
                260                 265                 270

Ala Ile Gln Gln Gln His Gln Leu Gln Glu Gln Tyr Ser Phe Tyr Ser
        275                 280                 285

Asn Ser Thr Gln Leu Ala Gly Thr Gly Ser Gln Asp Val Ser Ala Ser
    290                 295                 300

Ala Ala Ala Leu Glu Leu Ser Leu Ser Ser Trp Cys Ser Pro Tyr Pro
305                 310                 315                 320

Ala Ala Gly Ser Met
            325

<210> SEQ ID NO 3
<211> LENGTH: 791
<212> TYPE: DNA
<213> ORGANISM: Zea mays

<400> SEQUENCE: 3
aaatggccgt gacaacgtat actattatcg agtaaaaggt cgccacttta gtagtacatg      60
tacatgcatg cgcagataca tcatcaggta ctcatatatg ggcacacata tagacatgtt     120
ttgaggaaaa tgagacaaag tatagtggag acttccctag aaagcagaag aaaaagaagt     180
ggtttatgtt ccgttaaatc atactacaac ttttttttat tatactctcc attttgtcat     240
cattaggtac tcatatatgg gcacacatat agtactgcca attttcttg ctaaaaaaag      300 ttccactata tatatgtatg tatgcacaaa taaactaatt ttcttagaaa agaaaaccgg     360
tgtaatacat actaagggct agtttgggaa ccctggtttt ctaaggaatt ttatttttcc     420

```
aaaaaaaata gtttattttt ccttcggaaa ttaggaatct cttataaaat tcgagttccc      480
aaactattcc taatatatat atcatactct ccatcagtct atatatagat tacatatagt      540
aagtatagag tatctcgcta tcacatagtg ccactaatct tctggagtgt accagttgta      600
taaatatcta tcagtatcag cactactgtt tgctgaatac cccaaaactc tctgcttgac      660
ttctcttccc taacctttgc actgtccaaa atggcttcct gatcccctca cttcctcgaa      720
tcattctaag aagaaactca agccgctacc attaggggca gattaattgc tgcactttca      780
gataatctac c                                                           791
```

<210> SEQ ID NO 4
<211> LENGTH: 609
<212> TYPE: DNA
<213> ORGANISM: Zea mays

<400> SEQUENCE: 4

```
cattgaacaa tggagctgca agagcaatga tgcactagct agtgtaatgc agtgcatgca       60
tggtagattg gtagctagcc tttgcagttt gcaccaggca ccagcagcag ctagaagacg      120
acagacgaca ggggcttgac taggttgcgg aagggcagtt gccagttgcc acaaggggag      180
cctggacctc tgcatcctcc tcatgatagc tctgtctctc tcacacacac acacagtcac      240
acagagacac gcaaatgact tctgtctcta actcttccaa atttcgaagc ggccaatgca      300
agagccagcc cccggccgta tgtcaacttc acttgtctct ctccaaaaga tatcgtatca      360
cccatgggca atggccatga ccccctccc agccccaacc tatatcacct agcgcagcta      420
cgctctcttc tcccgctctc gctctctgct ggctgcatgc tagctacctt ctagctatct      480
agcctctagc tccaatgcac tcctcctta taaacaagga accctccttc ggctctcttg      540
ccatagaccg gacaccggag agctaggtca cagaagcgct caggaaggcc gctgcgctga      600
gatagaggc                                                              609
```

<210> SEQ ID NO 5
<211> LENGTH: 176
<212> TYPE: PRT
<213> ORGANISM: Artificial sequence
<220> FEATURE:
<223> OTHER INFORMATION: synthetic

<400> SEQUENCE: 5

```
Leu Glu Pro Gly Glu Lys Pro Tyr Lys Cys Pro Glu Cys Gly Lys Ser
1               5                   10                  15

Phe Ser Gln Ser Ser Leu Val Arg His Gln Arg Thr His Thr Gly
                20                  25                  30

Glu Lys Pro Tyr Lys Cys Pro Glu Cys Gly Lys Ser Phe Ser Arg Ala
                35                  40                  45

Asp Asn Leu Thr Glu His Gln Arg Thr His Thr Gly Glu Lys Pro Tyr
            50                  55                  60

Lys Cys Pro Glu Cys Gly Lys Ser Phe Ser Thr Ser Gly Asn Leu Thr
65                  70                  75                  80

Glu His Gln Arg Thr His Thr Gly Glu Lys Pro Tyr Lys Cys Pro Glu
                85                  90                  95

Cys Gly Lys Ser Phe Ser Thr Ser Gly Asn Leu Thr Glu His Gln Arg
                100                 105                 110

Thr His Thr Gly Glu Lys Pro Tyr Lys Cys Pro Glu Cys Gly Lys Ser
                115                 120                 125
```

```
Phe Ser Gln Lys Ser Ser Leu Ile Ala His Gln Arg Thr His Thr Gly
        130                 135                 140
Glu Lys Pro Tyr Lys Cys Pro Glu Cys Gly Lys Ser Phe Ser Arg Ala
145                 150                 155                 160
Asp Asn Leu Thr Glu His Gln Arg Thr His Thr Gly Lys Lys Thr Ser
                165                 170                 175
```

<210> SEQ ID NO 6
<211> LENGTH: 18
<212> TYPE: DNA
<213> ORGANISM: Zea mays

<400> SEQUENCE: 6
cagatacatc atcaggta                                              18

<210> SEQ ID NO 7
<211> LENGTH: 260
<212> TYPE: PRT
<213> ORGANISM: Artificial sequence
<220> FEATURE:
<223> OTHER INFORMATION: synthetic

<400> SEQUENCE: 7

```
Met Arg Lys Arg Lys Glu Ser Asn Arg Glu Ser Ala Arg Arg Ser Arg
1               5                   10                  15
Arg Ser Arg Tyr Arg Lys Lys Val Leu Glu Pro Gly Glu Lys Pro Tyr
                20                  25                  30
Lys Cys Pro Glu Cys Gly Lys Ser Phe Ser Gln Ser Ser Leu Val
            35                  40                  45
Arg His Gln Arg Thr His Thr Gly Glu Lys Pro Tyr Lys Cys Pro Glu
        50                  55                  60
Cys Gly Lys Ser Phe Ser Arg Ala Asp Asn Leu Thr Glu His Gln Arg
65                  70                  75                  80
Thr His Thr Gly Glu Lys Pro Tyr Lys Cys Pro Glu Cys Gly Lys Ser
                85                  90                  95
Phe Ser Thr Ser Gly Asn Leu Thr Glu His Gln Arg Thr His Thr Gly
            100                 105                 110
Glu Lys Pro Tyr Lys Cys Pro Glu Cys Gly Lys Ser Phe Ser Thr Ser
        115                 120                 125
Gly Asn Leu Thr Glu His Gln Arg Thr His Thr Gly Glu Lys Pro Tyr
    130                 135                 140
Lys Cys Pro Glu Cys Gly Lys Ser Phe Ser Gln Lys Ser Ser Leu Ile
145                 150                 155                 160
Ala His Gln Arg Thr His Thr Gly Glu Lys Pro Tyr Lys Cys Pro Glu
                165                 170                 175
Cys Gly Lys Ser Phe Ser Arg Ala Asp Asn Leu Thr Glu His Gln Arg
            180                 185                 190
Thr His Thr Gly Lys Lys Thr Ser Ala Gly Ser Ser Asp Asp Cys Ser
        195                 200                 205
Ser Ala Ala Ser Val Ser Leu Arg Val Gly Ser His Asp Glu Pro Cys
    210                 215                 220
Phe Ser Gly Asp Gly Asp Gly Asp Trp Met Asp Asp Val Arg Ala Leu
225                 230                 235                 240
Ala Ser Phe Leu Glu Ser Asp Glu Asp Trp Leu Arg Cys Gln Thr Ala
                245                 250                 255
Gly Gln Leu Ala
        260
```

<210> SEQ ID NO 8
<211> LENGTH: 176
<212> TYPE: PRT
<213> ORGANISM: Artificial sequence
<220> FEATURE:
<223> OTHER INFORMATION: synthetic

<400> SEQUENCE: 8

```
Leu Glu Pro Gly Glu Lys Pro Tyr Lys Cys Pro Glu Cys Gly Lys Ser
1               5                   10                  15

Phe Ser Gln Ser Gly Asp Leu Arg Arg His Gln Arg Thr His Thr Gly
            20                  25                  30

Glu Lys Pro Tyr Lys Cys Pro Glu Cys Gly Lys Ser Phe Ser Thr Ser
        35                  40                  45

Gly Asn Leu Thr Glu His Gln Arg Thr His Thr Gly Glu Lys Pro Tyr
    50                  55                  60

Lys Cys Pro Glu Cys Gly Lys Ser Phe Ser Gln Ser Ser Ser Leu Val
65                  70                  75                  80

Arg His Gln Arg Thr His Thr Gly Glu Lys Pro Tyr Lys Cys Pro Glu
                85                  90                  95

Cys Gly Lys Ser Phe Ser Thr Ser Gly Asn Leu Thr Glu His Gln Arg
            100                 105                 110

Thr His Thr Gly Glu Lys Pro Tyr Lys Cys Pro Glu Cys Gly Lys Ser
        115                 120                 125

Phe Ser Gln Ser Ser Ser Leu Val Arg His Gln Arg Thr His Thr Gly
    130                 135                 140

Glu Lys Pro Tyr Lys Cys Pro Glu Cys Gly Lys Ser Phe Ser Gln Ser
145                 150                 155                 160

Ser Ser Leu Val Arg His Gln Arg Thr His Thr Gly Lys Lys Thr Ser
                165                 170                 175
```

<210> SEQ ID NO 9
<211> LENGTH: 18
<212> TYPE: DNA
<213> ORGANISM: Zea mays

<400> SEQUENCE: 9
gtagtacatg tacatgca                                                      18

<210> SEQ ID NO 10
<211> LENGTH: 260
<212> TYPE: PRT
<213> ORGANISM: Artificial sequence
<220> FEATURE:
<223> OTHER INFORMATION: synthetic

<400> SEQUENCE: 10

```
Met Arg Lys Arg Lys Glu Ser Asn Arg Glu Ser Ala Arg Arg Ser Arg
1               5                   10                  15

Arg Ser Arg Tyr Arg Lys Val Leu Glu Pro Gly Glu Lys Pro Tyr
            20                  25                  30

Lys Cys Pro Glu Cys Gly Lys Ser Phe Ser Gln Ser Gly Asp Leu Arg
        35                  40                  45

Arg His Gln Arg Thr His Thr Gly Glu Lys Pro Tyr Lys Cys Pro Glu
    50                  55                  60

Cys Gly Lys Ser Phe Ser Thr Ser Gly Asn Leu Thr Glu His Gln Arg
65                  70                  75                  80
```

```
Thr His Thr Gly Glu Lys Pro Tyr Lys Cys Pro Glu Cys Gly Lys Ser
                85                  90                  95

Phe Ser Gln Ser Ser Ser Leu Val Arg His Gln Arg Thr His Thr Gly
            100                 105                 110

Glu Lys Pro Tyr Lys Cys Pro Glu Cys Gly Lys Ser Phe Ser Thr Ser
        115                 120                 125

Gly Asn Leu Thr Glu His Gln Arg Thr His Thr Gly Glu Lys Pro Tyr
    130                 135                 140

Lys Cys Pro Glu Cys Gly Lys Ser Phe Ser Gln Ser Ser Ser Leu Val
145                 150                 155                 160

Arg His Gln Arg Thr His Thr Gly Glu Lys Pro Tyr Lys Cys Pro Glu
                165                 170                 175

Cys Gly Lys Ser Phe Ser Gln Ser Ser Ser Leu Val Arg His Gln Arg
            180                 185                 190

Thr His Thr Gly Lys Lys Thr Ser Ala Gly Ser Ser Asp Asp Cys Ser
        195                 200                 205

Ser Ala Ala Ser Val Ser Leu Arg Val Gly Ser His Asp Glu Pro Cys
    210                 215                 220

Phe Ser Gly Asp Gly Asp Gly Asp Trp Met Asp Val Arg Ala Leu
225                 230                 235                 240

Ala Ser Phe Leu Glu Ser Asp Glu Asp Trp Leu Arg Cys Gln Thr Ala
                245                 250                 255

Gly Gln Leu Ala
        260

<210> SEQ ID NO 11
<211> LENGTH: 176
<212> TYPE: PRT
<213> ORGANISM: Artificial sequence
<220> FEATURE:
<223> OTHER INFORMATION: synthetic

<400> SEQUENCE: 11

Leu Glu Pro Gly Glu Lys Pro Tyr Lys Cys Pro Glu Cys Gly Lys Ser
1               5                   10                  15

Phe Ser Gln Ala Gly His Leu Ala Ser His Gln Arg Thr His Thr Gly
            20                  25                  30

Glu Lys Pro Tyr Lys Cys Pro Glu Cys Gly Lys Ser Phe Ser Thr Ser
        35                  40                  45

Gly Asn Leu Thr Glu His Gln Arg Thr His Thr Gly Glu Lys Pro Tyr
    50                  55                  60

Lys Cys Pro Glu Cys Gly Lys Ser Phe Ser Arg Ser Asp Lys Leu Thr
65                  70                  75                  80

Glu His Gln Arg Thr His Thr Gly Glu Lys Pro Tyr Lys Cys Pro Glu
                85                  90                  95

Cys Gly Lys Ser Phe Ser Arg Asn Asp Ala Leu Thr Glu His Gln Arg
            100                 105                 110

Thr His Thr Gly Glu Lys Pro Tyr Lys Cys Pro Glu Cys Gly Lys Ser
        115                 120                 125

Phe Ser Gln Ser Ser Asn Leu Val Arg His Gln Arg Thr His Thr Gly
    130                 135                 140

Glu Lys Pro Tyr Lys Cys Pro Glu Cys Gly Lys Ser Phe Ser Thr Thr
145                 150                 155                 160

Gly Asn Leu Thr Val His Gln Arg Thr His Thr Gly Lys Lys Thr Ser
                165                 170                 175
```

<210> SEQ ID NO 12
<211> LENGTH: 18
<212> TYPE: DNA
<213> ORGANISM: Zea mays

<400> SEQUENCE: 12
aatgaactgc ggcattga                                                     18

<210> SEQ ID NO 13
<211> LENGTH: 260
<212> TYPE: PRT
<213> ORGANISM: Artificial sequence
<220> FEATURE:
<223> OTHER INFORMATION: synthetic

<400> SEQUENCE: 13

Met Arg Lys Arg Lys Glu Ser Asn Arg Glu Ser Ala Arg Arg Ser Arg
1               5                   10                  15

Arg Ser Arg Tyr Arg Lys Lys Val Leu Glu Pro Gly Glu Lys Pro Tyr
            20                  25                  30

Lys Cys Pro Glu Cys Gly Lys Ser Phe Ser Gln Ala Gly His Leu Ala
        35                  40                  45

Ser His Gln Arg Thr His Thr Gly Glu Lys Pro Tyr Lys Cys Pro Glu
    50                  55                  60

Cys Gly Lys Ser Phe Ser Thr Ser Gly Asn Leu Thr Glu His Gln Arg
65                  70                  75                  80

Thr His Thr Gly Glu Lys Pro Tyr Lys Cys Pro Glu Cys Gly Lys Ser
                85                  90                  95

Phe Ser Arg Ser Asp Lys Leu Thr Glu His Gln Arg Thr His Thr Gly
            100                 105                 110

Glu Lys Pro Tyr Lys Cys Pro Glu Cys Gly Lys Ser Phe Ser Arg Asn
        115                 120                 125

Asp Ala Leu Thr Glu His Gln Arg Thr His Thr Gly Glu Lys Pro Tyr
    130                 135                 140

Lys Cys Pro Glu Cys Gly Lys Ser Phe Ser Gln Ser Ser Asn Leu Val
145                 150                 155                 160

Arg His Gln Arg Thr His Thr Gly Glu Lys Pro Tyr Lys Cys Pro Glu
                165                 170                 175

Cys Gly Lys Ser Phe Ser Thr Thr Gly Asn Leu Thr Val His Gln Arg
            180                 185                 190

Thr His Thr Gly Lys Lys Thr Ser Ala Gly Ser Ser Asp Asp Cys Ser
        195                 200                 205

Ser Ala Ala Ser Val Ser Leu Arg Val Gly Ser His Asp Glu Pro Cys
    210                 215                 220

Phe Ser Gly Asp Gly Asp Gly Asp Trp Met Asp Asp Val Arg Ala Leu
225                 230                 235                 240

Ala Ser Phe Leu Glu Ser Asp Glu Asp Trp Leu Arg Cys Gln Thr Ala
                245                 250                 255

Gly Gln Leu Ala
        260

<210> SEQ ID NO 14
<211> LENGTH: 176
<212> TYPE: PRT
<213> ORGANISM: Artificial sequence
<220> FEATURE:
<223> OTHER INFORMATION: synthetic

<400> SEQUENCE: 14

| Leu | Glu | Pro | Gly | Glu | Lys | Pro | Tyr | Lys | Cys | Pro | Glu | Cys | Gly | Lys | Ser |
| 1 | | | | 5 | | | | | 10 | | | | | 15 | |

| Phe | Ser | Arg | Ser | Asp | Asn | Leu | Val | Arg | His | Gln | Arg | Thr | His | Thr | Gly |
| | | | 20 | | | | | 25 | | | | | 30 | | |

| Glu | Lys | Pro | Tyr | Lys | Cys | Pro | Glu | Cys | Gly | Lys | Ser | Phe | Ser | Arg | Arg |
| | | | 35 | | | | | 40 | | | | | 45 | | |

| Asp | Glu | Leu | Asn | Val | His | Gln | Arg | Thr | His | Thr | Gly | Glu | Lys | Pro | Tyr |
| | | 50 | | | | | 55 | | | | | 60 | | | |

| Lys | Cys | Pro | Glu | Cys | Gly | Lys | Ser | Phe | Ser | Pro | Ala | Asp | Leu | Thr |
| 65 | | | | 70 | | | | | 75 | | | | | 80 |

| Arg | His | Gln | Arg | Thr | His | Thr | Gly | Glu | Lys | Pro | Tyr | Lys | Cys | Pro | Glu |
| | | | | 85 | | | | | 90 | | | | | 95 | |

| Cys | Gly | Lys | Ser | Phe | Ser | Gln | Ala | Gly | His | Leu | Ala | Ser | His | Gln | Arg |
| | | | 100 | | | | | 105 | | | | | 110 | | |

| Thr | His | Thr | Gly | Glu | Lys | Pro | Tyr | Lys | Cys | Pro | Glu | Cys | Gly | Lys | Ser |
| | | | 115 | | | | | 120 | | | | | 125 | | |

| Phe | Ser | Thr | Ser | Gly | Asn | Leu | Thr | Glu | His | Gln | Arg | Thr | His | Thr | Gly |
| | | | 130 | | | | | 135 | | | | | 140 | | |

| Glu | Lys | Pro | Tyr | Lys | Cys | Pro | Glu | Cys | Gly | Lys | Ser | Phe | Ser | Arg | Ser |
| 145 | | | | 150 | | | | | 155 | | | | | 160 |

| Asp | Lys | Leu | Thr | Glu | His | Gln | Arg | Thr | His | Thr | Gly | Lys | Lys | Thr | Ser |
| | | | 165 | | | | | 170 | | | | | 175 | | |

<210> SEQ ID NO 15
<211> LENGTH: 18
<212> TYPE: DNA
<213> ORGANISM: Zea mays

<400> SEQUENCE: 15
cggcattgaa caatggag                                                   18

<210> SEQ ID NO 16
<211> LENGTH: 260
<212> TYPE: PRT
<213> ORGANISM: Artificial sequence
<220> FEATURE:
<223> OTHER INFORMATION: synthetic

<400> SEQUENCE: 16

| Met | Arg | Lys | Arg | Lys | Glu | Ser | Asn | Arg | Glu | Ser | Ala | Arg | Arg | Ser | Arg |
| 1 | | | | 5 | | | | | 10 | | | | | 15 | |

| Arg | Ser | Arg | Tyr | Arg | Lys | Lys | Val | Leu | Glu | Pro | Gly | Glu | Lys | Pro | Tyr |
| | | | 20 | | | | | 25 | | | | | 30 | | |

| Lys | Cys | Pro | Glu | Cys | Gly | Lys | Ser | Phe | Ser | Arg | Ser | Asp | Asn | Leu | Val |
| | | | 35 | | | | | 40 | | | | | 45 | | |

| Arg | His | Gln | Arg | Thr | His | Thr | Gly | Glu | Lys | Pro | Tyr | Lys | Cys | Pro | Glu |
| | | 50 | | | | | 55 | | | | | 60 | | | |

| Cys | Gly | Lys | Ser | Phe | Ser | Arg | Arg | Asp | Glu | Leu | Asn | Val | His | Gln | Arg |
| 65 | | | | 70 | | | | | 75 | | | | | 80 |

| Thr | His | Thr | Gly | Glu | Lys | Pro | Tyr | Lys | Cys | Pro | Glu | Cys | Gly | Lys | Ser |
| | | | | 85 | | | | | 90 | | | | | 95 | |

| Phe | Ser | Ser | Pro | Ala | Asp | Leu | Thr | Arg | His | Gln | Arg | Thr | His | Thr | Gly |
| | | | 100 | | | | | 105 | | | | | 110 | | |

| Glu | Lys | Pro | Tyr | Lys | Cys | Pro | Glu | Cys | Gly | Lys | Ser | Phe | Ser | Gln | Ala |
| | | | 115 | | | | | 120 | | | | | 125 | | |

Gly His Leu Ala Ser His Gln Arg Thr His Thr Gly Glu Lys Pro Tyr
    130                 135                 140

Lys Cys Pro Glu Cys Gly Lys Ser Phe Ser Thr Ser Gly Asn Leu Thr
145                 150                 155                 160

Glu His Gln Arg Thr His Thr Gly Glu Lys Pro Tyr Lys Cys Pro Glu
                165                 170                 175

Cys Gly Lys Ser Phe Ser Arg Ser Asp Lys Leu Thr Glu His Gln Arg
                180                 185                 190

Thr His Thr Gly Lys Lys Thr Ser Ala Gly Ser Ser Asp Asp Cys Ser
            195                 200                 205

Ser Ala Ala Ser Val Ser Leu Arg Val Gly Ser His Asp Glu Pro Cys
210                 215                 220

Phe Ser Gly Asp Gly Asp Gly Asp Trp Met Asp Asp Val Arg Ala Leu
225                 230                 235                 240

Ala Ser Phe Leu Glu Ser Asp Glu Asp Trp Leu Arg Cys Gln Thr Ala
                245                 250                 255

Gly Gln Leu Ala
        260

<210> SEQ ID NO 17
<211> LENGTH: 1173
<212> TYPE: PRT
<213> ORGANISM: Artificial sequence
<220> FEATURE:
<223> OTHER INFORMATION: synthetic

<400> SEQUENCE: 17

Met Ala Pro Lys Lys Arg Lys Val Asp Tyr Lys Asp His Asp Gly
1               5                   10                  15

Asp Tyr Lys Asp His Asp Ile Asp Tyr Lys Asp Asp Asp Lys Gly
                20                  25                  30

Thr Val Asp Leu Arg Thr Leu Gly Tyr Ser Gln Gln Gln Gln Glu Lys
            35                  40                  45

Ile Lys Pro Lys Val Arg Ser Thr Val Ala Gln His His Glu Ala Leu
50                  55                  60

Val Gly His Gly Phe Thr His Ala His Ile Val Ala Leu Ser Gln His
65                  70                  75                  80

Pro Ala Ala Leu Gly Thr Val Ala Val Lys Tyr Gln Asp Met Ile Ala
                85                  90                  95

Ala Leu Pro Glu Ala Thr His Glu Ala Ile Val Gly Val Gly Lys Gln
                100                 105                 110

Trp Ser Gly Ala Arg Ala Leu Glu Ala Leu Leu Thr Val Ala Gly Glu
            115                 120                 125

Leu Arg Gly Pro Pro Leu Gln Leu Asp Thr Gly Gln Leu Leu Lys Ile
    130                 135                 140

Ala Lys Arg Gly Gly Val Thr Ala Val Glu Ala Val His Ala Trp Arg
145                 150                 155                 160

Asn Ala Leu Thr Gly Ala Pro Leu Asn Leu Thr Pro Glu Gln Val Val
                165                 170                 175

Ala Ile Leu Thr Pro Glu Gln Val Val Ala Ile Ala Ser Asn His Gly
            180                 185                 190

Gly Lys Gln Ala Leu Glu Thr Val Gln Arg Leu Leu Pro Val Leu Cys
        195                 200                 205

Gln Ala His Gly Leu Thr Pro Glu Gln Val Val Ala Ile Ala Ser Asn
    210                 215                 220

```
His Gly Gly Lys Gln Ala Leu Glu Thr Val Gln Arg Leu Leu Pro Val
225                 230                 235                 240

Leu Cys Gln Ala His Gly Leu Thr Pro Glu Gln Val Val Ala Ile Ala
            245                 250                 255

Ser His Asp Gly Gly Lys Gln Ala Leu Glu Thr Val Gln Arg Leu Leu
        260                 265                 270

Pro Val Leu Cys Gln Ala His Gly Leu Thr Pro Glu Gln Val Val Ala
    275                 280                 285

Ile Ala Ser His Asp Gly Gly Lys Gln Ala Leu Glu Thr Val Gln Arg
290                 295                 300

Leu Leu Pro Val Leu Cys Gln Ala His Gly Leu Thr Pro Glu Gln Val
305                 310                 315                 320

Val Ala Ile Ala Ser His Asp Gly Gly Lys Gln Ala Leu Glu Thr Val
                325                 330                 335

Gln Arg Leu Leu Pro Val Leu Cys Gln Ala His Gly Leu Thr Pro Glu
            340                 345                 350

Gln Val Val Ala Ile Ala Ser Asn Gly Gly Lys Gln Ala Leu Glu
        355                 360                 365

Thr Val Gln Arg Leu Leu Pro Val Leu Cys Gln Ala His Leu Thr Pro
370                 375                 380

Glu Gln Val Val Ala Ile Ala Ser His Asp Gly Gly Lys Gln Ala Leu
385                 390                 395                 400

Glu Thr Val Gln Arg Leu Leu Pro Val Leu Cys Gln Ala His Gly Leu
                405                 410                 415

Thr Pro Glu Gln Val Val Ala Ile Ala Ser Asn Gly Gly Lys Gln
        420                 425                 430

Ala Leu Glu Thr Val Gln Arg Leu Leu Pro Val Leu Cys Gln Ala His
            435                 440                 445

Gly Leu Thr Pro Glu Gln Val Val Ala Ile Ala Ser His Gly Gly
        450                 455                 460

Lys Gln Ala Leu Glu Thr Val Gln Arg Leu Leu Pro Val Leu Cys Gln
465                 470                 475                 480

Ala His Gly Leu Thr Pro Glu Gln Val Val Ala Ile Ala Ser His Asp
                485                 490                 495

Gly Gly Lys Gln Ala Leu Glu Thr Val Gln Arg Leu Leu Pro Val Leu
        500                 505                 510

Cys Gln Ala His Gly Leu Thr Pro Glu Gln Val Val Ala Ile Ala Ser
            515                 520                 525

Asn Ile Gly Gly Lys Gln Ala Leu Glu Thr Val Gln Arg Leu Leu Pro
530                 535                 540

Val Leu Cys Gln Ala His Gly Leu Thr Pro Glu Gln Val Val Ala Ile
545                 550                 555                 560

Ala Ser Asn Gly Gly Lys Gln Ala Leu Glu Thr Val Gln Arg Leu
                565                 570                 575

Leu Pro Val Leu Cys Gln Ala His Gly Leu Thr Pro Glu Gln Val Val
            580                 585                 590

Ala Ile Ala Ser His Asp Gly Gly Lys Gln Ala Leu Glu Thr Val Gln
        595                 600                 605

Arg Leu Leu Pro Val Leu Cys Gln Ala His Gly Leu Thr Pro Glu Gln
    610                 615                 620

Val Val Ala Ile Ala Ser His Asp Gly Gly Lys Gln Ala Leu Glu Thr
625                 630                 635                 640

Val Gln Arg Leu Leu Pro Val Leu Cys Gln Ala His Gly Leu Thr Pro
```

-continued

```
                645                 650                 655
Glu Gln Val Val Ala Ile Ala Ser Asn Gly Gly Gly Lys Gln Ala Leu
                660                 665                 670

Glu Thr Val Gln Arg Leu Leu Pro Val Leu Cys Gln Ala His Gly Leu
                675                 680                 685

Thr Pro Glu Gln Val Val Ala Ile Ala Ser His Asp Gly Gly Lys Gln
    690                 695                 700

Ala Leu Glu Thr Val Gln Arg Leu Leu Pro Val Leu Cys Gln Ala His
705                 710                 715                 720

Gly Leu Thr Pro Glu Gln Val Val Ala Ile Ala Ser His Asp Gly Gly
                    725                 730                 735

Lys Gln Ala Leu Glu Thr Val Gln Arg Leu Leu Pro Val Leu Cys Gln
                740                 745                 750

Ala His Gly Leu Thr Pro Glu Gln Val Val Ala Ile Ala Ser Asn Gly
                755                 760                 765

Gly Gly Lys Gln Ala Leu Glu Thr Val Gln Arg Leu Leu Pro Val Leu
                770                 775                 780

Cys Gln Ala His Gly Leu Thr Pro Glu Gln Val Val Ala Ile Ala Ser
785                 790                 795                 800

His Asp Gly Gly Lys Gln Ala Leu Glu Thr Val Gln Arg Leu Leu Pro
                    805                 810                 815

Val Leu Cys Gln Ala His Gly Leu Thr Pro Glu Gln Val Val Ala Ile
                820                 825                 830

Ala Ser Asn Ile Gly Gly Lys Gln Ala Leu Glu Thr Val Gln Arg Leu
                835                 840                 845

Leu Pro Val Leu Cys Gln Ala His Gly Leu Thr Pro Glu Gln Val Val
850                 855                 860

Ala Ile Ala Ser Asn Gly Gly Gly Lys Gln Ala Leu Glu Thr Val Gln
865                 870                 875                 880

Arg Leu Leu Pro Val Leu Cys Gln Ala His Gly Leu Thr Pro Glu Gln
                885                 890                 895

Val Val Ala Ile Ala Ser Asn His Gly Gly Lys Gln Ala Leu Glu Thr
                900                 905                 910

Val Gln Arg Leu Leu Pro Val Leu Cys Gln Ala His Gly Leu Thr Pro
                915                 920                 925

Glu Gln Val Val Ala Ile Ala Ser Asn Ile Gly Gly Lys Gln Ala Leu
                930                 935                 940

Glu Thr Val Gln Arg Leu Leu Pro Val Leu Cys Gln Ala His Gly Leu
945                 950                 955                 960

Thr Pro Glu Gln Val Val Ala Ile Ala Ser Asn Gly Gly Gly Lys Gln
                    965                 970                 975

Ala Leu Glu Thr Val Gln Arg Leu Leu Pro Val Leu Cys Gln Ala His
                980                 985                 990

Gly Leu Thr Pro Glu Gln Val Val Ala Ile Ala Ser Asn Ile Gly Gly
                995                 1000                1005

Lys Gln Ala Leu Glu Thr Val Gln Arg Leu Leu Pro Val Leu Cys
                1010                1015                1020

Gln Ala His Gly Leu Thr Pro Glu Gln Val Val Ala Ile Ala Ser
                1025                1030                1035

Asn His Gly Gly Lys Gln Ala Leu Glu Thr Val Gln Arg Leu Leu
                1040                1045                1050

Pro Val Leu Cys Gln Ala His Gly Leu Thr Pro Glu Gln Val Val
                1055                1060                1065
```

```
Ala Ile Ala Ser His Asp Gly Gly Lys Gln Ala Leu Glu Thr Val
        1070            1075                1080

Gln Arg Leu Leu Pro Val Leu Cys Gln Ala His Gly Leu Thr Pro
1085                1090                1095

Glu Gln Val Val Ala Ile Ala Ser Asn Gly Gly Gly Ser Ile Val
1100                1105                1110

Ala Gln Leu Ser Arg Pro Asp Pro Ala Leu Ala Ala Leu Thr Asn
1115                1120                1125

Asp His Leu Val Ala Leu Ala Cys Leu Gly Gly Arg Pro Ala Leu
1130                1135                1140

Asp Ala Val Lys Lys Gly Leu Pro His Ala Pro Ala Leu Ile Lys
1145                1150                1155

Arg Thr Asn Arg Arg Ile Pro Glu Arg Thr Ser His Arg Val Ala
1160                1165                1170
```

<210> SEQ ID NO 18
<211> LENGTH: 1270
<212> TYPE: PRT
<213> ORGANISM: Artificial sequence
<220> FEATURE:
<223> OTHER INFORMATION: synthetic

<400> SEQUENCE: 18

```
Met Ala Pro Lys Lys Arg Lys Val Asp Tyr Lys Asp His Asp Gly
1               5                   10                  15

Asp Tyr Lys Asp His Asp Ile Asp Tyr Lys Asp Asp Asp Lys Gly
                20                  25                  30

Thr Val Asp Leu Arg Thr Leu Gly Tyr Ser Gln Gln Gln Gln Glu Lys
        35                  40                  45

Ile Lys Pro Lys Val Arg Ser Thr Val Ala Gln His His Glu Ala Leu
50                  55                  60

Val Gly His Gly Phe Thr His Ala His Ile Val Ala Leu Ser Gln His
65                  70                  75                  80

Pro Ala Ala Leu Gly Thr Val Ala Val Lys Tyr Gln Asp Met Ile Ala
                85                  90                  95

Ala Leu Pro Glu Ala Thr His Glu Ala Ile Val Gly Val Gly Lys Gln
                100                 105                 110

Trp Ser Gly Ala Arg Ala Leu Glu Ala Leu Leu Thr Val Ala Gly Glu
                115                 120                 125

Leu Arg Gly Pro Pro Leu Gln Leu Asp Thr Gly Gln Leu Leu Lys Ile
130                 135                 140

Ala Lys Arg Gly Gly Val Thr Ala Val Glu Ala Val His Ala Trp Arg
145                 150                 155                 160

Asn Ala Leu Thr Gly Ala Pro Leu Asn Leu Thr Pro Glu Gln Val Val
                165                 170                 175

Ala Ile Leu Thr Pro Glu Gln Val Val Ala Ile Ala Ser Asn His Gly
                180                 185                 190

Gly Lys Gln Ala Leu Glu Thr Val Gln Arg Leu Leu Pro Val Leu Cys
                195                 200                 205

Gln Ala His Gly Leu Thr Pro Glu Gln Val Val Ala Ile Ala Ser Asn
210                 215                 220

His Gly Gly Lys Gln Ala Leu Glu Thr Val Gln Arg Leu Leu Pro Val
225                 230                 235                 240

Leu Cys Gln Ala His Gly Leu Thr Pro Glu Gln Val Val Ala Ile Ala
                245                 250                 255
```

-continued

```
Ser His Asp Gly Gly Lys Gln Ala Leu Glu Thr Val Gln Arg Leu Leu
            260                 265                 270

Pro Val Leu Cys Gln Ala His Gly Leu Thr Pro Glu Gln Val Val Ala
        275                 280                 285

Ile Ala Ser His Asp Gly Gly Lys Gln Ala Leu Glu Thr Val Gln Arg
290                 295                 300

Leu Leu Pro Val Leu Cys Gln Ala His Gly Leu Thr Pro Glu Gln Val
305                 310                 315                 320

Val Ala Ile Ala Ser His Asp Gly Gly Lys Gln Ala Leu Glu Thr Val
                325                 330                 335

Gln Arg Leu Leu Pro Val Leu Cys Gln Ala His Gly Leu Thr Pro Glu
            340                 345                 350

Gln Val Val Ala Ile Ala Ser Asn Gly Gly Lys Gln Ala Leu Glu
        355                 360                 365

Thr Val Gln Arg Leu Leu Pro Val Leu Cys Gln Ala His Leu Thr Pro
    370                 375                 380

Glu Gln Val Val Ala Ile Ala Ser His Asp Gly Gly Lys Gln Ala Leu
385                 390                 395                 400

Glu Thr Val Gln Arg Leu Leu Pro Val Leu Cys Gln Ala His Gly Leu
                405                 410                 415

Thr Pro Glu Gln Val Val Ala Ile Ala Ser Asn Gly Gly Lys Gln
            420                 425                 430

Ala Leu Glu Thr Val Gln Arg Leu Leu Pro Val Leu Cys Gln Ala His
        435                 440                 445

Gly Leu Thr Pro Glu Gln Val Val Ala Ile Ala Ser Asn His Gly Gly
    450                 455                 460

Lys Gln Ala Leu Glu Thr Val Gln Arg Leu Leu Pro Val Leu Cys Gln
465                 470                 475                 480

Ala His Gly Leu Thr Pro Glu Gln Val Val Ala Ile Ala Ser His Asp
                485                 490                 495

Gly Gly Lys Gln Ala Leu Glu Thr Val Gln Arg Leu Leu Pro Val Leu
            500                 505                 510

Cys Gln Ala His Gly Leu Thr Pro Glu Gln Val Val Ala Ile Ala Ser
        515                 520                 525

Asn Ile Gly Gly Lys Gln Ala Leu Glu Thr Val Gln Arg Leu Leu Pro
    530                 535                 540

Val Leu Cys Gln Ala His Gly Leu Thr Pro Glu Gln Val Val Ala Ile
545                 550                 555                 560

Ala Ser Asn Gly Gly Lys Gln Ala Leu Glu Thr Val Gln Arg Leu
                565                 570                 575

Leu Pro Val Leu Cys Gln Ala His Gly Leu Thr Pro Glu Gln Val Val
            580                 585                 590

Ala Ile Ala Ser His Asp Gly Gly Lys Gln Ala Leu Glu Thr Val Gln
        595                 600                 605

Arg Leu Leu Pro Val Leu Cys Gln Ala His Gly Leu Thr Pro Glu Gln
    610                 615                 620

Val Val Ala Ile Ala Ser His Asp Gly Gly Lys Gln Ala Leu Glu Thr
625                 630                 635                 640

Val Gln Arg Leu Leu Pro Val Leu Cys Gln Ala His Gly Leu Thr Pro
                645                 650                 655

Glu Gln Val Val Ala Ile Ala Ser Asn Gly Gly Lys Gln Ala Leu
            660                 665                 670
```

-continued

```
Glu Thr Val Gln Arg Leu Leu Pro Val Leu Cys Gln Ala His Gly Leu
            675                 680                 685

Thr Pro Glu Gln Val Val Ala Ile Ala Ser His Asp Gly Gly Lys Gln
    690                 695                 700

Ala Leu Glu Thr Val Gln Arg Leu Leu Pro Val Leu Cys Gln Ala His
705                 710                 715                 720

Gly Leu Thr Pro Glu Gln Val Val Ala Ile Ala Ser His Asp Gly Gly
                725                 730                 735

Lys Gln Ala Leu Glu Thr Val Gln Arg Leu Leu Pro Val Leu Cys Gln
            740                 745                 750

Ala His Gly Leu Thr Pro Glu Gln Val Val Ala Ile Ala Ser Asn Gly
        755                 760                 765

Gly Gly Lys Gln Ala Leu Glu Thr Val Gln Arg Leu Leu Pro Val Leu
    770                 775                 780

Cys Gln Ala His Gly Leu Thr Pro Glu Gln Val Val Ala Ile Ala Ser
785                 790                 795                 800

His Asp Gly Gly Lys Gln Ala Leu Glu Thr Val Gln Arg Leu Leu Pro
                805                 810                 815

Val Leu Cys Gln Ala His Gly Leu Thr Pro Glu Gln Val Val Ala Ile
            820                 825                 830

Ala Ser Asn Ile Gly Gly Lys Gln Ala Leu Glu Thr Val Gln Arg Leu
        835                 840                 845

Leu Pro Val Leu Cys Gln Ala His Gly Leu Thr Pro Glu Gln Val Val
    850                 855                 860

Ala Ile Ala Ser Asn Gly Gly Lys Gln Ala Leu Glu Thr Val Gln
865                 870                 875                 880

Arg Leu Leu Pro Val Leu Cys Gln Ala His Gly Leu Thr Pro Glu Gln
                885                 890                 895

Val Val Ala Ile Ala Ser Asn His Gly Gly Lys Gln Ala Leu Glu Thr
            900                 905                 910

Val Gln Arg Leu Leu Pro Val Leu Cys Gln Ala His Gly Leu Thr Pro
        915                 920                 925

Glu Gln Val Val Ala Ile Ala Ser Asn Ile Gly Gly Lys Gln Ala Leu
    930                 935                 940

Glu Thr Val Gln Arg Leu Leu Pro Val Leu Cys Gln Ala His Gly Leu
945                 950                 955                 960

Thr Pro Glu Gln Val Val Ala Ile Ala Ser Asn Gly Gly Lys Gln
                965                 970                 975

Ala Leu Glu Thr Val Gln Arg Leu Leu Pro Val Leu Cys Gln Ala His
            980                 985                 990

Gly Leu Thr Pro Glu Gln Val Val Ala Ile Ala Ser Asn Ile Gly Gly
        995                 1000                1005

Lys Gln Ala Leu Glu Thr Val Gln Arg Leu Leu Pro Val Leu Cys
    1010                1015                1020

Gln Ala His Gly Leu Thr Pro Glu Gln Val Val Ala Ile Ala Ser
    1025                1030                1035

Asn His Gly Gly Lys Gln Ala Leu Glu Thr Val Gln Arg Leu Leu
    1040                1045                1050

Pro Val Leu Cys Gln Ala His Gly Leu Thr Pro Glu Gln Val Val
    1055                1060                1065

Ala Ile Ala Ser His Asp Gly Gly Lys Gln Ala Leu Glu Thr Val
    1070                1075                1080

Gln Arg Leu Leu Pro Val Leu Cys Gln Ala His Gly Leu Thr Pro
```

-continued

```
            1085                1090                1095
Glu Gln Val Val Ala Ile Ala Ser Asn Gly Gly Gly Ser Ile Val
        1100                1105                1110
Ala Gln Leu Ser Arg Pro Asp Pro Ala Leu Ala Ala Leu Thr Asn
        1115                1120                1125
Asp His Leu Val Ala Leu Ala Cys Leu Gly Gly Arg Pro Ala Leu
        1130                1135                1140
Asp Ala Val Lys Lys Gly Leu Pro His Ala Pro Ala Leu Ile Lys
        1145                1150                1155
Arg Thr Asn Arg Arg Ile Pro Glu Arg Thr Ser His Arg Val Ala
        1160                1165                1170
Pro Lys Lys Lys Arg Lys Val Ser Ser Asp Tyr Lys Asp His Asp
        1175                1180                1185
Gly Asp Tyr Lys Asp His Asp Ile Asp Tyr Lys Asp Asp Asp Asp
        1190                1195                1200
Lys Ala Ala Gly Gly Gly Gly Ser Gly Arg Ala Asp Ala Leu Asp
        1205                1210                1215
Asp Phe Asp Leu Asp Met Leu Gly Ser Asp Ala Leu Asp Asp Phe
        1220                1225                1230
Asp Leu Asp Met Leu Gly Ser Asp Ala Leu Asp Asp Phe Asp Leu
        1235                1240                1245
Asp Met Leu Gly Ser Asp Ala Leu Asp Asp Phe Asp Leu Asp Met
        1250                1255                1260
Leu His His His His His His
        1265                1270

<210> SEQ ID NO 19
<211> LENGTH: 1208
<212> TYPE: PRT
<213> ORGANISM: Artificial sequence
<220> FEATURE:
<223> OTHER INFORMATION: synthetic

<400> SEQUENCE: 19

Met Ala Pro Lys Lys Lys Arg Lys Val Asp Tyr Lys Asp His Asp Gly
1               5                   10                  15
Asp Tyr Lys Asp His Asp Ile Asp Tyr Lys Asp Asp Asp Asp Lys Gly
                20                  25                  30
Thr Val Asp Leu Arg Thr Leu Gly Tyr Ser Gln Gln Gln Gln Glu Lys
            35                  40                  45
Ile Lys Pro Lys Val Arg Ser Thr Val Ala Gln His His Glu Ala Leu
        50                  55                  60
Val Gly His Gly Phe Thr His Ala His Ile Val Ala Leu Ser Gln His
65                  70                  75                  80
Pro Ala Ala Leu Gly Thr Val Ala Val Lys Tyr Gln Asp Met Ile Ala
                85                  90                  95
Ala Leu Pro Glu Ala Thr His Glu Ala Ile Val Gly Val Gly Lys Gln
                100                 105                 110
Trp Ser Gly Ala Arg Ala Leu Glu Ala Leu Leu Thr Val Ala Gly Glu
            115                 120                 125
Leu Arg Gly Pro Pro Leu Gln Leu Asp Thr Gly Gln Leu Leu Lys Ile
        130                 135                 140
Ala Lys Arg Gly Gly Val Thr Ala Val Glu Ala Val His Ala Trp Arg
145                 150                 155                 160
Asn Ala Leu Thr Gly Ala Pro Leu Asn Leu Thr Pro Glu Gln Val Val
```

-continued

```
                165                 170                 175
Ala Ile Leu Thr Pro Glu Gln Val Val Ala Ile Ala Ser His Asp Gly
            180                 185                 190

Gly Lys Gln Ala Leu Glu Thr Val Gln Arg Leu Leu Pro Val Leu Cys
        195                 200                 205

Gln Ala His Gly Leu Thr Pro Glu Gln Val Val Ala Ile Ala Ser Asn
    210                 215                 220

Gly Gly Lys Gln Ala Leu Glu Thr Val Gln Arg Leu Leu Pro Val
225                 230                 235                 240

Leu Cys Gln Ala His Gly Leu Thr Pro Glu Gln Val Val Ala Ile Ala
            245                 250                 255

Ser Asn Gly Gly Lys Gln Ala Leu Glu Thr Val Gln Arg Leu Leu
        260                 265                 270

Pro Val Leu Cys Gln Ala His Gly Leu Thr Pro Glu Gln Val Val Ala
    275                 280                 285

Ile Ala Ser His Asp Gly Gly Lys Gln Ala Leu Glu Thr Val Gln Arg
290                 295                 300

Leu Leu Pro Val Leu Cys Gln Ala His Gly Leu Thr Pro Glu Gln Val
305                 310                 315                 320

Val Ala Ile Ala Ser His Asp Gly Gly Lys Gln Ala Leu Glu Thr Val
            325                 330                 335

Gln Arg Leu Leu Pro Val Leu Cys Gln Ala His Gly Leu Thr Pro Glu
        340                 345                 350

Gln Val Val Ala Ile Ala Ser Asn Ile Gly Gly Lys Gln Ala Leu Glu
    355                 360                 365

Thr Val Gln Arg Leu Leu Pro Val Leu Cys Gln Ala His Gly Leu Thr
370                 375                 380

Pro Glu Gln Val Val Ala Ile Ala Ser Asn Ile Gly Gly Lys Gln Ala
385                 390                 395                 400

Leu Glu Thr Val Gln Arg Leu Leu Pro Val Leu Cys Gln Ala His Gly
            405                 410                 415

Leu Thr Pro Glu Gln Val Val Ala Ile Ala Ser Asn Ile Gly Gly Lys
        420                 425                 430

Gln Ala Leu Glu Thr Val Gln Arg Leu Leu Pro Val Leu Cys Gln Ala
    435                 440                 445

His Gly Leu Thr Pro Glu Gln Val Val Ala Ile Ala Ser Asn Gly Gly
        450                 455                 460

Gly Lys Gln Ala Leu Glu Thr Val Gln Arg Leu Leu Pro Val Leu Cys
465                 470                 475                 480

Gln Ala His Gly Leu Thr Pro Glu Gln Val Val Ala Ile Ala Ser Asn
            485                 490                 495

Gly Gly Gly Lys Gln Ala Leu Glu Thr Val Gln Arg Leu Leu Pro Val
        500                 505                 510

Leu Cys Gln Ala His Gly Leu Thr Pro Glu Gln Val Val Ala Ile Ala
    515                 520                 525

Ser His Asp Gly Gly Lys Gln Ala Leu Glu Thr Val Gln Arg Leu Leu
    530                 535                 540

Pro Val Leu Cys Gln Ala His Gly Leu Thr Pro Glu Gln Val Val Ala
545                 550                 555                 560

Ile Ala Ser His Asp Gly Gly Lys Gln Ala Leu Glu Thr Val Gln Arg
            565                 570                 575

Leu Leu Pro Val Leu Cys Gln Ala His Gly Leu Thr Pro Glu Gln Val
        580                 585                 590
```

Val Ala Ile Ala Ser Asn His Gly Gly Lys Gln Ala Leu Glu Thr Val
            595                 600                 605

Gln Arg Leu Leu Pro Val Leu Cys Gln Ala His Gly Leu Thr Pro Glu
            610                 615                 620

Gln Val Val Ala Ile Ala Ser Asn Ile Gly Gly Lys Gln Ala Leu Glu
625                 630                 635                 640

Thr Val Gln Arg Leu Leu Pro Val Leu Cys Gln Ala His Gly Leu Thr
                645                 650                 655

Pro Glu Gln Val Val Ala Ile Ala Ser Asn Ile Gly Gly Lys Gln Ala
            660                 665                 670

Leu Glu Thr Val Gln Arg Leu Leu Pro Val Leu Cys Gln Ala His Gly
            675                 680                 685

Leu Thr Pro Glu Gln Val Val Ala Ile Ala Ser Asn His Gly Gly Lys
            690                 695                 700

Gln Ala Leu Glu Thr Val Gln Arg Leu Leu Pro Val Leu Cys Gln Ala
705                 710                 715                 720

His Gly Leu Thr Pro Glu Gln Val Val Ala Ile Ala Ser His Asp Gly
                725                 730                 735

Gly Lys Gln Ala Leu Glu Thr Val Gln Arg Leu Leu Pro Val Leu Cys
            740                 745                 750

Gln Ala His Gly Leu Thr Pro Glu Gln Val Val Ala Ile Ala Ser Asn
            755                 760                 765

His Gly Gly Lys Gln Ala Leu Glu Thr Val Gln Arg Leu Leu Pro Val
            770                 775                 780

Leu Cys Gln Ala His Gly Leu Thr Pro Glu Gln Val Val Ala Ile Ala
785                 790                 795                 800

Ser Asn His Gly Gly Lys Gln Ala Leu Glu Thr Val Gln Arg Leu Leu
                805                 810                 815

Pro Val Leu Cys Gln Ala His Gly Leu Thr Pro Glu Gln Val Val Ala
            820                 825                 830

Ile Ala Ser His Asp Gly Gly Lys Gln Ala Leu Glu Thr Val Gln Arg
            835                 840                 845

Leu Leu Pro Val Leu Cys Gln Ala His Gly Leu Thr Pro Glu Gln Val
            850                 855                 860

Val Ala Ile Ala Ser His Asp Gly Gly Lys Gln Ala Leu Glu Thr Val
865                 870                 875                 880

Gln Arg Leu Leu Pro Val Leu Cys Gln Ala His Gly Leu Thr Pro Glu
                885                 890                 895

Gln Val Val Ala Ile Ala Ser Asn Ile Gly Gly Lys Gln Ala Leu Glu
            900                 905                 910

Thr Val Gln Arg Leu Leu Pro Val Leu Cys Gln Ala His Gly Leu Thr
            915                 920                 925

Pro Glu Gln Val Val Ala Ile Ala Ser Asn Ile Gly Gly Lys Gln Ala
            930                 935                 940

Leu Glu Thr Val Gln Arg Leu Leu Pro Val Leu Cys Gln Ala His Gly
945                 950                 955                 960

Leu Thr Pro Glu Gln Val Val Ala Ile Ala Ser Asn Gly Gly Gly Lys
                965                 970                 975

Gln Ala Leu Glu Thr Val Gln Arg Leu Leu Pro Val Leu Cys Gln Ala
            980                 985                 990

His Gly Leu Thr Pro Glu Gln Val  Val Ala Ile Ala Ser  Asn His Gly
            995                 1000                1005

```
Gly Lys Gln Ala Leu Glu Thr Val Gln Arg Leu Leu Pro Val Leu
    1010                1015                1020

Cys Gln Ala His Gly Leu Thr Pro Glu Gln Val Val Ala Ile Ala
    1025                1030                1035

Ser His Asp Gly Gly Lys Gln Ala Leu Glu Thr Val Gln Arg Leu
    1040                1045                1050

Leu Pro Val Leu Cys Gln Ala His Gly Leu Thr Pro Glu Gln Val
    1055                1060                1065

Val Ala Ile Ala Ser Asn Ile Gly Gly Lys Gln Ala Leu Glu Thr
    1070                1075                1080

Val Gln Arg Leu Leu Pro Val Leu Cys Gln Ala His Gly Leu Thr
    1085                1090                1095

Pro Glu Gln Val Val Ala Ile Ala Ser Asn Ile Gly Gly Lys Gln
    1100                1105                1110

Ala Leu Glu Thr Val Gln Arg Leu Leu Pro Val Leu Cys Gln Ala
    1115                1120                1125

His Gly Leu Thr Pro Glu Gln Val Val Ala Ile Ala Ser Asn Gly
    1130                1135                1140

Gly Gly Ser Ile Val Ala Gln Leu Ser Arg Pro Asp Pro Ala Leu
    1145                1150                1155

Ala Ala Leu Thr Asn Asp His Leu Val Ala Leu Ala Cys Leu Gly
    1160                1165                1170

Gly Arg Pro Ala Leu Asp Ala Val Lys Lys Gly Leu Pro His Ala
    1175                1180                1185

Pro Ala Leu Ile Lys Arg Thr Asn Arg Arg Ile Pro Glu Arg Thr
    1190                1195                1200

Ser His Arg Val Ala
    1205

<210> SEQ ID NO 20
<211> LENGTH: 1305
<212> TYPE: PRT
<213> ORGANISM: Artificial sequence
<220> FEATURE:
<223> OTHER INFORMATION: synthetic

<400> SEQUENCE: 20

Met Ala Pro Lys Lys Lys Arg Lys Val Asp Tyr Lys Asp His Asp
1               5                   10                  15

Asp Tyr Lys Asp His Asp Ile Asp Tyr Lys Asp Asp Asp Lys Gly
                20                  25                  30

Thr Val Asp Leu Arg Thr Leu Gly Tyr Ser Gln Gln Gln Glu Lys
            35                  40                  45

Ile Lys Pro Lys Val Arg Ser Thr Val Ala Gln His His Glu Ala Leu
    50                  55                  60

Val Gly His Gly Phe Thr His Ala His Ile Val Ala Leu Ser Gln His
65              70                  75                      80

Pro Ala Ala Leu Gly Thr Val Ala Val Lys Tyr Gln Asp Met Ile Ala
                85                  90                      95

Ala Leu Pro Glu Ala Thr His Glu Ala Ile Val Gly Val Gly Lys Gln
                100                 105                 110

Trp Ser Gly Ala Arg Ala Leu Glu Ala Leu Leu Thr Val Ala Gly Glu
            115                 120                 125

Leu Arg Gly Pro Pro Leu Gln Leu Asp Thr Gly Gln Leu Leu Lys Ile
        130                 135                 140
```

```
Ala Lys Arg Gly Gly Val Thr Ala Val Glu Val His Ala Trp Arg
145                 150                 155                 160

Asn Ala Leu Thr Gly Ala Pro Leu Asn Leu Thr Pro Glu Gln Val Val
                165                 170                 175

Ala Ile Leu Thr Pro Glu Gln Val Val Ala Ile Ala Ser His Asp Gly
            180                 185                 190

Gly Lys Gln Ala Leu Glu Thr Val Gln Arg Leu Leu Pro Val Leu Cys
        195                 200                 205

Gln Ala His Gly Leu Thr Pro Glu Gln Val Val Ala Ile Ala Ser Asn
    210                 215                 220

Gly Gly Gly Lys Gln Ala Leu Glu Thr Val Gln Arg Leu Leu Pro Val
225                 230                 235                 240

Leu Cys Gln Ala His Gly Leu Thr Pro Glu Gln Val Val Ala Ile Ala
            245                 250                 255

Ser Asn Gly Gly Gly Lys Gln Ala Leu Glu Thr Val Gln Arg Leu Leu
        260                 265                 270

Pro Val Leu Cys Gln Ala His Gly Leu Thr Pro Glu Gln Val Val Ala
    275                 280                 285

Ile Ala Ser His Asp Gly Gly Lys Gln Ala Leu Glu Thr Val Gln Arg
290                 295                 300

Leu Leu Pro Val Leu Cys Gln Ala His Gly Leu Thr Pro Glu Gln Val
305                 310                 315                 320

Val Ala Ile Ala Ser His Asp Gly Gly Lys Gln Ala Leu Glu Thr Val
            325                 330                 335

Gln Arg Leu Leu Pro Val Leu Cys Gln Ala His Gly Leu Thr Pro Glu
        340                 345                 350

Gln Val Val Ala Ile Ala Ser Asn Ile Gly Gly Lys Gln Ala Leu Glu
    355                 360                 365

Thr Val Gln Arg Leu Leu Pro Val Leu Cys Gln Ala His Gly Leu Thr
370                 375                 380

Pro Glu Gln Val Val Ala Ile Ala Ser Asn Ile Gly Gly Lys Gln Ala
385                 390                 395                 400

Leu Glu Thr Val Gln Arg Leu Leu Pro Val Leu Cys Gln Ala His Gly
            405                 410                 415

Leu Thr Pro Glu Gln Val Val Ala Ile Ala Ser Asn Ile Gly Gly Lys
        420                 425                 430

Gln Ala Leu Glu Thr Val Gln Arg Leu Leu Pro Val Leu Cys Gln Ala
    435                 440                 445

His Gly Leu Thr Pro Glu Gln Val Val Ala Ile Ala Ser Asn Gly Gly
450                 455                 460

Gly Lys Gln Ala Leu Glu Thr Val Gln Arg Leu Leu Pro Val Leu Cys
465                 470                 475                 480

Gln Ala His Gly Leu Thr Pro Glu Gln Val Val Ala Ile Ala Ser Asn
            485                 490                 495

Gly Gly Gly Lys Gln Ala Leu Glu Thr Val Gln Arg Leu Leu Pro Val
        500                 505                 510

Leu Cys Gln Ala His Gly Leu Thr Pro Glu Gln Val Val Ala Ile Ala
    515                 520                 525

Ser His Asp Gly Gly Lys Gln Ala Leu Glu Thr Val Gln Arg Leu Leu
530                 535                 540

Pro Val Leu Cys Gln Ala His Gly Leu Thr Pro Glu Gln Val Val Ala
545                 550                 555                 560

Ile Ala Ser His Asp Gly Gly Lys Gln Ala Leu Glu Thr Val Gln Arg
```

```
              565                 570                 575
Leu Leu Pro Val Leu Cys Gln Ala His Gly Leu Thr Pro Glu Gln Val
            580                 585                 590

Val Ala Ile Ala Ser Asn His Gly Gly Lys Gln Ala Leu Glu Thr Val
            595                 600                 605

Gln Arg Leu Leu Pro Val Leu Cys Gln Ala His Gly Leu Thr Pro Glu
            610                 615                 620

Gln Val Ala Ile Ala Ser Asn Ile Gly Gly Lys Gln Ala Leu Glu
625                 630                 635                 640

Thr Val Gln Arg Leu Leu Pro Val Leu Cys Gln Ala His Gly Leu Thr
                645                 650                 655

Pro Glu Gln Val Val Ala Ile Ala Ser Asn Ile Gly Gly Lys Gln Ala
            660                 665                 670

Leu Glu Thr Val Gln Arg Leu Leu Pro Val Leu Cys Gln Ala His Gly
            675                 680                 685

Leu Thr Pro Glu Gln Val Val Ala Ile Ala Ser Asn His Gly Gly Lys
            690                 695                 700

Gln Ala Leu Glu Thr Val Gln Arg Leu Leu Pro Val Leu Cys Gln Ala
705                 710                 715                 720

His Gly Leu Thr Pro Glu Gln Val Val Ala Ile Ala Ser His Asp Gly
                725                 730                 735

Gly Lys Gln Ala Leu Glu Thr Val Gln Arg Leu Leu Pro Val Leu Cys
            740                 745                 750

Gln Ala His Gly Leu Thr Pro Glu Gln Val Val Ala Ile Ala Ser Asn
            755                 760                 765

His Gly Gly Lys Gln Ala Leu Glu Thr Val Gln Arg Leu Leu Pro Val
            770                 775                 780

Leu Cys Gln Ala His Gly Leu Thr Pro Glu Gln Val Val Ala Ile Ala
785                 790                 795                 800

Ser Asn His Gly Gly Lys Gln Ala Leu Glu Thr Val Gln Arg Leu Leu
                805                 810                 815

Pro Val Leu Cys Gln Ala His Gly Leu Thr Pro Glu Gln Val Val Ala
            820                 825                 830

Ile Ala Ser His Asp Gly Gly Lys Gln Ala Leu Glu Thr Val Gln Arg
            835                 840                 845

Leu Leu Pro Val Leu Cys Gln Ala His Gly Leu Thr Pro Glu Gln Val
            850                 855                 860

Val Ala Ile Ala Ser His Asp Gly Gly Lys Gln Ala Leu Glu Thr Val
865                 870                 875                 880

Gln Arg Leu Leu Pro Val Leu Cys Gln Ala His Gly Leu Thr Pro Glu
                885                 890                 895

Gln Val Val Ala Ile Ala Ser Asn Ile Gly Gly Lys Gln Ala Leu Glu
            900                 905                 910

Thr Val Gln Arg Leu Leu Pro Val Leu Cys Gln Ala His Gly Leu Thr
            915                 920                 925

Pro Glu Gln Val Val Ala Ile Ala Ser Asn Ile Gly Gly Lys Gln Ala
            930                 935                 940

Leu Glu Thr Val Gln Arg Leu Leu Pro Val Leu Cys Gln Ala His Gly
945                 950                 955                 960

Leu Thr Pro Glu Gln Val Val Ala Ile Ala Ser Asn Gly Gly Gly Lys
                965                 970                 975

Gln Ala Leu Glu Thr Val Gln Arg Leu Leu Pro Val Leu Cys Gln Ala
            980                 985                 990
```

-continued

```
His Gly Leu Thr Pro Glu Gln Val  Val Ala Ile Ala Ser  Asn His Gly
        995                 1000                1005

Gly Lys  Gln Ala Leu Glu Thr  Val Gln Arg Leu Leu  Pro Val Leu
    1010                 1015                1020

Cys Gln  Ala His Gly Leu Thr  Pro Glu Gln Val Val  Ala Ile Ala
    1025                 1030                1035

Ser His  Asp Gly Gly Lys Gln  Ala Leu Glu Thr Val  Gln Arg Leu
    1040                 1045                1050

Leu Pro  Val Leu Cys Gln Ala  His Gly Leu Thr Pro  Glu Gln Val
    1055                 1060                1065

Val Ala  Ile Ala Ser Asn Ile  Gly Gly Lys Gln Ala  Leu Glu Thr
    1070                 1075                1080

Val Gln  Arg Leu Leu Pro Val  Leu Cys Gln Ala His  Gly Leu Thr
    1085                 1090                1095

Pro Glu  Gln Val Val Ala Ile  Ala Ser Asn Ile Gly  Gly Lys Gln
    1100                 1105                1110

Ala Leu  Glu Thr Val Gln Arg  Leu Leu Pro Val Leu  Cys Gln Ala
    1115                 1120                1125

His Gly  Leu Thr Pro Glu Gln  Val Val Ala Ile Ala  Ser Asn Gly
    1130                 1135                1140

Gly Gly  Ser Ile Val Ala Gln  Leu Ser Arg Pro Asp  Pro Ala Leu
    1145                 1150                1155

Ala Ala  Leu Thr Asn Asp His  Leu Val Ala Leu Ala  Cys Leu Gly
    1160                 1165                1170

Gly Arg  Pro Ala Leu Asp Ala  Val Lys Lys Gly Leu  Pro His Ala
    1175                 1180                1185

Pro Ala  Leu Ile Lys Arg Thr  Asn Arg Arg Ile Pro  Glu Arg Thr
    1190                 1195                1200

Ser His  Arg Val Ala Pro Lys  Lys Lys Arg Lys Val  Ser Ser Asp
    1205                 1210                1215

Tyr Lys  Asp His Asp Gly Asp  Tyr Lys Asp His Asp  Ile Asp Tyr
    1220                 1225                1230

Lys Asp  Asp Asp Asp Lys Ala  Ala Gly Gly Gly Gly  Ser Gly Arg
    1235                 1240                1245

Ala Asp  Ala Leu Asp Asp Phe  Asp Leu Asp Met Leu  Gly Ser Asp
    1250                 1255                1260

Ala Leu  Asp Asp Phe Asp Leu  Asp Met Leu Gly Ser  Asp Ala Leu
    1265                 1270                1275

Asp Asp  Phe Asp Leu Asp Met  Leu Gly Ser Asp Ala  Leu Asp Asp
    1280                 1285                1290

Phe Asp  Leu Asp Met Leu His  His His His His
    1295                 1300                1305
```

<210> SEQ ID NO 21
<211> LENGTH: 1174
<212> TYPE: PRT
<213> ORGANISM: Artificial sequence
<220> FEATURE:
<223> OTHER INFORMATION: synthetic

<400> SEQUENCE: 21

```
Met Ala Pro Lys Lys Lys Arg Lys Val Asp Tyr Lys Asp His Asp Gly
1               5                   10                  15

Asp Tyr Lys Asp His Asp Ile Asp Tyr Lys Asp Asp Asp Asp Lys Gly
            20                  25                  30
```

Thr Val Asp Leu Arg Thr Leu Gly Tyr Ser Gln Gln Gln Gln Glu Lys
        35                  40                  45

Ile Lys Pro Lys Val Arg Ser Thr Val Ala Gln His His Glu Ala Leu
50                  55                  60

Val Gly His Gly Phe Thr His Ala His Ile Val Ala Leu Ser Gln His
65                  70                  75                  80

Pro Ala Ala Leu Gly Thr Val Ala Val Lys Tyr Gln Asp Met Ile Ala
                85                  90                  95

Ala Leu Pro Glu Ala Thr His Glu Ala Ile Val Gly Val Gly Lys Gln
            100                 105                 110

Trp Ser Gly Ala Arg Ala Leu Glu Ala Leu Leu Thr Val Ala Gly Glu
        115                 120                 125

Leu Arg Gly Pro Pro Leu Gln Leu Asp Thr Gly Gln Leu Leu Lys Ile
    130                 135                 140

Ala Lys Arg Gly Gly Val Thr Ala Val Glu Ala Val His Ala Trp Arg
145                 150                 155                 160

Asn Ala Leu Thr Gly Ala Pro Leu Asn Leu Thr Pro Glu Gln Val Val
                165                 170                 175

Ala Ile Leu Thr Pro Glu Gln Val Val Ala Ile Ala Ser Asn Ile Gly
            180                 185                 190

Gly Lys Gln Ala Leu Glu Thr Val Gln Arg Leu Leu Pro Val Leu Cys
        195                 200                 205

Gln Ala His Gly Leu Thr Pro Glu Gln Val Val Ala Ile Ala Ser Asn
    210                 215                 220

Gly Gly Gly Lys Gln Ala Leu Glu Thr Val Gln Arg Leu Leu Pro Val
225                 230                 235                 240

Leu Cys Gln Ala His Gly Leu Thr Pro Glu Gln Val Val Ala Ile Ala
                245                 250                 255

Ser His Asp Gly Gly Lys Gln Ala Leu Glu Thr Val Gln Arg Leu Leu
            260                 265                 270

Pro Val Leu Cys Gln Ala His Gly Leu Thr Pro Glu Gln Val Val Ala
        275                 280                 285

Ile Ala Ser Asn His Gly Gly Lys Gln Ala Leu Glu Thr Val Gln Arg
    290                 295                 300

Leu Leu Pro Val Leu Cys Gln Ala His Gly Leu Thr Pro Glu Gln Val
305                 310                 315                 320

Val Ala Ile Ala Ser Asn Gly Gly Gly Lys Gln Ala Leu Glu Thr Val
                325                 330                 335

Gln Arg Leu Leu Pro Val Leu Cys Gln Ala His Gly Leu Thr Pro Glu
            340                 345                 350

Gln Val Val Ala Ile Ala Ser Asn Ile Gly Gly Lys Gln Ala Leu Glu
        355                 360                 365

Thr Val Gln Arg Leu Leu Pro Val Leu Cys Gln Ala His Gly Leu Thr
    370                 375                 380

Pro Glu Gln Val Val Ala Ile Ala Ser Asn Gly Gly Lys Gln Ala
385                 390                 395                 400

Leu Glu Thr Val Gln Arg Leu Leu Pro Val Leu Cys Gln Ala His Gly
                405                 410                 415

Leu Thr Pro Glu Gln Val Val Ala Ile Ala Ser His Asp Gly Gly Lys
            420                 425                 430

Gln Ala Leu Glu Thr Val Gln Arg Leu Leu Pro Val Leu Cys Gln Ala
        435                 440                 445

His Gly Leu Thr Pro Glu Gln Val Val Ala Ile Ala Ser Asn Ile Gly
        450                 455                 460

Gly Lys Gln Ala Leu Glu Thr Val Gln Arg Leu Leu Pro Val Leu Cys
465                 470                 475                 480

Gln Ala His Gly Leu Thr Pro Glu Gln Val Val Ala Ile Ala Ser His
            485                 490                 495

Asp Gly Gly Lys Gln Ala Leu Glu Thr Val Gln Arg Leu Leu Pro Val
        500                 505                 510

Leu Cys Gln Ala His Gly Leu Thr Pro Glu Gln Val Val Ala Ile Ala
            515                 520                 525

Ser His Asp Gly Gly Lys Gln Ala Leu Glu Thr Val Gln Arg Leu Leu
530                 535                 540

Pro Val Leu Cys Gln Ala His Gly Leu Thr Pro Glu Gln Val Val Ala
545                 550                 555                 560

Ile Ala Ser His Asp Gly Gly Lys Gln Ala Leu Glu Thr Val Gln Arg
            565                 570                 575

Leu Leu Pro Val Leu Cys Gln Ala His Gly Leu Thr Pro Glu Gln Val
                580                 585                 590

Val Ala Ile Ala Ser Asn Ile Gly Gly Lys Gln Ala Leu Glu Thr Val
            595                 600                 605

Gln Arg Leu Leu Pro Val Leu Cys Gln Ala His Gly Leu Thr Pro Glu
    610                 615                 620

Gln Val Val Ala Ile Ala Ser Asn Gly Gly Lys Gln Ala Leu Glu
625                 630                 635                 640

Thr Val Gln Arg Leu Leu Pro Val Leu Cys Gln Ala His Gly Leu Thr
                645                 650                 655

Pro Glu Gln Val Val Ala Ile Ala Ser Asn His Gly Gly Lys Gln Ala
            660                 665                 670

Leu Glu Thr Val Gln Arg Leu Leu Pro Val Leu Cys Gln Ala His Gly
        675                 680                 685

Leu Thr Pro Glu Gln Val Val Ala Ile Ala Ser Asn His Gly Gly Lys
    690                 695                 700

Gln Ala Leu Glu Thr Val Gln Arg Leu Leu Pro Val Leu Cys Gln Ala
705                 710                 715                 720

His Gly Leu Thr Pro Glu Gln Val Val Ala Ile Ala Ser His Asp Gly
            725                 730                 735

Gly Lys Gln Ala Leu Glu Thr Val Gln Arg Leu Leu Pro Val Leu Cys
        740                 745                 750

Gln Ala His Gly Leu Thr Pro Glu Gln Val Val Ala Ile Ala Ser Asn
            755                 760                 765

Ile Gly Gly Lys Gln Ala Leu Glu Thr Val Gln Arg Leu Leu Pro Val
770                 775                 780

Leu Cys Gln Ala His Gly Leu Thr Pro Glu Gln Val Val Ala Ile Ala
785                 790                 795                 800

Ser Asn Gly Gly Gly Lys Gln Ala Leu Glu Thr Val Gln Arg Leu Leu
            805                 810                 815

Pro Val Leu Cys Gln Ala His Gly Leu Thr Pro Glu Gln Val Val Ala
        820                 825                 830

Ile Ala Ser Asn His Gly Gly Lys Gln Ala Leu Glu Thr Val Gln Arg
            835                 840                 845

Leu Leu Pro Val Leu Cys Gln Ala His Gly Leu Thr Pro Glu Gln Val
    850                 855                 860

Val Ala Ile Ala Ser Asn Ile Gly Gly Lys Gln Ala Leu Glu Thr Val

```
                865                 870                 875                 880
Gln Arg Leu Leu Pro Val Leu Cys Gln Ala His Gly Leu Thr Pro Glu
                    885                 890                 895
Gln Val Val Ala Ile Ala Ser His Asp Gly Gly Lys Gln Ala Leu Glu
                900                 905                 910
Thr Val Gln Arg Leu Leu Pro Val Leu Cys Gln Ala His Gly Leu Thr
            915                 920                 925
Pro Glu Gln Val Val Ala Ile Ala Ser His Asp Gly Gly Lys Gln Ala
        930                 935                 940
Leu Glu Thr Val Gln Arg Leu Leu Pro Val Leu Cys Gln Ala His Gly
945                 950                 955                 960
Leu Thr Pro Glu Gln Val Val Ala Ile Ala Ser His Asp Gly Gly Lys
                965                 970                 975
Gln Ala Leu Glu Thr Val Gln Arg Leu Leu Pro Val Leu Cys Gln Ala
            980                 985                 990
His Gly Leu Thr Pro Glu Gln Val Val Ala Ile Ala Ser His Asp Gly
        995                 1000                1005
Gly Lys Gln Ala Leu Glu Thr Val Gln Arg Leu Leu Pro Val Leu
    1010                1015                1020
Cys Gln Ala His Gly Leu Thr Pro Glu Gln Val Val Ala Ile Ala
    1025                1030                1035
Ser His Asp Gly Gly Lys Gln Ala Leu Glu Thr Val Gln Arg Leu
    1040                1045                1050
Leu Pro Val Leu Cys Gln Ala His Gly Leu Thr Pro Glu Gln Val
    1055                1060                1065
Val Ala Ile Ala Ser His Asp Gly Gly Lys Gln Ala Leu Glu Thr
    1070                1075                1080
Val Gln Arg Leu Leu Pro Val Leu Cys Gln Ala His Gly Leu Thr
    1085                1090                1095
Pro Glu Gln Val Val Ala Ile Ala Ser Asn Gly Gly Gly Ser Ile
    1100                1105                1110
Val Ala Gln Leu Ser Arg Pro Asp Pro Ala Leu Ala Ala Leu Thr
    1115                1120                1125
Asn Asp His Leu Val Ala Leu Ala Cys Leu Gly Gly Arg Pro Ala
    1130                1135                1140
Leu Asp Ala Val Lys Lys Gly Leu Pro His Ala Pro Ala Leu Ile
    1145                1150                1155
Lys Arg Thr Asn Arg Arg Ile Pro Glu Arg Thr Ser His Arg Val
    1160                1165                1170
Ala
```

<210> SEQ ID NO 22
<211> LENGTH: 1271
<212> TYPE: PRT
<213> ORGANISM: Artificial sequence
<220> FEATURE:
<223> OTHER INFORMATION: synthetic

<400> SEQUENCE: 22

```
Met Ala Pro Lys Lys Lys Arg Lys Val Asp Tyr Lys Asp His Asp Gly
1               5                   10                  15
Asp Tyr Lys Asp His Asp Ile Asp Tyr Lys Asp Asp Asp Lys Gly
            20                  25                  30
Thr Val Asp Leu Arg Thr Leu Gly Tyr Ser Gln Gln Gln Gln Glu Lys
        35                  40                  45
```

```
Ile Lys Pro Lys Val Arg Ser Thr Val Ala Gln His His Glu Ala Leu
 50                  55                  60
Val Gly His Gly Phe Thr His Ala His Ile Val Ala Leu Ser Gln His
 65                  70                  75                  80
Pro Ala Ala Leu Gly Thr Val Ala Val Lys Tyr Gln Asp Met Ile Ala
                 85                  90                  95
Ala Leu Pro Glu Ala Thr His Glu Ala Ile Val Gly Val Gly Lys Gln
            100                 105                 110
Trp Ser Gly Ala Arg Ala Leu Glu Ala Leu Leu Thr Val Ala Gly Glu
        115                 120                 125
Leu Arg Gly Pro Pro Leu Gln Leu Asp Thr Gly Gln Leu Leu Lys Ile
130                 135                 140
Ala Lys Arg Gly Gly Val Thr Ala Val Glu Ala Val His Ala Trp Arg
145                 150                 155                 160
Asn Ala Leu Thr Gly Ala Pro Leu Asn Leu Thr Pro Glu Gln Val Val
                165                 170                 175
Ala Ile Leu Thr Pro Glu Gln Val Val Ala Ile Ala Ser Asn Ile Gly
            180                 185                 190
Gly Lys Gln Ala Leu Glu Thr Val Gln Arg Leu Leu Pro Val Leu Cys
        195                 200                 205
Gln Ala His Gly Leu Thr Pro Glu Gln Val Val Ala Ile Ala Ser Asn
210                 215                 220
Gly Gly Gly Lys Gln Ala Leu Glu Thr Val Gln Arg Leu Leu Pro Val
225                 230                 235                 240
Leu Cys Gln Ala His Gly Leu Thr Pro Glu Gln Val Val Ala Ile Ala
                245                 250                 255
Ser His Asp Gly Gly Lys Gln Ala Leu Glu Thr Val Gln Arg Leu Leu
            260                 265                 270
Pro Val Leu Cys Gln Ala His Gly Leu Thr Pro Glu Gln Val Val Ala
        275                 280                 285
Ile Ala Ser Asn His Gly Gly Lys Gln Ala Leu Glu Thr Val Gln Arg
290                 295                 300
Leu Leu Pro Val Leu Cys Gln Ala His Gly Leu Thr Pro Glu Gln Val
305                 310                 315                 320
Val Ala Ile Ala Ser Asn Gly Gly Gly Lys Gln Ala Leu Glu Thr Val
                325                 330                 335
Gln Arg Leu Leu Pro Val Leu Cys Gln Ala His Gly Leu Thr Pro Glu
            340                 345                 350
Gln Val Val Ala Ile Ala Ser Asn Ile Gly Gly Lys Gln Ala Leu Glu
        355                 360                 365
Thr Val Gln Arg Leu Leu Pro Val Leu Cys Gln Ala His Gly Leu Thr
370                 375                 380
Pro Glu Gln Val Val Ala Ile Ala Ser Asn Gly Gly Gly Lys Gln Ala
385                 390                 395                 400
Leu Glu Thr Val Gln Arg Leu Leu Pro Val Leu Cys Gln Ala His Gly
                405                 410                 415
Leu Thr Pro Glu Gln Val Val Ala Ile Ala Ser His Asp Gly Gly Lys
            420                 425                 430
Gln Ala Leu Glu Thr Val Gln Arg Leu Leu Pro Val Leu Cys Gln Ala
        435                 440                 445
His Gly Leu Thr Pro Glu Gln Val Val Ala Ile Ala Ser Asn Ile Gly
450                 455                 460
```

-continued

```
Gly Lys Gln Ala Leu Glu Thr Val Gln Arg Leu Pro Val Leu Cys
465                 470                 475                 480

Gln Ala His Gly Leu Thr Pro Glu Gln Val Val Ala Ile Ala Ser His
                485                 490                 495

Asp Gly Gly Lys Gln Ala Leu Glu Thr Val Gln Arg Leu Leu Pro Val
            500                 505                 510

Leu Cys Gln Ala His Gly Leu Thr Pro Glu Gln Val Val Ala Ile Ala
        515                 520                 525

Ser His Asp Gly Gly Lys Gln Ala Leu Glu Thr Val Gln Arg Leu Leu
    530                 535                 540

Pro Val Leu Cys Gln Ala His Gly Leu Thr Pro Glu Gln Val Val Ala
545                 550                 555                 560

Ile Ala Ser His Asp Gly Gly Lys Gln Ala Leu Glu Thr Val Gln Arg
                565                 570                 575

Leu Leu Pro Val Leu Cys Gln Ala His Gly Leu Thr Pro Glu Gln Val
                580                 585                 590

Val Ala Ile Ala Ser Asn Ile Gly Gly Lys Gln Ala Leu Glu Thr Val
            595                 600                 605

Gln Arg Leu Leu Pro Val Leu Cys Gln Ala His Gly Leu Thr Pro Glu
        610                 615                 620

Gln Val Val Ala Ile Ala Ser Asn Gly Gly Gly Lys Gln Ala Leu Glu
625                 630                 635                 640

Thr Val Gln Arg Leu Leu Pro Val Leu Cys Gln Ala His Gly Leu Thr
                645                 650                 655

Pro Glu Gln Val Val Ala Ile Ala Ser Asn His Gly Gly Lys Gln Ala
                660                 665                 670

Leu Glu Thr Val Gln Arg Leu Leu Pro Val Leu Cys Gln Ala His Gly
            675                 680                 685

Leu Thr Pro Glu Gln Val Val Ala Ile Ala Ser Asn His Gly Gly Lys
        690                 695                 700

Gln Ala Leu Glu Thr Val Gln Arg Leu Leu Pro Val Leu Cys Gln Ala
705                 710                 715                 720

His Gly Leu Thr Pro Glu Gln Val Val Ala Ile Ala Ser His Asp Gly
                725                 730                 735

Gly Lys Gln Ala Leu Glu Thr Val Gln Arg Leu Leu Pro Val Leu Cys
                740                 745                 750

Gln Ala His Gly Leu Thr Pro Glu Gln Val Val Ala Ile Ala Ser Asn
            755                 760                 765

Ile Gly Gly Lys Gln Ala Leu Glu Thr Val Gln Arg Leu Leu Pro Val
        770                 775                 780

Leu Cys Gln Ala His Gly Leu Thr Pro Glu Gln Val Val Ala Ile Ala
785                 790                 795                 800

Ser Asn Gly Gly Gly Lys Gln Ala Leu Glu Thr Val Gln Arg Leu Leu
                805                 810                 815

Pro Val Leu Cys Gln Ala His Gly Leu Thr Pro Glu Gln Val Val Ala
                820                 825                 830

Ile Ala Ser Asn His Gly Gly Lys Gln Ala Leu Glu Thr Val Gln Arg
            835                 840                 845

Leu Leu Pro Val Leu Cys Gln Ala His Gly Leu Thr Pro Glu Gln Val
        850                 855                 860

Val Ala Ile Ala Ser Asn Ile Gly Gly Lys Gln Ala Leu Glu Thr Val
865                 870                 875                 880

Gln Arg Leu Leu Pro Val Leu Cys Gln Ala His Gly Leu Thr Pro Glu
```

```
                        885                 890                 895
Gln Val Val Ala Ile Ala Ser His Asp Gly Gly Lys Gln Ala Leu Glu
            900                 905                 910
Thr Val Gln Arg Leu Leu Pro Val Leu Cys Gln Ala His Gly Leu Thr
            915                 920                 925
Pro Glu Gln Val Val Ala Ile Ala Ser His Asp Gly Gly Lys Gln Ala
            930                 935                 940
Leu Glu Thr Val Gln Arg Leu Leu Pro Val Leu Cys Gln Ala His Gly
945                 950                 955                 960
Leu Thr Pro Glu Gln Val Val Ala Ile Ala Ser His Asp Gly Gly Lys
                965                 970                 975
Gln Ala Leu Glu Thr Val Gln Arg Leu Leu Pro Val Leu Cys Gln Ala
            980                 985                 990
His Gly Leu Thr Pro Glu Gln Val Val Ala Ile Ala Ser His Asp Gly
            995                 1000                1005
Gly Lys Gln Ala Leu Glu Thr Val Gln Arg Leu Leu Pro Val Leu
        1010                1015                1020
Cys Gln Ala His Gly Leu Thr Pro Glu Gln Val Val Ala Ile Ala
        1025                1030                1035
Ser His Asp Gly Gly Lys Gln Ala Leu Glu Thr Val Gln Arg Leu
        1040                1045                1050
Leu Pro Val Leu Cys Gln Ala His Gly Leu Thr Pro Glu Gln Val
        1055                1060                1065
Val Ala Ile Ala Ser His Asp Gly Gly Lys Gln Ala Leu Glu Thr
        1070                1075                1080
Val Gln Arg Leu Leu Pro Val Leu Cys Gln Ala His Gly Leu Thr
        1085                1090                1095
Pro Glu Gln Val Val Ala Ile Ala Ser Asn Gly Gly Gly Ser Ile
        1100                1105                1110
Val Ala Gln Leu Ser Arg Pro Asp Pro Ala Leu Ala Ala Leu Thr
        1115                1120                1125
Asn Asp His Leu Val Ala Leu Ala Cys Leu Gly Gly Arg Pro Ala
        1130                1135                1140
Leu Asp Ala Val Lys Lys Gly Leu Pro His Ala Pro Ala Leu Ile
        1145                1150                1155
Lys Arg Thr Asn Arg Arg Ile Pro Glu Arg Thr Ser His Arg Val
        1160                1165                1170
Ala Pro Lys Lys Lys Arg Lys Val Ser Ser Asp Tyr Lys Asp His
        1175                1180                1185
Asp Gly Asp Tyr Lys Asp His Asp Ile Asp Tyr Lys Asp Asp Asp
        1190                1195                1200
Asp Lys Ala Ala Gly Gly Gly Ser Gly Arg Ala Asp Ala Leu
        1205                1210                1215
Asp Asp Phe Asp Leu Asp Met Leu Gly Ser Asp Ala Leu Asp Asp
        1220                1225                1230
Phe Asp Leu Asp Met Leu Gly Ser Asp Ala Leu Asp Asp Phe Asp
        1235                1240                1245
Leu Asp Met Leu Gly Ser Asp Ala Leu Asp Asp Phe Asp Leu Asp
        1250                1255                1260
Met Leu His His His His His His
        1265                1270

<210> SEQ ID NO 23
```

<211> LENGTH: 1208
<212> TYPE: PRT
<213> ORGANISM: Artificial sequence
<220> FEATURE:
<223> OTHER INFORMATION: synthetic

<400> SEQUENCE: 23

```
Met Ala Pro Lys Lys Arg Lys Val Asp Tyr Lys Asp His Asp Gly
1               5                   10                  15

Asp Tyr Lys Asp His Asp Ile Asp Tyr Lys Asp Asp Asp Lys Gly
            20                  25                  30

Thr Val Asp Leu Arg Thr Leu Gly Tyr Ser Gln Gln Gln Gln Glu Lys
            35                  40                      45

Ile Lys Pro Lys Val Arg Ser Thr Val Ala Gln His His Glu Ala Leu
50                  55                      60

Val Gly His Gly Phe Thr His Ala His Ile Val Ala Leu Ser Gln His
65                      70                  75                  80

Pro Ala Ala Leu Gly Thr Val Ala Val Lys Tyr Gln Asp Met Ile Ala
                85                  90                  95

Ala Leu Pro Glu Ala Thr His Glu Ala Ile Val Gly Val Gly Lys Gln
            100                 105                 110

Trp Ser Gly Ala Arg Ala Leu Glu Ala Leu Leu Thr Val Ala Gly Glu
            115                 120                 125

Leu Arg Gly Pro Pro Leu Gln Leu Asp Thr Gly Gln Leu Leu Lys Ile
130                 135                 140

Ala Lys Arg Gly Gly Val Thr Ala Val Glu Ala Val His Ala Trp Arg
145                 150                 155                 160

Asn Ala Leu Thr Gly Ala Pro Leu Asn Leu Thr Pro Glu Gln Val Val
                165                 170                 175

Ala Ile Leu Thr Pro Glu Gln Val Val Ala Ile Ala Ser Asn Ile Gly
            180                 185                 190

Gly Lys Gln Ala Leu Glu Thr Val Gln Arg Leu Leu Pro Val Leu Cys
            195                 200                 205

Gln Ala His Gly Leu Thr Pro Glu Gln Val Val Ala Ile Ala Ser Asn
210                 215                 220

Gly Gly Gly Lys Gln Ala Leu Glu Thr Val Gln Arg Leu Leu Pro Val
225                 230                 235                 240

Leu Cys Gln Ala His Gly Leu Thr Pro Glu Gln Val Val Ala Ile Ala
                245                 250                 255

Ser Asn Gly Gly Gly Lys Gln Ala Leu Glu Thr Val Gln Arg Leu Leu
            260                 265                 270

Pro Val Leu Cys Gln Ala His Gly Leu Thr Pro Glu Gln Val Val Ala
            275                 280                 285

Ile Ala Ser His Asp Gly Gly Lys Gln Ala Leu Glu Thr Val Gln Arg
290                 295                 300

Leu Leu Pro Val Leu Cys Gln Ala His Gly Leu Thr Pro Glu Gln Val
305                 310                 315                 320

Val Ala Ile Ala Ser His Asp Gly Gly Lys Gln Ala Leu Glu Thr Val
                325                 330                 335

Gln Arg Leu Leu Pro Val Leu Cys Gln Ala His Gly Leu Thr Pro Glu
            340                 345                 350

Gln Val Val Ala Ile Ala Ser Asn Gly Gly Gly Lys Gln Ala Leu Glu
            355                 360                 365

Thr Val Gln Arg Leu Leu Pro Val Leu Cys Gln Ala His Gly Leu Thr
370                 375                 380
```

```
Pro Glu Gln Val Val Ala Ile Ala Ser Asn Ile Gly Gly Lys Gln Ala
385                 390                 395                 400

Leu Glu Thr Val Gln Arg Leu Leu Pro Val Leu Cys Gln Ala His Gly
            405                 410                 415

Leu Thr Pro Glu Gln Val Val Ala Ile Ala Ser Asn Ile Gly Gly Lys
            420                 425                 430

Gln Ala Leu Glu Thr Val Gln Arg Leu Leu Pro Val Leu Cys Gln Ala
            435                 440                 445

His Gly Leu Thr Pro Glu Gln Val Val Ala Ile Ala Ser Asn Gly Gly
            450                 455                 460

Gly Lys Gln Ala Leu Glu Thr Val Gln Arg Leu Leu Pro Val Leu Cys
465                 470                 475                 480

Gln Ala His Gly Leu Thr Pro Glu Gln Val Val Ala Ile Ala Ser Asn
            485                 490                 495

Ile Gly Gly Lys Gln Ala Leu Glu Thr Val Gln Arg Leu Leu Pro Val
            500                 505                 510

Leu Cys Gln Ala His Gly Leu Thr Pro Glu Gln Val Val Ala Ile Ala
            515                 520                 525

Ser Asn Gly Gly Gly Lys Gln Ala Leu Glu Thr Val Gln Arg Leu Leu
530                 535                 540

Pro Val Leu Cys Gln Ala His Gly Leu Thr Pro Glu Gln Val Val Ala
545                 550                 555                 560

Ile Ala Ser Asn Ile Gly Gly Lys Gln Ala Leu Glu Thr Val Gln Arg
            565                 570                 575

Leu Leu Pro Val Leu Cys Gln Ala His Gly Leu Thr Pro Glu Gln Val
            580                 585                 590

Val Ala Ile Ala Ser Asn Gly Gly Gly Lys Gln Ala Leu Glu Thr Val
            595                 600                 605

Gln Arg Leu Leu Pro Val Leu Cys Gln Ala His Gly Leu Thr Pro Glu
610                 615                 620

Gln Val Val Ala Ile Ala Ser Asn Ile Gly Gly Lys Gln Ala Leu Glu
625                 630                 635                 640

Thr Val Gln Arg Leu Leu Pro Val Leu Cys Gln Ala His Gly Leu Thr
            645                 650                 655

Pro Glu Gln Val Val Ala Ile Ala Ser Asn Gly Gly Gly Lys Gln Ala
            660                 665                 670

Leu Glu Thr Val Gln Arg Leu Leu Pro Val Leu Cys Gln Ala His Gly
            675                 680                 685

Leu Thr Pro Glu Gln Val Val Ala Ile Ala Ser Asn Ile Gly Gly Lys
            690                 695                 700

Gln Ala Leu Glu Thr Val Gln Arg Leu Leu Pro Val Leu Cys Gln Ala
705                 710                 715                 720

His Gly Leu Thr Pro Glu Gln Val Val Ala Ile Ala Ser Asn Gly Gly
            725                 730                 735

Gly Lys Gln Ala Leu Glu Thr Val Gln Arg Leu Leu Pro Val Leu Cys
            740                 745                 750

Gln Ala His Gly Leu Thr Pro Glu Gln Val Val Ala Ile Ala Ser His
            755                 760                 765

Asp Gly Gly Lys Gln Ala Leu Glu Thr Val Gln Arg Leu Leu Pro Val
            770                 775                 780

Leu Cys Gln Ala His Gly Leu Thr Pro Glu Gln Val Val Ala Ile Ala
785                 790                 795                 800
```

```
Ser Asn Ile Gly Gly Lys Gln Ala Leu Glu Thr Val Gln Arg Leu Leu
                805                 810                 815

Pro Val Leu Cys Gln Ala His Gly Leu Thr Pro Glu Gln Val Val Ala
            820                 825                 830

Ile Ala Ser Asn Gly Gly Lys Gln Ala Leu Glu Thr Val Gln Arg
        835                 840                 845

Leu Leu Pro Val Leu Cys Gln Ala His Gly Leu Thr Pro Glu Gln Val
850                 855                 860

Val Ala Ile Ala Ser Asn Ile Gly Gly Lys Gln Ala Leu Glu Thr Val
865                 870                 875                 880

Gln Arg Leu Leu Pro Val Leu Cys Gln Ala His Gly Leu Thr Pro Glu
                885                 890                 895

Gln Val Val Ala Ile Ala Ser His Asp Gly Gly Lys Gln Ala Leu Glu
            900                 905                 910

Thr Val Gln Arg Leu Leu Pro Val Leu Cys Gln Ala His Gly Leu Thr
        915                 920                 925

Pro Glu Gln Val Val Ala Ile Ala Ser Asn Gly Gly Lys Gln Ala
    930                 935                 940

Leu Glu Thr Val Gln Arg Leu Leu Pro Val Leu Cys Gln Ala His Gly
945                 950                 955                 960

Leu Thr Pro Glu Gln Val Val Ala Ile Ala Ser His Asp Gly Gly Lys
                965                 970                 975

Gln Ala Leu Glu Thr Val Gln Arg Leu Leu Pro Val Leu Cys Gln Ala
            980                 985                 990

His Gly Leu Thr Pro Glu Gln Val Val Ala Ile Ala Ser Asn Gly Gly
        995                 1000                1005

Gly Lys Gln Ala Leu Glu Thr Val Gln Arg Leu Leu Pro Val Leu
    1010                1015                1020

Cys Gln Ala His Gly Leu Thr Pro Glu Gln Val Ala Ile Ala
    1025                1030                1035

Ser His Asp Gly Gly Lys Gln Ala Leu Glu Thr Val Gln Arg Leu
    1040                1045                1050

Leu Pro Val Leu Cys Gln Ala His Gly Leu Thr Pro Glu Gln Val
    1055                1060                1065

Val Ala Ile Ala Ser His Asp Gly Gly Lys Gln Ala Leu Glu Thr
    1070                1075                1080

Val Gln Arg Leu Leu Pro Val Leu Cys Gln Ala His Gly Leu Thr
    1085                1090                1095

Pro Glu Gln Val Val Ala Ile Ala Ser Asn Ile Gly Gly Lys Gln
    1100                1105                1110

Ala Leu Glu Thr Val Gln Arg Leu Leu Pro Val Leu Cys Gln Ala
    1115                1120                1125

His Gly Leu Thr Pro Glu Gln Val Val Ala Ile Ala Ser Asn Gly
    1130                1135                1140

Gly Gly Ser Ile Val Ala Gln Leu Ser Arg Pro Asp Pro Ala Leu
    1145                1150                1155

Ala Ala Leu Thr Asn Asp His Leu Val Ala Leu Ala Cys Leu Gly
    1160                1165                1170

Gly Arg Pro Ala Leu Asp Ala Val Lys Lys Gly Leu Pro His Ala
    1175                1180                1185

Pro Ala Leu Ile Lys Arg Thr Asn Arg Arg Ile Pro Glu Arg Thr
    1190                1195                1200

Ser His Arg Val Ala
```

<210> SEQ ID NO 24
<211> LENGTH: 1305
<212> TYPE: PRT
<213> ORGANISM: Artificial sequence
<220> FEATURE:
<223> OTHER INFORMATION: synthetic

<400> SEQUENCE: 24

```
Met Ala Pro Lys Lys Arg Lys Val Asp Tyr Lys Asp His Asp Gly
1               5                   10                  15

Asp Tyr Lys Asp His Asp Ile Asp Tyr Lys Asp Asp Asp Lys Gly
                20                  25                  30

Thr Val Asp Leu Arg Thr Leu Gly Tyr Ser Gln Gln Gln Gln Glu Lys
                35                  40                  45

Ile Lys Pro Lys Val Arg Ser Thr Val Ala Gln His His Glu Ala Leu
50                  55                  60

Val Gly His Gly Phe Thr His Ala His Ile Val Ala Leu Ser Gln His
65                  70                  75                  80

Pro Ala Ala Leu Gly Thr Val Ala Val Lys Tyr Gln Asp Met Ile Ala
                85                  90                  95

Ala Leu Pro Glu Ala Thr His Glu Ala Ile Val Gly Val Gly Lys Gln
                100                 105                 110

Trp Ser Gly Ala Arg Ala Leu Glu Ala Leu Leu Thr Val Ala Gly Glu
                115                 120                 125

Leu Arg Gly Pro Pro Leu Gln Leu Asp Thr Gly Gln Leu Leu Lys Ile
130                 135                 140

Ala Lys Arg Gly Gly Val Thr Ala Val Glu Ala Val His Ala Trp Arg
145                 150                 155                 160

Asn Ala Leu Thr Gly Ala Pro Leu Asn Leu Thr Pro Glu Gln Val Val
                165                 170                 175

Ala Ile Leu Thr Pro Glu Gln Val Val Ala Ile Ala Ser Asn Ile Gly
                180                 185                 190

Gly Lys Gln Ala Leu Glu Thr Val Gln Arg Leu Leu Pro Val Leu Cys
                195                 200                 205

Gln Ala His Gly Leu Thr Pro Glu Gln Val Val Ala Ile Ala Ser Asn
210                 215                 220

Gly Gly Gly Lys Gln Ala Leu Glu Thr Val Gln Arg Leu Leu Pro Val
225                 230                 235                 240

Leu Cys Gln Ala His Gly Leu Thr Pro Glu Gln Val Val Ala Ile Ala
                245                 250                 255

Ser Asn Gly Gly Gly Lys Gln Ala Leu Glu Thr Val Gln Arg Leu Leu
                260                 265                 270

Pro Val Leu Cys Gln Ala His Gly Leu Thr Pro Glu Gln Val Val Ala
                275                 280                 285

Ile Ala Ser His Asp Gly Gly Lys Gln Ala Leu Glu Thr Val Gln Arg
290                 295                 300

Leu Leu Pro Val Leu Cys Gln Ala His Gly Leu Thr Pro Glu Gln Val
305                 310                 315                 320

Val Ala Ile Ala Ser His Asp Gly Gly Lys Gln Ala Leu Glu Thr Val
                325                 330                 335

Gln Arg Leu Leu Pro Val Leu Cys Gln Ala His Gly Leu Thr Pro Glu
                340                 345                 350

Gln Val Val Ala Ile Ala Ser Asn Gly Gly Gly Lys Gln Ala Leu Glu
```

```
                    355                 360                 365
Thr Val Gln Arg Leu Leu Pro Val Leu Cys Gln Ala His Gly Leu Thr
        370                 375                 380
Pro Glu Gln Val Val Ala Ile Ala Ser Asn Ile Gly Gly Lys Gln Ala
385                 390                 395                 400
Leu Glu Thr Val Gln Arg Leu Leu Pro Val Leu Cys Gln Ala His Gly
                405                 410                 415
Leu Thr Pro Glu Gln Val Val Ala Ile Ala Ser Asn Ile Gly Gly Lys
            420                 425                 430
Gln Ala Leu Glu Thr Val Gln Arg Leu Leu Pro Val Leu Cys Gln Ala
        435                 440                 445
His Gly Leu Thr Pro Glu Gln Val Val Ala Ile Ala Ser Asn Gly Gly
        450                 455                 460
Gly Lys Gln Ala Leu Glu Thr Val Gln Arg Leu Leu Pro Val Leu Cys
465                 470                 475                 480
Gln Ala His Gly Leu Thr Pro Glu Gln Val Val Ala Ile Ala Ser Asn
                485                 490                 495
Ile Gly Gly Lys Gln Ala Leu Glu Thr Val Gln Arg Leu Leu Pro Val
            500                 505                 510
Leu Cys Gln Ala His Gly Leu Thr Pro Glu Gln Val Val Ala Ile Ala
        515                 520                 525
Ser Asn Gly Gly Lys Gln Ala Leu Glu Thr Val Gln Arg Leu Leu
        530                 535                 540
Pro Val Leu Cys Gln Ala His Gly Leu Thr Pro Glu Gln Val Val Ala
545                 550                 555                 560
Ile Ala Ser Asn Ile Gly Gly Lys Gln Ala Leu Glu Thr Val Gln Arg
                565                 570                 575
Leu Leu Pro Val Leu Cys Gln Ala His Gly Leu Thr Pro Glu Gln Val
            580                 585                 590
Val Ala Ile Ala Ser Asn Gly Gly Gly Lys Gln Ala Leu Glu Thr Val
        595                 600                 605
Gln Arg Leu Leu Pro Val Leu Cys Gln Ala His Gly Leu Thr Pro Glu
    610                 615                 620
Gln Val Val Ala Ile Ala Ser Asn Ile Gly Gly Lys Gln Ala Leu Glu
625                 630                 635                 640
Thr Val Gln Arg Leu Leu Pro Val Leu Cys Gln Ala His Gly Leu Thr
                645                 650                 655
Pro Glu Gln Val Val Ala Ile Ala Ser Asn Gly Gly Lys Gln Ala
            660                 665                 670
Leu Glu Thr Val Gln Arg Leu Leu Pro Val Leu Cys Gln Ala His Gly
        675                 680                 685
Leu Thr Pro Glu Gln Val Val Ala Ile Ala Ser Asn Ile Gly Gly Lys
        690                 695                 700
Gln Ala Leu Glu Thr Val Gln Arg Leu Leu Pro Val Leu Cys Gln Ala
705                 710                 715                 720
His Gly Leu Thr Pro Glu Gln Val Val Ala Ile Ala Ser Asn Gly Gly
                725                 730                 735
Gly Lys Gln Ala Leu Glu Thr Val Gln Arg Leu Leu Pro Val Leu Cys
            740                 745                 750
Gln Ala His Gly Leu Thr Pro Glu Gln Val Val Ala Ile Ala Ser His
        755                 760                 765
Asp Gly Gly Lys Gln Ala Leu Glu Thr Val Gln Arg Leu Leu Pro Val
    770                 775                 780
```

Leu Cys Gln Ala His Gly Leu Thr Pro Glu Gln Val Val Ala Ile Ala
785                 790                 795                 800

Ser Asn Ile Gly Gly Lys Gln Ala Leu Glu Thr Val Gln Arg Leu Leu
            805                 810                 815

Pro Val Leu Cys Gln Ala His Gly Leu Thr Pro Glu Gln Val Val Ala
        820                 825                 830

Ile Ala Ser Asn Gly Gly Lys Gln Ala Leu Glu Thr Val Gln Arg
            835                 840                 845

Leu Leu Pro Val Leu Cys Gln Ala His Gly Leu Thr Pro Glu Gln Val
850                 855                 860

Val Ala Ile Ala Ser Asn Ile Gly Gly Lys Gln Ala Leu Glu Thr Val
865                 870                 875                 880

Gln Arg Leu Leu Pro Val Leu Cys Gln Ala His Gly Leu Thr Pro Glu
                885                 890                 895

Gln Val Val Ala Ile Ala Ser His Asp Gly Gly Lys Gln Ala Leu Glu
        900                 905                 910

Thr Val Gln Arg Leu Leu Pro Val Leu Cys Gln Ala His Gly Leu Thr
        915                 920                 925

Pro Glu Gln Val Val Ala Ile Ala Ser Asn Gly Gly Lys Gln Ala
        930                 935                 940

Leu Glu Thr Val Gln Arg Leu Leu Pro Val Leu Cys Gln Ala His Gly
945                 950                 955                 960

Leu Thr Pro Glu Gln Val Val Ala Ile Ala Ser His Asp Gly Gly Lys
            965                 970                 975

Gln Ala Leu Glu Thr Val Gln Arg Leu Leu Pro Val Leu Cys Gln Ala
            980                 985                 990

His Gly Leu Thr Pro Glu Gln Val  Val Ala Ile Ala Ser  Asn Gly Gly
            995                 1000                1005

Gly Lys  Gln Ala Leu Glu Thr  Val Gln Arg Leu Leu  Pro Val Leu
    1010                1015                1020

Cys Gln  Ala His Gly Leu Thr  Pro Glu Gln Val  Ala Ile Ala
    1025                1030                1035

Ser His Asp Gly Gly Lys Gln  Ala Leu Glu Thr Val  Gln Arg Leu
    1040                1045                1050

Leu Pro  Val Leu Cys Gln Ala  His Gly Leu Thr Pro  Glu Gln Val
    1055                1060                1065

Val Ala  Ile Ala Ser His Asp  Gly Gly Lys Gln Ala  Leu Glu Thr
    1070                1075                1080

Val Gln  Arg Leu Leu Pro Val  Leu Cys Gln Ala His  Gly Leu Thr
    1085                1090                1095

Pro Glu  Gln Val Val Ala Ile  Ala Ser Asn Ile Gly  Gly Lys Gln
    1100                1105                1110

Ala Leu  Glu Thr Val Gln Arg  Leu Leu Pro Val Leu  Cys Gln Ala
    1115                1120                1125

His Gly  Leu Thr Pro Glu Gln  Val Val Ala Ile Ala  Ser Asn Gly
    1130                1135                1140

Gly Gly  Ser Ile Val Ala Gln  Leu Ser Arg Pro Asp  Pro Ala Leu
    1145                1150                1155

Ala Ala  Leu Thr Asn Asp His  Leu Val Ala Leu Ala  Cys Leu Gly
    1160                1165                1170

Gly Arg  Pro Ala Leu Asp Ala  Val Lys Lys Gly Leu  Pro His Ala
    1175                1180                1185

-continued

```
Pro Ala Leu Ile Lys Arg Thr Asn Arg Arg Ile Pro Glu Arg Thr
    1190                1195                1200

Ser His Arg Val Ala Pro Lys Lys Arg Lys Val Ser Ser Asp
    1205                1210                1215

Tyr Lys Asp His Asp Gly Asp Tyr Lys Asp His Asp Ile Asp Tyr
    1220                1225                1230

Lys Asp Asp Asp Asp Lys Ala Ala Gly Gly Gly Ser Gly Arg
    1235                1240                1245

Ala Asp Ala Leu Asp Asp Phe Asp Leu Asp Met Leu Gly Ser Asp
    1250                1255                1260

Ala Leu Asp Asp Phe Asp Leu Asp Met Leu Gly Ser Asp Ala Leu
    1265                1270                1275

Asp Asp Phe Asp Leu Asp Met Leu Gly Ser Asp Ala Leu Asp Asp
    1280                1285                1290

Phe Asp Leu Asp Met Leu His His His His His His
    1295                1300                1305

<210> SEQ ID NO 25
<211> LENGTH: 1208
<212> TYPE: PRT
<213> ORGANISM: Artificial sequence
<220> FEATURE:
<223> OTHER INFORMATION: synthetic

<400> SEQUENCE: 25

Met Ala Pro Lys Lys Lys Arg Lys Val Asp Tyr Lys Asp His Asp Gly
1               5                   10                  15

Asp Tyr Lys Asp His Asp Ile Asp Tyr Lys Asp Asp Asp Lys Gly
                20                  25                  30

Thr Val Asp Leu Arg Thr Leu Gly Tyr Ser Gln Gln Gln Gln Glu Lys
            35                  40                  45

Ile Lys Pro Lys Val Arg Ser Thr Val Ala Gln His His Glu Ala Leu
        50                  55                  60

Val Gly His Gly Phe Thr His Ala His Ile Val Ala Leu Ser Gln His
65                  70                  75                  80

Pro Ala Ala Leu Gly Thr Val Ala Val Lys Tyr Gln Asp Met Ile Ala
                85                  90                  95

Ala Leu Pro Glu Ala Thr His Glu Ala Ile Val Gly Val Gly Lys Gln
            100                 105                 110

Trp Ser Gly Ala Arg Ala Leu Glu Ala Leu Leu Thr Val Ala Gly Glu
        115                 120                 125

Leu Arg Gly Pro Pro Leu Gln Leu Asp Thr Gly Gln Leu Leu Lys Ile
    130                 135                 140

Ala Lys Arg Gly Gly Val Thr Ala Val Glu Ala Val His Ala Trp Arg
145                 150                 155                 160

Asn Ala Leu Thr Gly Ala Pro Leu Asn Leu Thr Pro Glu Gln Val Val
                165                 170                 175

Ala Ile Leu Thr Pro Glu Gln Val Val Ala Ile Ala Ser His Asp Gly
            180                 185                 190

Gly Lys Gln Ala Leu Glu Thr Val Gln Arg Leu Leu Pro Val Leu Cys
        195                 200                 205

Gln Ala His Gly Leu Thr Pro Glu Gln Val Val Ala Ile Ala Ser Asn
    210                 215                 220

Gly Gly Gly Lys Gln Ala Leu Glu Thr Val Gln Arg Leu Leu Pro Val
225                 230                 235                 240
```

```
Leu Cys Gln Ala His Gly Leu Thr Pro Glu Gln Val Val Ala Ile Ala
                245                 250                 255

Ser Asn Gly Gly Gly Lys Gln Ala Leu Glu Thr Val Gln Arg Leu Leu
            260                 265                 270

Pro Val Leu Cys Gln Ala His Gly Leu Thr Pro Glu Gln Val Val Ala
        275                 280                 285

Ile Ala Ser His Asp Gly Gly Lys Gln Ala Leu Glu Thr Val Gln Arg
    290                 295                 300

Leu Leu Pro Val Leu Cys Gln Ala His Gly Leu Thr Pro Glu Gln Val
305                 310                 315                 320

Val Ala Ile Ala Ser Asn Gly Gly Gly Lys Gln Ala Leu Glu Thr Val
            325                 330                 335

Gln Arg Leu Leu Pro Val Leu Cys Gln Ala His Gly Leu Thr Pro Glu
        340                 345                 350

Gln Val Val Ala Ile Ala Ser Asn His Gly Gly Lys Gln Ala Leu Glu
    355                 360                 365

Thr Val Gln Arg Leu Leu Pro Val Leu Cys Gln Ala His Gly Leu Thr
370                 375                 380

Pro Glu Gln Val Val Ala Ile Ala Ser Asn His Gly Gly Lys Gln Ala
385                 390                 395                 400

Leu Glu Thr Val Gln Arg Leu Leu Pro Val Leu Cys Gln Ala His Gly
            405                 410                 415

Leu Thr Pro Glu Gln Val Val Ala Ile Ala Ser Asn Ile Gly Gly Lys
        420                 425                 430

Gln Ala Leu Glu Thr Val Gln Arg Leu Leu Pro Val Leu Cys Gln Ala
    435                 440                 445

His Gly Leu Thr Pro Glu Gln Val Val Ala Ile Ala Ser Asn His Gly
450                 455                 460

Gly Lys Gln Ala Leu Glu Thr Val Gln Arg Leu Leu Pro Val Leu Cys
465                 470                 475                 480

Gln Ala His Gly Leu Thr Pro Glu Gln Val Val Ala Ile Ala Ser Asn
            485                 490                 495

Gly Gly Gly Lys Gln Ala Leu Glu Thr Val Gln Arg Leu Leu Pro Val
        500                 505                 510

Leu Cys Gln Ala His Gly Leu Thr Pro Glu Gln Val Val Ala Ile Ala
    515                 520                 525

Ser Asn His Gly Gly Lys Gln Ala Leu Glu Thr Val Gln Arg Leu Leu
530                 535                 540

Pro Val Leu Cys Gln Ala His Gly Leu Thr Pro Glu Gln Val Val Ala
545                 550                 555                 560

Ile Ala Ser Asn Gly Gly Gly Lys Gln Ala Leu Glu Thr Val Gln Arg
            565                 570                 575

Leu Leu Pro Val Leu Cys Gln Ala His Gly Leu Thr Pro Glu Gln Val
        580                 585                 590

Val Ala Ile Ala Ser Asn Ile Gly Gly Lys Gln Ala Leu Glu Thr Val
    595                 600                 605

Gln Arg Leu Leu Pro Val Leu Cys Gln Ala His Gly Leu Thr Pro Glu
610                 615                 620

Gln Val Val Ala Ile Ala Ser His Asp Gly Gly Lys Gln Ala Leu Glu
625                 630                 635                 640

Thr Val Gln Arg Leu Leu Pro Val Leu Cys Gln Ala His Gly Leu Thr
            645                 650                 655

Pro Glu Gln Val Val Ala Ile Ala Ser His Asp Gly Gly Lys Gln Ala
```

```
                    660                 665                 670
Leu Glu Thr Val Gln Arg Leu Leu Pro Val Leu Cys Gln Ala His Gly
                675                 680                 685
Leu Thr Pro Glu Gln Val Val Ala Ile Ala Ser Asn Ile Gly Gly Lys
                690                 695                 700
Gln Ala Leu Glu Thr Val Gln Arg Leu Leu Pro Val Leu Cys Gln Ala
705                 710                 715                 720
His Gly Leu Thr Pro Glu Gln Val Val Ala Ile Ala Ser Asn His Gly
                725                 730                 735
Gly Lys Gln Ala Leu Glu Thr Val Gln Arg Leu Leu Pro Val Leu Cys
                740                 745                 750
Gln Ala His Gly Leu Thr Pro Glu Gln Val Val Ala Ile Ala Ser Asn
                755                 760                 765
Gly Gly Gly Lys Gln Ala Leu Glu Thr Val Gln Arg Leu Leu Pro Val
                770                 775                 780
Leu Cys Gln Ala His Gly Leu Thr Pro Glu Gln Val Val Ala Ile Ala
785                 790                 795                 800
Ser Asn Gly Gly Gly Lys Gln Ala Leu Glu Thr Val Gln Arg Leu Leu
                805                 810                 815
Pro Val Leu Cys Gln Ala His Gly Leu Thr Pro Glu Gln Val Val Ala
                820                 825                 830
Ile Ala Ser Asn His Gly Gly Lys Gln Ala Leu Glu Thr Val Gln Arg
                835                 840                 845
Leu Leu Pro Val Leu Cys Gln Ala His Gly Leu Thr Pro Glu Gln Val
                850                 855                 860
Val Ala Ile Ala Ser Asn Gly Gly Gly Lys Gln Ala Leu Glu Thr Val
865                 870                 875                 880
Gln Arg Leu Leu Pro Val Leu Cys Gln Ala His Gly Leu Thr Pro Glu
                885                 890                 895
Gln Val Val Ala Ile Ala Ser Asn Ile Gly Gly Lys Gln Ala Leu Glu
                900                 905                 910
Thr Val Gln Arg Leu Leu Pro Val Leu Cys Gln Ala His Gly Leu Thr
                915                 920                 925
Pro Glu Gln Val Val Ala Ile Ala Ser Asn Gly Gly Gly Lys Gln Ala
                930                 935                 940
Leu Glu Thr Val Gln Arg Leu Leu Pro Val Leu Cys Gln Ala His Gly
945                 950                 955                 960
Leu Thr Pro Glu Gln Val Val Ala Ile Ala Ser Asn Ile Gly Gly Lys
                965                 970                 975
Gln Ala Leu Glu Thr Val Gln Arg Leu Leu Pro Val Leu Cys Gln Ala
                980                 985                 990
His Gly Leu Thr Pro Glu Gln Val Val Ala Ile Ala Ser Asn Ile Gly
                995                1000                1005
Gly Lys Gln Ala Leu Glu Thr Val Gln Arg Leu Leu Pro Val Leu
                1010                1015                1020
Cys Gln Ala His Gly Leu Thr Pro Glu Gln Val Val Ala Ile Ala
                1025                1030                1035
Ser Asn Ile Gly Gly Lys Gln Ala Leu Glu Thr Val Gln Arg Leu
                1040                1045                1050
Leu Pro Val Leu Cys Gln Ala His Gly Leu Thr Pro Glu Gln Val
                1055                1060                1065
Val Ala Ile Ala Ser Asn Gly Gly Gly Lys Gln Ala Leu Glu Thr
                1070                1075                1080
```

```
Val Gln Arg Leu Leu Pro Val Leu Cys Gln Ala His Gly Leu Thr
    1085                1090                1095

Pro Glu Gln Val Val Ala Ile Ala Ser Asn Ile Gly Gly Lys Gln
    1100                1105                1110

Ala Leu Glu Thr Val Gln Arg Leu Leu Pro Val Leu Cys Gln Ala
    1115                1120                1125

His Gly Leu Thr Pro Glu Gln Val Val Ala Ile Ala Ser Asn Gly
    1130                1135                1140

Gly Gly Ser Ile Val Ala Gln Leu Ser Arg Pro Asp Pro Ala Leu
    1145                1150                1155

Ala Ala Leu Thr Asn Asp His Leu Val Ala Leu Ala Cys Leu Gly
    1160                1165                1170

Gly Arg Pro Ala Leu Asp Ala Val Lys Lys Gly Leu Pro His Ala
    1175                1180                1185

Pro Ala Leu Ile Lys Arg Thr Asn Arg Arg Ile Pro Glu Arg Thr
    1190                1195                1200

Ser His Arg Val Ala
    1205

<210> SEQ ID NO 26
<211> LENGTH: 1305
<212> TYPE: PRT
<213> ORGANISM: Artificial sequence
<220> FEATURE:
<223> OTHER INFORMATION: synthetic

<400> SEQUENCE: 26

Met Ala Pro Lys Lys Lys Arg Lys Val Asp Tyr Lys Asp His Asp Gly
1               5                   10                  15

Asp Tyr Lys Asp His Asp Ile Asp Tyr Lys Asp Asp Asp Lys Gly
                20                  25                  30

Thr Val Asp Leu Arg Thr Leu Gly Tyr Ser Gln Gln Gln Gln Glu Lys
            35                  40                  45

Ile Lys Pro Lys Val Arg Ser Thr Val Ala Gln His His Glu Ala Leu
    50                  55                  60

Val Gly His Gly Phe Thr His Ala His Ile Val Ala Leu Ser Gln His
65                  70                  75                  80

Pro Ala Ala Leu Gly Thr Val Ala Val Lys Tyr Gln Asp Met Ile Ala
                85                  90                  95

Ala Leu Pro Glu Ala Thr His Glu Ala Ile Val Gly Val Gly Lys Gln
            100                 105                 110

Trp Ser Gly Ala Arg Ala Leu Glu Ala Leu Leu Thr Val Ala Gly Glu
        115                 120                 125

Leu Arg Gly Pro Pro Leu Gln Leu Asp Thr Gly Gln Leu Leu Lys Ile
    130                 135                 140

Ala Lys Arg Gly Gly Val Thr Ala Val Glu Ala Val His Ala Trp Arg
145                 150                 155                 160

Asn Ala Leu Thr Gly Ala Pro Leu Asn Leu Thr Pro Glu Gln Val Val
                165                 170                 175

Ala Ile Leu Thr Pro Glu Gln Val Val Ala Ile Ala Ser His Asp Gly
            180                 185                 190

Gly Lys Gln Ala Leu Glu Thr Val Gln Arg Leu Leu Pro Val Leu Cys
        195                 200                 205

Gln Ala His Gly Leu Thr Pro Glu Gln Val Val Ala Ile Ala Ser Asn
    210                 215                 220
```

```
Gly Gly Gly Lys Gln Ala Leu Glu Thr Val Gln Arg Leu Leu Pro Val
225                 230                 235                 240

Leu Cys Gln Ala His Gly Leu Thr Pro Glu Gln Val Val Ala Ile Ala
            245                 250                 255

Ser Asn Gly Gly Gly Lys Gln Ala Leu Glu Thr Val Gln Arg Leu Leu
            260                 265                 270

Pro Val Leu Cys Gln Ala His Gly Leu Thr Pro Glu Gln Val Val Ala
        275                 280                 285

Ile Ala Ser His Asp Gly Gly Lys Gln Ala Leu Glu Thr Val Gln Arg
        290                 295                 300

Leu Leu Pro Val Leu Cys Gln Ala His Gly Leu Thr Pro Glu Gln Val
305                 310                 315                 320

Val Ala Ile Ala Ser Asn Gly Gly Gly Lys Gln Ala Leu Glu Thr Val
                325                 330                 335

Gln Arg Leu Leu Pro Val Leu Cys Gln Ala His Gly Leu Thr Pro Glu
                340                 345                 350

Gln Val Val Ala Ile Ala Ser Asn His Gly Gly Lys Gln Ala Leu Glu
            355                 360                 365

Thr Val Gln Arg Leu Leu Pro Val Leu Cys Gln Ala His Gly Leu Thr
370                 375                 380

Pro Glu Gln Val Val Ala Ile Ala Ser Asn His Gly Gly Lys Gln Ala
385                 390                 395                 400

Leu Glu Thr Val Gln Arg Leu Leu Pro Val Leu Cys Gln Ala His Gly
                405                 410                 415

Leu Thr Pro Glu Gln Val Val Ala Ile Ala Ser Asn Ile Gly Gly Lys
            420                 425                 430

Gln Ala Leu Glu Thr Val Gln Arg Leu Leu Pro Val Leu Cys Gln Ala
            435                 440                 445

His Gly Leu Thr Pro Glu Gln Val Val Ala Ile Ala Ser Asn His Gly
        450                 455                 460

Gly Lys Gln Ala Leu Glu Thr Val Gln Arg Leu Leu Pro Val Leu Cys
465                 470                 475                 480

Gln Ala His Gly Leu Thr Pro Glu Gln Val Val Ala Ile Ala Ser Asn
                485                 490                 495

Gly Gly Gly Lys Gln Ala Leu Glu Thr Val Gln Arg Leu Leu Pro Val
            500                 505                 510

Leu Cys Gln Ala His Gly Leu Thr Pro Glu Gln Val Val Ala Ile Ala
        515                 520                 525

Ser Asn His Gly Gly Lys Gln Ala Leu Glu Thr Val Gln Arg Leu Leu
        530                 535                 540

Pro Val Leu Cys Gln Ala His Gly Leu Thr Pro Glu Gln Val Val Ala
545                 550                 555                 560

Ile Ala Ser Asn Gly Gly Gly Lys Gln Ala Leu Glu Thr Val Gln Arg
                565                 570                 575

Leu Leu Pro Val Leu Cys Gln Ala His Gly Leu Thr Pro Glu Gln Val
                580                 585                 590

Val Ala Ile Ala Ser Asn Ile Gly Gly Lys Gln Ala Leu Glu Thr Val
            595                 600                 605

Gln Arg Leu Leu Pro Val Leu Cys Gln Ala His Gly Leu Thr Pro Glu
        610                 615                 620

Gln Val Val Ala Ile Ala Ser His Asp Gly Gly Lys Gln Ala Leu Glu
625                 630                 635                 640
```

-continued

Thr Val Gln Arg Leu Leu Pro Val Leu Cys Gln Ala His Gly Leu Thr
                645                 650                 655

Pro Glu Gln Val Val Ala Ile Ala Ser His Asp Gly Gly Lys Gln Ala
            660                 665                 670

Leu Glu Thr Val Gln Arg Leu Leu Pro Val Leu Cys Gln Ala His Gly
        675                 680                 685

Leu Thr Pro Glu Gln Val Val Ala Ile Ala Ser Asn Ile Gly Gly Lys
        690                 695                 700

Gln Ala Leu Glu Thr Val Gln Arg Leu Leu Pro Val Leu Cys Gln Ala
705                 710                 715                 720

His Gly Leu Thr Pro Glu Gln Val Val Ala Ile Ala Ser Asn His Gly
                725                 730                 735

Gly Lys Gln Ala Leu Glu Thr Val Gln Arg Leu Leu Pro Val Leu Cys
            740                 745                 750

Gln Ala His Gly Leu Thr Pro Glu Gln Val Val Ala Ile Ala Ser Asn
        755                 760                 765

Gly Gly Gly Lys Gln Ala Leu Glu Thr Val Gln Arg Leu Leu Pro Val
    770                 775                 780

Leu Cys Gln Ala His Gly Leu Thr Pro Glu Gln Val Val Ala Ile Ala
785                 790                 795                 800

Ser Asn Gly Gly Gly Lys Gln Ala Leu Glu Thr Val Gln Arg Leu Leu
                805                 810                 815

Pro Val Leu Cys Gln Ala His Gly Leu Thr Pro Glu Gln Val Val Ala
            820                 825                 830

Ile Ala Ser Asn His Gly Gly Lys Gln Ala Leu Glu Thr Val Gln Arg
        835                 840                 845

Leu Leu Pro Val Leu Cys Gln Ala His Gly Leu Thr Pro Glu Gln Val
    850                 855                 860

Val Ala Ile Ala Ser Asn Gly Gly Lys Gln Ala Leu Glu Thr Val
865                 870                 875                 880

Gln Arg Leu Leu Pro Val Leu Cys Gln Ala His Gly Leu Thr Pro Glu
                885                 890                 895

Gln Val Val Ala Ile Ala Ser Asn Ile Gly Gly Lys Gln Ala Leu Glu
            900                 905                 910

Thr Val Gln Arg Leu Leu Pro Val Leu Cys Gln Ala His Gly Leu Thr
        915                 920                 925

Pro Glu Gln Val Val Ala Ile Ala Ser Asn Gly Gly Gly Lys Gln Ala
    930                 935                 940

Leu Glu Thr Val Gln Arg Leu Leu Pro Val Leu Cys Gln Ala His Gly
945                 950                 955                 960

Leu Thr Pro Glu Gln Val Val Ala Ile Ala Ser Asn Ile Gly Gly Lys
                965                 970                 975

Gln Ala Leu Glu Thr Val Gln Arg Leu Leu Pro Val Leu Cys Gln Ala
            980                 985                 990

His Gly Leu Thr Pro Glu Gln Val Val Ala Ile Ala Ser Asn Ile Gly
        995                1000                1005

Gly Lys Gln Ala Leu Glu Thr Val Gln Arg Leu Leu Pro Val Leu
    1010                1015                1020

Cys Gln Ala His Gly Leu Thr Pro Glu Gln Val Val Ala Ile Ala
    1025                1030                1035

Ser Asn Ile Gly Gly Lys Gln Ala Leu Glu Thr Val Gln Arg Leu
    1040                1045                1050

Leu Pro Val Leu Cys Gln Ala His Gly Leu Thr Pro Glu Gln Val

```
              1055                1060                1065

Val Ala Ile Ala Ser Asn Gly Gly Gly Lys Gln Ala Leu Glu Thr
        1070                1075                1080

Val Gln Arg Leu Leu Pro Val Leu Cys Gln Ala His Gly Leu Thr
        1085                1090                1095

Pro Glu Gln Val Val Ala Ile Ala Ser Asn Ile Gly Gly Lys Gln
        1100                1105                1110

Ala Leu Glu Thr Val Gln Arg Leu Leu Pro Val Leu Cys Gln Ala
        1115                1120                1125

His Gly Leu Thr Pro Glu Gln Val Val Ala Ile Ala Ser Asn Gly
        1130                1135                1140

Gly Gly Ser Ile Val Ala Gln Leu Ser Arg Pro Asp Pro Ala Leu
        1145                1150                1155

Ala Ala Leu Thr Asn Asp His Leu Val Ala Leu Ala Cys Leu Gly
        1160                1165                1170

Gly Arg Pro Ala Leu Asp Ala Val Lys Lys Gly Leu Pro His Ala
        1175                1180                1185

Pro Ala Leu Ile Lys Arg Thr Asn Arg Arg Ile Pro Glu Arg Thr
        1190                1195                1200

Ser His Arg Val Ala Pro Lys Lys Arg Lys Val Ser Ser Asp
        1205                1210                1215

Tyr Lys Asp His Asp Gly Asp Tyr Lys Asp His Asp Ile Asp Tyr
        1220                1225                1230

Lys Asp Asp Asp Lys Ala Gly Gly Gly Ser Gly Arg
        1235                1240                1245

Ala Asp Ala Leu Asp Asp Phe Asp Leu Asp Met Leu Gly Ser Asp
        1250                1255                1260

Ala Leu Asp Asp Phe Asp Leu Asp Met Leu Gly Ser Asp Ala Leu
        1265                1270                1275

Asp Asp Phe Asp Leu Asp Met Leu Gly Ser Asp Ala Leu Asp Asp
        1280                1285                1290

Phe Asp Leu Asp Met Leu His His His His His
        1295                1300                1305

<210> SEQ ID NO 27
<211> LENGTH: 1242
<212> TYPE: PRT
<213> ORGANISM: Artificial sequence
<220> FEATURE:
<223> OTHER INFORMATION: synthetic

<400> SEQUENCE: 27

Met Ala Pro Lys Lys Lys Arg Lys Val Asp Tyr Lys Asp His Asp Gly
1               5                  10                  15

Asp Tyr Lys Asp His Asp Ile Asp Tyr Lys Asp Asp Asp Lys Gly
            20                  25                  30

Thr Val Asp Leu Arg Thr Leu Gly Tyr Ser Gln Gln Gln Gln Glu Lys
        35                  40                  45

Ile Lys Pro Lys Val Arg Ser Thr Val Ala Gln His His Glu Ala Leu
    50                  55                  60

Val Gly His Gly Phe Thr His Ala His Ile Val Ala Leu Ser Gln His
65                  70                  75                  80

Pro Ala Ala Leu Gly Thr Val Ala Val Lys Tyr Gln Asp Met Ile Ala
                85                  90                  95

Ala Leu Pro Glu Ala Thr His Glu Ala Ile Val Gly Val Gly Lys Gln
```

```
                100                 105                 110
Trp Ser Gly Ala Arg Ala Leu Glu Ala Leu Thr Val Ala Gly Glu
        115                 120                 125
Leu Arg Gly Pro Pro Leu Gln Leu Asp Thr Gly Gln Leu Leu Lys Ile
130                 135                 140
Ala Lys Arg Gly Gly Val Thr Ala Val Glu Ala Val His Ala Trp Arg
145                 150                 155                 160
Asn Ala Leu Thr Gly Ala Pro Leu Asn Leu Thr Pro Glu Gln Val Val
                165                 170                 175
Ala Ile Leu Thr Pro Glu Gln Val Val Ala Ile Ala Ser Asn His Gly
                180                 185                 190
Gly Lys Gln Ala Leu Glu Thr Val Gln Arg Leu Leu Pro Val Leu Cys
        195                 200                 205
Gln Ala His Gly Leu Thr Pro Glu Gln Val Val Ala Ile Ala Ser His
        210                 215                 220
Asp Gly Gly Lys Gln Ala Leu Glu Thr Val Gln Arg Leu Leu Pro Val
225                 230                 235                 240
Leu Cys Gln Ala His Gly Leu Thr Pro Glu Gln Val Val Ala Ile Ala
                245                 250                 255
Ser Asn Ile Gly Gly Lys Gln Ala Leu Glu Thr Val Gln Arg Leu Leu
                260                 265                 270
Pro Val Leu Cys Gln Ala His Gly Leu Thr Pro Glu Gln Val Val Ala
        275                 280                 285
Ile Ala Ser His Asp Gly Gly Lys Gln Ala Leu Glu Thr Val Gln Arg
        290                 295                 300
Leu Leu Pro Val Leu Cys Gln Ala His Gly Leu Thr Pro Glu Gln Val
305                 310                 315                 320
Val Ala Ile Ala Ser Asn Gly Gly Gly Lys Gln Ala Leu Glu Thr Val
                325                 330                 335
Gln Arg Leu Leu Pro Val Leu Cys Gln Ala His Gly Leu Thr Pro Glu
                340                 345                 350
Gln Val Val Ala Ile Ala Ser Asn His Gly Gly Lys Gln Ala Leu Glu
        355                 360                 365
Thr Val Gln Arg Leu Leu Pro Val Leu Cys Gln Ala His Gly Leu Thr
370                 375                 380
Pro Glu Gln Val Val Ala Ile Ala Ser Asn Gly Gly Gly Lys Gln Ala
385                 390                 395                 400
Leu Glu Thr Val Gln Arg Leu Leu Pro Val Leu Cys Gln Ala His Gly
                405                 410                 415
Leu Thr Pro Glu Gln Val Val Ala Ile Ala Ser His Asp Gly Gly Lys
                420                 425                 430
Gln Ala Leu Glu Thr Val Gln Arg Leu Leu Pro Val Leu Cys Gln Ala
        435                 440                 445
His Gly Leu Thr Pro Glu Gln Val Val Ala Ile Ala Ser His Asp Gly
        450                 455                 460
Gly Lys Gln Ala Leu Glu Thr Val Gln Arg Leu Leu Pro Val Leu Cys
465                 470                 475                 480
Gln Ala His Gly Leu Thr Pro Glu Gln Val Val Ala Ile Ala Ser Asn
                485                 490                 495
Ile Gly Gly Lys Gln Ala Leu Glu Thr Val Gln Arg Leu Leu Pro Val
                500                 505                 510
Leu Cys Gln Ala His Gly Leu Thr Pro Glu Gln Val Val Ala Ile Ala
        515                 520                 525
```

-continued

```
Ser Asn Ile Gly Gly Lys Gln Ala Leu Glu Thr Val Gln Arg Leu Leu
    530                 535                 540
Pro Val Leu Cys Gln Ala His Gly Leu Thr Pro Glu Gln Val Val Ala
545                 550                 555                 560
Ile Ala Ser Asn Ile Gly Gly Lys Gln Ala Leu Glu Thr Val Gln Arg
                565                 570                 575
Leu Leu Pro Val Leu Cys Gln Ala His Gly Leu Thr Pro Glu Gln Val
            580                 585                 590
Val Ala Ile Ala Ser Asn Ile Gly Gly Lys Gln Ala Leu Glu Thr Val
        595                 600                 605
Gln Arg Leu Leu Pro Val Leu Cys Gln Ala His Gly Leu Thr Pro Glu
    610                 615                 620
Gln Val Val Ala Ile Ala Ser Asn Gly Gly Lys Gln Ala Leu Glu
625                 630                 635                 640
Thr Val Gln Arg Leu Leu Pro Val Leu Cys Gln Ala His Gly Leu Thr
                645                 650                 655
Pro Glu Gln Val Val Ala Ile Ala Ser Asn His Gly Gly Lys Gln Ala
            660                 665                 670
Leu Glu Thr Val Gln Arg Leu Leu Pro Val Leu Cys Gln Ala His Gly
        675                 680                 685
Leu Thr Pro Glu Gln Val Val Ala Ile Ala Ser Asn His Gly Gly Lys
    690                 695                 700
Gln Ala Leu Glu Thr Val Gln Arg Leu Leu Pro Val Leu Cys Gln Ala
705                 710                 715                 720
His Gly Leu Thr Pro Glu Gln Val Val Ala Ile Ala Ser His Asp Gly
                725                 730                 735
Gly Lys Gln Ala Leu Glu Thr Val Gln Arg Leu Leu Pro Val Leu Cys
            740                 745                 750
Gln Ala His Gly Leu Thr Pro Glu Gln Val Val Ala Ile Ala Ser Asn
        755                 760                 765
Gly Gly Gly Lys Gln Ala Leu Glu Thr Val Gln Arg Leu Leu Pro Val
    770                 775                 780
Leu Cys Gln Ala His Gly Leu Thr Pro Glu Gln Val Val Ala Ile Ala
785                 790                 795                 800
Ser Asn Gly Gly Gly Lys Gln Ala Leu Glu Thr Val Gln Arg Leu Leu
                805                 810                 815
Pro Val Leu Cys Gln Ala His Gly Leu Thr Pro Glu Gln Val Val Ala
            820                 825                 830
Ile Ala Ser His Asp Gly Gly Lys Gln Ala Leu Glu Thr Val Gln Arg
        835                 840                 845
Leu Leu Pro Val Leu Cys Gln Ala His Gly Leu Thr Pro Glu Gln Val
    850                 855                 860
Val Ala Ile Ala Ser His Asp Gly Gly Lys Gln Ala Leu Glu Thr Val
865                 870                 875                 880
Gln Arg Leu Leu Pro Val Leu Cys Gln Ala His Gly Leu Thr Pro Glu
                885                 890                 895
Gln Val Val Ala Ile Ala Ser Asn Gly Gly Gly Lys Gln Ala Leu Glu
            900                 905                 910
Thr Val Gln Arg Leu Leu Pro Val Leu Cys Gln Ala His Gly Leu Thr
        915                 920                 925
Pro Glu Gln Val Val Ala Ile Ala Ser Asn His Gly Gly Lys Gln Ala
    930                 935                 940
```

```
Leu Glu Thr Val Gln Arg Leu Leu Pro Val Leu Cys Gln Ala His Gly
945                 950                 955                 960

Leu Thr Pro Glu Gln Val Val Ala Ile Ala Ser Asn Ile Gly Gly Lys
            965                 970                 975

Gln Ala Leu Glu Thr Val Gln Arg Leu Leu Pro Val Leu Cys Gln Ala
            980                 985                 990

His Gly Leu Thr Pro Glu Gln Val Val Ala Ile Ala Ser Asn Gly Gly
        995                 1000                1005

Gly Lys Gln Ala Leu Glu Thr Val Gln Arg Leu Leu Pro Val Leu
    1010                1015                1020

Cys Gln Ala His Gly Leu Thr Pro Glu Gln Val Val Ala Ile Ala
    1025                1030                1035

Ser His Asp Gly Gly Lys Gln Ala Leu Glu Thr Val Gln Arg Leu
    1040                1045                1050

Leu Pro Val Leu Cys Gln Ala His Gly Leu Thr Pro Glu Gln Val
    1055                1060                1065

Val Ala Ile Ala Ser His Asp Gly Gly Lys Gln Ala Leu Glu Thr
    1070                1075                1080

Val Gln Arg Leu Leu Pro Val Leu Cys Gln Ala His Gly Leu Thr
    1085                1090                1095

Pro Glu Gln Val Val Ala Ile Ala Ser His Asp Gly Gly Lys Gln
    1100                1105                1110

Ala Leu Glu Thr Val Gln Arg Leu Leu Pro Val Leu Cys Gln Ala
    1115                1120                1125

His Gly Leu Thr Pro Glu Gln Val Val Ala Ile Ala Ser His Asp
    1130                1135                1140

Gly Gly Lys Gln Ala Leu Glu Thr Val Gln Arg Leu Leu Pro Val
    1145                1150                1155

Leu Cys Gln Ala His Gly Leu Thr Pro Glu Gln Val Val Ala Ile
    1160                1165                1170

Ala Ser Asn Gly Gly Gly Ser Ile Val Ala Gln Leu Ser Arg Pro
    1175                1180                1185

Asp Pro Ala Leu Ala Ala Leu Thr Asn Asp His Leu Val Ala Leu
    1190                1195                1200

Ala Cys Leu Gly Gly Arg Pro Ala Leu Asp Ala Val Lys Lys Gly
    1205                1210                1215

Leu Pro His Ala Pro Ala Leu Ile Lys Arg Thr Asn Arg Arg Ile
    1220                1225                1230

Pro Glu Arg Thr Ser His Arg Val Ala
    1235                1240

<210> SEQ ID NO 28
<211> LENGTH: 1339
<212> TYPE: PRT
<213> ORGANISM: Artificial sequence
<220> FEATURE:
<223> OTHER INFORMATION: synthetic

<400> SEQUENCE: 28

Met Ala Pro Lys Lys Lys Arg Lys Val Asp Tyr Lys Asp His Asp Gly
1               5                   10                  15

Asp Tyr Lys Asp His Asp Ile Asp Tyr Lys Asp Asp Asp Asp Lys Gly
            20                  25                  30

Thr Val Asp Leu Arg Thr Leu Gly Tyr Ser Gln Gln Gln Gln Glu Lys
        35                  40                  45
```

-continued

```
Ile Lys Pro Lys Val Arg Ser Thr Val Ala Gln His His Glu Ala Leu
 50                  55                  60

Val Gly His Gly Phe Thr His Ala His Ile Val Ala Leu Ser Gln His
 65                  70                  75                  80

Pro Ala Ala Leu Gly Thr Val Ala Val Lys Tyr Gln Asp Met Ile Ala
                 85                  90                  95

Ala Leu Pro Glu Ala Thr His Glu Ala Ile Val Gly Val Gly Lys Gln
            100                 105                 110

Trp Ser Gly Ala Arg Ala Leu Glu Ala Leu Leu Thr Val Ala Gly Glu
        115                 120                 125

Leu Arg Gly Pro Pro Leu Gln Leu Asp Thr Gly Gln Leu Leu Lys Ile
130                 135                 140

Ala Lys Arg Gly Gly Val Thr Ala Val Glu Ala Val His Ala Trp Arg
145                 150                 155                 160

Asn Ala Leu Thr Gly Ala Pro Leu Asn Leu Thr Pro Glu Gln Val Val
                165                 170                 175

Ala Ile Leu Thr Pro Glu Gln Val Val Ala Ile Ala Ser Asn His Gly
            180                 185                 190

Gly Lys Gln Ala Leu Glu Thr Val Gln Arg Leu Leu Pro Val Leu Cys
        195                 200                 205

Gln Ala His Gly Leu Thr Pro Glu Gln Val Val Ala Ile Ala Ser His
210                 215                 220

Asp Gly Gly Lys Gln Ala Leu Glu Thr Val Gln Arg Leu Leu Pro Val
225                 230                 235                 240

Leu Cys Gln Ala His Gly Leu Thr Pro Glu Gln Val Val Ala Ile Ala
                245                 250                 255

Ser Asn Ile Gly Gly Lys Gln Ala Leu Glu Thr Val Gln Arg Leu Leu
            260                 265                 270

Pro Val Leu Cys Gln Ala His Gly Leu Thr Pro Glu Gln Val Val Ala
        275                 280                 285

Ile Ala Ser His Asp Gly Gly Lys Gln Ala Leu Glu Thr Val Gln Arg
290                 295                 300

Leu Leu Pro Val Leu Cys Gln Ala His Gly Leu Thr Pro Glu Gln Val
305                 310                 315                 320

Val Ala Ile Ala Ser Asn Gly Gly Gly Lys Gln Ala Leu Glu Thr Val
                325                 330                 335

Gln Arg Leu Leu Pro Val Leu Cys Gln Ala His Gly Leu Thr Pro Glu
            340                 345                 350

Gln Val Val Ala Ile Ala Ser Asn His Gly Gly Lys Gln Ala Leu Glu
        355                 360                 365

Thr Val Gln Arg Leu Leu Pro Val Leu Cys Gln Ala His Gly Leu Thr
370                 375                 380

Pro Glu Gln Val Val Ala Ile Ala Ser Asn Gly Gly Gly Lys Gln Ala
385                 390                 395                 400

Leu Glu Thr Val Gln Arg Leu Leu Pro Val Leu Cys Gln Ala His Gly
                405                 410                 415

Leu Thr Pro Glu Gln Val Val Ala Ile Ala Ser His Asp Gly Gly Lys
            420                 425                 430

Gln Ala Leu Glu Thr Val Gln Arg Leu Leu Pro Val Leu Cys Gln Ala
        435                 440                 445

His Gly Leu Thr Pro Glu Gln Val Val Ala Ile Ala Ser His Asp Gly
450                 455                 460

Gly Lys Gln Ala Leu Glu Thr Val Gln Arg Leu Leu Pro Val Leu Cys
```

```
                465                 470                 475                 480
        Gln Ala His Gly Leu Thr Pro Glu Gln Val Ala Ile Ala Ser Asn
                        485                 490                 495

Ile Gly Gly Lys Gln Ala Leu Glu Thr Val Gln Arg Leu Leu Pro Val
                        500                 505                 510

Leu Cys Gln Ala His Gly Leu Thr Pro Glu Gln Val Ala Ile Ala
                        515                 520                 525

Ser Asn Ile Gly Gly Lys Gln Ala Leu Glu Thr Val Gln Arg Leu Leu
                        530                 535                 540

Pro Val Leu Cys Gln Ala His Gly Leu Thr Pro Glu Gln Val Val Ala
        545                 550                 555                 560

Ile Ala Ser Asn Ile Gly Gly Lys Gln Ala Leu Glu Thr Val Gln Arg
                        565                 570                 575

Leu Leu Pro Val Leu Cys Gln Ala His Gly Leu Thr Pro Glu Gln Val
                        580                 585                 590

Val Ala Ile Ala Ser Asn Ile Gly Gly Lys Gln Ala Leu Glu Thr Val
                        595                 600                 605

Gln Arg Leu Leu Pro Val Leu Cys Gln Ala His Gly Leu Thr Pro Glu
                        610                 615                 620

Gln Val Val Ala Ile Ala Ser Asn Gly Gly Gly Lys Gln Ala Leu Glu
        625                 630                 635                 640

Thr Val Gln Arg Leu Leu Pro Val Leu Cys Gln Ala His Gly Leu Thr
                        645                 650                 655

Pro Glu Gln Val Val Ala Ile Ala Ser Asn His Gly Gly Lys Gln Ala
                        660                 665                 670

Leu Glu Thr Val Gln Arg Leu Leu Pro Val Leu Cys Gln Ala His Gly
                        675                 680                 685

Leu Thr Pro Glu Gln Val Val Ala Ile Ala Ser Asn His Gly Gly Lys
                        690                 695                 700

Gln Ala Leu Glu Thr Val Gln Arg Leu Leu Pro Val Leu Cys Gln Ala
        705                 710                 715                 720

His Gly Leu Thr Pro Glu Gln Val Val Ala Ile Ala Ser His Asp Gly
                        725                 730                 735

Gly Lys Gln Ala Leu Glu Thr Val Gln Arg Leu Leu Pro Val Leu Cys
                        740                 745                 750

Gln Ala His Gly Leu Thr Pro Glu Gln Val Val Ala Ile Ala Ser Asn
                        755                 760                 765

Gly Gly Gly Lys Gln Ala Leu Glu Thr Val Gln Arg Leu Leu Pro Val
                        770                 775                 780

Leu Cys Gln Ala His Gly Leu Thr Pro Glu Gln Val Val Ala Ile Ala
        785                 790                 795                 800

Ser Asn Gly Gly Gly Lys Gln Ala Leu Glu Thr Val Gln Arg Leu Leu
                        805                 810                 815

Pro Val Leu Cys Gln Ala His Gly Leu Thr Pro Glu Gln Val Val Ala
                        820                 825                 830

Ile Ala Ser His Asp Gly Gly Lys Gln Ala Leu Glu Thr Val Gln Arg
                        835                 840                 845

Leu Leu Pro Val Leu Cys Gln Ala His Gly Leu Thr Pro Glu Gln Val
                        850                 855                 860

Val Ala Ile Ala Ser His Asp Gly Gly Lys Gln Ala Leu Glu Thr Val
        865                 870                 875                 880

Gln Arg Leu Leu Pro Val Leu Cys Gln Ala His Gly Leu Thr Pro Glu
                        885                 890                 895
```

```
Gln Val Val Ala Ile Ala Ser Asn Gly Gly Lys Gln Ala Leu Glu
                900                 905                 910

Thr Val Gln Arg Leu Leu Pro Val Leu Cys Gln Ala His Gly Leu Thr
        915                 920                 925

Pro Glu Gln Val Val Ala Ile Ala Ser Asn His Gly Gly Lys Gln Ala
    930                 935                 940

Leu Glu Thr Val Gln Arg Leu Leu Pro Val Leu Cys Gln Ala His Gly
945                 950                 955                 960

Leu Thr Pro Glu Gln Val Val Ala Ile Ala Ser Asn Ile Gly Lys
                965                 970                 975

Gln Ala Leu Glu Thr Val Gln Arg Leu Leu Pro Val Leu Cys Gln Ala
            980                 985                 990

His Gly Leu Thr Pro Glu Gln Val Val Ala Ile Ala Ser Asn Gly Gly
            995                1000                1005

Gly Lys Gln Ala Leu Glu Thr Val Gln Arg Leu Leu Pro Val Leu
   1010                1015                1020

Cys Gln Ala His Gly Leu Thr Pro Glu Gln Val Val Ala Ile Ala
   1025                1030                1035

Ser His Asp Gly Gly Lys Gln Ala Leu Glu Thr Val Gln Arg Leu
   1040                1045                1050

Leu Pro Val Leu Cys Gln Ala His Gly Leu Thr Pro Glu Gln Val
   1055                1060                1065

Val Ala Ile Ala Ser His Asp Gly Gly Lys Gln Ala Leu Glu Thr
   1070                1075                1080

Val Gln Arg Leu Leu Pro Val Leu Cys Gln Ala His Gly Leu Thr
   1085                1090                1095

Pro Glu Gln Val Val Ala Ile Ala Ser His Asp Gly Gly Lys Gln
   1100                1105                1110

Ala Leu Glu Thr Val Gln Arg Leu Leu Pro Val Leu Cys Gln Ala
   1115                1120                1125

His Gly Leu Thr Pro Glu Gln Val Val Ala Ile Ala Ser His Asp
   1130                1135                1140

Gly Gly Lys Gln Ala Leu Glu Thr Val Gln Arg Leu Leu Pro Val
   1145                1150                1155

Leu Cys Gln Ala His Gly Leu Thr Pro Glu Gln Val Val Ala Ile
   1160                1165                1170

Ala Ser Asn Gly Gly Gly Ser Ile Val Ala Gln Leu Ser Arg Pro
   1175                1180                1185

Asp Pro Ala Leu Ala Ala Leu Thr Asn Asp His Leu Val Ala Leu
   1190                1195                1200

Ala Cys Leu Gly Gly Arg Pro Ala Leu Asp Ala Val Lys Lys Gly
   1205                1210                1215

Leu Pro His Ala Pro Ala Leu Ile Lys Arg Thr Asn Arg Arg Ile
   1220                1225                1230

Pro Glu Arg Thr Ser His Arg Val Ala Pro Lys Lys Lys Arg Lys
   1235                1240                1245

Val Ser Ser Asp Tyr Lys Asp His Asp Gly Asp Tyr Lys Asp His
   1250                1255                1260

Asp Ile Asp Tyr Lys Asp Asp Asp Lys Ala Ala Gly Gly Gly
   1265                1270                1275

Gly Ser Gly Arg Ala Asp Ala Leu Asp Asp Phe Asp Leu Asp Met
   1280                1285                1290
```

```
Leu Gly Ser Asp Ala Leu Asp Asp Phe Asp Leu Asp Met Leu Gly
    1295                1300                1305

Ser Asp Ala Leu Asp Asp Phe Asp Leu Asp Met Leu Gly Ser Asp
    1310                1315                1320

Ala Leu Asp Asp Phe Asp Leu Asp Met Leu His His His His His
    1325                1330                1335

His
```

<210> SEQ ID NO 29
<211> LENGTH: 1368
<212> TYPE: PRT
<213> ORGANISM: Artificial sequence
<220> FEATURE:
<223> OTHER INFORMATION: synthetic

<400> SEQUENCE: 29

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
```

```
              305                 310                 315                 320
         Met Ile Lys Arg Tyr Asp Glu His His Gln Asp Leu Thr Leu Leu Lys
                         325                 330                 335
         Ala Leu Val Arg Gln Gln Leu Pro Glu Lys Tyr Lys Glu Ile Phe Phe
                         340                 345                 350
         Asp Gln Ser Lys Asn Gly Tyr Ala Gly Tyr Ile Asp Gly Gly Ala Ser
                         355                 360                 365
         Gln Glu Glu Phe Tyr Lys Phe Ile Lys Pro Ile Leu Glu Lys Met Asp
                         370                 375                 380
         Gly Thr Glu Glu Leu Leu Val Lys Leu Asn Arg Glu Asp Leu Leu Arg
         385                 390                 395                 400
         Lys Gln Arg Thr Phe Asp Asn Gly Ser Ile Pro His Gln Ile His Leu
                         405                 410                 415
         Gly Glu Leu His Ala Ile Leu Arg Arg Gln Glu Asp Phe Tyr Pro Phe
                         420                 425                 430
         Leu Lys Asp Asn Arg Glu Lys Ile Glu Lys Ile Leu Thr Phe Arg Ile
                         435                 440                 445
         Pro Tyr Tyr Val Gly Pro Leu Ala Arg Gly Asn Ser Arg Phe Ala Trp
                         450                 455                 460
         Met Thr Arg Lys Ser Glu Glu Thr Ile Thr Pro Trp Asn Phe Glu Glu
         465                 470                 475                 480
         Val Val Asp Lys Gly Ala Ser Ala Gln Ser Phe Ile Glu Arg Met Thr
                         485                 490                 495
         Asn Phe Asp Lys Asn Leu Pro Asn Glu Lys Val Leu Pro Lys His Ser
                         500                 505                 510
         Leu Leu Tyr Glu Tyr Phe Thr Val Tyr Asn Glu Leu Thr Lys Val Lys
                         515                 520                 525
         Tyr Val Thr Glu Gly Met Arg Lys Pro Ala Phe Leu Ser Gly Glu Gln
                         530                 535                 540
         Lys Lys Ala Ile Val Asp Leu Leu Phe Lys Thr Asn Arg Lys Val Thr
         545                 550                 555                 560
         Val Lys Gln Leu Lys Glu Asp Tyr Phe Lys Lys Ile Glu Cys Phe Asp
                         565                 570                 575
         Ser Val Glu Ile Ser Gly Val Glu Asp Arg Phe Asn Ala Ser Leu Gly
                         580                 585                 590
         Thr Tyr His Asp Leu Leu Lys Ile Ile Lys Asp Lys Asp Phe Leu Asp
                         595                 600                 605
         Asn Glu Glu Asn Glu Asp Ile Leu Glu Asp Ile Val Leu Thr Leu Thr
                         610                 615                 620
         Leu Phe Glu Asp Arg Glu Met Ile Glu Glu Arg Leu Lys Thr Tyr Ala
         625                 630                 635                 640
         His Leu Phe Asp Asp Lys Val Met Lys Gln Leu Lys Arg Arg Arg Tyr
                         645                 650                 655
         Thr Gly Trp Gly Arg Leu Ser Arg Lys Leu Ile Asn Gly Ile Arg Asp
                         660                 665                 670
         Lys Gln Ser Gly Lys Thr Ile Leu Asp Phe Leu Lys Ser Asp Gly Phe
                         675                 680                 685
         Ala Asn Arg Asn Phe Met Gln Leu Ile His Asp Ser Leu Thr Phe
                         690                 695                 700
         Lys Glu Asp Ile Gln Lys Ala Gln Val Ser Gly Gln Gly Asp Ser Leu
         705                 710                 715                 720
         His Glu His Ile Ala Asn Leu Ala Gly Ser Pro Ala Ile Lys Lys Gly
                         725                 730                 735
```

```
Ile Leu Gln Thr Val Lys Val Asp Glu Leu Val Lys Val Met Gly
                740             745             750

Arg His Lys Pro Glu Asn Ile Val Ile Glu Met Ala Arg Glu Asn Gln
                755             760             765

Thr Thr Gln Lys Gly Lys Asn Ser Arg Glu Arg Met Lys Arg Ile
770             775             780

Glu Glu Gly Ile Lys Glu Leu Gly Ser Gln Ile Leu Lys Glu His Pro
785             790             795             800

Val Glu Asn Thr Gln Leu Gln Asn Glu Lys Leu Tyr Leu Tyr Tyr Leu
                805             810             815

Gln Asn Gly Arg Asp Met Tyr Val Asp Gln Glu Leu Asp Ile Asn Arg
                820             825             830

Leu Ser Asp Tyr Asp Val Asp Ala Ile Val Pro Gln Ser Phe Leu Lys
                835             840             845

Asp Asp Ser Ile Asp Asn Lys Val Leu Thr Arg Ser Asp Lys Asn Arg
                850             855             860

Gly Lys Ser Asp Asn Val Pro Ser Glu Glu Val Val Lys Lys Met Lys
865             870             875             880

Asn Tyr Trp Arg Gln Leu Leu Asn Ala Lys Leu Ile Thr Gln Arg Lys
                885             890             895

Phe Asp Asn Leu Thr Lys Ala Glu Arg Gly Gly Leu Ser Glu Leu Asp
                900             905             910

Lys Ala Gly Phe Ile Lys Arg Gln Leu Val Glu Thr Arg Gln Ile Thr
                915             920             925

Lys His Val Ala Gln Ile Leu Asp Ser Arg Met Asn Thr Lys Tyr Asp
                930             935             940

Glu Asn Asp Lys Leu Ile Arg Glu Val Lys Val Ile Thr Leu Lys Ser
945             950             955             960

Lys Leu Val Ser Asp Phe Arg Lys Asp Phe Gln Phe Tyr Lys Val Arg
                965             970             975

Glu Ile Asn Asn Tyr His His Ala His Asp Ala Tyr Leu Asn Ala Val
                980             985             990

Val Gly Thr Ala Leu Ile Lys Lys Tyr Pro Lys Leu Glu Ser Glu Phe
                995             1000            1005

Val Tyr Gly Asp Tyr Lys Val Tyr Asp Val Arg Lys Met Ile Ala
                1010            1015            1020

Lys Ser Glu Gln Glu Ile Gly Lys Ala Thr Ala Lys Tyr Phe Phe
1025            1030            1035

Tyr Ser Asn Ile Met Asn Phe Phe Lys Thr Glu Ile Thr Leu Ala
1040            1045            1050

Asn Gly Glu Ile Arg Lys Arg Pro Leu Ile Glu Thr Asn Gly Glu
1055            1060            1065

Thr Gly Glu Ile Val Trp Asp Lys Gly Arg Asp Phe Ala Thr Val
1070            1075            1080

Arg Lys Val Leu Ser Met Pro Gln Val Asn Ile Val Lys Lys Thr
1085            1090            1095

Glu Val Gln Thr Gly Gly Phe Ser Lys Glu Ser Ile Leu Pro Lys
1100            1105            1110

Arg Asn Ser Asp Lys Leu Ile Ala Arg Lys Lys Asp Trp Asp Pro
1115            1120            1125

Lys Lys Tyr Gly Gly Phe Asp Ser Pro Thr Val Ala Tyr Ser Val
1130            1135            1140
```

Leu Val Val Ala Lys Val Glu Lys Gly Lys Ser Lys Lys Leu Lys
1145                1150                1155

Ser Val Lys Glu Leu Leu Gly Ile Thr Ile Met Glu Arg Ser Ser
1160                1165                1170

Phe Glu Lys Asn Pro Ile Asp Phe Leu Glu Ala Lys Gly Tyr Lys
1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

<210> SEQ ID NO 30
<211> LENGTH: 1467
<212> TYPE: PRT
<213> ORGANISM: Artificial sequence
<220> FEATURE:
<223> OTHER INFORMATION: synthetic

<400> SEQUENCE: 30

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

-continued

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr

```
545                 550                 555                 560
Val Lys Gln Leu Lys Glu Asp Tyr Phe Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
                595                 600                 605
Asn Glu Glu Asn Glu Asp Ile Leu Glu Asp Ile Val Leu Thr Leu Thr
610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
                675                 680                 685
Ala Asn Arg Asn Phe Met Gln Leu Ile His Asp Asp Ser Leu Thr Phe
                690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
                740                 745                 750
Arg His Lys Pro Glu Asn Ile Val Ile Glu Met Ala Arg Glu Asn Gln
                755                 760                 765
Thr Thr Gln Lys Gly Gln Lys Asn Ser Arg Glu Arg Met Lys Arg Ile
770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp Ala Ile Val Pro Gln Ser Phe Leu Lys
                835                 840                 845
Asp Asp Ser Ile Asp Asn Lys Val Leu Thr Arg Ser Asp Lys Asn Arg
850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
                915                 920                 925
Lys His Val Ala Gln Ile Leu Asp Ser Arg Met Asn Thr Lys Tyr Asp
                930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
```

-continued

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
        1295                1300                1305

Ile Ile His Leu Phe Thr Leu Thr Asn Leu Gly Ala Pro Ala Ala
        1310                1315                1320

Phe Lys Tyr Phe Asp Thr Thr Ile Asp Arg Lys Arg Tyr Thr Ser
        1325                1330                1335

Thr Lys Glu Val Leu Asp Ala Thr Leu Ile His Gln Ser Ile Thr
        1340                1345                1350

Gly Leu Tyr Glu Thr Arg Ile Asp Leu Ser Gln Leu Gly Gly Asp
        1355                1360                1365

-continued

```
Gly Ser Pro Lys Lys Lys Arg Lys Val Ser Ser Asp Tyr Lys Asp
    1370                1375                1380

His Asp Gly Asp Tyr Lys Asp His Asp Ile Asp Tyr Lys Asp Asp
    1385                1390                1395

Asp Asp Lys Ala Ala Gly Gly Gly Ser Gly Arg Ala Asp Ala
    1400                1405                1410

Leu Asp Asp Phe Asp Leu Asp Met Leu Gly Ser Asp Ala Leu Asp
    1415                1420                1425

Asp Phe Asp Leu Asp Met Leu Gly Ser Asp Ala Leu Asp Asp Phe
    1430                1435                1440

Asp Leu Asp Met Leu Gly Ser Asp Ala Leu Asp Asp Phe Asp Leu
    1445                1450                1455

Asp Met Leu His His His His His His
    1460                1465
```

<210> SEQ ID NO 31
<211> LENGTH: 20
<212> TYPE: DNA
<213> ORGANISM: Artificial sequence
<220> FEATURE:
<223> OTHER INFORMATION: synthetic

<400> SEQUENCE: 31
ttatttttcc ttcggaaatt     20

<210> SEQ ID NO 32
<211> LENGTH: 20
<212> TYPE: DNA
<213> ORGANISM: Artificial sequence
<220> FEATURE:
<223> OTHER INFORMATION: synthetic

<400> SEQUENCE: 32
aaaatagttt atttttcctt     20

<210> SEQ ID NO 33
<211> LENGTH: 20
<212> TYPE: DNA
<213> ORGANISM: Artificial sequence
<220> FEATURE:
<223> OTHER INFORMATION: synthetic

<400> SEQUENCE: 33
ttgggaaccc tggttttcta     20

<210> SEQ ID NO 34
<211> LENGTH: 20
<212> TYPE: DNA
<213> ORGANISM: Artificial sequence
<220> FEATURE:
<223> OTHER INFORMATION: synthetic

<400> SEQUENCE: 34
aagggctagt ttgggaaccc     20

<210> SEQ ID NO 35
<211> LENGTH: 20
<212> TYPE: DNA
<213> ORGANISM: Artificial sequence
<220> FEATURE:
<223> OTHER INFORMATION: synthetic

<400> SEQUENCE: 35
tacatactaa gggctagttt                                                    20

<210> SEQ ID NO 36
<211> LENGTH: 20
<212> TYPE: DNA
<213> ORGANISM: Artificial sequence
<220> FEATURE:
<223> OTHER INFORMATION: synthetic

<400> SEQUENCE: 36
aaaagatatc gtatcaccca                                                    20

<210> SEQ ID NO 37
<211> LENGTH: 20
<212> TYPE: DNA
<213> ORGANISM: Artificial sequence
<220> FEATURE:
<223> OTHER INFORMATION: synthetic

<400> SEQUENCE: 37
gcaatgcaag agccagcccc                                                    20

<210> SEQ ID NO 38
<211> LENGTH: 20
<212> TYPE: DNA
<213> ORGANISM: Artificial sequence
<220> FEATURE:
<223> OTHER INFORMATION: synthetic

<400> SEQUENCE: 38
gactcttcca aattccgaag                                                    20

<210> SEQ ID NO 39
<211> LENGTH: 20
<212> TYPE: DNA
<213> ORGANISM: Artificial sequence
<220> FEATURE:
<223> OTHER INFORMATION: synthetic

<400> SEQUENCE: 39
cagttgccac aaggggagcc                                                    20

<210> SEQ ID NO 40
<211> LENGTH: 20
<212> TYPE: DNA
<213> ORGANISM: Artificial sequence
<220> FEATURE:
<223> OTHER INFORMATION: synthetic

<400> SEQUENCE: 40
ggcagttacc agttgccaca                                                    20

<210> SEQ ID NO 41
<211> LENGTH: 408
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (307)..(326)
<223> OTHER INFORMATION: n is a, c, g, or t

<400> SEQUENCE: 41
aaaataaatg gtaaaatgtc aaatcaaaac taggctgcag tatgcagagc agagtcatga        60
tgatactact tactacaccg attcttgtgt gcagaaaaat atgttaaaat aattgaatct       120

```
ttctctagcc aaatttgaca acaatgtaca ccgttcatat tgagagacga tgcttcttgt    180
ttgctttcgg tggaagctgc atatactcaa cattactcct tcagcgagtt ttccaactga    240
gtcccacatt gcccagacct aacacggtat tcttgtttat aatgaaatgt gccaccacat    300
ggattgnnnn nnnnnnnnnn nnnnnngttt tagagctaga aatagcaagt taaaataagg    360
ctagtccgtt atcaacttga aaaagtggca ccgagtcggt gcttttttt               408
```

```
<210> SEQ ID NO 42
<211> LENGTH: 23
<212> TYPE: PRT
<213> ORGANISM: Zea mays

<400> SEQUENCE: 42

Arg Lys Arg Lys Glu Ser Asn Arg Glu Ser Ala Arg Arg Ser Arg Arg
1               5                   10                  15

Ser Arg Tyr Arg Lys Lys Val
            20

<210> SEQ ID NO 43
<211> LENGTH: 60
<212> TYPE: PRT
<213> ORGANISM: Zea mays

<400> SEQUENCE: 43

Ala Gly Ser Ser Asp Asp Cys Ser Ser Ala Ala Ser Val Ser Leu Arg
1               5                   10                  15

Val Gly Ser His Asp Glu Pro Cys Phe Ser Gly Asp Gly Asp Gly Asp
            20                  25                  30

Trp Met Asp Asp Val Arg Ala Leu Ala Ser Phe Leu Glu Ser Asp Glu
        35                  40                  45

Asp Trp Leu Arg Cys Gln Thr Ala Gly Gln Leu Ala
    50                  55                  60

<210> SEQ ID NO 44
<211> LENGTH: 1307
<212> TYPE: PRT
<213> ORGANISM: Unknown
<220> FEATURE:
<223> OTHER INFORMATION: a bacterium in the genus Aminococcus

<400> SEQUENCE: 44

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125
```

```
Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
                260                 265                 270

Lys Ile Lys Gly Leu Asn Glu Val Leu Asn Leu Ala Ile Gln Lys Asn
            275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
                340                 345                 350

Phe Asn Glu Leu Asn Ser Ile Asp Leu Thr His Ile Phe Ile Ser His
            355                 360                 365

Lys Lys Leu Glu Thr Ile Ser Ser Ala Leu Cys Asp His Trp Asp Thr
370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
                435                 440                 445

Ala Leu Asp Gln Pro Leu Pro Thr Thr Leu Lys Lys Gln Glu Glu Lys
450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
                500                 505                 510

Phe Tyr Asn Lys Ala Arg Asn Tyr Ala Thr Lys Lys Pro Tyr Ser Val
            515                 520                 525

Glu Lys Phe Lys Leu Asn Phe Gln Met Pro Thr Leu Ala Ser Gly Trp
530                 535                 540

Asp Val Asn Lys Glu Lys Asn Asn Gly Ala Ile Leu Phe Val Lys Asn
```

```
             545                 550                 555                 560
        Gly Leu Tyr Tyr Leu Gly Ile Met Pro Lys Gln Lys Gly Arg Tyr Lys
                         565                 570                 575
        Ala Leu Ser Phe Glu Pro Thr Glu Lys Thr Ser Glu Gly Phe Asp Lys
                         580                 585                 590
        Met Tyr Tyr Asp Tyr Phe Pro Asp Ala Ala Lys Met Ile Pro Lys Cys
                         595                 600                 605
        Ser Thr Gln Leu Lys Ala Val Thr Ala His Phe Gln Thr His Thr Thr
                         610                 615                 620
        Pro Ile Leu Leu Ser Asn Asn Phe Ile Glu Pro Leu Glu Ile Thr Lys
        625                 630                 635                 640
        Glu Ile Tyr Asp Leu Asn Asn Pro Glu Lys Glu Pro Lys Lys Phe Gln
                         645                 650                 655
        Thr Ala Tyr Ala Lys Lys Thr Gly Asp Gln Lys Gly Tyr Arg Glu Ala
                         660                 665                 670
        Leu Cys Lys Trp Ile Asp Phe Thr Arg Asp Phe Leu Ser Lys Tyr Thr
                         675                 680                 685
        Lys Thr Thr Ser Ile Asp Leu Ser Ser Leu Arg Pro Ser Ser Gln Tyr
                         690                 695                 700
        Lys Asp Leu Gly Glu Tyr Tyr Ala Glu Leu Asn Pro Leu Leu Tyr His
        705                 710                 715                 720
        Ile Ser Phe Gln Arg Ile Ala Glu Lys Glu Ile Met Asp Ala Val Glu
                         725                 730                 735
        Thr Gly Lys Leu Tyr Leu Phe Gln Ile Tyr Asn Lys Asp Phe Ala Lys
                         740                 745                 750
        Gly His His Gly Lys Pro Asn Leu His Thr Leu Tyr Trp Thr Gly Leu
                         755                 760                 765
        Phe Ser Pro Glu Asn Leu Ala Lys Thr Ser Ile Lys Leu Asn Gly Gln
                         770                 775                 780
        Ala Glu Leu Phe Tyr Arg Pro Lys Ser Arg Met Lys Arg Met Ala His
        785                 790                 795                 800
        Arg Leu Gly Glu Lys Met Leu Asn Lys Lys Leu Lys Asp Gln Lys Thr
                         805                 810                 815
        Pro Ile Pro Asp Thr Leu Tyr Gln Glu Leu Tyr Asp Tyr Val Asn His
                         820                 825                 830
        Arg Leu Ser His Asp Leu Ser Asp Glu Ala Arg Ala Leu Leu Pro Asn
                         835                 840                 845
        Val Ile Thr Lys Glu Val Ser His Glu Ile Ile Lys Asp Arg Arg Phe
        850                 855                 860
        Thr Ser Asp Lys Phe Phe Phe His Val Pro Ile Thr Leu Asn Tyr Gln
        865                 870                 875                 880
        Ala Ala Asn Ser Pro Ser Lys Phe Asn Gln Arg Val Asn Ala Tyr Leu
                         885                 890                 895
        Lys Glu His Pro Glu Thr Pro Ile Ile Gly Ile Asp Arg Gly Glu Arg
                         900                 905                 910
        Asn Leu Ile Tyr Ile Thr Val Ile Asp Ser Thr Gly Lys Ile Leu Glu
                         915                 920                 925
        Gln Arg Ser Leu Asn Thr Ile Gln Gln Phe Asp Tyr Gln Lys Lys Leu
                         930                 935                 940
        Asp Asn Arg Glu Lys Glu Arg Val Ala Ala Arg Gln Ala Trp Ser Val
        945                 950                 955                 960
        Val Gly Thr Ile Lys Asp Leu Lys Gln Gly Tyr Leu Ser Gln Val Ile
                         965                 970                 975
```

His Glu Ile Val Asp Leu Met Ile His Tyr Gln Ala Val Val Leu
                980                 985                 990

Glu Asn Leu Asn Phe Gly Phe Lys Ser Lys Arg Thr Gly Ile Ala Glu
        995                 1000                1005

Lys Ala Val Tyr Gln Gln Phe Glu Lys Met Leu Ile Asp Lys Leu
    1010                1015                1020

Asn Cys Leu Val Leu Lys Asp Tyr Pro Ala Glu Lys Val Gly Gly
    1025                1030                1035

Val Leu Asn Pro Tyr Gln Leu Thr Asp Gln Phe Thr Ser Phe Ala
    1040                1045                1050

Lys Met Gly Thr Gln Ser Gly Phe Leu Phe Tyr Val Pro Ala Pro
    1055                1060                1065

Tyr Thr Ser Lys Ile Asp Pro Leu Thr Gly Phe Val Asp Pro Phe
    1070                1075                1080

Val Trp Lys Thr Ile Lys Asn His Glu Ser Arg Lys His Phe Leu
    1085                1090                1095

Glu Gly Phe Asp Phe Leu His Tyr Asp Val Lys Thr Gly Asp Phe
    1100                1105                1110

Ile Leu His Phe Lys Met Asn Arg Asn Leu Ser Phe Gln Arg Gly
    1115                1120                1125

Leu Pro Gly Phe Met Pro Ala Trp Asp Ile Val Phe Glu Lys Asn
    1130                1135                1140

Glu Thr Gln Phe Asp Ala Lys Gly Thr Pro Phe Ile Ala Gly Lys
    1145                1150                1155

Arg Ile Val Pro Val Ile Glu Asn His Arg Phe Thr Gly Arg Tyr
    1160                1165                1170

Arg Asp Leu Tyr Pro Ala Asn Glu Leu Ile Ala Leu Leu Glu Glu
    1175                1180                1185

Lys Gly Ile Val Phe Arg Asp Gly Ser Asn Ile Leu Pro Lys Leu
    1190                1195                1200

Leu Glu Asn Asp Asp Ser His Ala Ile Asp Thr Met Val Ala Leu
    1205                1210                1215

Ile Arg Ser Val Leu Gln Met Arg Asn Ser Asn Ala Ala Thr Gly
    1220                1225                1230

Glu Asp Tyr Ile Asn Ser Pro Val Arg Asp Leu Asn Gly Val Cys
    1235                1240                1245

Phe Asp Ser Arg Phe Gln Asn Pro Glu Trp Pro Met Asp Ala Asp
    1250                1255                1260

Ala Asn Gly Ala Tyr His Ile Ala Leu Lys Gly Gln Leu Leu Leu
    1265                1270                1275

Asn His Leu Lys Glu Ser Lys Asp Leu Lys Leu Gln Asn Gly Ile
    1280                1285                1290

Ser Asn Gln Asp Trp Leu Ala Tyr Ile Gln Glu Leu Arg Asn
    1295                1300                1305

<210> SEQ ID NO 45
<211> LENGTH: 1228
<212> TYPE: PRT
<213> ORGANISM: Unknown
<220> FEATURE:
<223> OTHER INFORMATION: a bacterium in the genus Lachnospiraceae

<400> SEQUENCE: 45

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

```
Glu Lys Leu Phe Asp Ala Asp Phe Val Leu Glu Lys Ser Leu Lys Lys
            435                 440                 445

Asn Asp Ala Val Val Ala Ile Met Lys Asp Leu Leu Asp Ser Val Lys
450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
                500                 505                 510

Gln Lys Pro Tyr Ser Lys Asp Lys Phe Lys Leu Tyr Phe Gln Asn Pro
            515                 520                 525

Gln Phe Met Gly Gly Trp Asp Lys Asp Lys Glu Thr Asp Tyr Arg Ala
            530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Val Asn Gly
                565                 570                 575

Asn Tyr Glu Lys Ile Asn Tyr Lys Leu Leu Pro Gly Pro Asn Lys Met
                580                 585                 590

Leu Pro Lys Val Phe Phe Ser Lys Lys Trp Met Ala Tyr Tyr Asn Pro
            595                 600                 605

Ser Glu Asp Ile Gln Lys Ile Tyr Lys Asn Gly Thr Phe Lys Lys Gly
            610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
                660                 665                 670

Val Glu Glu Gln Gly Tyr Lys Val Ser Phe Glu Ser Ala Ser Lys Lys
            675                 680                 685

Glu Val Asp Lys Leu Val Glu Glu Gly Lys Leu Tyr Met Phe Gln Ile
            690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
                740                 745                 750

Lys Glu Glu Leu Val Val His Pro Ala Asn Ser Pro Ile Ala Asn Lys
            755                 760                 765

Asn Pro Asp Asn Pro Lys Lys Thr Thr Thr Leu Ser Tyr Asp Val Tyr
            770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
                820                 825                 830

Arg Gly Glu Arg Asn Leu Leu Tyr Ile Val Val Val Asp Gly Lys Gly
                835                 840                 845

Asn Ile Val Glu Gln Tyr Ser Leu Asn Glu Ile Ile Asn Asn Phe Asn
```

850                 855                 860
Gly Ile Arg Ile Lys Thr Asp Tyr His Ser Leu Leu Asp Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Glu Asp Leu Asn
            915                 920                 925

Ser Gly Phe Lys Asn Ser Arg Val Lys Val Glu Lys Gln Val Tyr Gln
        930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu Thr Ser Lys Ile Asp Pro Ser Thr
            995                 1000                1005

Gly Phe Val Asn Leu Leu Lys Thr Lys Tyr Thr Ser Ile Ala Asp
        1010                1015                1020

Ser Lys Lys Phe Ile Ser Ser Phe Asp Arg Ile Met Tyr Val Pro
        1025                1030                1035

Glu Glu Asp Leu Phe Glu Phe Ala Leu Asp Tyr Lys Asn Phe Ser
        1040                1045                1050

Arg Thr Asp Ala Asp Tyr Ile Lys Lys Trp Lys Leu Tyr Ser Tyr
        1055                1060                1065

Gly Asn Arg Ile Arg Ile Phe Arg Asn Pro Lys Lys Asn Asn Val
        1070                1075                1080

Phe Asp Trp Glu Glu Val Cys Leu Thr Ser Ala Tyr Lys Glu Leu
        1085                1090                1095

Phe Asn Lys Tyr Gly Ile Asn Tyr Gln Gln Gly Asp Ile Arg Ala
        1100                1105                1110

Leu Leu Cys Glu Gln Ser Asp Lys Ala Phe Tyr Ser Ser Phe Met
        1115                1120                1125

Ala Leu Met Ser Leu Met Leu Gln Met Arg Asn Ser Ile Thr Gly
        1130                1135                1140

Arg Thr Asp Val Asp Phe Leu Ile Ser Pro Val Lys Asn Ser Asp
        1145                1150                1155

Gly Ile Phe Tyr Asp Ser Arg Asn Tyr Glu Ala Gln Glu Asn Ala
        1160                1165                1170

Ile Leu Pro Lys Asn Ala Asp Ala Asn Gly Ala Tyr Asn Ile Ala
        1175                1180                1185

Arg Lys Val Leu Trp Ala Ile Gly Gln Phe Lys Lys Ala Glu Asp
        1190                1195                1200

Glu Lys Leu Asp Lys Val Lys Ile Ala Ile Ser Asn Lys Glu Trp
        1205                1210                1215

Leu Glu Tyr Ala Gln Thr Ser Val Lys His
        1220                1225

<210> SEQ ID NO 46
<211> LENGTH: 1300
<212> TYPE: PRT
<213> ORGANISM: Francisella novicida

<400> SEQUENCE: 46

```
Met Ser Ile Tyr Gln Glu Phe Val Asn Lys Tyr Ser Leu Ser Lys Thr
1               5                   10                  15
Leu Arg Phe Glu Leu Ile Pro Gln Gly Lys Thr Leu Glu Asn Ile Lys
            20                  25                  30
Ala Arg Gly Leu Ile Leu Asp Asp Glu Lys Arg Ala Lys Asp Tyr Lys
        35                  40                  45
Lys Ala Lys Gln Ile Ile Asp Lys Tyr His Gln Phe Phe Ile Glu Glu
    50                  55                  60
Ile Leu Ser Ser Val Cys Ile Ser Glu Asp Leu Leu Gln Asn Tyr Ser
65                  70                  75                  80
Asp Val Tyr Phe Lys Leu Lys Lys Ser Asp Asp Asn Leu Gln Lys
            85                  90                  95
Asp Phe Lys Ser Ala Lys Asp Thr Ile Lys Lys Gln Ile Ser Glu Tyr
            100                 105                 110
Ile Lys Asp Ser Glu Lys Phe Lys Asn Leu Phe Asn Gln Asn Leu Ile
        115                 120                 125
Asp Ala Lys Lys Gly Gln Glu Ser Asp Leu Ile Leu Trp Leu Lys Gln
    130                 135                 140
Ser Lys Asp Asn Gly Ile Glu Leu Phe Lys Ala Asn Ser Asp Ile Thr
145                 150                 155                 160
Asp Ile Asp Glu Ala Leu Glu Ile Ile Lys Ser Phe Lys Gly Trp Thr
            165                 170                 175
Thr Tyr Phe Lys Gly Phe His Glu Asn Arg Lys Asn Val Tyr Ser Ser
            180                 185                 190
Asn Asp Ile Pro Thr Ser Ile Ile Tyr Arg Ile Val Asp Asp Asn Leu
        195                 200                 205
Pro Lys Phe Leu Glu Asn Lys Ala Lys Tyr Glu Ser Leu Lys Asp Lys
    210                 215                 220
Ala Pro Glu Ala Ile Asn Tyr Glu Gln Ile Lys Lys Asp Leu Ala Glu
225                 230                 235                 240
Glu Leu Thr Phe Asp Ile Asp Tyr Lys Thr Ser Glu Val Asn Gln Arg
            245                 250                 255
Val Phe Ser Leu Asp Glu Val Phe Glu Ile Ala Asn Phe Asn Asn Tyr
            260                 265                 270
Leu Asn Gln Ser Gly Ile Thr Lys Phe Asn Thr Ile Ile Gly Gly Lys
        275                 280                 285
Phe Val Asn Gly Glu Asn Thr Lys Arg Lys Gly Ile Asn Glu Tyr Ile
    290                 295                 300
Asn Leu Tyr Ser Gln Gln Ile Asn Asp Lys Thr Leu Lys Lys Tyr Lys
305                 310                 315                 320
Met Ser Val Leu Phe Lys Gln Ile Leu Ser Asp Thr Glu Ser Lys Ser
            325                 330                 335
Phe Val Ile Asp Lys Leu Glu Asp Asp Ser Asp Val Val Thr Thr Met
            340                 345                 350
Gln Ser Phe Tyr Glu Gln Ile Ala Ala Phe Lys Thr Val Glu Glu Lys
        355                 360                 365
Ser Ile Lys Glu Thr Leu Ser Leu Leu Phe Asp Asp Leu Lys Ala Gln
    370                 375                 380
Lys Leu Asp Leu Ser Lys Ile Tyr Phe Lys Asn Asp Lys Ser Leu Thr
385                 390                 395                 400
Asp Leu Ser Gln Gln Val Phe Asp Asp Tyr Ser Val Ile Gly Thr Ala
```

-continued

```
                405                 410                 415
Val Leu Glu Tyr Ile Thr Gln Gln Ile Ala Pro Lys Asn Leu Asp Asn
            420                 425                 430

Pro Ser Lys Lys Glu Gln Leu Ile Ala Lys Lys Thr Glu Lys Ala
            435                 440                 445

Lys Tyr Leu Ser Leu Glu Thr Ile Lys Leu Ala Leu Glu Glu Phe Asn
            450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Val Lys Ala Ile Lys Asp
            515                 520                 525

Leu Leu Asp Gln Thr Asn Asn Leu Leu His Lys Leu Lys Ile Phe His
            530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
            595                 600                 605

Trp Asp Lys Asn Lys Glu Pro Asp Asn Thr Ala Ile Leu Phe Ile Lys
            610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
            675                 680                 685

Leu Arg Ile Arg Asn His Ser Thr His Thr Lys Asn Gly Ser Pro Gln
            690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
            755                 760                 765

Ile Ser Glu Ser Tyr Ile Asp Ser Val Val Asn Gln Gly Lys Leu Tyr
            770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830
```

```
Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
            915                 920                 925

Val Asp Gly Lys Gly Asn Ile Ile Lys Gln Asp Thr Phe Asn Ile Ile
930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn Ala Ile Val Val Phe Glu Asp Leu
            995                 1000                1005

Asn Phe Gly Phe Lys Arg Gly Arg Phe Lys Val Glu Lys Gln Val
    1010                1015                1020

Tyr Gln Lys Leu Glu Lys Met Leu Ile Glu Lys Leu Asn Tyr Leu
    1025                1030                1035

Val Phe Lys Asp Asn Glu Phe Asp Lys Thr Gly Gly Val Leu Arg
    1040                1045                1050

Ala Tyr Gln Leu Thr Ala Pro Phe Glu Thr Phe Lys Lys Met Gly
    1055                1060                1065

Lys Gln Thr Gly Ile Ile Tyr Tyr Val Pro Ala Gly Phe Thr Ser
    1070                1075                1080

Lys Ile Cys Pro Val Thr Gly Phe Val Asn Gln Leu Tyr Pro Lys
    1085                1090                1095

Tyr Glu Ser Val Ser Lys Ser Gln Glu Phe Phe Ser Lys Phe Asp
    1100                1105                1110

Lys Ile Cys Tyr Asn Leu Asp Lys Gly Tyr Phe Glu Phe Ser Phe
    1115                1120                1125

Asp Tyr Lys Asn Phe Gly Asp Lys Ala Ala Lys Gly Lys Trp Thr
    1130                1135                1140

Ile Ala Ser Phe Gly Ser Arg Leu Ile Asn Phe Arg Asn Ser Asp
    1145                1150                1155

Lys Asn His Asn Trp Asp Thr Arg Glu Val Tyr Pro Thr Lys Glu
    1160                1165                1170

Leu Glu Lys Leu Leu Lys Asp Tyr Ser Ile Glu Tyr Gly His Gly
    1175                1180                1185

Glu Cys Ile Lys Ala Ala Ile Cys Gly Glu Ser Asp Lys Lys Phe
    1190                1195                1200

Phe Ala Lys Leu Thr Ser Val Leu Asn Thr Ile Leu Gln Met Arg
    1205                1210                1215

Asn Ser Lys Thr Gly Thr Glu Leu Asp Tyr Leu Ile Ser Pro Val
    1220                1225                1230
```

```
Ala Asp Val Asn Gly Asn Phe Phe Asp Ser Arg Gln Ala Pro Lys
    1235                1240                1245

Asn Met Pro Gln Asp Ala Asp Ala Asn Gly Ala Tyr His Ile Gly
    1250                1255                1260

Leu Lys Gly Leu Met Leu Leu Gly Arg Ile Lys Asn Asn Gln Glu
    1265                1270                1275

Gly Lys Lys Leu Asn Leu Val Ile Lys Asn Glu Glu Tyr Phe Glu
    1280                1285                1290

Phe Val Gln Asn Arg Asn Asn
    1295                1300

<210> SEQ ID NO 47
<211> LENGTH: 1320
<212> TYPE: PRT
<213> ORGANISM: Unknown
<220> FEATURE:
<223> OTHER INFORMATION: bacterial

<400> SEQUENCE: 47

Met Gln Gln Tyr Gln Val Ser Lys Thr Val Arg Phe Gly Leu Thr Leu
1               5                   10                  15

Lys Asn Ser Glu Lys Lys His Ala Thr His Leu Leu Leu Lys Asp Leu
            20                  25                  30

Val Asn Val Ser Glu Glu Arg Ile Lys Asn Glu Ile Thr Lys Asp Asp
        35                  40                  45

Lys Asn Gln Ser Glu Leu Ser Phe Phe Asn Glu Val Ile Glu Thr Leu
    50                  55                  60

Asp Leu Met Asp Lys Tyr Ile Lys Asp Trp Glu Asn Cys Phe Tyr Arg
65                  70                  75                  80

Thr Asp Gln Ile Gln Leu Thr Lys Glu Tyr Tyr Lys Val Ile Ala Lys
                85                  90                  95

Lys Ala Cys Phe Asp Trp Phe Trp Thr Asn Asp Arg Gly Met Lys Phe
            100                 105                 110

Pro Thr Ser Ser Ile Ile Ser Phe Asn Ser Leu Lys Ser Ser Asp Lys
        115                 120                 125

Ser Lys Thr Ser Asp Asn Leu Asp Arg Lys Lys Ile Leu Asp Tyr
    130                 135                 140

Trp Lys Gly Asn Ile Phe Lys Thr Gln Lys Ala Ile Lys Asp Val Leu
145                 150                 155                 160

Asp Ile Thr Glu Asp Ile Gln Lys Ala Ile Glu Glu Lys Ser His
                165                 170                 175

Arg Glu Ile Asn Arg Val Asn His Arg Lys Met Gly Ile His Leu Ile
            180                 185                 190

His Leu Ile Asn Asp Thr Leu Val Pro Leu Cys Asn Gly Ser Ile Phe
        195                 200                 205

Phe Gly Asn Ile Ser Lys Leu Asp Phe Cys Glu Ser Glu Asn Glu Lys
    210                 215                 220

Leu Ile Asp Phe Ala Ser Thr Glu Lys Gln Asp Glu Arg Lys Phe Leu
225                 230                 235                 240

Leu Ser Lys Ile Asn Glu Ile Lys Gln Tyr Phe Glu Asp Asn Gly Gly
                245                 250                 255

Asn Val Pro Phe Ala Arg Ala Thr Leu Asn Arg His Thr Ala Asn Gln
            260                 265                 270

Lys Pro Asp Arg Tyr Asn Glu Glu Ile Lys Lys Leu Val Asn Glu Leu
        275                 280                 285
```

Gly Val Asn Ser Leu Val Arg Ser Leu Lys Ser Lys Thr Ile Glu Glu
290                 295                 300

Ile Lys Thr His Phe Glu Phe Glu Asn Lys Asn Lys Ile Asn Glu Leu
305                 310                 315                 320

Lys Asn Ser Phe Val Leu Ser Ile Val Glu Lys Ile Gln Leu Phe Lys
                325                 330                 335

Tyr Lys Thr Ile Pro Ala Ser Val Arg Phe Leu Leu Ala Asp Tyr Phe
            340                 345                 350

Glu Glu Gln Lys Leu Ser Thr Lys Glu Ala Leu Thr Ile Phe Glu
        355                 360                 365

Glu Ile Gly Lys Pro Gln Asn Ile Gly Phe Asp Tyr Ile Gln Leu Lys
370                 375                 380

Glu Lys Asp Asn Phe Thr Leu Lys Lys Tyr Pro Leu Lys Gln Ala Phe
385                 390                 395                 400

Asp Tyr Ala Trp Glu Asn Leu Ala Arg Leu Asp Gln Asn Pro Lys Ala
                405                 410                 415

Asn Gln Phe Ser Val Asp Glu Cys Lys Arg Phe Phe Lys Glu Val Phe
            420                 425                 430

Ser Met Glu Met Asp Asn Ile Asn Phe Lys Thr Tyr Ala Leu Leu Leu
        435                 440                 445

Ala Leu Lys Glu Lys Thr Thr Ala Phe Asp Lys Lys Gly Glu Gly Ala
450                 455                 460

Ala Lys Asn Lys Ser Glu Ile Ile Glu Gln Ile Lys Gly Val Phe Glu
465                 470                 475                 480

Glu Leu Asp Gln Pro Phe Lys Ile Ile Ala Asn Thr Leu Arg Glu Glu
                485                 490                 495

Val Ile Lys Lys Glu Asp Glu Leu Asn Val Leu Lys Arg Gln Tyr Arg
            500                 505                 510

Glu Thr Asp Arg Lys Ile Lys Thr Leu Gln Asn Glu Ile Lys Lys Ile
        515                 520                 525

Lys Asn Gln Ile Lys Asn Leu Glu Asn Ser Lys Lys Tyr Ser Phe Pro
530                 535                 540

Glu Ile Ile Lys Trp Ile Asp Leu Thr Glu Gln Glu Gln Leu Leu Asp
545                 550                 555                 560

Lys Asn Lys Gln Ala Lys Ser Asn Tyr Gln Lys Ala Lys Gly Asp Leu
                565                 570                 575

Gly Leu Ile Arg Gly Ser Gln Lys Thr Ser Ile Asn Asp Tyr Phe Tyr
            580                 585                 590

Leu Thr Asp Lys Val Tyr Arg Lys Leu Ala Gln Asp Phe Gly Lys Lys
        595                 600                 605

Met Ala Asp Leu Arg Glu Lys Leu Leu Asp Lys Asn Asp Val Asn Lys
610                 615                 620

Ile Lys Tyr Leu Ser Tyr Ile Val Lys Asp Asn Gln Gly Tyr Gln Tyr
625                 630                 635                 640

Thr Leu Leu Lys Pro Leu Glu Asp Lys Asn Ala Glu Ile Ile Glu Leu
                645                 650                 655

Lys Ser Glu Pro Asn Gly Asp Leu Lys Leu Phe Glu Ile Lys Ser Leu
            660                 665                 670

Thr Ser Lys Thr Leu Asn Lys Phe Ile Lys Asn Lys Gly Ala Tyr Lys
        675                 680                 685

Glu Phe His Ser Ala Glu Phe Glu His Lys Lys Ile Lys Glu Asp Trp
690                 695                 700

Lys Asn Tyr Lys Tyr Asn Ser Asp Phe Ile Val Lys Leu Lys Lys Cys

-continued

```
            705                 710                 715                 720
Leu Ser His Ser Asp Met Ala Asn Thr Gln Asn Trp Lys Ala Phe Gly
                725                 730                 735
Trp Asp Leu Asp Lys Cys Lys Ser Tyr Glu Thr Ile Glu Lys Glu Ile
                740                 745                 750
Asp Gln Lys Ser Tyr Gln Leu Val Glu Ile Lys Leu Ser Lys Thr Thr
                755                 760                 765
Ile Glu Lys Trp Val Lys Glu Asn Asn Tyr Leu Leu Leu Pro Ile Val
                770                 775                 780
Asn Gln Asp Ile Thr Ala Glu Lys Leu Lys Val Asn Thr Asn Gln Phe
785                 790                 795                 800
Thr Lys Asp Trp Gln His Ile Phe Glu Lys Asn Pro Asn His Arg Leu
                805                 810                 815
His Pro Glu Phe Asn Ile Ala Tyr Arg Gln Pro Thr Lys Asp Tyr Ala
                820                 825                 830
Lys Glu Gly Glu Lys Arg Tyr Ser Arg Phe Gln Leu Thr Gly Gln Phe
                835                 840                 845
Met Tyr Glu Tyr Ile Pro Gln Asp Ala Asn Tyr Ile Ser Arg Lys Glu
                850                 855                 860
Gln Ile Thr Leu Phe Asn Asp Lys Glu Glu Gln Lys Ile Gln Val Glu
865                 870                 875                 880
Thr Phe Asn Asn Gln Ile Ala Lys Ile Leu Asn Ala Glu Asp Phe Tyr
                885                 890                 895
Val Ile Gly Ile Asp Arg Gly Ile Thr Gln Leu Ala Thr Leu Cys Val
                900                 905                 910
Leu Asn Lys Asn Gly Val Ile Gln Gly Gly Phe Glu Ile Phe Thr Arg
                915                 920                 925
Glu Phe Asp Tyr Thr Asn Lys Gln Trp Lys His Thr Lys Leu Lys Glu
                930                 935                 940
Asn Arg Asn Ile Leu Asp Ile Ser Asn Leu Lys Val Glu Thr Thr Val
945                 950                 955                 960
Asn Gly Glu Lys Val Leu Val Asp Leu Ser Glu Val Lys Thr Tyr Leu
                965                 970                 975
Arg Asp Glu Asn Gly Glu Pro Met Lys Asn Glu Lys Gly Val Ile Leu
                980                 985                 990
Thr Lys Asp Asn Leu Gln Lys Ile Lys Leu Lys Gln Leu Ala Tyr Asp
                995                 1000                1005
Arg Lys Leu Gln Tyr Lys Met Gln His Glu Pro Glu Leu Val Leu
                1010                1015               1020
Ser Phe Leu Asp Arg Leu Glu Asn Lys Glu Gln Ile Pro Asn Leu
                1025                1030               1035
Leu Ala Ser Thr Lys Leu Ile Ser Ala Tyr Lys Glu Gly Thr Ala
                1040                1045               1050
Tyr Ala Asp Ile Asp Ile Glu Gln Phe Trp Asn Ile Leu Gln Thr
                1055                1060               1065
Phe Gln Thr Ile Val Asp Lys Phe Gly Gly Ile Glu Asn Ala Lys
                1070                1075               1080
Lys Thr Met Glu Phe Arg Gln Tyr Thr Glu Leu Asp Ala Ser Phe
                1085                1090               1095
Asp Leu Lys Asn Gly Val Val Ala Asn Met Val Gly Val Val Lys
                1100                1105               1110
Phe Ile Met Glu Lys Tyr Asn Tyr Lys Thr Phe Ile Ala Leu Glu
                1115                1120               1125
```

-continued

Asp Leu Thr Phe Ala Phe Gly Gln Ser Ile Asp Gly Ile Asn Gly
    1130                1135                1140

Glu Arg Leu Arg Ser Thr Lys Glu Asp Lys Glu Val Asp Phe Lys
    1145                1150                1155

Glu Gln Glu Asn Ser Thr Leu Ala Gly Leu Gly Thr Tyr His Phe
    1160                1165                1170

Phe Glu Met Gln Leu Leu Lys Lys Leu Ser Lys Thr Gln Ile Gly
    1175                1180                1185

Asn Glu Ile Lys His Phe Val Pro Ala Phe Arg Ser Thr Glu Asn
    1190                1195                1200

Tyr Glu Lys Ile Val Arg Lys Asp Lys Asn Val Lys Ala Lys Ile
    1205                1210                1215

Val Ser Tyr Pro Phe Gly Ile Val Ser Phe Val Asn Pro Arg Asn
    1220                1225                1230

Thr Ser Ile Ser Cys Pro Asn Cys Lys Asn Ala Asn Lys Ser Asn
    1235                1240                1245

Arg Ile Lys Lys Glu Asn Asp Arg Ile Leu Cys Lys His Asn Ile
    1250                1255                1260

Glu Lys Thr Lys Gly Asn Cys Gly Phe Asp Thr Ala Asn Phe Asp
    1265                1270                1275

Glu Asn Lys Leu Arg Ala Glu Asn Lys Gly Lys Asn Phe Lys Tyr
    1280                1285                1290

Ile Ser Ser Gly Asp Ala Asn Ala Ala Tyr Asn Ile Ala Val Lys
    1295                1300                1305

Leu Leu Glu Asp Lys Ile Phe Glu Ile Asn Lys Lys
    1310                1315                1320

<210> SEQ ID NO 48
<211> LENGTH: 5
<212> TYPE: PRT
<213> ORGANISM: Artificial sequence
<220> FEATURE:
<223> OTHER INFORMATION: synthetic

<400> SEQUENCE: 48

Thr Gly Glu Lys Pro
1               5

<210> SEQ ID NO 49
<211> LENGTH: 7
<212> TYPE: PRT
<213> ORGANISM: Simian virus 40

<400> SEQUENCE: 49

Pro Lys Lys Lys Arg Lys Val
1               5

<210> SEQ ID NO 50
<211> LENGTH: 4
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (2)..(2)
<223> OTHER INFORMATION: Xaa is lysine or arginine
<220> FEATURE:
<221> NAME/KEY: VARIANT
<222> LOCATION: (3)..(3)
<223> OTHER INFORMATION: Xaa is any amino acid

```
<220> FEATURE:
<221> NAME/KEY: VARIANT
<222> LOCATION: (4)..(4)
<223> OTHER INFORMATION: Xaa is  lysine or arginine

<400> SEQUENCE: 50

Lys Xaa Xaa Xaa
1

<210> SEQ ID NO 51
<211> LENGTH: 19
<212> TYPE: PRT
<213> ORGANISM: Artificial sequence
<220> FEATURE:
<223> OTHER INFORMATION: synthetic
<220> FEATURE:
<221> NAME/KEY: VARIANT
<222> LOCATION: (1)..(1)
<223> OTHER INFORMATION: Xaa is lysine or arginine
<220> FEATURE:
<221> NAME/KEY: VARIANT
<222> LOCATION: (2)..(2)
<223> OTHER INFORMATION: Xaa is lysine or arginine
<220> FEATURE:
<221> NAME/KEY: VARIANT
<222> LOCATION: (3)..(12)
<223> OTHER INFORMATION: Xaa is any amino acid
<220> FEATURE:
<221> NAME/KEY: VARIANT
<222> LOCATION: (13)..(14)
<223> OTHER INFORMATION: Xaa is any amino acid or is absent
<220> FEATURE:
<221> NAME/KEY: VARIANT
<222> LOCATION: (15)..(19)
<223> OTHER INFORMATION: 3 of the 5 amino acids are lysine or arginine

<400> SEQUENCE: 51

Xaa Xaa Xaa Xaa Xaa Xaa Xaa Xaa Xaa Xaa Xaa Xaa Xaa Xaa Xaa Xaa
1               5                   10                  15

Xaa Xaa Xaa

<210> SEQ ID NO 52
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: VARIANT
<222> LOCATION: (5)..(5)
<223> OTHER INFORMATION: Xaa is lysine or arginine
<220> FEATURE:
<221> NAME/KEY: VARIANT
<222> LOCATION: (6)..(6)
<223> OTHER INFORMATION: Xaa is tryptophan, phenylalanine, or tyrosine

<400> SEQUENCE: 52

Leu Gly Lys Arg Xaa Xaa
1               5

<210> SEQ ID NO 53
<211> LENGTH: 5
<212> TYPE: PRT
<213> ORGANISM: Artificial sequence
<220> FEATURE:
<223> OTHER INFORMATION: synthetic

<400> SEQUENCE: 53

Gly Gly Gly Gly Ser
1               5
```

<210> SEQ ID NO 54
<211> LENGTH: 6
<212> TYPE: PRT
<213> ORGANISM: Artificial sequence
<220> FEATURE:
<223> OTHER INFORMATION: synthetic

<400> SEQUENCE: 54

Ser Gly Gly Gly Gly Ser
1               5

<210> SEQ ID NO 55
<211> LENGTH: 11
<212> TYPE: PRT
<213> ORGANISM: Artificial sequence
<220> FEATURE:
<223> OTHER INFORMATION: synthetic

<400> SEQUENCE: 55

Tyr Gly Arg Lys Lys Arg Arg Gln Arg Arg Arg
1               5                   10

<210> SEQ ID NO 56
<211> LENGTH: 12
<212> TYPE: PRT
<213> ORGANISM: Artificial sequence
<220> FEATURE:
<223> OTHER INFORMATION: synthetic

<400> SEQUENCE: 56

Arg Arg Gln Arg Arg Thr Ser Lys Leu Met Lys Arg
1               5                   10

<210> SEQ ID NO 57
<211> LENGTH: 27
<212> TYPE: PRT
<213> ORGANISM: Artificial sequence
<220> FEATURE:
<223> OTHER INFORMATION: synthetic

<400> SEQUENCE: 57

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 58
<211> LENGTH: 33
<212> TYPE: PRT
<213> ORGANISM: Artificial sequence
<220> FEATURE:
<223> OTHER INFORMATION: synthetic

<400> SEQUENCE: 58

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 59
<211> LENGTH: 16
<212> TYPE: PRT
<213> ORGANISM: Artificial sequence
<220> FEATURE:

<223> OTHER INFORMATION: synthetic

<400> SEQUENCE: 59

Arg Gln Ile Lys Ile Trp Phe Gln Asn Arg Arg Met Lys Trp Lys Lys
1               5                   10                  15

<210> SEQ ID NO 60
<211> LENGTH: 11
<212> TYPE: PRT
<213> ORGANISM: Artificial sequence
<220> FEATURE:
<223> OTHER INFORMATION: synthetic

<400> SEQUENCE: 60

Tyr Gly Arg Lys Lys Arg Arg Gln Arg Arg Arg
1               5                   10

<210> SEQ ID NO 61
<211> LENGTH: 8
<212> TYPE: PRT
<213> ORGANISM: Artificial sequence
<220> FEATURE:
<223> OTHER INFORMATION: synthetic

<400> SEQUENCE: 61

Arg Lys Lys Arg Arg Gln Arg Arg
1               5

<210> SEQ ID NO 62
<211> LENGTH: 11
<212> TYPE: PRT
<213> ORGANISM: Artificial sequence
<220> FEATURE:
<223> OTHER INFORMATION: synthetic

<400> SEQUENCE: 62

Tyr Ala Arg Ala Ala Ala Arg Gln Ala Arg Ala
1               5                   10

<210> SEQ ID NO 63
<211> LENGTH: 11
<212> TYPE: PRT
<213> ORGANISM: Artificial sequence
<220> FEATURE:
<223> OTHER INFORMATION: synthetic

<400> SEQUENCE: 63

Thr His Arg Leu Pro Arg Arg Arg Arg Arg Arg
1               5                   10

<210> SEQ ID NO 64
<211> LENGTH: 11
<212> TYPE: PRT
<213> ORGANISM: Artificial sequence
<220> FEATURE:
<223> OTHER INFORMATION: synthetic

<400> SEQUENCE: 64

Gly Gly Arg Arg Ala Arg Arg Arg Arg Arg Arg
1               5                   10

<210> SEQ ID NO 65
<211> LENGTH: 29
<212> TYPE: PRT
<213> ORGANISM: Zea mays

<400> SEQUENCE: 65

```
Thr Gly Gly Cys Cys Cys Thr Cys Thr Gly Cys Ala Thr Cys Cys Thr
1               5                   10                  15
Cys Cys Thr Cys Ala Thr Gly Ala Thr Ala Gly Cys Thr
            20                  25
```

<210> SEQ ID NO 66
<211> LENGTH: 30
<212> TYPE: PRT
<213> ORGANISM: Zea mays

<400> SEQUENCE: 66

```
Thr Cys Thr Thr Cys Cys Ala Ala Ala Thr Cys Cys Gly Ala Ala
1               5                   10                  15
Gly Cys Gly Gly Cys Cys Ala Ala Thr Gly Cys Ala Ala Thr
            20                  25                  30
```

<210> SEQ ID NO 67
<211> LENGTH: 30
<212> TYPE: PRT
<213> ORGANISM: Zea mays

<400> SEQUENCE: 67

```
Thr Ala Thr Cys Gly Thr Ala Thr Cys Ala Cys Cys Cys Ala Thr Gly
1               5                   10                  15
Gly Cys Cys Ala Thr Gly Ala Cys Cys Cys Cys Cys Thr
            20                  25                  30
```

<210> SEQ ID NO 68
<211> LENGTH: 30
<212> TYPE: PRT
<213> ORGANISM: Zea mays

<400> SEQUENCE: 68

```
Thr Ala Thr Thr Cys Cys Thr Ala Ala Thr Ala Thr Ala Thr Ala Thr
1               5                   10                  15
Ala Thr Cys Ala Thr Ala Cys Thr Cys Thr Cys Cys Ala Thr
            20                  25                  30
```

<210> SEQ ID NO 69
<211> LENGTH: 30
<212> TYPE: DNA
<213> ORGANISM: Zea mays

<400> SEQUENCE: 69
tcttctggag tgtaccagtt gtataaatat                                30

<210> SEQ ID NO 70
<211> LENGTH: 31
<212> TYPE: DNA
<213> ORGANISM: Zea mays

<400> SEQUENCE: 70
tgcactgtcc aaaatggctt cctgatcccc t                              31

<210> SEQ ID NO 71
<211> LENGTH: 311
<212> TYPE: DNA
<213> ORGANISM: Zea mays

<400> SEQUENCE: 71
gtactcatat atgggcacac atatagacat gttttgagga aaatgagaca agtatagtg  60

-continued

```
gagacttccc tagaaagcag aagaaaaaga agtggtttat gttccgttaa atcatactac    120 aactttttt tattatactc tccattttgt catcattagg tactcatata tgggcacaca    180
tatagtactg ccaattttc ttgctaaaaa aagttccact atatatatgt atgtatgcac    240
aaataaacta attttcttag aaaagaaaac cggtgtaata catactaagg gctagtttgg    300
gaaccctggt t                                                         311
```

<210> SEQ ID NO 72
<211> LENGTH: 1023
<212> TYPE: PRT
<213> ORGANISM: Artificial sequence
<220> FEATURE:
<223> OTHER INFORMATION: synthetic

<400> SEQUENCE: 72

```
Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
        35                  40                  45

Thr Glu Ala Ala Thr Gly Glu Trp Asp Glu Val Gln Ser Gly Leu Arg
    50                  55                  60

Ala Ala Asp Ala Pro Pro Pro Thr Met Arg Val Ala Val Thr Ala Ala
65                  70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
            100                 105                 110

Ser Gln Gln Gln Gln Glu Lys Ile Lys Pro Lys Val Arg Ser Thr Val
            115                 120                 125

Ala Gln His His Glu Ala Leu Val Gly His Gly Phe Thr His Ala His
        130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
            180                 185                 190

Leu Leu Thr Val Ala Gly Glu Leu Arg Gly Pro Pro Leu Gln Leu Asp
        195                 200                 205

Thr Gly Gln Leu Leu Lys Ile Ala Lys Arg Gly Gly Val Thr Ala Val
    210                 215                 220

Glu Ala Val His Ala Trp Arg Asn Ala Leu Thr Gly Ala Pro Leu Asn
225                 230                 235                 240

Leu Thr Glu Thr Leu Thr Pro Glu Gln Val Val Ala Ile Ala Ser Asn
                245                 250                 255

His Gly Gly Lys Gln Ala Leu Glu Thr Val Gln Arg Leu Leu Pro Val
            260                 265                 270

Leu Cys Gln Ala His Gly Leu Thr Pro Glu Gln Val Val Ala Ile Ala
        275                 280                 285

Ser Asn His Gly Gly Lys Gln Ala Leu Glu Thr Val Gln Arg Leu Leu
    290                 295                 300

Pro Val Leu Cys Gln Ala His Gly Leu Thr Pro Glu Gln Val Val Ala
305                 310                 315                 320
```

```
Ile Ala Ser His Asp Gly Gly Lys Gln Ala Leu Glu Thr Val Gln Arg
                325                 330                 335

Leu Leu Pro Val Leu Cys Gln Ala His Gly Leu Thr Pro Glu Gln Val
            340                 345                 350

Val Ala Ile Ala Ser His Asp Gly Gly Lys Gln Ala Leu Glu Thr Val
                355                 360                 365

Gln Arg Leu Leu Pro Val Leu Cys Gln Ala His Gly Leu Thr Pro Glu
370                 375                 380

Gln Val Val Ala Ile Ala Ser His Asp Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Glu Gln Val Val Ala Ile Ala Ser Asn Gly Gly Lys Gln Ala
            420                 425                 430

Leu Glu Thr Val Gln Arg Leu Leu Pro Val Leu Cys Gln Ala His Gly
            435                 440                 445

Leu Thr Pro Glu Gln Val Val Ala Ile Ala Ser His Asp Gly Gly Lys
            450                 455                 460

Gln Ala Leu Glu Thr Val Gln Arg Leu Leu Pro Val Leu Cys Gln Ala
465                 470                 475                 480

His Gly Leu Thr Pro Glu Gln Val Val Ala Ile Ala Ser Asn Gly Gly
                485                 490                 495

Gly Lys Gln Ala Leu Glu Thr Val Gln Arg Leu Leu Pro Val Leu Cys
                500                 505                 510

Gln Ala His Gly Leu Thr Pro Glu Gln Val Val Ala Ile Ala Ser Asn
                515                 520                 525

His Gly Gly Lys Gln Ala Leu Glu Thr Val Gln Arg Leu Leu Pro Val
                530                 535                 540

Leu Cys Gln Ala His Gly Leu Thr Pro Glu Gln Val Val Ala Ile Ala
545                 550                 555                 560

Ser His Asp Gly Gly Lys Gln Ala Leu Glu Thr Val Gln Arg Leu Leu
                565                 570                 575

Pro Val Leu Cys Gln Ala His Gly Leu Thr Pro Glu Gln Val Val Ala
            580                 585                 590

Ile Ala Ser Asn Ile Gly Gly Lys Gln Ala Leu Glu Thr Val Gln Arg
            595                 600                 605

Leu Leu Pro Val Leu Cys Gln Ala His Gly Leu Thr Pro Glu Gln Val
            610                 615                 620

Val Ala Ile Ala Ser Asn Gly Gly Gly Lys Gln Ala Leu Glu Thr Val
625                 630                 635                 640

Gln Arg Leu Leu Pro Val Leu Cys Gln Ala His Gly Leu Thr Pro Glu
                645                 650                 655

Gln Val Val Ala Ile Ala Ser His Asp Gly Gly Lys Gln Ala Leu Glu
            660                 665                 670

Thr Val Gln Arg Leu Leu Pro Val Leu Cys Gln Ala His Gly Leu Thr
            675                 680                 685

Pro Glu Gln Val Val Ala Ile Ala Ser His Asp Gly Gly Lys Gln Ala
            690                 695                 700

Leu Glu Thr Val Gln Arg Leu Leu Pro Val Leu Cys Gln Ala His Gly
705                 710                 715                 720

Leu Thr Pro Glu Gln Val Val Ala Ile Ala Ser Asn Gly Gly Gly Lys
                725                 730                 735
```

-continued

Gln Ala Leu Glu Thr Val Gln Arg Leu Leu Pro Val Leu Cys Gln Ala
                740                 745                 750

His Gly Leu Thr Pro Glu Gln Val Val Ala Ile Ala Ser His Asp Gly
            755                 760                 765

Gly Lys Gln Ala Leu Glu Thr Val Gln Arg Leu Leu Pro Val Leu Cys
        770                 775                 780

Gln Ala His Gly Leu Thr Pro Glu Gln Val Val Ala Ile Ala Ser His
785                 790                 795                 800

Asp Gly Gly Lys Gln Ala Leu Glu Thr Val Gln Arg Leu Leu Pro Val
                805                 810                 815

Leu Cys Gln Ala His Gly Ala Ser Gln Leu Thr Pro Glu Gln Val Val
            820                 825                 830

Ala Ile Ala Ser Asn Gly Gly Arg Pro Ala Leu Glu Ser Ile Val
        835                 840                 845

Ala Gln Leu Ser Arg Pro Asp Pro Ala Leu Ala Ala Leu Thr Asn Asp
    850                 855                 860

His Leu Val Ala Leu Ala Cys Leu Gly Gly Arg Pro Ala Leu Asp Ala
865                 870                 875                 880

Val Lys Lys Gly Leu Pro His Ala Pro Ala Leu Ile Lys Arg Thr Asn
                885                 890                 895

Arg Arg Ile Pro Glu Arg Thr Ser His Arg Val Ala Asp His Ala Gln
            900                 905                 910

Val Val Arg Val Leu Gly Phe Phe Gln Cys His Ser His Pro Ala Gln
        915                 920                 925

Ala Phe Asp Asp Ala Met Thr Gln Phe Gly Met Ser Arg His Gly Leu
    930                 935                 940

Leu Gln Leu Phe Arg Arg Val Gly Val Thr Glu Leu Glu Ala Arg Ser
945                 950                 955                 960

Gly Thr Leu Pro Pro Ala Ser Gln Arg Trp Asp Arg Ile Leu Gln Ala
                965                 970                 975

Ser Gly Met Lys Arg Ala Lys Pro Ser Pro Thr Ser Thr Gln Thr Pro
            980                 985                 990

Asp Gln Ala Ser Leu His Ala Phe Ala Asp Ser Leu Glu Arg Asp Leu
        995                 1000                1005

Asp Ala Pro Ser Pro Met His Glu Gly Asp Gln Thr Arg Ala Ser
    1010                1015                1020

<210> SEQ ID NO 73
<211> LENGTH: 1097
<212> TYPE: PRT
<213> ORGANISM: Artificial sequence
<220> FEATURE:
<223> OTHER INFORMATION: synthetic

<400> SEQUENCE: 73

Met His His His His His Met Ser Arg Thr Arg Leu Pro Ser Pro
1               5                   10                  15

Pro Ala Pro Ser Pro Ala Phe Ser Ala Asp Ser Phe Ser Asp Leu Leu
            20                  25                  30

Arg Gln Phe Asp Pro Ser Leu Phe Asn Thr Ser Leu Phe Asp Ser Leu
        35                  40                  45

Pro Pro Phe Gly Ala His His Thr Glu Ala Thr Gly Glu Trp Asp
    50                  55                  60

Glu Val Gln Ser Gly Leu Arg Ala Ala Asp Ala Pro Pro Thr Met
65                  70                  75                  80

Arg Val Ala Val Thr Ala Ala Arg Pro Pro Arg Ala Lys Pro Ala Pro
                 85                  90                  95

Arg Arg Arg Ala Ala Gln Pro Ser Asp Ala Ser Pro Ala Ala Gln Val
            100                 105                 110

Asp Leu Arg Thr Leu Gly Tyr Ser Gln Gln Gln Glu Lys Ile Lys
        115                 120                 125

Pro Lys Val Arg Ser Thr Val Ala Gln His His Glu Ala Leu Val Gly
    130                 135                 140

His Gly Phe Thr His Ala His Ile Val Ala Leu Ser Gln His Pro Ala
145                 150                 155                 160

Ala Leu Gly Thr Val Ala Val Lys Tyr Gln Asp Met Ile Ala Ala Leu
                165                 170                 175

Pro Glu Ala Thr His Glu Ala Ile Val Gly Val Gly Lys Gln Trp Ser
            180                 185                 190

Gly Ala Arg Ala Leu Glu Ala Leu Leu Thr Val Ala Gly Glu Leu Arg
        195                 200                 205

Gly Pro Pro Leu Gln Leu Asp Thr Gly Gln Leu Leu Lys Ile Ala Lys
    210                 215                 220

Arg Gly Gly Val Thr Ala Val Glu Ala Val His Ala Trp Arg Asn Ala
225                 230                 235                 240

Leu Thr Gly Ala Pro Leu Asn Leu Thr Glu Thr Leu Thr Pro Glu Gln
                245                 250                 255

Val Val Ala Ile Ala Ser Asn His Gly Gly Lys Gln Ala Leu Glu Thr
            260                 265                 270

Val Gln Arg Leu Leu Pro Val Leu Cys Gln Ala His Gly Leu Thr Pro
        275                 280                 285

Glu Gln Val Val Ala Ile Ala Ser Asn His Gly Gly Lys Gln Ala Leu
    290                 295                 300

Glu Thr Val Gln Arg Leu Leu Pro Val Leu Cys Gln Ala His Gly Leu
305                 310                 315                 320

Thr Pro Glu Gln Val Val Ala Ile Ala Ser His Asp Gly Gly Lys Gln
                325                 330                 335

Ala Leu Glu Thr Val Gln Arg Leu Leu Pro Val Leu Cys Gln Ala His
            340                 345                 350

Gly Leu Thr Pro Glu Gln Val Val Ala Ile Ala Ser His Asp Gly Gly
        355                 360                 365

Lys Gln Ala Leu Glu Thr Val Gln Arg Leu Leu Pro Val Leu Cys Gln
    370                 375                 380

Ala His Gly Leu Thr Pro Glu Gln Val Val Ala Ile Ala Ser His Asp
385                 390                 395                 400

Gly Gly Lys Gln Ala Leu Glu Thr Val Gln Arg Leu Leu Pro Val Leu
                405                 410                 415

Cys Gln Ala His Gly Leu Thr Pro Glu Gln Val Val Ala Ile Ala Ser
            420                 425                 430

Asn Gly Gly Gly Lys Gln Ala Leu Glu Thr Val Gln Arg Leu Leu Pro
        435                 440                 445

Val Leu Cys Gln Ala His Gly Leu Thr Pro Glu Gln Val Val Ala Ile
    450                 455                 460

Ala Ser His Asp Gly Gly Lys Gln Ala Leu Glu Thr Val Gln Arg Leu
465                 470                 475                 480

Leu Pro Val Leu Cys Gln Ala His Gly Leu Thr Pro Glu Gln Val Val
                485                 490                 495

Ala Ile Ala Ser Asn Gly Gly Gly Lys Gln Ala Leu Glu Thr Val Gln

```
                500             505             510
Arg Leu Leu Pro Val Leu Cys Gln Ala His Gly Leu Thr Pro Glu Gln
            515             520             525

Val Val Ala Ile Ala Ser Asn His Gly Gly Lys Gln Ala Leu Glu Thr
        530             535             540

Val Gln Arg Leu Leu Pro Val Leu Cys Gln Ala His Gly Leu Thr Pro
545             550             555             560

Glu Gln Val Val Ala Ile Ala Ser His Asp Gly Gly Lys Gln Ala Leu
            565             570             575

Glu Thr Val Gln Arg Leu Leu Pro Val Leu Cys Gln Ala His Gly Leu
        580             585             590

Thr Pro Glu Gln Val Val Ala Ile Ala Ser Asn Ile Gly Gly Lys Gln
        595             600             605

Ala Leu Glu Thr Val Gln Arg Leu Leu Pro Val Leu Cys Gln Ala His
        610             615             620

Gly Leu Thr Pro Glu Gln Val Val Ala Ile Ala Ser Asn Gly Gly Gly
625             630             635             640

Lys Gln Ala Leu Glu Thr Val Gln Arg Leu Leu Pro Val Leu Cys Gln
            645             650             655

Ala His Gly Leu Thr Pro Glu Gln Val Val Ala Ile Ala Ser His Asp
            660             665             670

Gly Gly Lys Gln Ala Leu Glu Thr Val Gln Arg Leu Leu Pro Val Leu
        675             680             685

Cys Gln Ala His Gly Leu Thr Pro Glu Gln Val Val Ala Ile Ala Ser
        690             695             700

His Asp Gly Gly Lys Gln Ala Leu Glu Thr Val Gln Arg Leu Leu Pro
705             710             715             720

Val Leu Cys Gln Ala His Gly Leu Thr Pro Glu Gln Val Val Ala Ile
            725             730             735

Ala Ser Asn Gly Gly Gly Lys Gln Ala Leu Glu Thr Val Gln Arg Leu
            740             745             750

Leu Pro Val Leu Cys Gln Ala His Gly Leu Thr Pro Glu Gln Val Val
        755             760             765

Ala Ile Ala Ser His Asp Gly Gly Lys Gln Ala Leu Glu Thr Val Gln
        770             775             780

Arg Leu Leu Pro Val Leu Cys Gln Ala His Gly Leu Thr Pro Glu Gln
785             790             795             800

Val Val Ala Ile Ala Ser His Asp Gly Gly Lys Gln Ala Leu Glu Thr
            805             810             815

Val Gln Arg Leu Leu Pro Val Leu Cys Gln Ala His Gly Ala Ser Gln
            820             825             830

Leu Thr Pro Glu Gln Val Val Ala Ile Ala Ser Asn Gly Gly Gly Arg
        835             840             845

Pro Ala Leu Glu Ser Ile Val Ala Gln Leu Ser Arg Pro Asp Pro Ala
        850             855             860

Leu Ala Ala Leu Thr Asn Asp His Leu Val Ala Leu Ala Cys Leu Gly
865             870             875             880

Gly Arg Pro Ala Leu Asp Ala Val Lys Lys Gly Leu Pro His Ala Pro
            885             890             895

Ala Leu Ile Lys Arg Thr Asn Arg Arg Ile Pro Glu Arg Thr Ser His
            900             905             910

Arg Val Ala Asp His Ala Gln Val Val Arg Val Leu Gly Phe Phe Gln
            915             920             925
```

```
Cys His Ser His Pro Ala Gln Ala Phe Asp Asp Ala Met Thr Gln Phe
    930                 935                 940

Gly Met Ser Arg His Gly Leu Leu Gln Leu Phe Arg Arg Val Gly Val
945                 950                 955                 960

Thr Glu Leu Glu Ala Arg Ser Gly Thr Leu Pro Pro Ala Ser Gln Arg
                965                 970                 975

Trp Asp Arg Ile Leu Gln Ala Ser Gly Met Lys Arg Ala Lys Pro Ser
            980                 985                 990

Pro Thr Ser Thr Gln Thr Pro Asp Gln Ala Ser Leu His Ala Phe Ala
        995                 1000                1005

Asp Ser Leu Glu Arg Asp Leu Asp Ala Pro Ser Pro Met His Glu
    1010                1015                1020

Gly Asp Gln Thr Arg Ala Ser Ala Ser Pro Lys Lys Lys Arg Lys
    1025                1030                1035

Val Glu Ala Ser Gly Ser Gly Arg Ala Asp Ala Leu Asp Asp Phe
    1040                1045                1050

Asp Leu Asp Met Leu Gly Ser Asp Ala Leu Asp Asp Phe Asp Leu
    1055                1060                1065

Asp Met Leu Gly Ser Asp Ala Leu Asp Asp Phe Asp Leu Asp Met
    1070                1075                1080

Leu Gly Ser Asp Ala Leu Asp Asp Phe Asp Leu Asp Met Leu
    1085                1090                1095
```

<210> SEQ ID NO 74
<211> LENGTH: 19
<212> TYPE: DNA
<213> ORGANISM: Zea mays

<400> SEQUENCE: 74
tggccctctg catcctcct                                                19

<210> SEQ ID NO 75
<211> LENGTH: 988
<212> TYPE: PRT
<213> ORGANISM: Artificial sequence
<220> FEATURE:
<223> OTHER INFORMATION: synthetic

<400> SEQUENCE: 75

```
Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
        35                  40                  45

Thr Glu Ala Ala Thr Gly Glu Trp Asp Glu Val Gln Ser Gly Leu Arg
    50                  55                  60

Ala Ala Asp Ala Pro Pro Pro Thr Met Arg Val Ala Val Thr Ala Ala
65                  70                  75                  80

Arg Pro Pro Arg Ala Lys Pro Ala Pro Arg Arg Arg Ala Ala Gln Pro
                85                  90                  95

Ser Asp Ala Ser Pro Ala Ala Gln Val Asp Leu Arg Thr Leu Gly Tyr
            100                 105                 110

Ser Gln Gln Gln Gln Glu Lys Ile Lys Pro Lys Val Arg Ser Thr Val
        115                 120                 125

Ala Gln His His Glu Ala Leu Val Gly His Gly Phe Thr His Ala His
```

```
              130                 135                 140
Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
            180                 185                 190

Leu Leu Thr Val Ala Gly Glu Leu Arg Gly Pro Leu Gln Leu Asp
                195                 200                 205

Thr Gly Gln Leu Leu Lys Ile Ala Lys Arg Gly Gly Val Thr Ala Val
        210                 215                 220

Glu Ala Val His Ala Trp Arg Asn Ala Leu Thr Gly Ala Pro Leu Asn
225                 230                 235                 240

Leu Thr Glu Thr Leu Thr Pro Glu Gln Val Val Ala Ile Ala Ser Asn
                245                 250                 255

His Gly Gly Lys Gln Ala Leu Glu Thr Val Gln Arg Leu Leu Pro Val
            260                 265                 270

Leu Cys Gln Ala His Gly Leu Thr Pro Glu Gln Val Val Ala Ile Ala
        275                 280                 285

Ser Asn Gly Gly Lys Gln Ala Leu Glu Thr Val Gln Arg Leu Leu
            290                 295                 300

Pro Val Leu Cys Gln Ala His Gly Leu Thr Pro Glu Gln Val Val Ala
305                 310                 315                 320

Ile Ala Ser Asn His Gly Gly Lys Gln Ala Leu Glu Thr Val Gln Arg
                325                 330                 335

Leu Leu Pro Val Leu Cys Gln Ala His Gly Leu Thr Pro Glu Gln Val
            340                 345                 350

Val Ala Ile Ala Ser Asn Gly Gly Lys Gln Ala Leu Glu Thr Val
        355                 360                 365

Gln Arg Leu Leu Pro Val Leu Cys Gln Ala His Gly Leu Thr Pro Glu
    370                 375                 380

Gln Val Val Ala Ile Ala Ser His Asp Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Glu Gln Val Val Ala Ile Ala Ser Asn Ile Gly Gly Lys Gln Ala
            420                 425                 430

Leu Glu Thr Val Gln Arg Leu Leu Pro Val Leu Cys Gln Ala His Leu
        435                 440                 445

Thr Pro Glu Gln Val Val Ala Ile Ala Ser Asn Ile Gly Gly Lys Gln
    450                 455                 460

Ala Leu Glu Thr Val Gln Arg Leu Leu Pro Val Leu Cys Gln Ala His
465                 470                 475                 480

Gly Leu Thr Pro Glu Gln Val Val Ala Ile Ala Ser His Asp Gly Gly
                485                 490                 495

Lys Gln Ala Leu Glu Thr Val Gln Arg Leu Leu Pro Val Leu Cys Gln
            500                 505                 510

Ala His Gly Leu Thr Pro Glu Gln Val Val Ala Ile Ala Ser Asn Gly
        515                 520                 525

Gly Gly Lys Gln Ala Leu Glu Thr Val Gln Arg Leu Leu Pro Val Leu
    530                 535                 540

Cys Gln Ala His Gly Leu Thr Pro Glu Gln Val Val Ala Ile Ala Ser
545                 550                 555                 560
```

-continued

```
Asn Gly Gly Gly Lys Gln Ala Leu Glu Thr Val Gln Arg Leu Leu Pro
            565                 570                 575
Val Leu Cys Gln Ala His Gly Leu Thr Pro Glu Gln Val Val Ala Ile
        580                 585                 590
Ala Ser His Asp Gly Gly Lys Gln Ala Leu Glu Thr Val Gln Arg Leu
    595                 600                 605
Leu Pro Val Leu Cys Gln Ala His Gly Leu Thr Pro Glu Gln Val Val
610                 615                 620
Ala Ile Ala Ser Asn Ile Gly Gly Lys Gln Ala Leu Glu Thr Val Gln
625                 630                 635                 640
Arg Leu Leu Pro Val Leu Cys Gln Ala His Gly Leu Thr Pro Glu Gln
                645                 650                 655
Val Val Ala Ile Ala Ser His Asp Gly Gly Lys Gln Ala Leu Glu Thr
            660                 665                 670
Val Gln Arg Leu Leu Pro Val Leu Cys Gln Ala His Gly Leu Thr Pro
        675                 680                 685
Glu Gln Val Val Ala Ile Ala Ser Asn Gly Gly Lys Gln Ala Leu
    690                 695                 700
Glu Thr Val Gln Arg Leu Leu Pro Val Leu Cys Gln Ala His Gly Leu
705                 710                 715                 720
Thr Pro Glu Gln Val Val Ala Ile Ala Ser Asn Gly Gly Lys Gln
                725                 730                 735
Ala Leu Glu Thr Val Gln Arg Leu Leu Pro Val Leu Cys Gln Ala His
            740                 745                 750
Gly Leu Thr Pro Glu Gln Val Val Ala Ile Ala Ser Asn His Gly Gly
        755                 760                 765
Lys Gln Ala Leu Glu Thr Val Gln Arg Leu Leu Pro Val Leu Cys Gln
    770                 775                 780
Ala His Gly Ala Ser Gln Leu Thr Pro Glu Gln Val Val Ala Ile Ala
785                 790                 795                 800
Ser Asn Gly Gly Gly Arg Pro Ala Leu Glu Ser Ile Val Ala Gln Leu
                805                 810                 815
Ser Arg Pro Asp Pro Ala Leu Ala Ala Leu Thr Asn Asp His Leu Val
            820                 825                 830
Ala Leu Ala Cys Leu Gly Gly Arg Pro Ala Leu Asp Ala Val Lys Lys
        835                 840                 845
Gly Leu Pro His Ala Pro Ala Leu Ile Lys Arg Thr Asn Arg Arg Ile
    850                 855                 860
Pro Glu Arg Thr Ser His Arg Val Ala Asp His Ala Gln Val Val Arg
865                 870                 875                 880
Val Leu Gly Phe Phe Gln Cys His Ser His Pro Ala Gln Ala Phe Asp
                885                 890                 895
Asp Ala Met Thr Gln Phe Gly Met Ser Arg His Gly Leu Leu Gln Leu
            900                 905                 910
Phe Arg Arg Val Gly Val Thr Glu Leu Glu Ala Arg Ser Gly Thr Leu
        915                 920                 925
Pro Pro Ala Ser Gln Arg Trp Asp Arg Ile Leu Gln Ala Ser Gly Met
    930                 935                 940
Lys Arg Ala Lys Pro Ser Pro Thr Ser Thr Gln Thr Pro Asp Gln Ala
945                 950                 955                 960
Ser Leu His Ala Phe Ala Asp Ser Leu Glu Arg Asp Leu Asp Ala Pro
                965                 970                 975
```

```
Ser Pro Met His Glu Gly Asp Gln Thr Arg Ala Ser
        980                 985

<210> SEQ ID NO 76
<211> LENGTH: 1062
<212> TYPE: PRT
<213> ORGANISM: Artificial sequence
<220> FEATURE:
<223> OTHER INFORMATION: synthetic

<400> SEQUENCE: 76

Met His His His His His Met Ser Arg Thr Arg Leu Pro Ser Pro
1               5                   10                  15

Pro Ala Pro Ser Pro Ala Phe Ser Ala Asp Ser Phe Ser Asp Leu Leu
            20                  25                  30

Arg Gln Phe Asp Pro Ser Leu Phe Asn Thr Ser Leu Phe Asp Ser Leu
        35                  40                  45

Pro Pro Phe Gly Ala His His Thr Glu Ala Ala Thr Gly Glu Trp Asp
50                  55                  60

Glu Val Gln Ser Gly Leu Arg Ala Ala Asp Ala Pro Pro Pro Thr Met
65                  70                  75                  80

Arg Val Ala Val Thr Ala Ala Arg Pro Pro Arg Ala Lys Pro Ala Pro
                85                  90                  95

Arg Arg Arg Ala Ala Gln Pro Ser Asp Ala Ser Pro Ala Ala Gln Val
            100                 105                 110

Asp Leu Arg Thr Leu Gly Tyr Ser Gln Gln Gln Gln Glu Lys Ile Lys
        115                 120                 125

Pro Lys Val Arg Ser Thr Val Ala Gln His His Glu Ala Leu Val Gly
    130                 135                 140

His Gly Phe Thr His Ala His Ile Val Ala Leu Ser Gln His Pro Ala
145                 150                 155                 160

Ala Leu Gly Thr Val Ala Val Lys Tyr Gln Asp Met Ile Ala Ala Leu
                165                 170                 175

Pro Glu Ala Thr His Glu Ala Ile Val Gly Val Gly Lys Gln Trp Ser
            180                 185                 190

Gly Ala Arg Ala Leu Glu Ala Leu Leu Thr Val Ala Gly Glu Leu Arg
        195                 200                 205

Gly Pro Pro Leu Gln Leu Asp Thr Gly Gln Leu Leu Lys Ile Ala Lys
    210                 215                 220

Arg Gly Gly Val Thr Ala Val Glu Ala Val His Ala Trp Arg Asn Ala
225                 230                 235                 240

Leu Thr Gly Ala Pro Leu Asn Leu Thr Glu Thr Leu Thr Pro Glu Gln
                245                 250                 255

Val Val Ala Ile Ala Ser Asn His Gly Gly Lys Gln Ala Leu Glu Thr
            260                 265                 270

Val Gln Arg Leu Leu Pro Val Leu Cys Gln Ala His Gly Leu Thr Pro
        275                 280                 285

Glu Gln Val Val Ala Ile Ala Ser Asn Gly Gly Gly Lys Gln Ala Leu
    290                 295                 300

Glu Thr Val Gln Arg Leu Leu Pro Val Leu Cys Gln Ala His Gly Leu
305                 310                 315                 320

Thr Pro Glu Gln Val Val Ala Ile Ala Ser Asn His Gly Gly Lys Gln
                325                 330                 335

Ala Leu Glu Thr Val Gln Arg Leu Leu Pro Val Leu Cys Gln Ala His
            340                 345                 350
```

```
Gly Leu Thr Pro Glu Gln Val Val Ala Ile Ala Ser Asn Gly Gly
            355                 360                 365
Lys Gln Ala Leu Glu Thr Val Gln Arg Leu Leu Pro Val Leu Cys Gln
    370                 375                 380
Ala His Gly Leu Thr Pro Glu Gln Val Val Ala Ile Ala Ser His Asp
385                 390                 395                 400
Gly Gly Lys Gln Ala Leu Glu Thr Val Gln Arg Leu Leu Pro Val Leu
                405                 410                 415
Cys Gln Ala His Gly Leu Thr Pro Glu Gln Val Val Ala Ile Ala Ser
                420                 425                 430
Asn Ile Gly Gly Lys Gln Ala Leu Glu Thr Val Gln Arg Leu Leu Pro
            435                 440                 445
Val Leu Cys Gln Ala His Leu Thr Pro Glu Gln Val Val Ala Ile Ala
        450                 455                 460
Ser Asn Ile Gly Gly Lys Gln Ala Leu Glu Thr Val Gln Arg Leu Leu
465                 470                 475                 480
Pro Val Leu Cys Gln Ala His Gly Leu Thr Pro Glu Gln Val Val Ala
                485                 490                 495
Ile Ala Ser His Asp Gly Gly Lys Gln Ala Leu Glu Thr Val Gln Arg
                500                 505                 510
Leu Leu Pro Val Leu Cys Gln Ala His Gly Leu Thr Pro Glu Gln Val
            515                 520                 525
Val Ala Ile Ala Ser Asn Gly Gly Lys Gln Ala Leu Glu Thr Val
        530                 535                 540
Gln Arg Leu Leu Pro Val Leu Cys Gln Ala His Gly Leu Thr Pro Glu
545                 550                 555                 560
Gln Val Val Ala Ile Ala Ser Asn Gly Gly Lys Gln Ala Leu Glu
                565                 570                 575
Thr Val Gln Arg Leu Leu Pro Val Leu Cys Gln Ala His Gly Leu Thr
                580                 585                 590
Pro Glu Gln Val Val Ala Ile Ala Ser His Asp Gly Gly Lys Gln Ala
            595                 600                 605
Leu Glu Thr Val Gln Arg Leu Leu Pro Val Leu Cys Gln Ala His Gly
    610                 615                 620
Leu Thr Pro Glu Gln Val Val Ala Ile Ala Ser Asn Ile Gly Gly Lys
625                 630                 635                 640
Gln Ala Leu Glu Thr Val Gln Arg Leu Leu Pro Val Leu Cys Gln Ala
                645                 650                 655
His Gly Leu Thr Pro Glu Gln Val Val Ala Ile Ala Ser His Asp Gly
                660                 665                 670
Gly Lys Gln Ala Leu Glu Thr Val Gln Arg Leu Leu Pro Val Leu Cys
            675                 680                 685
Gln Ala His Gly Leu Thr Pro Glu Gln Val Val Ala Ile Ala Ser Asn
    690                 695                 700
Gly Gly Gly Lys Gln Ala Leu Glu Thr Val Gln Arg Leu Leu Pro Val
705                 710                 715                 720
Leu Cys Gln Ala His Gly Leu Thr Pro Glu Gln Val Val Ala Ile Ala
                725                 730                 735
Ser Asn Gly Gly Gly Lys Gln Ala Leu Glu Thr Val Gln Arg Leu Leu
                740                 745                 750
Pro Val Leu Cys Gln Ala His Gly Leu Thr Pro Glu Gln Val Val Ala
            755                 760                 765
Ile Ala Ser Asn His Gly Gly Lys Gln Ala Leu Glu Thr Val Gln Arg
```

```
                        770                 775                 780
Leu Leu Pro Val Leu Cys Gln Ala His Gly Ala Ser Gln Leu Thr Pro
785                 790                 795                 800

Glu Gln Val Val Ala Ile Ala Ser Asn Gly Gly Arg Pro Ala Leu
                805                 810                 815

Glu Ser Ile Val Ala Gln Leu Ser Arg Pro Asp Pro Ala Leu Ala Ala
                820                 825                 830

Leu Thr Asn Asp His Leu Val Ala Leu Ala Cys Leu Gly Gly Arg Pro
                835                 840                 845

Ala Leu Asp Ala Val Lys Lys Gly Leu Pro His Ala Pro Ala Leu Ile
850                 855                 860

Lys Arg Thr Asn Arg Arg Ile Pro Glu Arg Thr Ser His Arg Val Ala
865                 870                 875                 880

Asp His Ala Gln Val Val Arg Val Leu Gly Phe Phe Gln Cys His Ser
                885                 890                 895

His Pro Ala Gln Ala Phe Asp Asp Ala Met Thr Gln Phe Gly Met Ser
                900                 905                 910

Arg His Gly Leu Leu Gln Leu Phe Arg Arg Val Gly Val Thr Glu Leu
                915                 920                 925

Glu Ala Arg Ser Gly Thr Leu Pro Pro Ala Ser Gln Arg Trp Asp Arg
930                 935                 940

Ile Leu Gln Ala Ser Gly Met Lys Arg Ala Lys Pro Ser Pro Thr Ser
945                 950                 955                 960

Thr Gln Thr Pro Asp Gln Ala Ser Leu His Ala Phe Ala Asp Ser Leu
                965                 970                 975

Glu Arg Asp Leu Asp Ala Pro Ser Pro Met His Glu Gly Asp Gln Thr
                980                 985                 990

Arg Ala Ser Ala Ser Pro Lys Lys Lys Arg Lys Val Glu Ala Ser Gly
                995                 1000                1005

Ser Gly Arg Ala Asp Ala Leu Asp Asp Phe Asp Leu Asp Met Leu
        1010                1015                1020

Gly Ser Asp Ala Leu Asp Asp Phe Asp Leu Asp Met Leu Gly Ser
        1025                1030                1035

Asp Ala Leu Asp Asp Phe Asp Leu Asp Met Leu Gly Ser Asp Ala
        1040                1045                1050

Leu Asp Asp Phe Asp Leu Asp Met Leu
        1055                1060

<210> SEQ ID NO 77
<211> LENGTH: 18
<212> TYPE: DNA
<213> ORGANISM: Zea mays

<400> SEQUENCE: 77
tgtgtcaact tcacttgt                                                18

<210> SEQ ID NO 78
<211> LENGTH: 1023
<212> TYPE: PRT
<213> ORGANISM: Artificial sequence
<220> FEATURE:
<223> OTHER INFORMATION: synthetic

<400> SEQUENCE: 78

Met Ser Arg Thr Arg Leu Pro Ser Pro Pro Ala Pro Ser Pro Ala Phe
1               5                   10                  15
```

```
Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
        35                  40                  45

Thr Glu Ala Ala Thr Gly Glu Trp Asp Glu Val Gln Ser Gly Leu Arg
50                  55                  60

Ala Ala Asp Ala Pro Pro Thr Met Arg Val Ala Val Thr Ala Ala
65                  70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
            100                 105                 110

Ser Gln Gln Gln Glu Lys Ile Lys Pro Lys Val Arg Ser Thr Val
        115                 120                 125

Ala Gln His His Glu Ala Leu Val Gly His Gly Phe Thr His Ala His
130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
            180                 185                 190

Leu Leu Thr Val Ala Gly Glu Leu Arg Gly Pro Pro Leu Gln Leu Asp
        195                 200                 205

Thr Gly Gln Leu Leu Lys Ile Ala Lys Arg Gly Gly Val Thr Ala Val
210                 215                 220

Glu Ala Val His Ala Trp Arg Asn Ala Leu Thr Gly Ala Pro Leu Asn
225                 230                 235                 240

Leu Thr Glu Thr Leu Thr Pro Glu Gln Val Val Ala Ile Ala Ser His
                245                 250                 255

Asp Gly Gly Lys Gln Ala Leu Glu Thr Val Gln Arg Leu Leu Pro Val
            260                 265                 270

Leu Cys Gln Ala His Gly Leu Thr Pro Glu Gln Val Val Ala Ile Ala
        275                 280                 285

Ser Asn His Gly Gly Lys Gln Ala Leu Glu Thr Val Gln Arg Leu Leu
290                 295                 300

Pro Val Leu Cys Gln Ala His Gly Leu Thr Pro Glu Gln Val Val Ala
305                 310                 315                 320

Ile Ala Ser Asn Gly Gly Gly Lys Gln Ala Leu Glu Thr Val Gln Arg
                325                 330                 335

Leu Leu Pro Val Leu Cys Gln Ala His Gly Leu Thr Pro Glu Gln Val
            340                 345                 350

Val Ala Ile Ala Ser Asn Ile Gly Gly Lys Gln Ala Leu Glu Thr Val
        355                 360                 365

Gln Arg Leu Leu Pro Val Leu Cys Gln Ala His Gly Leu Thr Pro Glu
370                 375                 380

Gln Val Val Ala Ile Ala Ser Asn Gly Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Glu Gln Val Val Ala Ile Ala Ser His Asp Gly Gly Lys Gln Ala
            420                 425                 430

Leu Glu Thr Val Gln Arg Leu Leu Pro Val Leu Cys Gln Ala His Gly
```

-continued

```
            435                 440                 445
Leu Thr Pro Glu Gln Val Val Ala Ile Ala Ser Asn Ile Gly Gly Lys
450                 455                 460

Gln Ala Leu Glu Thr Val Gln Arg Leu Leu Pro Val Leu Cys Gln Ala
465                 470                 475                 480

His Gly Leu Thr Pro Glu Gln Val Val Ala Ile Ala Ser His Asp Gly
                    485                 490                 495

Gly Lys Gln Ala Leu Glu Thr Val Gln Arg Leu Leu Pro Val Leu Cys
                500                 505                 510

Gln Ala His Gly Leu Thr Pro Glu Gln Val Val Ala Ile Ala Ser His
            515                 520                 525

Asp Gly Gly Lys Gln Ala Leu Glu Thr Val Gln Arg Leu Leu Pro Val
530                 535                 540

Leu Cys Gln Ala His Gly Leu Thr Pro Glu Gln Val Val Ala Ile Ala
545                 550                 555                 560

Ser His Asp Gly Gly Lys Gln Ala Leu Glu Thr Val Gln Arg Leu Leu
                565                 570                 575

Pro Val Leu Cys Gln Ala His Gly Leu Thr Pro Glu Gln Val Val Ala
            580                 585                 590

Ile Ala Ser Asn Ile Gly Gly Lys Gln Ala Leu Glu Thr Val Gln Arg
            595                 600                 605

Leu Leu Pro Val Leu Cys Gln Ala His Gly Leu Thr Pro Glu Gln Val
610                 615                 620

Val Ala Ile Ala Ser Asn Gly Gly Gly Lys Gln Ala Leu Glu Thr Val
625                 630                 635                 640

Gln Arg Leu Leu Pro Val Leu Cys Gln Ala His Gly Leu Thr Pro Glu
                645                 650                 655

Gln Val Val Ala Ile Ala Ser Asn His Gly Gly Lys Gln Ala Leu Glu
            660                 665                 670

Thr Val Gln Arg Leu Leu Pro Val Leu Cys Gln Ala His Gly Leu Thr
            675                 680                 685

Pro Glu Gln Val Val Ala Ile Ala Ser Asn His Gly Gly Lys Gln Ala
        690                 695                 700

Leu Glu Thr Val Gln Arg Leu Leu Pro Val Leu Cys Gln Ala His Gly
705                 710                 715                 720

Leu Thr Pro Glu Gln Val Val Ala Ile Ala Ser His Asp Gly Gly Lys
                725                 730                 735

Gln Ala Leu Glu Thr Val Gln Arg Leu Leu Pro Val Leu Cys Gln Ala
                740                 745                 750

His Gly Leu Thr Pro Glu Gln Val Val Ala Ile Ala Ser His Asp Gly
            755                 760                 765

Gly Lys Gln Ala Leu Glu Thr Val Gln Arg Leu Leu Pro Val Leu Cys
        770                 775                 780

Gln Ala His Gly Leu Thr Pro Glu Gln Val Val Ala Ile Ala Ser Asn
785                 790                 795                 800

Ile Gly Gly Lys Gln Ala Leu Glu Thr Val Gln Arg Leu Leu Pro Val
                805                 810                 815

Leu Cys Gln Ala His Gly Ala Ser Gln Leu Thr Pro Glu Gln Val Val
            820                 825                 830

Ala Ile Ala Ser Asn Gly Gly Gly Arg Pro Ala Leu Glu Ser Ile Val
            835                 840                 845

Ala Gln Leu Ser Arg Pro Asp Pro Ala Leu Ala Ala Leu Thr Asn Asp
        850                 855                 860
```

His Leu Val Ala Leu Ala Cys Leu Gly Gly Arg Pro Ala Leu Asp Ala
865                 870                 875                 880

Val Lys Lys Gly Leu Pro His Ala Pro Ala Leu Ile Lys Arg Thr Asn
            885                 890                 895

Arg Arg Ile Pro Glu Arg Thr Ser His Arg Val Ala Asp His Ala Gln
        900                 905                 910

Val Val Arg Val Leu Gly Phe Phe Gln Cys His Ser His Pro Ala Gln
        915                 920                 925

Ala Phe Asp Asp Ala Met Thr Gln Phe Gly Met Ser Arg His Gly Leu
        930                 935                 940

Leu Gln Leu Phe Arg Arg Val Gly Val Thr Glu Leu Glu Ala Arg Ser
945                 950                 955                 960

Gly Thr Leu Pro Pro Ala Ser Gln Arg Trp Asp Arg Ile Leu Gln Ala
            965                 970                 975

Ser Gly Met Lys Arg Ala Lys Pro Ser Pro Thr Ser Thr Gln Thr Pro
            980                 985                 990

Asp Gln Ala Ser Leu His Ala Phe Ala Asp Ser Leu Glu Arg Asp Leu
        995                 1000                1005

Asp Ala Pro Ser Pro Met His Glu Gly Asp Gln Thr Arg Ala Ser
    1010                1015                1020

<210> SEQ ID NO 79
<211> LENGTH: 1097
<212> TYPE: PRT
<213> ORGANISM: Artificial sequence
<220> FEATURE:
<223> OTHER INFORMATION: synthetic

<400> SEQUENCE: 79

Met His His His His His Met Ser Arg Thr Arg Leu Pro Ser Pro
1               5                   10                  15

Pro Ala Pro Ser Pro Ala Phe Ser Ala Asp Ser Phe Ser Asp Leu Leu
            20                  25                  30

Arg Gln Phe Asp Pro Ser Leu Phe Asn Thr Ser Leu Phe Asp Ser Leu
        35                  40                  45

Pro Pro Phe Gly Ala His His Thr Glu Ala Ala Thr Gly Glu Trp Asp
    50                  55                  60

Glu Val Gln Ser Gly Leu Arg Ala Ala Asp Ala Pro Pro Pro Thr Met
65                  70                  75                  80

Arg Val Ala Val Thr Ala Ala Arg Pro Pro Arg Ala Lys Pro Ala Pro
                85                  90                  95

Arg Arg Arg Ala Ala Gln Pro Ser Asp Ala Ser Pro Ala Ala Gln Val
            100                 105                 110

Asp Leu Arg Thr Leu Gly Tyr Ser Gln Gln Gln Gln Glu Lys Ile Lys
        115                 120                 125

Pro Lys Val Arg Ser Thr Val Ala Gln His His Glu Ala Leu Val Gly
    130                 135                 140

His Gly Phe Thr His Ala His Ile Val Ala Leu Ser Gln His Pro Ala
145                 150                 155                 160

Ala Leu Gly Thr Val Ala Val Lys Tyr Gln Asp Met Ile Ala Ala Leu
                165                 170                 175

Pro Glu Ala Thr His Glu Ala Ile Val Gly Val Gly Lys Gln Trp Ser
            180                 185                 190

Gly Ala Arg Ala Leu Glu Ala Leu Leu Thr Val Ala Gly Glu Leu Arg
        195                 200                 205

```
Gly Pro Pro Leu Gln Leu Asp Thr Gly Gln Leu Leu Lys Ile Ala Lys
    210                 215                 220

Arg Gly Gly Val Thr Ala Val Glu Ala Val His Ala Trp Arg Asn Ala
225                 230                 235                 240

Leu Thr Gly Ala Pro Leu Asn Leu Thr Glu Thr Leu Thr Pro Glu Gln
                245                 250                 255

Val Val Ala Ile Ala Ser His Asp Gly Gly Lys Gln Ala Leu Glu Thr
                260                 265                 270

Val Gln Arg Leu Leu Pro Val Leu Cys Gln Ala His Gly Leu Thr Pro
        275                 280                 285

Glu Gln Val Val Ala Ile Ala Ser Asn His Gly Gly Lys Gln Ala Leu
    290                 295                 300

Glu Thr Val Gln Arg Leu Leu Pro Val Leu Cys Gln Ala His Gly Leu
305                 310                 315                 320

Thr Pro Glu Gln Val Val Ala Ile Ala Ser Asn Gly Gly Lys Gln
                325                 330                 335

Ala Leu Glu Thr Val Gln Arg Leu Leu Pro Val Leu Cys Gln Ala His
                340                 345                 350

Gly Leu Thr Pro Glu Gln Val Val Ala Ile Ala Ser Asn Ile Gly Gly
                355                 360                 365

Lys Gln Ala Leu Glu Thr Val Gln Arg Leu Leu Pro Val Leu Cys Gln
    370                 375                 380

Ala His Gly Leu Thr Pro Glu Gln Val Val Ala Ile Ala Ser Asn Gly
385                 390                 395                 400

Gly Gly Lys Gln Ala Leu Glu Thr Val Gln Arg Leu Leu Pro Val Leu
                405                 410                 415

Cys Gln Ala His Gly Leu Thr Pro Glu Gln Val Val Ala Ile Ala Ser
                420                 425                 430

His Asp Gly Gly Lys Gln Ala Leu Glu Thr Val Gln Arg Leu Leu Pro
                435                 440                 445

Val Leu Cys Gln Ala His Gly Leu Thr Pro Glu Gln Val Val Ala Ile
    450                 455                 460

Ala Ser Asn Ile Gly Gly Lys Gln Ala Leu Glu Thr Val Gln Arg Leu
465                 470                 475                 480

Leu Pro Val Leu Cys Gln Ala His Gly Leu Thr Pro Glu Gln Val Val
                485                 490                 495

Ala Ile Ala Ser His Asp Gly Gly Lys Gln Ala Leu Glu Thr Val Gln
                500                 505                 510

Arg Leu Leu Pro Val Leu Cys Gln Ala His Gly Leu Thr Pro Glu Gln
                515                 520                 525

Val Val Ala Ile Ala Ser His Asp Gly Gly Lys Gln Ala Leu Glu Thr
    530                 535                 540

Val Gln Arg Leu Leu Pro Val Leu Cys Gln Ala His Gly Leu Thr Pro
545                 550                 555                 560

Glu Gln Val Val Ala Ile Ala Ser His Asp Gly Gly Lys Gln Ala Leu
                565                 570                 575

Glu Thr Val Gln Arg Leu Leu Pro Val Leu Cys Gln Ala His Gly Leu
                580                 585                 590

Thr Pro Glu Gln Val Val Ala Ile Ala Ser Asn Ile Gly Gly Lys Gln
                595                 600                 605

Ala Leu Glu Thr Val Gln Arg Leu Leu Pro Val Leu Cys Gln Ala His
    610                 615                 620
```

```
Gly Leu Thr Pro Glu Gln Val Val Ala Ile Ala Ser Asn Gly Gly Gly
625                 630                 635                 640

Lys Gln Ala Leu Glu Thr Val Gln Arg Leu Leu Pro Val Leu Cys Gln
            645                 650                 655

Ala His Gly Leu Thr Pro Glu Gln Val Val Ala Ile Ala Ser Asn His
                660                 665                 670

Gly Gly Lys Gln Ala Leu Glu Thr Val Gln Arg Leu Leu Pro Val Leu
        675                 680                 685

Cys Gln Ala His Gly Leu Thr Pro Glu Gln Val Val Ala Ile Ala Ser
    690                 695                 700

Asn His Gly Gly Lys Gln Ala Leu Glu Thr Val Gln Arg Leu Pro
705                 710                 715                 720

Val Leu Cys Gln Ala His Gly Leu Thr Pro Glu Gln Val Val Ala Ile
                725                 730                 735

Ala Ser His Asp Gly Gly Lys Gln Ala Leu Glu Thr Val Gln Arg Leu
            740                 745                 750

Leu Pro Val Leu Cys Gln Ala His Gly Leu Thr Pro Glu Gln Val Val
        755                 760                 765

Ala Ile Ala Ser His Asp Gly Gly Lys Gln Ala Leu Glu Thr Val Gln
    770                 775                 780

Arg Leu Leu Pro Val Leu Cys Gln Ala His Gly Leu Thr Pro Glu Gln
785                 790                 795                 800

Val Val Ala Ile Ala Ser Asn Ile Gly Gly Lys Gln Ala Leu Glu Thr
                805                 810                 815

Val Gln Arg Leu Leu Pro Val Leu Cys Gln Ala His Gly Ala Ser Gln
            820                 825                 830

Leu Thr Pro Glu Gln Val Val Ala Ile Ala Ser Asn Gly Gly Gly Arg
        835                 840                 845

Pro Ala Leu Glu Ser Ile Val Ala Gln Leu Ser Arg Pro Asp Pro Ala
    850                 855                 860

Leu Ala Ala Leu Thr Asn Asp His Leu Val Ala Leu Ala Cys Leu Gly
865                 870                 875                 880

Gly Arg Pro Ala Leu Asp Ala Val Lys Lys Gly Leu Pro His Ala Pro
                885                 890                 895

Ala Leu Ile Lys Arg Thr Asn Arg Arg Ile Pro Glu Arg Thr Ser His
            900                 905                 910

Arg Val Ala Asp His Ala Gln Val Val Arg Val Leu Gly Phe Phe Gln
        915                 920                 925

Cys His Ser His Pro Ala Gln Ala Phe Asp Asp Ala Met Thr Gln Phe
    930                 935                 940

Gly Met Ser Arg His Gly Leu Leu Gln Leu Phe Arg Arg Val Gly Val
945                 950                 955                 960

Thr Glu Leu Glu Ala Arg Ser Gly Thr Leu Pro Pro Ala Ser Gln Arg
                965                 970                 975

Trp Asp Arg Ile Leu Gln Ala Ser Gly Met Lys Arg Ala Lys Pro Ser
            980                 985                 990

Pro Thr Ser Thr Gln Thr Pro Asp  Gln Ala Ser Leu His  Ala Phe Ala
        995                 1000                1005

Asp Ser  Leu Glu Arg Asp  Leu Asp Ala Pro Ser Pro  Met His Glu
    1010                1015                1020

Gly Asp  Gln Thr Arg Ala Ser  Ala Ser Pro Lys Lys  Lys Arg Lys
    1025                1030                1035

Val Glu  Ala Ser Gly Ser Gly  Arg Ala Asp Ala Leu  Asp Asp Phe
```

```
                1040                1045                1050

Asp Leu Asp Met Leu Gly Ser Asp Ala Leu Asp Phe Asp Leu
        1055                1060                1065

Asp Met Leu Gly Ser Asp Ala Leu Asp Asp Phe Asp Leu Asp Met
    1070                1075                1080

Leu Gly Ser Asp Ala Leu Asp Asp Phe Asp Leu Asp Met Leu
        1085                1090                1095

<210> SEQ ID NO 80
<211> LENGTH: 19
<212> TYPE: DNA
<213> ORGANISM: Zea mays

<400> SEQUENCE: 80
tcgtatcacc catggccat                                              19

<210> SEQ ID NO 81
<211> LENGTH: 989
<212> TYPE: PRT
<213> ORGANISM: Artificial sequence
<220> FEATURE:
<223> OTHER INFORMATION: synthetic

<400> SEQUENCE: 81

Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
        35                  40                  45

Thr Glu Ala Ala Thr Gly Glu Trp Asp Glu Val Gln Ser Gly Leu Arg
    50                  55                  60

Ala Ala Asp Ala Pro Pro Pro Thr Met Arg Val Ala Val Thr Ala Ala
65                  70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
            100                 105                 110

Ser Gln Gln Gln Gln Glu Lys Ile Lys Pro Lys Val Arg Ser Thr Val
        115                 120                 125

Ala Gln His His Glu Ala Leu Val Gly His Gly Phe Thr His Ala His
    130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
            180                 185                 190

Leu Leu Thr Val Ala Gly Glu Leu Arg Gly Pro Pro Leu Gln Leu Asp
        195                 200                 205

Thr Gly Gln Leu Leu Lys Ile Ala Lys Arg Gly Gly Val Thr Ala Val
    210                 215                 220

Glu Ala Val His Ala Trp Arg Asn Ala Leu Thr Gly Ala Pro Leu Asn
225                 230                 235                 240

Leu Thr Glu Thr Leu Thr Pro Glu Gln Val Val Ala Ile Ala Ser His
                245                 250                 255
```

-continued

Asp Gly Gly Lys Gln Ala Leu Glu Thr Val Gln Arg Leu Leu Pro Val
            260                 265                 270

Leu Cys Gln Ala His Gly Leu Thr Pro Glu Gln Val Val Ala Ile Ala
        275                 280                 285

Ser His Asp Gly Gly Lys Gln Ala Leu Glu Thr Val Gln Arg Leu Leu
    290                 295                 300

Pro Val Leu Cys Gln Ala His Gly Leu Thr Pro Glu Gln Val Val Ala
305                 310                 315                 320

Ile Ala Ser Asn Gly Gly Lys Gln Ala Leu Glu Thr Val Gln Arg
                325                 330                 335

Leu Leu Pro Val Leu Cys Gln Ala His Gly Leu Thr Pro Glu Gln Val
            340                 345                 350

Val Ala Ile Ala Ser Asn Ile Gly Gly Lys Gln Ala Leu Glu Thr Val
        355                 360                 365

Gln Arg Leu Leu Pro Val Leu Cys Gln Ala His Gly Leu Thr Pro Glu
    370                 375                 380

Gln Val Val Ala Ile Ala Ser Asn Ile Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Glu Gln Val Val Ala Ile Ala Ser Asn Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser Asn Ile Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Glu Gln Val Val Ala Ile Ala Ser Asn Gly Gly
                485                 490                 495

Gly Lys Gln Ala Leu Glu Thr Val Gln Arg Leu Leu Pro Val Leu Cys
            500                 505                 510

Gln Ala His Gly Leu Thr Pro Glu Gln Val Val Ala Ile Ala Ser Asn
        515                 520                 525

Ile Gly Gly Lys Gln Ala Leu Glu Thr Val Gln Arg Leu Leu Pro Val
    530                 535                 540

Leu Cys Gln Ala His Gly Leu Thr Pro Glu Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Ala His Gly Leu Thr Pro Glu Gln Val Val Ala
            580                 585                 590

Ile Ala Ser Asn Ile Gly Gly Lys Gln Ala Leu Glu Thr Val Gln Arg
        595                 600                 605

Leu Leu Pro Val Leu Cys Gln Ala His Gly Leu Thr Pro Glu Gln Val
    610                 615                 620

Val Ala Ile Ala Ser Asn Gly Gly Gly Lys Gln Ala Leu Glu Thr Val
625                 630                 635                 640

Gln Arg Leu Leu Pro Val Leu Cys Gln Ala His Gly Leu Thr Pro Glu
                645                 650                 655

Gln Val Val Ala Ile Ala Ser Asn Ile Gly Gly Lys Gln Ala Leu Glu
            660                 665                 670

Thr Val Gln Arg Leu Leu Pro Val Leu Cys Gln Ala His Gly Leu Thr

```
                675                 680                 685
Pro Glu Gln Val Val Ala Ile Ala Ser Asn Gly Gly Gly Lys Gln Ala
        690                 695                 700

Leu Glu Thr Val Gln Arg Leu Leu Pro Val Leu Cys Gln Ala His Gly
705                 710                 715                 720

Leu Thr Pro Glu Gln Val Val Ala Ile Ala Ser His Asp Gly Gly Lys
                725                 730                 735

Gln Ala Leu Glu Thr Val Gln Arg Leu Leu Pro Val Leu Cys Gln Ala
            740                 745                 750

His Gly Leu Thr Pro Glu Gln Val Val Ala Ile Ala Ser Asn Ile Gly
        755                 760                 765

Gly Lys Gln Ala Leu Glu Thr Val Gln Arg Leu Leu Pro Val Leu Cys
770                 775                 780

Gln Ala His Gly Ala Ser Gln Leu Thr Pro Glu Gln Val Val Ala Ile
785                 790                 795                 800

Ala Ser Asn Gly Gly Arg Pro Ala Leu Glu Ser Ile Val Ala Gln
                805                 810                 815

Leu Ser Arg Pro Asp Pro Ala Leu Ala Ala Leu Thr Asn Asp His Leu
            820                 825                 830

Val Ala Leu Ala Cys Leu Gly Gly Arg Pro Ala Leu Asp Ala Val Lys
        835                 840                 845

Lys Gly Leu Pro His Ala Pro Ala Leu Ile Lys Arg Thr Asn Arg Arg
850                 855                 860

Ile Pro Glu Arg Thr Ser His Arg Val Ala Asp His Ala Gln Val Val
865                 870                 875                 880

Arg Val Leu Gly Phe Phe Gln Cys His Ser His Pro Ala Gln Ala Phe
                885                 890                 895

Asp Asp Ala Met Thr Gln Phe Gly Met Ser Arg His Gly Leu Leu Gln
            900                 905                 910

Leu Phe Arg Arg Val Gly Val Thr Glu Leu Glu Ala Arg Ser Gly Thr
        915                 920                 925

Leu Pro Pro Ala Ser Gln Arg Trp Asp Arg Ile Leu Gln Ala Ser Gly
    930                 935                 940

Met Lys Arg Ala Lys Pro Ser Pro Thr Ser Thr Gln Thr Pro Asp Gln
945                 950                 955                 960

Ala Ser Leu His Ala Phe Ala Asp Ser Leu Glu Arg Asp Leu Asp Ala
                965                 970                 975

Pro Ser Pro Met His Glu Gly Asp Gln Thr Arg Ala Ser
            980                 985

<210> SEQ ID NO 82
<211> LENGTH: 1063
<212> TYPE: PRT
<213> ORGANISM: Artificial sequence
<220> FEATURE:
<223> OTHER INFORMATION: synthetic

<400> SEQUENCE: 82

Met His His His His His Met Ser Arg Thr Arg Leu Pro Ser Pro
1               5                   10                  15

Pro Ala Pro Ser Pro Ala Phe Ser Ala Asp Ser Phe Ser Asp Leu Leu
                20                  25                  30

Arg Gln Phe Asp Pro Ser Leu Phe Asn Thr Ser Leu Phe Asp Ser Leu
            35                  40                  45

Pro Pro Phe Gly Ala His His Thr Glu Ala Ala Thr Gly Glu Trp Asp
```

```
                50                  55                  60
Glu Val Gln Ser Gly Leu Arg Ala Ala Asp Ala Pro Pro Thr Met
 65                  70                  75                  80

Arg Val Ala Val Thr Ala Ala Arg Pro Pro Arg Ala Lys Pro Ala Pro
                 85                  90                  95

Arg Arg Arg Ala Ala Gln Pro Ser Asp Ala Ser Pro Ala Ala Gln Val
                100                 105                 110

Asp Leu Arg Thr Leu Gly Tyr Ser Gln Gln Gln Glu Lys Ile Lys
                115                 120                 125

Pro Lys Val Arg Ser Thr Val Ala Gln His His Glu Ala Leu Val Gly
                130                 135                 140

His Gly Phe Thr His Ala His Ile Val Ala Leu Ser Gln His Pro Ala
145                 150                 155                 160

Ala Leu Gly Thr Val Ala Val Lys Tyr Gln Asp Met Ile Ala Ala Leu
                165                 170                 175

Pro Glu Ala Thr His Glu Ala Ile Val Gly Val Gly Lys Gln Trp Ser
                180                 185                 190

Gly Ala Arg Ala Leu Glu Ala Leu Leu Thr Val Ala Gly Glu Leu Arg
                195                 200                 205

Gly Pro Pro Leu Gln Leu Asp Thr Gly Gln Leu Leu Lys Ile Ala Lys
                210                 215                 220

Arg Gly Gly Val Thr Ala Val Glu Ala Val His Ala Trp Arg Asn Ala
225                 230                 235                 240

Leu Thr Gly Ala Pro Leu Asn Leu Thr Glu Thr Leu Thr Pro Glu Gln
                245                 250                 255

Val Val Ala Ile Ala Ser His Asp Gly Gly Lys Gln Ala Leu Glu Thr
                260                 265                 270

Val Gln Arg Leu Leu Pro Val Leu Cys Gln Ala His Gly Leu Thr Pro
                275                 280                 285

Glu Gln Val Val Ala Ile Ala Ser His Asp Gly Gly Lys Gln Ala Leu
                290                 295                 300

Glu Thr Val Gln Arg Leu Leu Pro Val Leu Cys Gln Ala His Gly Leu
305                 310                 315                 320

Thr Pro Glu Gln Val Val Ala Ile Ala Ser Asn Gly Gly Lys Gln
                325                 330                 335

Ala Leu Glu Thr Val Gln Arg Leu Leu Pro Val Leu Cys Gln Ala His
                340                 345                 350

Gly Leu Thr Pro Glu Gln Val Val Ala Ile Ala Ser Asn Ile Gly Gly
                355                 360                 365

Lys Gln Ala Leu Glu Thr Val Gln Arg Leu Leu Pro Val Leu Cys Gln
                370                 375                 380

Ala His Gly Leu Thr Pro Glu Gln Val Val Ala Ile Ala Ser Asn Ile
385                 390                 395                 400

Gly Gly Lys Gln Ala Leu Glu Thr Val Gln Arg Leu Leu Pro Val Leu
                405                 410                 415

Cys Gln Ala His Gly Leu Thr Pro Glu Gln Val Val Ala Ile Ala Ser
                420                 425                 430

Asn Gly Gly Lys Gln Ala Leu Glu Thr Val Gln Arg Leu Leu Pro
                435                 440                 445

Val Leu Cys Gln Ala His Gly Leu Thr Pro Glu Gln Val Val Ala Ile
                450                 455                 460

Ala Ser Asn Ile Gly Gly Lys Gln Ala Leu Glu Thr Val Gln Arg Leu
465                 470                 475                 480
```

```
Leu Pro Val Leu Cys Gln Ala His Gly Leu Thr Pro Glu Gln Val Val
            485                 490                 495

Ala Ile Ala Ser Asn Gly Gly Lys Gln Ala Leu Glu Thr Val Gln
        500                 505                 510

Arg Leu Leu Pro Val Leu Cys Gln Ala His Gly Leu Thr Pro Glu Gln
        515                 520                 525

Val Val Ala Ile Ala Ser Asn Ile Gly Gly Lys Gln Ala Leu Glu Thr
530                 535                 540

Val Gln Arg Leu Leu Pro Val Leu Cys Gln Ala His Gly Leu Thr Pro
545                 550                 555                 560

Glu Gln Val Val Ala Ile Ala Ser Asn Gly Gly Lys Gln Ala Leu
                565                 570                 575

Glu Thr Val Gln Arg Leu Leu Pro Val Leu Cys Gln Ala His Gly Leu
            580                 585                 590

Thr Pro Glu Gln Val Val Ala Ile Ala Ser Asn Ile Gly Gly Lys Gln
            595                 600                 605

Ala Leu Glu Thr Val Gln Arg Leu Leu Pro Val Leu Cys Gln Ala His
        610                 615                 620

Gly Leu Thr Pro Glu Gln Val Val Ala Ile Ala Ser Asn Gly Gly
625                 630                 635                 640

Lys Gln Ala Leu Glu Thr Val Gln Arg Leu Leu Pro Val Leu Cys Gln
            645                 650                 655

Ala His Gly Leu Thr Pro Glu Gln Val Val Ala Ile Ala Ser Asn Ile
            660                 665                 670

Gly Gly Lys Gln Ala Leu Glu Thr Val Gln Arg Leu Leu Pro Val Leu
        675                 680                 685

Cys Gln Ala His Gly Leu Thr Pro Glu Gln Val Val Ala Ile Ala Ser
        690                 695                 700

Asn Gly Gly Gly Lys Gln Ala Leu Glu Thr Val Gln Arg Leu Leu Pro
705                 710                 715                 720

Val Leu Cys Gln Ala His Gly Leu Thr Pro Glu Gln Val Val Ala Ile
            725                 730                 735

Ala Ser His Asp Gly Gly Lys Gln Ala Leu Glu Thr Val Gln Arg Leu
            740                 745                 750

Leu Pro Val Leu Cys Gln Ala His Gly Leu Thr Pro Glu Gln Val Val
            755                 760                 765

Ala Ile Ala Ser Asn Ile Gly Gly Lys Gln Ala Leu Glu Thr Val Gln
            770                 775                 780

Arg Leu Leu Pro Val Leu Cys Gln Ala His Gly Ala Ser Gln Leu Thr
785                 790                 795                 800

Pro Glu Gln Val Val Ala Ile Ala Ser Asn Gly Gly Gly Arg Pro Ala
            805                 810                 815

Leu Glu Ser Ile Val Ala Gln Leu Ser Arg Pro Asp Pro Ala Leu Ala
            820                 825                 830

Ala Leu Thr Asn Asp His Leu Val Ala Leu Ala Cys Leu Gly Gly Arg
        835                 840                 845

Pro Ala Leu Asp Ala Val Lys Lys Gly Leu Pro His Ala Pro Ala Leu
850                 855                 860

Ile Lys Arg Thr Asn Arg Arg Ile Pro Glu Arg Thr Ser His Arg Val
865                 870                 875                 880

Ala Asp His Ala Gln Val Val Arg Val Leu Gly Phe Phe Gln Cys His
            885                 890                 895
```

```
Ser His Pro Ala Gln Ala Phe Asp Asp Ala Met Thr Gln Phe Gly Met
            900                 905                 910

Ser Arg His Gly Leu Leu Gln Leu Phe Arg Arg Val Gly Val Thr Glu
        915                 920                 925

Leu Glu Ala Arg Ser Gly Thr Leu Pro Pro Ala Ser Gln Arg Trp Asp
    930                 935                 940

Arg Ile Leu Gln Ala Ser Gly Met Lys Arg Ala Lys Pro Ser Pro Thr
945                 950                 955                 960

Ser Thr Gln Thr Pro Asp Gln Ala Ser Leu His Ala Phe Ala Asp Ser
                965                 970                 975

Leu Glu Arg Asp Leu Asp Ala Pro Ser Pro Met His Glu Gly Asp Gln
            980                 985                 990

Thr Arg Ala Ser Ala Ser Pro Lys Lys Lys Arg Lys Val Glu Ala Ser
        995                 1000                1005

Gly Ser Gly Arg Ala Asp Ala Leu Asp Asp Phe Asp Leu Asp Met
    1010                1015                1020

Leu Gly Ser Asp Ala Leu Asp Asp Phe Asp Leu Asp Met Leu Gly
    1025                1030                1035

Ser Asp Ala Leu Asp Asp Phe Asp Leu Asp Met Leu Gly Ser Asp
    1040                1045                1050

Ala Leu Asp Asp Phe Asp Leu Asp Met Leu
    1055                1060

<210> SEQ ID NO 83
<211> LENGTH: 18
<212> TYPE: DNA
<213> ORGANISM: Zea mays

<400> SEQUENCE: 83
tcctaatata tatatcat                                                  18

<210> SEQ ID NO 84
<211> LENGTH: 989
<212> TYPE: PRT
<213> ORGANISM: Artificial sequence
<220> FEATURE:
<223> OTHER INFORMATION: synthetic

<400> SEQUENCE: 84

Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
        35                  40                  45

Thr Glu Ala Ala Thr Gly Glu Trp Asp Glu Val Gln Ser Gly Leu Arg
    50                  55                  60

Ala Ala Asp Ala Pro Pro Thr Met Arg Val Ala Val Thr Ala Ala
65                  70                  75                  80

Arg Pro Pro Arg Ala Lys Pro Ala Pro Arg Arg Arg Ala Ala Gln Pro
                85                  90                  95

Ser Asp Ala Ser Pro Ala Ala Gln Val Asp Leu Arg Thr Leu Gly Tyr
            100                 105                 110

Ser Gln Gln Gln Gln Glu Lys Ile Lys Pro Lys Val Arg Ser Thr Val
        115                 120                 125

Ala Gln His His Glu Ala Leu Val Gly His Gly Phe Thr His Ala His
    130                 135                 140
```

```
Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
            180                 185                 190

Leu Leu Thr Val Ala Gly Glu Leu Arg Gly Pro Pro Leu Gln Leu Asp
        195                 200                 205

Thr Gly Gln Leu Leu Lys Ile Ala Lys Arg Gly Gly Val Thr Ala Val
210                 215                 220

Glu Ala Val His Ala Trp Arg Asn Ala Leu Thr Gly Ala Pro Leu Asn
225                 230                 235                 240

Leu Thr Glu Thr Leu Thr Pro Glu Gln Val Ala Ile Ala Ser Asn
                245                 250                 255

His Gly Gly Lys Gln Ala Leu Glu Thr Val Gln Arg Leu Leu Pro Val
            260                 265                 270

Leu Cys Gln Ala His Gly Leu Thr Pro Glu Gln Val Ala Ile Ala
        275                 280                 285

Ser Asn Gly Gly Gly Lys Gln Ala Leu Glu Thr Val Gln Arg Leu Leu
290                 295                 300

Pro Val Leu Cys Gln Ala His Gly Leu Thr Pro Glu Gln Val Val Ala
305                 310                 315                 320

Ile Ala Ser Asn Ile Gly Gly Lys Gln Ala Leu Glu Thr Val Gln Arg
                325                 330                 335

Leu Leu Pro Val Leu Cys Gln Ala His Gly Leu Thr Pro Glu Gln Val
            340                 345                 350

Val Ala Ile Ala Ser His Asp Gly Gly Lys Gln Ala Leu Glu Thr Val
        355                 360                 365

Gln Arg Leu Leu Pro Val Leu Cys Gln Ala His Gly Leu Thr Pro Glu
370                 375                 380

Gln Val Val Ala Ile Ala Ser His Asp Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Glu Gln Val Val Ala Ile Ala Ser Asn Ile Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser Asn His Gly Gly Lys
450                 455                 460

Gln Ala Leu Glu Thr Val Gln Arg Leu Leu Pro Val Leu Cys Gln Ala
465                 470                 475                 480

His Gly Leu Thr Pro Glu Gln Val Val Ala Ile Ala Ser Asn Gly Gly
                485                 490                 495

Gly Lys Gln Ala Leu Glu Thr Val Gln Arg Leu Leu Pro Val Leu Cys
            500                 505                 510

Gln Ala His Gly Leu Thr Pro Glu Gln Val Val Ala Ile Ala Ser Asn
        515                 520                 525

Gly Gly Gly Lys Gln Ala Leu Glu Thr Val Gln Arg Leu Leu Pro Val
530                 535                 540

Leu Cys Gln Ala His Gly Leu Thr Pro Glu Gln Val Val Ala Ile Ala
545                 550                 555                 560
```

```
Ser Asn His Gly Gly Lys Gln Ala Leu Glu Thr Val Gln Arg Leu Leu
                565                 570                 575
Pro Val Leu Cys Gln Ala His Gly Leu Thr Pro Glu Gln Val Val Ala
            580                 585                 590
Ile Ala Ser Asn Gly Gly Lys Gln Ala Leu Glu Thr Val Gln Arg
        595                 600                 605
Leu Leu Pro Val Leu Cys Gln Ala His Gly Leu Thr Pro Glu Gln Val
    610                 615                 620
Val Ala Ile Ala Ser Asn Ile Gly Gly Lys Gln Ala Leu Glu Thr Val
625                 630                 635                 640
Gln Arg Leu Leu Pro Val Leu Cys Gln Ala His Gly Leu Thr Pro Glu
                645                 650                 655
Gln Val Val Ala Ile Ala Ser Asn Gly Gly Lys Gln Ala Leu Glu
            660                 665                 670
Thr Val Gln Arg Leu Leu Pro Val Leu Cys Gln Ala His Gly Leu Thr
            675                 680                 685
Pro Glu Gln Val Val Ala Ile Ala Ser Asn Ile Gly Gly Lys Gln Ala
        690                 695                 700
Leu Glu Thr Val Gln Arg Leu Leu Pro Val Leu Cys Gln Ala His Gly
705                 710                 715                 720
Leu Thr Pro Glu Gln Val Val Ala Ile Ala Ser Asn Ile Gly Gly Lys
                725                 730                 735
Gln Ala Leu Glu Thr Val Gln Arg Leu Leu Pro Val Leu Cys Gln Ala
            740                 745                 750
His Gly Leu Thr Pro Glu Gln Val Val Ala Ile Ala Ser Asn Ile Gly
            755                 760                 765
Gly Lys Gln Ala Leu Glu Thr Val Gln Arg Leu Leu Pro Val Leu Cys
770                 775                 780
Gln Ala His Gly Ala Ser Gln Leu Thr Pro Glu Gln Val Val Ala Ile
785                 790                 795                 800
Ala Ser Asn Gly Gly Arg Pro Ala Leu Glu Ser Ile Val Ala Gln
            805                 810                 815
Leu Ser Arg Pro Asp Pro Ala Leu Ala Ala Leu Thr Asn Asp His Leu
            820                 825                 830
Val Ala Leu Ala Cys Leu Gly Gly Arg Pro Ala Leu Asp Ala Val Lys
            835                 840                 845
Lys Gly Leu Pro His Ala Pro Ala Leu Ile Lys Arg Thr Asn Arg Arg
            850                 855                 860
Ile Pro Glu Arg Thr Ser His Arg Val Ala Asp His Ala Gln Val Val
865                 870                 875                 880
Arg Val Leu Gly Phe Phe Gln Cys His Ser His Pro Ala Gln Ala Phe
                885                 890                 895
Asp Asp Ala Met Thr Gln Phe Gly Met Ser Arg His Gly Leu Leu Gln
            900                 905                 910
Leu Phe Arg Arg Val Gly Val Thr Glu Leu Glu Ala Arg Ser Gly Thr
            915                 920                 925
Leu Pro Pro Ala Ser Gln Arg Trp Asp Arg Ile Leu Gln Ala Ser Gly
        930                 935                 940
Met Lys Arg Ala Lys Pro Ser Pro Thr Ser Thr Gln Thr Pro Asp Gln
945                 950                 955                 960
Ala Ser Leu His Ala Phe Ala Asp Ser Leu Glu Arg Asp Leu Asp Ala
                965                 970                 975
Pro Ser Pro Met His Glu Gly Asp Gln Thr Arg Ala Ser
```

```
                980             985
```

<210> SEQ ID NO 85
<211> LENGTH: 1063
<212> TYPE: PRT
<213> ORGANISM: Artificial sequence
<220> FEATURE:
<223> OTHER INFORMATION: synthetic

<400> SEQUENCE: 85

```
Met His His His His His Met Ser Arg Thr Arg Leu Pro Ser Pro
1               5                   10                  15

Pro Ala Pro Ser Pro Ala Phe Ser Ala Asp Ser Phe Ser Asp Leu Leu
            20                  25                  30

Arg Gln Phe Asp Pro Ser Leu Phe Asn Thr Ser Leu Phe Asp Ser Leu
        35                  40                  45

Pro Pro Phe Gly Ala His His Thr Glu Ala Ala Thr Gly Glu Trp Asp
    50                  55                  60

Glu Val Gln Ser Gly Leu Arg Ala Ala Asp Ala Pro Pro Pro Thr Met
65                  70                  75                  80

Arg Val Ala Val Thr Ala Ala Arg Pro Pro Arg Ala Lys Pro Ala Pro
                85                  90                  95

Arg Arg Arg Ala Ala Gln Pro Ser Asp Ala Ser Pro Ala Ala Gln Val
            100                 105                 110

Asp Leu Arg Thr Leu Gly Tyr Ser Gln Gln Gln Gln Glu Lys Ile Lys
        115                 120                 125

Pro Lys Val Arg Ser Thr Val Ala Gln His His Glu Ala Leu Val Gly
    130                 135                 140

His Gly Phe Thr His Ala His Ile Val Ala Leu Ser Gln His Pro Ala
145                 150                 155                 160

Ala Leu Gly Thr Val Ala Val Lys Tyr Gln Asp Met Ile Ala Ala Leu
                165                 170                 175

Pro Glu Ala Thr His Glu Ala Ile Val Gly Val Gly Lys Gln Trp Ser
            180                 185                 190

Gly Ala Arg Ala Leu Glu Ala Leu Leu Thr Val Ala Gly Glu Leu Arg
        195                 200                 205

Gly Pro Pro Leu Gln Leu Asp Thr Gly Gln Leu Leu Lys Ile Ala Lys
    210                 215                 220

Arg Gly Gly Val Thr Ala Val Glu Ala Val His Ala Trp Arg Asn Ala
225                 230                 235                 240

Leu Thr Gly Ala Pro Leu Asn Leu Thr Glu Thr Leu Thr Pro Glu Gln
                245                 250                 255

Val Val Ala Ile Ala Ser Asn His Gly Gly Lys Gln Ala Leu Glu Thr
            260                 265                 270

Val Gln Arg Leu Leu Pro Val Leu Cys Gln Ala His Gly Leu Thr Pro
        275                 280                 285

Glu Gln Val Val Ala Ile Ala Ser Asn Gly Gly Gly Lys Gln Ala Leu
    290                 295                 300

Glu Thr Val Gln Arg Leu Leu Pro Val Leu Cys Gln Ala His Gly Leu
305                 310                 315                 320

Thr Pro Glu Gln Val Val Ala Ile Ala Ser Asn Ile Gly Gly Lys Gln
                325                 330                 335

Ala Leu Glu Thr Val Gln Arg Leu Leu Pro Val Leu Cys Gln Ala His
            340                 345                 350

Gly Leu Thr Pro Glu Gln Val Val Ala Ile Ala Ser His Asp Gly Gly
```

|  |  |  |  |  | 355 |  |  |  |  | 360 |  |  |  |  | 365 |
|---|---|---|---|---|---|---|---|---|---|---|---|---|---|---|---|

Lys Gln Ala Leu Glu Thr Val Gln Arg Leu Leu Pro Val Leu Cys Gln
370                     375                 380

Ala His Gly Leu Thr Pro Glu Gln Val Val Ala Ile Ala Ser His Asp
385                 390                 395                 400

Gly Gly Lys Gln Ala Leu Glu Thr Val Gln Arg Leu Leu Pro Val Leu
            405                 410                 415

Cys Gln Ala His Gly Leu Thr Pro Glu Gln Val Val Ala Ile Ala Ser
        420                 425                 430

Asn Ile Gly Gly Lys Gln Ala Leu Glu Thr Val Gln Arg Leu Leu Pro
            435                 440                 445

Val Leu Cys Gln Ala His Gly Leu Thr Pro Glu Gln Val Val Ala Ile
    450                 455                 460

Ala Ser Asn His Gly Gly Lys Gln Ala Leu Glu Thr Val Gln Arg Leu
465                 470                 475                 480

Leu Pro Val Leu Cys Gln Ala His Gly Leu Thr Pro Glu Gln Val Val
                485                 490                 495

Ala Ile Ala Ser Asn Gly Gly Gly Lys Gln Ala Leu Glu Thr Val Gln
            500                 505                 510

Arg Leu Leu Pro Val Leu Cys Gln Ala His Gly Leu Thr Pro Glu Gln
        515                 520                 525

Val Val Ala Ile Ala Ser Asn Gly Gly Gly Lys Gln Ala Leu Glu Thr
    530                 535                 540

Val Gln Arg Leu Leu Pro Val Leu Cys Gln Ala His Gly Leu Thr Pro
545                 550                 555                 560

Glu Gln Val Val Ala Ile Ala Ser Asn His Gly Gly Lys Gln Ala Leu
                565                 570                 575

Glu Thr Val Gln Arg Leu Leu Pro Val Leu Cys Gln Ala His Gly Leu
            580                 585                 590

Thr Pro Glu Gln Val Val Ala Ile Ala Ser Asn Gly Gly Gly Lys Gln
        595                 600                 605

Ala Leu Glu Thr Val Gln Arg Leu Leu Pro Val Leu Cys Gln Ala His
    610                 615                 620

Gly Leu Thr Pro Glu Gln Val Val Ala Ile Ala Ser Asn Ile Gly Gly
625                 630                 635                 640

Lys Gln Ala Leu Glu Thr Val Gln Arg Leu Leu Pro Val Leu Cys Gln
                645                 650                 655

Ala His Gly Leu Thr Pro Glu Gln Val Val Ala Ile Ala Ser Asn Gly
            660                 665                 670

Gly Gly Lys Gln Ala Leu Glu Thr Val Gln Arg Leu Leu Pro Val Leu
        675                 680                 685

Cys Gln Ala His Gly Leu Thr Pro Glu Gln Val Val Ala Ile Ala Ser
    690                 695                 700

Asn Ile Gly Gly Lys Gln Ala Leu Glu Thr Val Gln Arg Leu Leu Pro
705                 710                 715                 720

Val Leu Cys Gln Ala His Gly Leu Thr Pro Glu Gln Val Val Ala Ile
                725                 730                 735

Ala Ser Asn Ile Gly Gly Lys Gln Ala Leu Glu Thr Val Gln Arg Leu
            740                 745                 750

Leu Pro Val Leu Cys Gln Ala His Gly Leu Thr Pro Glu Gln Val Val
        755                 760                 765

Ala Ile Ala Ser Asn Ile Gly Gly Lys Gln Ala Leu Glu Thr Val Gln
    770                 775                 780

-continued

Arg Leu Leu Pro Val Leu Cys Gln Ala His Gly Ala Ser Gln Leu Thr
785                 790                 795                 800

Pro Glu Gln Val Val Ala Ile Ala Ser Asn Gly Gly Arg Pro Ala
            805                 810                 815

Leu Glu Ser Ile Val Ala Gln Leu Ser Arg Pro Asp Pro Ala Leu Ala
            820                 825                 830

Ala Leu Thr Asn Asp His Leu Val Ala Leu Ala Cys Leu Gly Gly Arg
            835                 840                 845

Pro Ala Leu Asp Ala Val Lys Lys Gly Leu Pro His Ala Pro Ala Leu
850                 855                 860

Ile Lys Arg Thr Asn Arg Arg Ile Pro Glu Arg Thr Ser His Arg Val
865                 870                 875                 880

Ala Asp His Ala Gln Val Val Arg Val Leu Gly Phe Phe Gln Cys His
            885                 890                 895

Ser His Pro Ala Gln Ala Phe Asp Asp Ala Met Thr Gln Phe Gly Met
            900                 905                 910

Ser Arg His Gly Leu Leu Gln Leu Phe Arg Arg Val Gly Val Thr Glu
            915                 920                 925

Leu Glu Ala Arg Ser Gly Thr Leu Pro Pro Ala Ser Gln Arg Trp Asp
930                 935                 940

Arg Ile Leu Gln Ala Ser Gly Met Lys Arg Ala Lys Pro Ser Pro Thr
945                 950                 955                 960

Ser Thr Gln Thr Pro Asp Gln Ala Ser Leu His Ala Phe Ala Asp Ser
            965                 970                 975

Leu Glu Arg Asp Leu Asp Ala Pro Ser Pro Met His Glu Gly Asp Gln
            980                 985                 990

Thr Arg Ala Ser Ala Ser Pro Lys Lys Lys Arg Lys Val Glu Ala Ser
            995                 1000                1005

Gly Ser Gly Arg Ala Asp Ala Leu Asp Asp Phe Asp Leu Asp Met
        1010                1015                1020

Leu Gly Ser Asp Ala Leu Asp Asp Phe Asp Leu Asp Met Leu Gly
        1025                1030                1035

Ser Asp Ala Leu Asp Asp Phe Asp Leu Asp Met Leu Gly Ser Asp
        1040                1045                1050

Ala Leu Asp Asp Phe Asp Leu Asp Met Leu
        1055                1060

<210> SEQ ID NO 86
<211> LENGTH: 18
<212> TYPE: DNA
<213> ORGANISM: Zea mays

<400> SEQUENCE: 86
tgtaccagtt gtataaat                                                    18

<210> SEQ ID NO 87
<211> LENGTH: 989
<212> TYPE: PRT
<213> ORGANISM: Artificial sequence
<220> FEATURE:
<223> OTHER INFORMATION: synthetic

<400> SEQUENCE: 87

Met Ser Arg Thr Arg Leu Pro Ser Pro Ala Pro Ser Pro Ala Phe
1               5                   10                  15

Ser Ala Asp Ser Phe Ser Asp Leu Leu Arg Gln Phe Asp Pro Ser Leu

```
                 20                  25                  30
Phe Asn Thr Ser Leu Phe Asp Ser Leu Pro Pro Phe Gly Ala His His
             35                  40                  45
Thr Glu Ala Ala Thr Gly Glu Trp Asp Glu Val Gln Ser Gly Leu Arg
         50                  55                  60
Ala Ala Asp Ala Pro Pro Thr Met Arg Val Ala Val Thr Ala Ala
 65                  70                  75                  80
Arg Pro Pro Arg Ala Lys Pro Ala Pro Arg Arg Ala Ala Gln Pro
                 85                  90                  95
Ser Asp Ala Ser Pro Ala Ala Gln Val Asp Leu Arg Thr Leu Gly Tyr
                100                 105                 110
Ser Gln Gln Gln Glu Lys Ile Lys Pro Lys Val Arg Ser Thr Val
             115                 120                 125
Ala Gln His His Glu Ala Leu Val Gly His Gly Phe Thr His Ala His
             130                 135                 140
Ile Val Ala Leu Ser Gln His Pro Ala Ala Leu Gly Thr Val Ala Val
145                 150                 155                 160
Lys Tyr Gln Asp Met Ile Ala Ala Leu Pro Glu Ala Thr His Glu Ala
                 165                 170                 175
Ile Val Gly Val Gly Lys Gln Trp Ser Gly Ala Arg Ala Leu Glu Ala
             180                 185                 190
Leu Leu Thr Val Ala Gly Glu Leu Arg Gly Pro Pro Leu Gln Leu Asp
             195                 200                 205
Thr Gly Gln Leu Leu Lys Ile Ala Lys Arg Gly Gly Val Thr Ala Val
         210                 215                 220
Glu Ala Val His Ala Trp Arg Asn Ala Leu Thr Gly Ala Pro Leu Asn
225                 230                 235                 240
Leu Thr Glu Thr Leu Thr Pro Glu Gln Val Val Ala Ile Ala Ser Asn
                 245                 250                 255
His Gly Gly Lys Gln Ala Leu Glu Thr Val Gln Arg Leu Leu Pro Val
             260                 265                 270
Leu Cys Gln Ala His Gly Leu Thr Pro Glu Gln Val Val Ala Ile Ala
             275                 280                 285
Ser Asn Gly Gly Gly Lys Gln Ala Leu Glu Thr Val Gln Arg Leu Leu
             290                 295                 300
Pro Val Leu Cys Gln Ala His Gly Leu Thr Pro Glu Gln Val Val Ala
305                 310                 315                 320
Ile Ala Ser His Asp Gly Gly Lys Gln Ala Leu Glu Thr Val Gln Arg
                 325                 330                 335
Leu Leu Pro Val Leu Cys Gln Ala His Gly Leu Thr Pro Glu Gln Val
             340                 345                 350
Val Ala Ile Ala Ser His Asp Gly Gly Lys Gln Ala Leu Glu Thr Val
             355                 360                 365
Gln Arg Leu Leu Pro Val Leu Cys Gln Ala His Gly Leu Thr Pro Glu
         370                 375                 380
Gln Val Val Ala Ile Ala Ser Asn Ile Gly Gly Lys Gln Ala Leu Glu
385                 390                 395                 400
Thr Val Gln Arg Leu Leu Pro Val Leu Cys Gln Ala His Gly Leu Thr
                 405                 410                 415
Pro Glu Gln Val Val Ala Ile Ala Ser Asn Ile Gly Gly Lys Gln Ala
             420                 425                 430
Leu Glu Thr Val Gln Arg Leu Leu Pro Val Leu Cys Gln Ala His Gly
             435                 440                 445
```

```
Leu Thr Pro Glu Gln Val Val Ala Ile Ala Ser Asn Ile Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Glu Gln Val Val Ala Ile Ala Ser Asn Ile Gly
            485                 490                 495

Gly Lys Gln Ala Leu Glu Thr Val Gln Arg Leu Leu Pro Val Leu Cys
        500                 505                 510

Gln Ala His Gly Leu Thr Pro Glu Gln Val Val Ala Ile Ala Ser Asn
    515                 520                 525

Gly Gly Gly Lys Gln Ala Leu Glu Thr Val Gln Arg Leu Leu Pro Val
530                 535                 540

Leu Cys Gln Ala His Gly Leu Thr Pro Glu Gln Val Val Ala Ile Ala
545                 550                 555                 560

Ser Asn His Gly Gly Lys Gln Ala Leu Glu Thr Val Gln Arg Leu Leu
            565                 570                 575

Pro Val Leu Cys Gln Ala His Gly Leu Thr Pro Glu Gln Val Val Ala
        580                 585                 590

Ile Ala Ser Asn His Gly Gly Lys Gln Ala Leu Glu Thr Val Gln Arg
    595                 600                 605

Leu Leu Pro Val Leu Cys Gln Ala His Gly Leu Thr Pro Glu Gln Val
610                 615                 620

Val Ala Ile Ala Ser His Asp Gly Gly Lys Gln Ala Leu Glu Thr Val
625                 630                 635                 640

Gln Arg Leu Leu Pro Val Leu Cys Gln Ala His Gly Leu Thr Pro Glu
            645                 650                 655

Gln Val Val Ala Ile Ala Ser Asn Gly Gly Gly Lys Gln Ala Leu Glu
        660                 665                 670

Thr Val Gln Arg Leu Leu Pro Val Leu Cys Gln Ala His Gly Leu Thr
    675                 680                 685

Pro Glu Gln Val Val Ala Ile Ala Ser Asn Gly Gly Gly Lys Gln Ala
690                 695                 700

Leu Glu Thr Val Gln Arg Leu Leu Pro Val Leu Cys Gln Ala His Gly
705                 710                 715                 720

Leu Thr Pro Glu Gln Val Val Ala Ile Ala Ser His Asp Gly Gly Lys
            725                 730                 735

Gln Ala Leu Glu Thr Val Gln Arg Leu Leu Pro Val Leu Cys Gln Ala
        740                 745                 750

His Gly Leu Thr Pro Glu Gln Val Val Ala Ile Ala Ser His Asp Gly
    755                 760                 765

Gly Lys Gln Ala Leu Glu Thr Val Gln Arg Leu Leu Pro Val Leu Cys
770                 775                 780

Gln Ala His Gly Ala Ser Gln Leu Thr Pro Glu Gln Val Val Ala Ile
785                 790                 795                 800

Ala Ser Asn Gly Gly Gly Arg Pro Ala Leu Glu Ser Ile Val Ala Gln
            805                 810                 815

Leu Ser Arg Pro Asp Pro Ala Leu Ala Ala Leu Thr Asn Asp His Leu
        820                 825                 830

Val Ala Leu Ala Cys Leu Gly Gly Arg Pro Ala Leu Asp Ala Val Lys
    835                 840                 845

Lys Gly Leu Pro His Ala Pro Ala Leu Ile Lys Arg Thr Asn Arg Arg
850                 855                 860
```

```
Ile Pro Glu Arg Thr Ser His Arg Val Ala Asp His Ala Gln Val Val
865                 870                 875                 880

Arg Val Leu Gly Phe Phe Gln Cys His Ser His Pro Ala Gln Ala Phe
                885                 890                 895

Asp Asp Ala Met Thr Gln Phe Gly Met Ser Arg His Gly Leu Leu Gln
            900                 905                 910

Leu Phe Arg Arg Val Gly Val Thr Glu Leu Glu Ala Arg Ser Gly Thr
        915                 920                 925

Leu Pro Pro Ala Ser Gln Arg Trp Asp Arg Ile Leu Gln Ala Ser Gly
    930                 935                 940

Met Lys Arg Ala Lys Pro Ser Pro Thr Ser Thr Gln Thr Pro Asp Gln
945                 950                 955                 960

Ala Ser Leu His Ala Phe Ala Asp Ser Leu Glu Arg Asp Leu Asp Ala
                965                 970                 975

Pro Ser Pro Met His Glu Gly Asp Gln Thr Arg Ala Ser
                980                 985

<210> SEQ ID NO 88
<211> LENGTH: 1063
<212> TYPE: PRT
<213> ORGANISM: Artificial sequence
<220> FEATURE:
<223> OTHER INFORMATION: synthetic

<400> SEQUENCE: 88

Met His His His His His Met Ser Arg Thr Arg Leu Pro Ser Pro
1               5                   10                  15

Pro Ala Pro Ser Pro Ala Phe Ser Ala Asp Ser Phe Ser Asp Leu Leu
                20                  25                  30

Arg Gln Phe Asp Pro Ser Leu Phe Asn Thr Ser Leu Phe Asp Ser Leu
            35                  40                  45

Pro Pro Phe Gly Ala His His Thr Glu Ala Ala Thr Gly Glu Trp Asp
        50                  55                  60

Glu Val Gln Ser Gly Leu Arg Ala Ala Asp Ala Pro Pro Pro Thr Met
65                  70                  75                  80

Arg Val Ala Val Thr Ala Ala Arg Pro Pro Arg Ala Lys Pro Ala Pro
                85                  90                  95

Arg Arg Arg Ala Ala Gln Pro Ser Asp Ala Ser Pro Ala Ala Gln Val
                100                 105                 110

Asp Leu Arg Thr Leu Gly Tyr Ser Gln Gln Gln Gln Glu Lys Ile Lys
            115                 120                 125

Pro Lys Val Arg Ser Thr Val Ala Gln His His Glu Ala Leu Val Gly
        130                 135                 140

His Gly Phe Thr His Ala His Ile Val Ala Leu Ser Gln His Pro Ala
145                 150                 155                 160

Ala Leu Gly Thr Val Ala Val Lys Tyr Gln Asp Met Ile Ala Ala Leu
                165                 170                 175

Pro Glu Ala Thr His Glu Ala Ile Val Gly Val Gly Lys Gln Trp Ser
            180                 185                 190

Gly Ala Arg Ala Leu Glu Ala Leu Leu Thr Val Ala Gly Glu Leu Arg
        195                 200                 205

Gly Pro Pro Leu Gln Leu Asp Thr Gly Gln Leu Leu Lys Ile Ala Lys
    210                 215                 220

Arg Gly Gly Val Thr Ala Val Glu Ala Val His Ala Trp Arg Asn Ala
225                 230                 235                 240
```

```
Leu Thr Gly Ala Pro Leu Asn Leu Thr Glu Thr Leu Thr Pro Glu Gln
                245                 250                 255

Val Val Ala Ile Ala Ser Asn His Gly Gly Lys Gln Ala Leu Glu Thr
            260                 265                 270

Val Gln Arg Leu Leu Pro Val Leu Cys Gln Ala His Gly Leu Thr Pro
        275                 280                 285

Glu Gln Val Val Ala Ile Ala Ser Asn Gly Gly Lys Gln Ala Leu
    290                 295                 300

Glu Thr Val Gln Arg Leu Leu Pro Val Leu Cys Gln Ala His Gly Leu
305                 310                 315                 320

Thr Pro Glu Gln Val Val Ala Ile Ala Ser His Asp Gly Gly Lys Gln
                325                 330                 335

Ala Leu Glu Thr Val Gln Arg Leu Leu Pro Val Leu Cys Gln Ala His
            340                 345                 350

Gly Leu Thr Pro Glu Gln Val Val Ala Ile Ala Ser His Asp Gly Gly
        355                 360                 365

Lys Gln Ala Leu Glu Thr Val Gln Arg Leu Leu Pro Val Leu Cys Gln
    370                 375                 380

Ala His Gly Leu Thr Pro Glu Gln Val Val Ala Ile Ala Ser Asn Ile
385                 390                 395                 400

Gly Gly Lys Gln Ala Leu Glu Thr Val Gln Arg Leu Leu Pro Val Leu
                405                 410                 415

Cys Gln Ala His Gly Leu Thr Pro Glu Gln Val Val Ala Ile Ala Ser
            420                 425                 430

Asn Ile Gly Gly Lys Gln Ala Leu Glu Thr Val Gln Arg Leu Leu Pro
        435                 440                 445

Val Leu Cys Gln Ala His Gly Leu Thr Pro Glu Gln Val Val Ala Ile
    450                 455                 460

Ala Ser Asn Ile Gly Gly Lys Gln Ala Leu Glu Thr Val Gln Arg Leu
465                 470                 475                 480

Leu Pro Val Leu Cys Gln Ala His Gly Leu Thr Pro Glu Gln Val Val
                485                 490                 495

Ala Ile Ala Ser Asn Ile Gly Gly Lys Gln Ala Leu Glu Thr Val Gln
            500                 505                 510

Arg Leu Leu Pro Val Leu Cys Gln Ala His Gly Leu Thr Pro Glu Gln
        515                 520                 525

Val Val Ala Ile Ala Ser Asn Gly Gly Lys Gln Ala Leu Glu Thr
    530                 535                 540

Val Gln Arg Leu Leu Pro Val Leu Cys Gln Ala His Gly Leu Thr Pro
545                 550                 555                 560

Glu Gln Val Val Ala Ile Ala Ser Asn His Gly Gly Lys Gln Ala Leu
                565                 570                 575

Glu Thr Val Gln Arg Leu Leu Pro Val Leu Cys Gln Ala His Gly Leu
            580                 585                 590

Thr Pro Glu Gln Val Val Ala Ile Ala Ser Asn His Gly Gly Lys Gln
        595                 600                 605

Ala Leu Glu Thr Val Gln Arg Leu Leu Pro Val Leu Cys Gln Ala His
    610                 615                 620

Gly Leu Thr Pro Glu Gln Val Val Ala Ile Ala Ser His Asp Gly Gly
625                 630                 635                 640

Lys Gln Ala Leu Glu Thr Val Gln Arg Leu Leu Pro Val Leu Cys Gln
                645                 650                 655

Ala His Gly Leu Thr Pro Glu Gln Val Val Ala Ile Ala Ser Asn Gly
```

```
                660                 665                 670
Gly Gly Lys Gln Ala Leu Glu Thr Val Gln Arg Leu Leu Pro Val Leu
            675                 680                 685
Cys Gln Ala His Gly Leu Thr Pro Glu Gln Val Val Ala Ile Ala Ser
690                 695                 700
Asn Gly Gly Gly Lys Gln Ala Leu Glu Thr Val Gln Arg Leu Leu Pro
705                 710                 715                 720
Val Leu Cys Gln Ala His Gly Leu Thr Pro Glu Gln Val Val Ala Ile
            725                 730                 735
Ala Ser His Asp Gly Gly Lys Gln Ala Leu Glu Thr Val Gln Arg Leu
            740                 745                 750
Leu Pro Val Leu Cys Gln Ala His Gly Leu Thr Pro Glu Gln Val Val
            755                 760                 765
Ala Ile Ala Ser His Asp Gly Gly Lys Gln Ala Leu Glu Thr Val Gln
            770                 775                 780
Arg Leu Leu Pro Val Leu Cys Gln Ala His Gly Ala Ser Gln Leu Thr
785                 790                 795                 800
Pro Glu Gln Val Val Ala Ile Ala Ser Asn Gly Gly Gly Arg Pro Ala
                805                 810                 815
Leu Glu Ser Ile Val Ala Gln Leu Ser Arg Pro Asp Pro Ala Leu Ala
                820                 825                 830
Ala Leu Thr Asn Asp His Leu Val Ala Leu Ala Cys Leu Gly Gly Arg
            835                 840                 845
Pro Ala Leu Asp Ala Val Lys Lys Gly Leu Pro His Ala Pro Ala Leu
            850                 855                 860
Ile Lys Arg Thr Asn Arg Arg Ile Pro Glu Arg Thr Ser His Arg Val
865                 870                 875                 880
Ala Asp His Ala Gln Val Val Arg Val Leu Gly Phe Phe Gln Cys His
                885                 890                 895
Ser His Pro Ala Gln Ala Phe Asp Asp Ala Met Thr Gln Phe Gly Met
                900                 905                 910
Ser Arg His Gly Leu Leu Gln Leu Phe Arg Arg Val Gly Val Thr Glu
            915                 920                 925
Leu Glu Ala Arg Ser Gly Thr Leu Pro Pro Ala Ser Gln Arg Trp Asp
            930                 935                 940
Arg Ile Leu Gln Ala Ser Gly Met Lys Arg Ala Lys Pro Ser Pro Thr
945                 950                 955                 960
Ser Thr Gln Thr Pro Asp Gln Ala Ser Leu His Ala Phe Ala Asp Ser
                965                 970                 975
Leu Glu Arg Asp Leu Asp Ala Pro Ser Pro Met His Glu Gly Asp Gln
            980                 985                 990
Thr Arg Ala Ser Ala Ser Pro Lys  Lys Lys Arg Lys Val  Glu Ala Ser
            995                 1000                1005
Gly Ser  Gly Arg Ala Asp Ala  Leu Asp Asp Phe Asp  Leu Asp Met
        1010                1015                1020
Leu Gly  Ser Asp Ala Leu  Asp Asp Phe Asp Leu Asp  Met Leu Gly
        1025                1030                1035
Ser Asp  Ala Leu Asp Asp Phe  Asp Leu Asp Met Leu  Gly Ser Asp
        1040                1045                1050
Ala Leu  Asp Asp Phe Asp Leu  Asp Met Leu
        1055                1060

<210> SEQ ID NO 89
```

```
<211> LENGTH: 18
<212> TYPE: DNA
<213> ORGANISM: Zea mays

<400> SEQUENCE: 89
tgtccaaaat ggcttcct                                                   18

<210> SEQ ID NO 90
<211> LENGTH: 1446
<212> TYPE: PRT
<213> ORGANISM: Artificial sequence
<220> FEATURE:
<223> OTHER INFORMATION: synthetic

<400> SEQUENCE: 90
```

| | | | | | | | | | | | | | | | |
|---|---|---|---|---|---|---|---|---|---|---|---|---|---|---|---|
| Met | His | His | His | His | His | Met | Asp | Lys | Lys | Tyr | Ser | Ile | Gly | Leu | |
| 1 | | | | 5 | | | | | 10 | | | | | 15 | |
| Ala | Ile | Gly | Thr | Asn | Ser | Val | Gly | Trp | Ala | Val | Ile | Thr | Asp | Glu | Tyr |
| | | | 20 | | | | | 25 | | | | | 30 | | |
| Lys | Val | Pro | Ser | Lys | Lys | Phe | Lys | Val | Leu | Gly | Asn | Thr | Asp | Arg | His |
| | | | 35 | | | | 40 | | | | | 45 | | | |
| Ser | Ile | Lys | Lys | Asn | Leu | Ile | Gly | Ala | Leu | Leu | Phe | Asp | Ser | Gly | Glu |
| | 50 | | | | | 55 | | | | | 60 | | | | |
| Thr | Ala | Glu | Ala | Thr | Arg | Leu | Lys | Arg | Thr | Ala | Arg | Arg | Arg | Tyr | Thr |
| 65 | | | | | 70 | | | | | 75 | | | | | 80 |
| Arg | Arg | Lys | Asn | Arg | Ile | Cys | Tyr | Leu | Gln | Glu | Ile | Phe | Ser | Asn | Glu |
| | | | | 85 | | | | | 90 | | | | | 95 | |
| Met | Ala | Lys | Val | Asp | Asp | Ser | Phe | Phe | His | Arg | Leu | Glu | Glu | Ser | Phe |
| | | | 100 | | | | | 105 | | | | | 110 | | |
| Leu | Val | Glu | Glu | Asp | Lys | Lys | His | Glu | Arg | His | Pro | Ile | Phe | Gly | Asn |
| | | | 115 | | | | 120 | | | | | 125 | | | |
| Ile | Val | Asp | Glu | Val | Ala | Tyr | His | Glu | Lys | Tyr | Pro | Thr | Ile | Tyr | His |
| | 130 | | | | | 135 | | | | | 140 | | | | |
| Leu | Arg | Lys | Lys | Leu | Val | Asp | Ser | Thr | Asp | Lys | Ala | Asp | Leu | Arg | Leu |
| 145 | | | | | 150 | | | | | 155 | | | | | 160 |
| Ile | Tyr | Leu | Ala | Leu | Ala | His | Met | Ile | Lys | Phe | Arg | Gly | His | Phe | Leu |
| | | | | 165 | | | | | 170 | | | | | 175 | |
| Ile | Glu | Gly | Asp | Leu | Asn | Pro | Asp | Asn | Ser | Asp | Val | Asp | Lys | Leu | Phe |
| | | | 180 | | | | | 185 | | | | | 190 | | |
| Ile | Gln | Leu | Val | Gln | Thr | Tyr | Asn | Gln | Leu | Phe | Glu | Glu | Asn | Pro | Ile |
| | | | 195 | | | | 200 | | | | | 205 | | | |
| Asn | Ala | Ser | Gly | Val | Asp | Ala | Lys | Ala | Ile | Leu | Ser | Ala | Arg | Leu | Ser |
| | 210 | | | | | 215 | | | | | 220 | | | | |
| Lys | Ser | Arg | Arg | Leu | Glu | Asn | Leu | Ile | Ala | Gln | Leu | Pro | Gly | Glu | Lys |
| 225 | | | | | 230 | | | | | 235 | | | | | 240 |
| Lys | Asn | Gly | Leu | Phe | Gly | Asn | Leu | Ile | Ala | Leu | Ser | Leu | Gly | Leu | Thr |
| | | | | 245 | | | | | 250 | | | | | 255 | |
| Pro | Asn | Phe | Lys | Ser | Asn | Phe | Asp | Leu | Ala | Glu | Asp | Ala | Lys | Leu | Gln |
| | | | 260 | | | | | 265 | | | | | 270 | | |
| Leu | Ser | Lys | Asp | Thr | Tyr | Asp | Asp | Asp | Leu | Asp | Asn | Leu | Leu | Ala | Gln |
| | | | 275 | | | | | 280 | | | | | 285 | | |
| Ile | Gly | Asp | Gln | Tyr | Ala | Asp | Leu | Phe | Leu | Ala | Ala | Lys | Asn | Leu | Ser |
| | | | 290 | | | | | 295 | | | | | 300 | | |
| Asp | Ala | Ile | Leu | Leu | Ser | Asp | Ile | Leu | Arg | Val | Asn | Thr | Glu | Ile | Thr |
| 305 | | | | | 310 | | | | | 315 | | | | | 320 |
| Lys | Ala | Pro | Leu | Ser | Ala | Ser | Met | Ile | Lys | Arg | Tyr | Asp | Glu | His | His |

```
                    325                 330                 335
Gln Asp Leu Thr Leu Leu Lys Ala Leu Val Arg Gln Leu Pro Glu
                340                 345                 350
Lys Tyr Lys Glu Ile Phe Phe Asp Gln Ser Lys Asn Gly Tyr Ala Gly
                355                 360                 365
Tyr Ile Asp Gly Gly Ala Ser Gln Glu Glu Phe Tyr Lys Phe Ile Lys
                370                 375                 380
Pro Ile Leu Glu Lys Met Asp Gly Thr Glu Glu Leu Leu Val Lys Leu
385                 390                 395                 400
Asn Arg Glu Asp Leu Leu Arg Lys Gln Arg Thr Phe Asp Asn Gly Ser
                405                 410                 415
Ile Pro His Gln Ile His Leu Gly Glu Leu His Ala Ile Leu Arg Arg
                420                 425                 430
Gln Glu Asp Phe Tyr Pro Phe Leu Lys Asp Asn Arg Glu Lys Ile Glu
                435                 440                 445
Lys Ile Leu Thr Phe Arg Ile Pro Tyr Tyr Val Gly Pro Leu Ala Arg
                450                 455                 460
Gly Asn Ser Arg Phe Ala Trp Met Thr Arg Lys Ser Glu Glu Thr Ile
465                 470                 475                 480
Thr Pro Trp Asn Phe Glu Glu Val Val Asp Lys Gly Ala Ser Ala Gln
                485                 490                 495
Ser Phe Ile Glu Arg Met Thr Asn Phe Asp Lys Asn Leu Pro Asn Glu
                500                 505                 510
Lys Val Leu Pro Lys His Ser Leu Leu Tyr Glu Tyr Phe Thr Val Tyr
                515                 520                 525
Asn Glu Leu Thr Lys Val Lys Tyr Val Thr Glu Gly Met Arg Lys Pro
530                 535                 540
Ala Phe Leu Ser Gly Glu Gln Lys Lys Ala Ile Val Asp Leu Leu Phe
545                 550                 555                 560
Lys Thr Asn Arg Lys Val Thr Val Lys Gln Leu Lys Glu Asp Tyr Phe
                565                 570                 575
Lys Lys Ile Glu Cys Phe Asp Ser Val Glu Ile Ser Gly Val Glu Asp
                580                 585                 590
Arg Phe Asn Ala Ser Leu Gly Thr Tyr His Asp Leu Leu Lys Ile Ile
                595                 600                 605
Lys Asp Lys Asp Phe Leu Asp Asn Glu Glu Asn Glu Asp Ile Leu Glu
                610                 615                 620
Asp Ile Val Leu Thr Leu Thr Leu Phe Glu Asp Arg Glu Met Ile Glu
625                 630                 635                 640
Glu Arg Leu Lys Thr Tyr Ala His Leu Phe Asp Asp Lys Val Met Lys
                645                 650                 655
Gln Leu Lys Arg Arg Arg Tyr Thr Gly Trp Gly Arg Leu Ser Arg Lys
                660                 665                 670
Leu Ile Asn Gly Ile Arg Asp Lys Gln Ser Gly Lys Thr Ile Leu Asp
                675                 680                 685
Phe Leu Lys Ser Asp Gly Phe Ala Asn Arg Asn Phe Met Gln Leu Ile
                690                 695                 700
His Asp Asp Ser Leu Thr Phe Lys Glu Asp Ile Gln Lys Ala Gln Val
705                 710                 715                 720
Ser Gly Gln Gly Asp Ser Leu His Glu His Ile Ala Asn Leu Ala Gly
                725                 730                 735
Ser Pro Ala Ile Lys Lys Gly Ile Leu Gln Thr Val Lys Val Val Asp
                740                 745                 750
```

```
Glu Leu Val Lys Val Met Gly Arg His Lys Pro Glu Asn Ile Val Ile
        755                 760                 765

Glu Met Ala Arg Glu Asn Gln Thr Thr Gln Lys Gly Gln Lys Asn Ser
        770                 775                 780

Arg Glu Arg Met Lys Arg Ile Glu Glu Gly Ile Lys Glu Leu Gly Ser
785                 790                 795                 800

Gln Ile Leu Lys Glu His Pro Val Glu Asn Thr Gln Leu Gln Asn Glu
        805                 810                 815

Lys Leu Tyr Leu Tyr Tyr Leu Gln Asn Gly Arg Asp Met Tyr Val Asp
        820                 825                 830

Gln Glu Leu Asp Ile Asn Arg Leu Ser Asp Tyr Asp Val Asp Ala Ile
        835                 840                 845

Val Pro Gln Ser Phe Leu Lys Asp Asp Ser Ile Asp Asn Lys Val Leu
        850                 855                 860

Thr Arg Ser Asp Lys Asn Arg Gly Lys Ser Asp Asn Val Pro Ser Glu
865                 870                 875                 880

Glu Val Val Lys Lys Met Lys Asn Tyr Trp Arg Gln Leu Leu Asn Ala
                885                 890                 895

Lys Leu Ile Thr Gln Arg Lys Phe Asp Asn Leu Thr Lys Ala Glu Arg
        900                 905                 910

Gly Gly Leu Ser Glu Leu Asp Lys Ala Gly Phe Ile Lys Arg Gln Leu
        915                 920                 925

Val Glu Thr Arg Gln Ile Thr Lys His Val Ala Gln Ile Leu Asp Ser
        930                 935                 940

Arg Met Asn Thr Lys Tyr Asp Glu Asn Asp Lys Leu Ile Arg Glu Val
945                 950                 955                 960

Lys Val Ile Thr Leu Lys Ser Lys Leu Val Ser Asp Phe Arg Lys Asp
                965                 970                 975

Phe Gln Phe Tyr Lys Val Arg Glu Ile Asn Asn Tyr His His Ala His
        980                 985                 990

Asp Ala Tyr Leu Asn Ala Val Val Gly Thr Ala Leu Ile Lys Lys Tyr
        995                 1000                1005

Pro Lys Leu Glu Ser Glu Phe Val Tyr Gly Asp Tyr Lys Val Tyr
        1010                1015                1020

Asp Val Arg Lys Met Ile Ala Lys Ser Glu Gln Glu Ile Gly Lys
        1025                1030                1035

Ala Thr Ala Lys Tyr Phe Phe Tyr Ser Asn Ile Met Asn Phe Phe
        1040                1045                1050

Lys Thr Glu Ile Thr Leu Ala Asn Gly Glu Ile Arg Lys Arg Pro
        1055                1060                1065

Leu Ile Glu Thr Asn Gly Glu Thr Gly Glu Ile Val Trp Asp Lys
        1070                1075                1080

Gly Arg Asp Phe Ala Thr Val Arg Lys Val Leu Ser Met Pro Gln
        1085                1090                1095

Val Asn Ile Val Lys Lys Thr Glu Val Gln Thr Gly Gly Phe Ser
        1100                1105                1110

Lys Glu Ser Ile Leu Pro Lys Arg Asn Ser Asp Lys Leu Ile Ala
        1115                1120                1125

Arg Lys Lys Asp Trp Asp Pro Lys Lys Tyr Gly Gly Phe Asp Ser
        1130                1135                1140

Pro Thr Val Ala Tyr Ser Val Leu Val Val Ala Lys Val Glu Lys
        1145                1150                1155
```

Gly Lys Ser Lys Lys Leu Lys Ser Val Lys Glu Leu Leu Gly Ile
            1160                1165                1170

Thr Ile Met Glu Arg Ser Ser Phe Glu Lys Asn Pro Ile Asp Phe
    1175                1180                1185

Leu Glu Ala Lys Gly Tyr Lys Glu Val Lys Lys Asp Leu Ile Ile
        1190                1195                1200

Lys Leu Pro Lys Tyr Ser Leu Phe Glu Leu Glu Asn Gly Arg Lys
    1205                1210                1215

Arg Met Leu Ala Ser Ala Gly Glu Leu Gln Lys Gly Asn Glu Leu
    1220                1225                1230

Ala Leu Pro Ser Lys Tyr Val Asn Phe Leu Tyr Leu Ala Ser His
    1235                1240                1245

Tyr Glu Lys Leu Lys Gly Ser Pro Glu Asp Asn Glu Gln Lys Gln
    1250                1255                1260

Leu Phe Val Glu Gln His Lys His Tyr Leu Asp Glu Ile Ile Glu
    1265                1270                1275

Gln Ile Ser Glu Phe Ser Lys Arg Val Ile Leu Ala Asp Ala Asn
    1280                1285                1290

Leu Asp Lys Val Leu Ser Ala Tyr Asn Lys His Arg Asp Lys Pro
    1295                1300                1305

Ile Arg Glu Gln Ala Glu Asn Ile Ile His Leu Phe Thr Leu Thr
    1310                1315                1320

Asn Leu Gly Ala Pro Ala Ala Phe Lys Tyr Phe Asp Thr Thr Ile
    1325                1330                1335

Asp Arg Lys Arg Tyr Thr Ser Thr Lys Glu Val Leu Asp Ala Thr
    1340                1345                1350

Leu Ile His Gln Ser Ile Thr Gly Leu Tyr Glu Thr Arg Ile Asp
    1355                1360                1365

Leu Ser Gln Leu Gly Gly Asp Gly Ser Pro Lys Lys Lys Arg Lys
    1370                1375                1380

Val Ser Ser Ala Ala Gly Gly Gly Ser Gly Arg Ala Asp Ala
    1385                1390                1395

Leu Asp Asp Phe Asp Leu Asp Met Leu Gly Ser Asp Ala Leu Asp
    1400                1405                1410

Asp Phe Asp Leu Asp Met Leu Gly Ser Asp Ala Leu Asp Asp Phe
    1415                1420                1425

Asp Leu Asp Met Leu Gly Ser Asp Ala Leu Asp Asp Phe Asp Leu
    1430                1435                1440

Asp Met Leu
    1445

<210> SEQ ID NO 91
<211> LENGTH: 531
<212> TYPE: PRT
<213> ORGANISM: Artificial sequence
<220> FEATURE:
<223> OTHER INFORMATION: synthetic

<400> SEQUENCE: 91

Glu Ala Ser Gly Ser Gly Arg Ala Asp Ala Leu Asp Asp Phe Asp Leu
1               5                   10                  15

Asp Met Leu Gly Ser Asp Ala Leu Asp Asp Phe Asp Leu Asp Met Leu
            20                  25                  30

Gly Ser Asp Ala Leu Asp Asp Phe Asp Leu Asp Met Leu Gly Ser Asp
        35                  40                  45

```
Ala Leu Asp Asp Phe Asp Leu Asp Met Leu Ile Asn Ser Arg Ser Ser
     50                  55                  60

Gly Ser Pro Lys Lys Arg Lys Val Gly Ser Gln Tyr Leu Pro Asp
 65              70                  75                  80

Thr Asp Asp Arg His Arg Ile Glu Glu Lys Arg Lys Arg Thr Tyr Glu
                 85                  90                  95

Thr Phe Lys Ser Ile Met Lys Lys Ser Pro Phe Ser Gly Pro Thr Asp
                100                 105                 110

Pro Arg Pro Pro Arg Arg Ile Ala Val Pro Ser Arg Ser Ser Ala
             115                 120                 125

Ser Val Pro Lys Pro Ala Pro Gln Pro Tyr Pro Phe Thr Ser Ser Leu
 130                 135                 140

Ser Thr Ile Asn Tyr Asp Glu Phe Pro Thr Met Val Phe Pro Ser Gly
 145                 150                 155                 160

Gln Ile Ser Gln Ala Ser Ala Leu Ala Pro Ala Pro Pro Gln Val Leu
                 165                 170                 175

Pro Gln Ala Pro Ala Pro Ala Pro Ala Pro Ala Met Val Ser Ala Leu
             180                 185                 190

Ala Gln Ala Pro Ala Pro Val Pro Val Leu Ala Pro Gly Pro Pro Gln
             195                 200                 205

Ala Val Ala Pro Pro Ala Pro Lys Pro Thr Gln Ala Gly Glu Gly Thr
 210                 215                 220

Leu Ser Glu Ala Leu Leu Gln Leu Gln Phe Asp Asp Glu Asp Leu Gly
 225                 230                 235                 240

Ala Leu Leu Gly Asn Ser Thr Asp Pro Ala Val Phe Thr Asp Leu Ala
                 245                 250                 255

Ser Val Asp Asn Ser Glu Phe Gln Gln Leu Leu Asn Gln Gly Ile Pro
             260                 265                 270

Val Ala Pro His Thr Thr Glu Pro Met Leu Met Glu Tyr Pro Glu Ala
             275                 280                 285

Ile Thr Arg Leu Val Thr Gly Ala Gln Arg Pro Pro Asp Pro Ala Pro
 290                 295                 300

Ala Pro Leu Gly Ala Pro Gly Leu Pro Asn Gly Leu Leu Ser Gly Asp
 305                 310                 315                 320

Glu Asp Phe Ser Ser Ile Ala Asp Met Asp Phe Ser Ala Leu Leu Gly
                 325                 330                 335

Ser Gly Ser Gly Ser Arg Asp Ser Arg Glu Gly Met Phe Leu Pro Lys
             340                 345                 350

Pro Glu Ala Gly Ser Ala Ile Ser Asp Val Phe Glu Gly Arg Glu Val
             355                 360                 365

Cys Gln Pro Lys Arg Ile Arg Pro Phe His Pro Pro Gly Ser Pro Trp
 370                 375                 380

Ala Asn Arg Pro Leu Pro Ala Ser Leu Ala Pro Thr Pro Thr Gly Pro
 385                 390                 395                 400

Val His Glu Pro Val Gly Ser Leu Thr Pro Ala Pro Val Pro Gln Pro
                 405                 410                 415

Leu Asp Pro Ala Pro Ala Val Thr Pro Glu Ala Ser His Leu Leu Glu
             420                 425                 430

Asp Pro Asp Glu Glu Thr Ser Gln Ala Val Lys Ala Leu Arg Glu Met
             435                 440                 445

Ala Asp Thr Val Ile Pro Gln Lys Glu Glu Ala Ala Ile Cys Gly Gln
 450                 455                 460

Met Asp Leu Ser His Pro Pro Pro Arg Gly His Leu Asp Glu Leu Thr
```

```
                465                 470                 475                 480
Thr Thr Leu Glu Ser Met Thr Glu Asp Leu Asn Leu Asp Ser Pro Leu
                    485                 490                 495

Thr Pro Glu Leu Asn Glu Ile Leu Asp Thr Phe Leu Asn Asp Glu Cys
                500                 505                 510

Leu Leu His Ala Met His Ile Ser Thr Gly Leu Ser Ile Phe Asp Thr
                515                 520                 525

Ser Leu Phe
        530

<210> SEQ ID NO 92
<211> LENGTH: 14
<212> TYPE: PRT
<213> ORGANISM: Simian Virus 40

<400> SEQUENCE: 92

Ala Ser Pro Lys Lys Lys Arg Lys Val Glu Ala Ser Gly Ser
1               5                   10

<210> SEQ ID NO 93
<211> LENGTH: 230
<212> TYPE: PRT
<213> ORGANISM: Artificial sequence
<220> FEATURE:
<223> OTHER INFORMATION: synthetic

<400> SEQUENCE: 93

Met Gly Pro Lys Lys Arg Lys Val Gly Arg Leu Glu Pro Gly Glu
1               5                   10                  15

Lys Pro Tyr Lys Cys Pro Glu Cys Gly Lys Ser Phe Ser Arg Ser Asp
                20                  25                  30

Lys Leu Val Arg His Gln Arg Thr His Thr Gly Glu Lys Pro Tyr Lys
                35                  40                  45

Cys Pro Glu Cys Gly Lys Ser Phe Ser Gln Ser Ser Asn Leu Val Arg
            50                  55                  60

His Gln Arg Thr His Thr Gly Glu Lys Pro Tyr Lys Cys Pro Glu Cys
65                  70                  75                  80

Gly Lys Ser Phe Ser Arg Ser Asp Asp Leu Val Arg His Gln Arg Thr
                85                  90                  95

His Thr Gly Glu Lys Pro Tyr Lys Cys Pro Glu Cys Gly Lys Ser Phe
                100                 105                 110

Ser Thr Ser Gly Ser Leu Val Arg His Gln Arg Thr His Thr Gly Glu
            115                 120                 125

Lys Pro Tyr Lys Cys Pro Glu Cys Gly Lys Ser Phe Ser Arg Glu Asp
        130                 135                 140

Asn Leu His Thr His Gln Arg Thr His Thr Gly Glu Lys Pro Tyr Lys
145                 150                 155                 160

Cys Pro Glu Cys Gly Lys Ser Phe Ser Asp Pro Gly Asn Leu Val Arg
                165                 170                 175

His Gln Arg Thr His Thr Gly Ala Ala Ala Asp Ala Leu Asp Asp Phe
                180                 185                 190

Asp Leu Asp Met Leu Asp Ala Leu Asp Asp Phe Asp Leu Asp Met Leu
            195                 200                 205

Asp Ala Leu Asp Asp Phe Asp Leu Asp Met Leu Asp Ala Leu Asp Asp
        210                 215                 220

Phe Asp Leu Asp Met Leu
225                 230
```

<210> SEQ ID NO 94
<211> LENGTH: 693
<212> TYPE: DNA
<213> ORGANISM: Artificial sequence
<220> FEATURE:
<223> OTHER INFORMATION: synthetic

<400> SEQUENCE: 94

```
atgggccta agaagaagcg caaggtcgga cgccttgagc ccggcgaaaa gccatataaa    60
tgcccagagt gtggcaagag cttcagccgc agcgacaagc ttgttcgcca tcaacgcact   120
cacaccggcg agaagcctta caagtgtcca gagtgcggca agagcttcag ccagagcagc   180
aacctcgttc gccatcaaag gacccacact ggagagaaac catataagtg cccagaatgc   240
ggaaaaagct ctcccgcag cgatgatctc gtccgccacc agaggactca caccggagag   300
aagccttata agtgcccaga gtgtggcaag tccttctcca ccagcggaag cctcgttcgc   360
catcagcgca cccatactgg agaaaaacct tacaagtgcc cagagtgtgg aaaaagcttt   420
agccgcgagg acaatctcca tacccatcaa cgcacccaca ctggcgaaaa gccttacaaa   480
tgtccagagt gcggcaagtc cttttccgac cccggcaacc ttgttaggca tcaaaggact   540
cataccggag ctgccgctga cgctcttgac gattttgatc tcgacatgct cgacgctctc   600
gatgatttcg accttgacat gcttgatgcc ctcgacgatt tcgatctcga tatgcttgat   660
gctcttgacg acttcgacct tgatatgctc tga                                693
```

<210> SEQ ID NO 95
<211> LENGTH: 230
<212> TYPE: PRT
<213> ORGANISM: Artificial sequence
<220> FEATURE:
<223> OTHER INFORMATION: synthetic

<400> SEQUENCE: 95

```
Met Gly Pro Lys Lys Arg Lys Val Gly Arg Leu Glu Pro Gly Glu
1               5                   10                  15

Lys Pro Tyr Lys Cys Pro Glu Cys Gly Lys Ser Phe Ser Asp Pro Gly
                20                  25                  30

Ala Leu Val Arg His Gln Arg Thr His Thr Gly Glu Lys Pro Tyr Lys
            35                  40                  45

Cys Pro Glu Cys Gly Lys Ser Phe Ser Arg Ser Asp Asn Leu Val Arg
        50                  55                  60

His Gln Arg Thr His Thr Gly Glu Lys Pro Tyr Lys Cys Pro Glu Cys
65                  70                  75                  80

Gly Lys Ser Phe Ser Gln Ser Gly Asp Leu Arg Arg His Gln Arg Thr
                85                  90                  95

His Thr Gly Glu Lys Pro Tyr Lys Cys Pro Glu Cys Gly Lys Ser Phe
            100                 105                 110

Ser Thr Ser Gly Asn Leu Val Arg His Gln Arg Thr His Thr Gly Glu
        115                 120                 125

Lys Pro Tyr Lys Cys Pro Glu Cys Gly Lys Ser Phe Ser Arg Ser Asp
    130                 135                 140

Asn Leu Val Arg His Gln Arg Thr His Thr Gly Glu Lys Pro Tyr Lys
145                 150                 155                 160

Cys Pro Glu Cys Gly Lys Ser Phe Ser Arg Ser Asp Asn Leu Val Arg
                165                 170                 175

His Gln Arg Thr His Thr Gly Ala Ala Ala Asp Ala Leu Asp Asp Phe
```

```
            180                 185                 190
Asp Leu Asp Met Leu Asp Ala Leu Asp Asp Phe Asp Leu Asp Met Leu
            195                 200                 205

Asp Ala Leu Asp Asp Phe Asp Leu Asp Met Leu Asp Ala Leu Asp Asp
            210                 215                 220

Phe Asp Leu Asp Met Leu
225                 230
```

<210> SEQ ID NO 96
<211> LENGTH: 693
<212> TYPE: DNA
<213> ORGANISM: Artificial sequence
<220> FEATURE:
<223> OTHER INFORMATION: synthetic

<400> SEQUENCE: 96

```
atgggaccaa aaagaagcg caaggtcgga cgccttgagc ccggcgaaaa gccatataag      60
tgcccagagt gcggcaagtc cttctccgat cccggcgccc tcgttaggca tcagaggacc    120
cacactggag agaagccata caagtgtcca gagtgcggaa aaagcttcag ccgctccgac    180
aacctcgtcc gccatcagcg cacccacacc ggagagaaac catacaagtg cccagagtgc    240
ggaaagtcct tcagccagtc cggagatctt cgccgccatc aaaggactca taccggcgag    300
aagccttata atgcccaga gtgtggaaaa tccttcagca ccagcggcaa tctcgttcgc    360
caccagagga ctcacactgg cgagaagcca tataaatgtc cagaatgtgg caaaagcttt    420
tctcgctccg ataacctcgt tgccaccaa cgcaccca ctggagaaaa accttacaaa      480
tgcccagagt gtggaaagag cttctctcgc agcgacaacc ttgtccgcca ccagcgcact    540
catactggag ctgccgccga cgccctcgac gatttcgacc tcgatatgct tgacgccctc    600
gatgatttcg accttgatat gcttgatgcc ctcgatgact tcgatctcga catgctcgac    660
gcccttgacg actttgatct cgatatgctc tga                                 693
```

<210> SEQ ID NO 97
<211> LENGTH: 230
<212> TYPE: PRT
<213> ORGANISM: Artificial sequence
<220> FEATURE:
<223> OTHER INFORMATION: synthetic

<400> SEQUENCE: 97

```
Met Gly Pro Lys Lys Arg Lys Val Gly Arg Leu Glu Pro Gly Glu
1               5                   10                  15

Lys Pro Tyr Lys Cys Pro Glu Cys Gly Lys Ser Phe Ser Gln Leu Ala
                20                  25                  30

His Leu Arg Ala His Gln Arg Thr His Thr Gly Glu Lys Pro Tyr Lys
            35                  40                  45

Cys Pro Glu Cys Gly Lys Ser Phe Ser Gln Ser Gly Asp Leu Arg Arg
        50                  55                  60

His Gln Arg Thr His Thr Gly Glu Lys Pro Tyr Lys Cys Pro Glu Cys
65                  70                  75                  80

Gly Lys Ser Phe Ser Thr Thr Gly Asn Leu Thr Val His Gln Arg Thr
                85                  90                  95

His Thr Gly Glu Lys Pro Tyr Lys Cys Pro Glu Cys Gly Lys Ser Phe
            100                 105                 110

Ser Asp Cys Arg Asp Leu Ala Arg His Gln Arg Thr His Thr Gly Glu
        115                 120                 125
```

Lys Pro Tyr Lys Cys Pro Glu Cys Gly Lys Ser Phe Ser Arg Ser Asp
            130                 135                 140

Asp Leu Val Arg His Gln Arg Thr His Thr Gly Glu Lys Pro Tyr Lys
145                 150                 155                 160

Cys Pro Glu Cys Gly Lys Ser Phe Ser Gln Ser Ser Asn Leu Val Arg
            165                 170                 175

His Gln Arg Thr His Thr Gly Ala Ala Ala Asp Ala Leu Asp Asp Phe
            180                 185                 190

Asp Leu Asp Met Leu Asp Ala Leu Asp Asp Phe Asp Leu Asp Met Leu
            195                 200                 205

Asp Ala Leu Asp Asp Phe Asp Leu Asp Met Leu Asp Ala Leu Asp Asp
            210                 215                 220

Phe Asp Leu Asp Met Leu
225                 230

<210> SEQ ID NO 98
<211> LENGTH: 693
<212> TYPE: DNA
<213> ORGANISM: Artificial sequence
<220> FEATURE:
<223> OTHER INFORMATION: synthetic

<400> SEQUENCE: 98
atgggcccta aaagaagcg caaggtcgga cgccttgagc ccggcgaaaa accttacaag      60
tgcccagaat gcggaaaatc ctttagccag ctcgcccacc ttcgcgccca tcagcgcact     120
cataccggag agaagccata taatgccca gagtgtggaa agtccttctc ccagagcggc     180
gatcttcgcc gccaccagcg cacccacact ggagaaaaac cttataagtg tccagaatgc     240
ggcaagagct tcagcaccac cggcaacctc accgttcacc agaggaccca taccggcgag     300
aagccataca gtgtccaga gtgtggcaaa agcttcagcg actgccgcga tcttgctcgc     360
catcaaagga ctcatactgg agagaagcct tacaagtgtc cagagtgcgg caagtccttc     420
agccgctccg atgacctcgt tcgccatcag cgcacccaca ccggcgaaaa gccatataag     480
tgtccagagt gcggaaagag cttttcccag agcagcaacc ttgttaggca ccaacgcacc     540
catactggag ctgccgctga tgctctcgac gacttcgacc tcgacatgct tgacgctctc     600
gacgatttcg atcttgatat gcttgatgcc ctcgatgatt tcgatctcga catgctcgat     660
gctctcgatg attttgacct tgacatgctt tga                                  693

<210> SEQ ID NO 99
<211> LENGTH: 230
<212> TYPE: PRT
<213> ORGANISM: Artificial sequence
<220> FEATURE:
<223> OTHER INFORMATION: synthetic

<400> SEQUENCE: 99

Met Gly Pro Lys Lys Arg Lys Val Gly Arg Leu Glu Pro Gly Glu
1               5                   10                  15

Lys Pro Tyr Lys Cys Pro Glu Cys Gly Lys Ser Phe Ser Arg Ser Asp
            20                  25                  30

Lys Leu Val Arg His Gln Arg Thr His Thr Gly Glu Lys Pro Tyr Lys
            35                  40                  45

Cys Pro Glu Cys Gly Lys Ser Phe Ser Thr Ser Gly Ser Leu Val Arg
            50                  55                  60

His Gln Arg Thr His Thr Gly Glu Lys Pro Tyr Lys Cys Pro Glu Cys
65                  70                  75                  80

| | | | | | | | | | | | |
|---|---|---|---|---|---|---|---|---|---|---|---|
|Gly|Lys|Ser|Phe|Ser|Arg|Glu|Asp|Asn|Leu|His|Thr|
| | | | |85| | | |90| | |95|

His Thr Gly Glu Lys Pro Tyr Lys Cys Pro Glu Cys Gly Lys Ser Phe
            100                 105                 110

Ser Gln Lys Ser Ser Leu Ile Ala His Gln Arg Thr His Thr Gly Glu
        115                 120                 125

Lys Pro Tyr Lys Cys Pro Glu Cys Gly Lys Ser Phe Ser Arg Ser Asp
    130                 135                 140

Glu Leu Val Arg His Gln Arg Thr His Thr Gly Lys Pro Tyr Lys
145                 150                 155                 160

Cys Pro Glu Cys Gly Lys Ser Phe Ser Arg Glu Asp Asn Leu His Thr
                165                 170                 175

His Gln Arg Thr His Thr Gly Ala Ala Ala Asp Ala Leu Asp Asp Phe
                180                 185                 190

Asp Leu Asp Met Leu Asp Ala Leu Asp Phe Asp Leu Asp Met Leu
            195                 200                 205

Asp Ala Leu Asp Asp Phe Asp Leu Asp Met Leu Asp Ala Leu Asp Asp
    210                 215                 220

Phe Asp Leu Asp Met Leu
225                 230

<210> SEQ ID NO 100
<211> LENGTH: 693
<212> TYPE: DNA
<213> ORGANISM: Artificial sequence
<220> FEATURE:
<223> OTHER INFORMATION: synthetic

<400> SEQUENCE: 100
atgggaccaa agaagaaaag gaaggtcggc cgccttgagc ccggcgaaaa gccttataag    60
tgtccagagt gtggaaaatc cttctctcgc agcgataagc tcgttaggca ccaacgcacc   120
catactggcg aaaaaccata aagtgccca gagtgtggaa agtcctttag cactagcggc   180
agccttgtta ggcaccagcg cacccacacc ggcgaaaagc cttacaagtg tccagaatgt   240
ggcaagagct ctcccgcga ggataatctc cacactcatc agcgcaccca taccggcgag   300
aaaccttaca gtgtccaga atgcggaaaa agcttcagcc aaaaaagcag cctcatcgct   360
catcagagga ctcataccgg agagaagcct tataaatgcc cagagtgcgg aaaatccttc   420
agccgcagcg acgaactcgt ccgccatcaa cgcactcaca ccggagaaaa accatacaaa   480
tgtccagagt gcggcaagtc ctttagccgc gaggacaacc tccacaccca tcaaggacc   540 cacactggag ccgctgctga tgccctcgac gacttcgatc ttgacatgct tgatgctctc   600
gatgatttcg atctcgacat gcttgacgcc ctcgacgatt tcgacctcga tatgctcgac   660
gcccttgacg actttgacct tgatatgctc tga                                693

<210> SEQ ID NO 101
<211> LENGTH: 18
<212> TYPE: DNA
<213> ORGANISM: Zea mays

<400> SEQUENCE: 101
gactaggttg cggaaggg                                                  18

<210> SEQ ID NO 102
<211> LENGTH: 18
<212> TYPE: DNA

-continued

<213> ORGANISM: Zea mays

<400> SEQUENCE: 102
gaggaggatg cagaggtc                                                   18

<210> SEQ ID NO 103
<211> LENGTH: 18
<212> TYPE: DNA
<213> ORGANISM: Zea mays

<400> SEQUENCE: 103
gaagcggcca atgcaaga                                                   18

<210> SEQ ID NO 104
<211> LENGTH: 18
<212> TYPE: DNA
<213> ORGANISM: Zea mays

<400> SEQUENCE: 104
taggtgatat aggttggg                                                   18

<210> SEQ ID NO 105
<211> LENGTH: 179
<212> TYPE: PRT
<213> ORGANISM: Artificial sequence
<220> FEATURE:
<223> OTHER INFORMATION: synthetic

<400> SEQUENCE: 105

Met Gly Gly Arg Leu Glu Pro Gly Glu Lys Pro Tyr Lys Cys Pro Glu
1               5                   10                  15
Cys Gly Lys Ser Phe Ser Arg Ser Asp Lys Leu Val Arg His Gln Arg
            20                  25                  30
Thr His Thr Gly Glu Lys Pro Tyr Lys Cys Pro Glu Cys Gly Lys Ser
        35                  40                  45
Phe Ser Gln Ser Ser Asn Leu Val Arg His Gln Arg Thr His Thr Gly
    50                  55                  60
Glu Lys Pro Tyr Lys Cys Pro Glu Cys Gly Lys Ser Phe Ser Arg Ser
65                  70                  75                  80
Asp Asp Leu Val Arg His Gln Arg Thr His Thr Gly Glu Lys Pro Tyr
                85                  90                  95
Lys Cys Pro Glu Cys Gly Lys Ser Phe Ser Thr Ser Gly Ser Leu Val
            100                 105                 110
Arg His Gln Arg Thr His Thr Gly Glu Lys Pro Tyr Lys Cys Pro Glu
        115                 120                 125
Cys Gly Lys Ser Phe Ser Arg Glu Asp Asn Leu His Thr His Gln Arg
    130                 135                 140
Thr His Thr Gly Glu Lys Pro Tyr Lys Cys Pro Glu Cys Gly Lys Ser
145                 150                 155                 160
Phe Ser Asp Pro Gly Asn Leu Val Arg His Gln Arg Thr His Thr Gly
                165                 170                 175
Ala Ala Ala

<210> SEQ ID NO 106
<211> LENGTH: 179
<212> TYPE: PRT
<213> ORGANISM: Artificial sequence
<220> FEATURE:
<223> OTHER INFORMATION: synthetic

<400> SEQUENCE: 106

Met Gly Gly Arg Leu Glu Pro Gly Glu Lys Pro Tyr Lys Cys Pro Glu
1               5                   10                  15

Cys Gly Lys Ser Phe Ser Asp Pro Gly Ala Leu Val Arg His Gln Arg
                20                  25                  30

Thr His Thr Gly Glu Lys Pro Tyr Lys Cys Pro Glu Cys Gly Lys Ser
            35                  40                  45

Phe Ser Arg Ser Asp Asn Leu Val Arg His Gln Arg Thr His Thr Gly
        50                  55                  60

Glu Lys Pro Tyr Lys Cys Pro Glu Cys Gly Lys Ser Phe Ser Gln Ser
65                  70                  75                  80

Gly Asp Leu Arg Arg His Gln Arg Thr His Thr Gly Glu Lys Pro Tyr
                85                  90                  95

Lys Cys Pro Glu Cys Gly Lys Ser Phe Ser Thr Ser Gly Asn Leu Val
            100                 105                 110

Arg His Gln Arg Thr His Thr Gly Glu Lys Pro Tyr Lys Cys Pro Glu
        115                 120                 125

Cys Gly Lys Ser Phe Ser Arg Ser Asp Asn Leu Val Arg His Gln Arg
    130                 135                 140

Thr His Thr Gly Glu Lys Pro Tyr Lys Cys Pro Glu Cys Gly Lys Ser
145                 150                 155                 160

Phe Ser Arg Ser Asp Asn Leu Val Arg His Gln Arg Thr His Thr Gly
                165                 170                 175

Ala Ala Ala

<210> SEQ ID NO 107
<211> LENGTH: 179
<212> TYPE: PRT
<213> ORGANISM: Artificial sequence
<220> FEATURE:
<223> OTHER INFORMATION: synthetic

<400> SEQUENCE: 107

Met Gly Gly Arg Leu Glu Pro Gly Glu Lys Pro Tyr Lys Cys Pro Glu
1               5                   10                  15

Cys Gly Lys Ser Phe Ser Gln Leu Ala His Leu Arg Ala His Gln Arg
                20                  25                  30

Thr His Thr Gly Glu Lys Pro Tyr Lys Cys Pro Glu Cys Gly Lys Ser
            35                  40                  45

Phe Ser Gln Ser Gly Asp Leu Arg Arg His Gln Arg Thr His Thr Gly
        50                  55                  60

Glu Lys Pro Tyr Lys Cys Pro Glu Cys Gly Lys Ser Phe Ser Thr Thr
65                  70                  75                  80

Gly Asn Leu Thr Val His Gln Arg Thr His Thr Gly Glu Lys Pro Tyr
                85                  90                  95

Lys Cys Pro Glu Cys Gly Lys Ser Phe Ser Asp Cys Arg Asp Leu Ala
            100                 105                 110

Arg His Gln Arg Thr His Thr Gly Glu Lys Pro Tyr Lys Cys Pro Glu
        115                 120                 125

Cys Gly Lys Ser Phe Ser Arg Ser Asp Asp Leu Val Arg His Gln Arg
    130                 135                 140

Thr His Thr Gly Glu Lys Pro Tyr Lys Cys Pro Glu Cys Gly Lys Ser
145                 150                 155                 160

Phe Ser Gln Ser Ser Asn Leu Val Arg His Gln Arg Thr His Thr Gly
                165                 170                 175

Ala Ala Ala

<210> SEQ ID NO 108
<211> LENGTH: 179
<212> TYPE: PRT
<213> ORGANISM: Artificial sequence
<220> FEATURE:
<223> OTHER INFORMATION: synthetic

<400> SEQUENCE: 108

Met Gly Gly Arg Leu Glu Pro Gly Glu Lys Pro Tyr Lys Cys Pro Glu
1               5                   10                  15

Cys Gly Lys Ser Phe Ser Arg Ser Asp Lys Leu Val Arg His Gln Arg
            20                  25                  30

Thr His Thr Gly Glu Lys Pro Tyr Lys Cys Pro Glu Cys Gly Lys Ser
        35                  40                  45

Phe Ser Thr Ser Gly Ser Leu Val Arg His Gln Arg Thr His Thr Gly
    50                  55                  60

Glu Lys Pro Tyr Lys Cys Pro Glu Cys Gly Lys Ser Phe Ser Arg Glu
65                  70                  75                  80

Asp Asn Leu His Thr His Gln Arg Thr His Thr Gly Glu Lys Pro Tyr
                85                  90                  95

Lys Cys Pro Glu Cys Gly Lys Ser Phe Ser Gln Lys Ser Ser Leu Ile
            100                 105                 110

Ala His Gln Arg Thr His Thr Gly Glu Lys Pro Tyr Lys Cys Pro Glu
        115                 120                 125

Cys Gly Lys Ser Phe Ser Arg Ser Asp Glu Leu Val Arg His Gln Arg
    130                 135                 140

Thr His Thr Gly Glu Lys Pro Tyr Lys Cys Pro Glu Cys Gly Lys Ser
145                 150                 155                 160

Phe Ser Arg Glu Asp Asn Leu His Thr His Gln Arg Thr His Thr Gly
                165                 170                 175

Ala Ala Ala

<210> SEQ ID NO 109
<211> LENGTH: 7
<212> TYPE: PRT
<213> ORGANISM: Artificial sequence
<220> FEATURE:
<223> OTHER INFORMATION: synthetic
<220> FEATURE:
<221> NAME/KEY: VARIANT
<222> LOCATION: (1)..(1)
<223> OTHER INFORMATION: Xaa is glutamate or arginine

<400> SEQUENCE: 109

Xaa Thr Leu Pro Leu Phe Pro
1               5

<210> SEQ ID NO 110
<211> LENGTH: 7
<212> TYPE: PRT
<213> ORGANISM: Artificial sequence
<220> FEATURE:
<223> OTHER INFORMATION: synthetic
<220> FEATURE:
<221> NAME/KEY: VARIANT
<222> LOCATION: (2)..(2)
<223> OTHER INFORMATION: Xaa is alanine or serine
<220> FEATURE:
<221> NAME/KEY: VARIANT
<222> LOCATION: (6)..(6)

```
<223> OTHER INFORMATION: Xaa is serine or threonine

<400> SEQUENCE: 110

Ala Xaa Leu Glu Leu Xaa Leu
1               5
```